(12) United States Patent
Wang et al.

(10) Patent No.: US 11,672,468 B2
(45) Date of Patent: Jun. 13, 2023

(54) SYSTEM AND METHOD FOR MULTI-MODALITY QUANTIFICATION OF NEUROINFLAMMATION IN CENTRAL NERVOUS SYSTEM DISEASES

(71) Applicant: WASHINGTON UNIVERSITY, St. Louis, MO (US)

(72) Inventors: Yong Wang, St. Louis, MO (US); Qing Wang, St. Louis, MO (US); Tammie Benzinger, St. Louis, MO (US)

(73) Assignee: Washington University, St. Louis, MO (US)

( * ) Notice: Subject to any disclaimer, the term of this patent is extended or adjusted under 35 U.S.C. 154(b) by 695 days.

(21) Appl. No.: 16/097,457

(22) PCT Filed: Apr. 28, 2017

(86) PCT No.: PCT/US2017/030161
§ 371 (c)(1),
(2) Date: Oct. 29, 2018

(87) PCT Pub. No.: WO2017/190029
PCT Pub. Date: Nov. 2, 2017

(65) Prior Publication Data
US 2019/0150822 A1    May 23, 2019
US 2020/0221991 A9    Jul. 16, 2020

Related U.S. Application Data

(60) Provisional application No. 62/353,159, filed on Jun. 22, 2016, provisional application No. 62/329,633, filed on Apr. 29, 2016.

(51) Int. Cl.
*A61B 5/00*    (2006.01)
*A61B 5/055*    (2006.01)
(Continued)

(52) U.S. Cl.
CPC ............ *A61B 5/4088* (2013.01); *A61B 5/055* (2013.01); *A61B 5/4064* (2013.01);
(Continued)

(58) Field of Classification Search
CPC ..... A61B 5/4088; A61B 5/4064; A61B 5/055; G01R 33/4806; G01R 33/56341; G01R 33/5616; G01R 33/5617; G01R 33/56509
See application file for complete search history.

(56) References Cited

U.S. PATENT DOCUMENTS

2002/0042569 A1    4/2002    Wedeen
2005/0068031 A1    3/2005    Frank
(Continued)

OTHER PUBLICATIONS

Yong Wang, Peng Sun, Qing Wang, Kathryn Trinkaus, Robert E. Schmidt, Robert T. Naismith, Anne H. Cross, Sheng-Kwei Song, Differentiation and quantification of inflammation, demyelination and axon injury or loss in multiple sclerosis, Brain, vol. 138, Issue 5, May 2015, pp. 1223-1238, (Year: 2015).*

(Continued)

*Primary Examiner* — Yi-Shan Yang
*Assistant Examiner* — Nicholas A Robinson
(74) *Attorney, Agent, or Firm* — Armstrong Teasdale LLP

(57) ABSTRACT

Methods and systems for diagnosing a condition of a central nervous system are provided. A method includes providing a DBSI-MRI data set obtained from the central nervous system of the subject, and transforming the DBSI-MRI data set to obtain at least one DBSI biomarker value. The method further includes comparing each DBSI biomarker value to at least one corresponding threshold value from a diagnostic database to obtain a relation between each DBSI biomarker value and the at least one corresponding threshold value, and diagnosing the condition according to at least one diagnostic rule, wherein each diagnostic rule defines a candidate con- (Continued)

dition in terms of the relations between the at least one DBSI biomarker value and the at least one corresponding threshold value.

6 Claims, 87 Drawing Sheets

(51) Int. Cl.
  *G01R 33/563* (2006.01)
  *G01R 33/48* (2006.01)
  *G01R 33/561* (2006.01)
  *G01R 33/565* (2006.01)

(52) U.S. Cl.
  CPC ... *G01R 33/4806* (2013.01); *G01R 33/56341* (2013.01); *G01R 33/5616* (2013.01); *G01R 33/5617* (2013.01); *G01R 33/56509* (2013.01)

(56) References Cited

U.S. PATENT DOCUMENTS

| | | | |
|---|---|---|---|
| 2009/0312625 | A1 | 12/2009 | Du |
| 2011/0282183 | A1* | 11/2011 | Song ............... G01R 33/56341 600/410 |
| 2012/0238936 | A1* | 9/2012 | Hyde ............... A61B 5/1459 604/8 |
| 2016/0326586 | A1* | 11/2016 | Scherer ............ G16B 20/10 |
| 2018/0310869 | A1* | 11/2018 | Yablonskiy ........ A61B 5/055 |

OTHER PUBLICATIONS

Seines P, Aarsland D, Bjørnerud A, Gjerstad L, Wallin A, Hessen E, Reinvang I, Grambaite R, Auning E, Kjævik VK, Due-Tonnessen P, Stenset V, Fladby T. Diffusion tensor imaging surpasses cerebrospinal fluid as predictor of cognitive decline and medial temporal lobe atrophy in subjective (Year: 2013).*

Acosta-Cabronero, J., Alley, S., Williams, G. B., Pengas, G., & Nestor, P. J. (2012). Diffusion tensor metrics as biomarkers in Alzheimer's disease. PloS one, 7(11), e49072. https://doi.org/10.1371/journal.pone.0049072 (Year: 2012).*

Seines P, Aarsland D, Bjørnerud A, Gjerstad L, Wallin A, Hessen E, Reinvang I, Grambaite R, Auning E, Kjærvik VK, Due-Tønnessen P, Stenset V, Fladby T. Diffusion tensor imaging surpasses cerebrospinal fluid as predictor of cognitive decline and medial temporal lobe atrophy in subjective (Year: 2013).*

International Search Report and Written Opinion for PCT/US2017/030161, dated Jul. 27, 2017, 8 pages.

* cited by examiner

FIG. 6
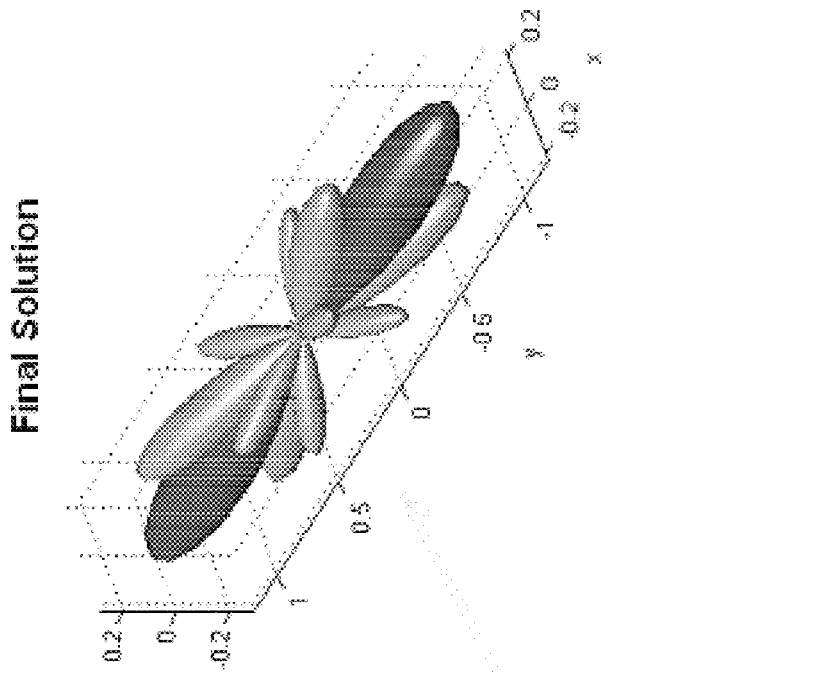
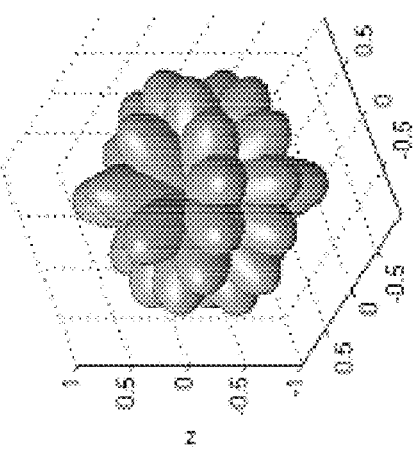
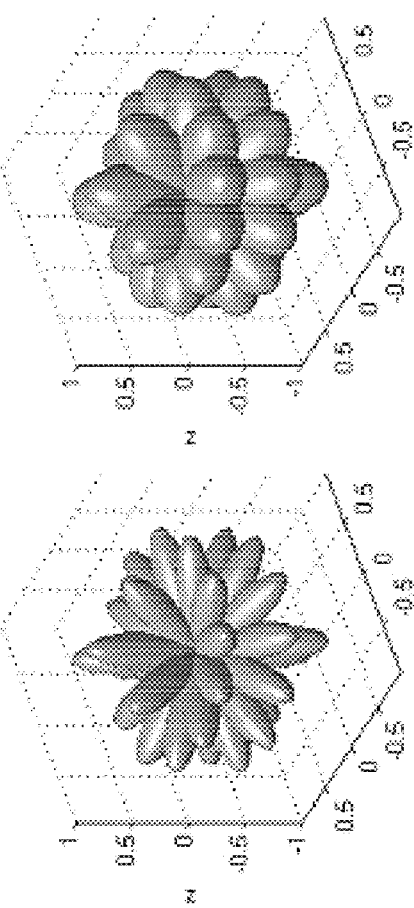
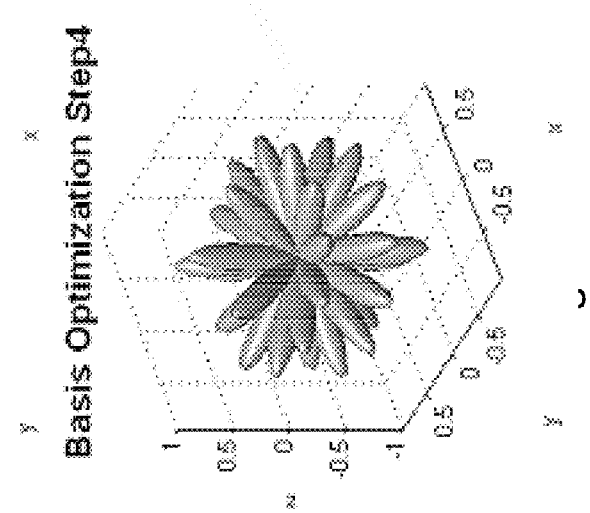

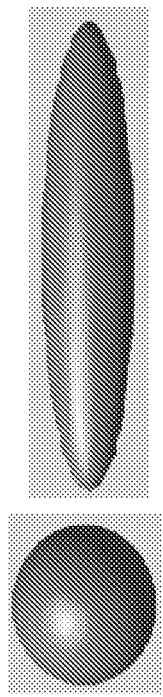
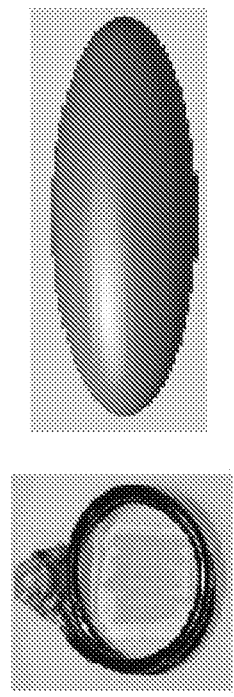
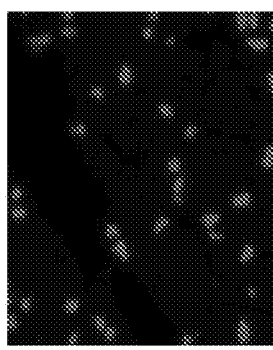
FIG. 18
| | |
|---|---|
| Axial Diffusivity (μm²/ms) | 1.06 |
| Radial Diffusivity (μm²/ms) | 0.16 |
| Gel Diffusivity (μm²/ms) | 1.89 |
| Cell Diffusivity (μm²/ms) | 0.01 |
| Fiber Ratio | 21.39% |
| Gel Ratio | 73.80% |
| Cell Ratio | 4.82% |
| | |
|---|---|
| Axial Diffusivity (μm²/ms) | 1.1+ |
| Radial Diffusivity (μm²/ms) | 0.54 |

FIG. 24A  MBP
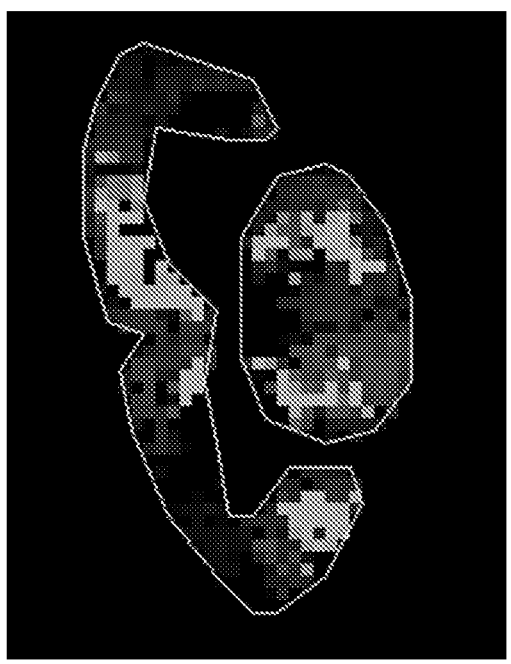
FIG. 24B  SMI-31
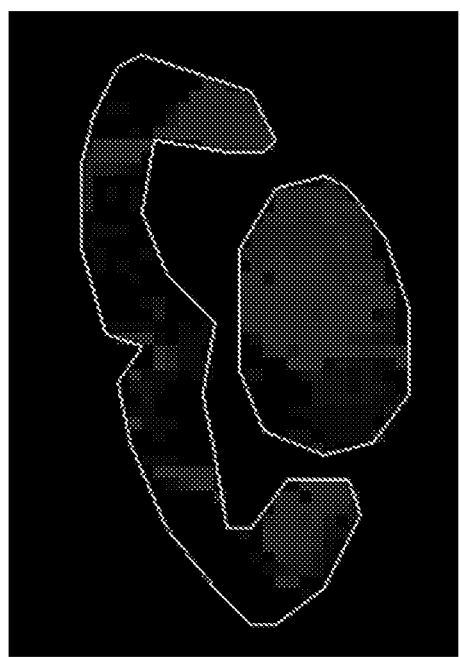
FIG. 24C  DAPI
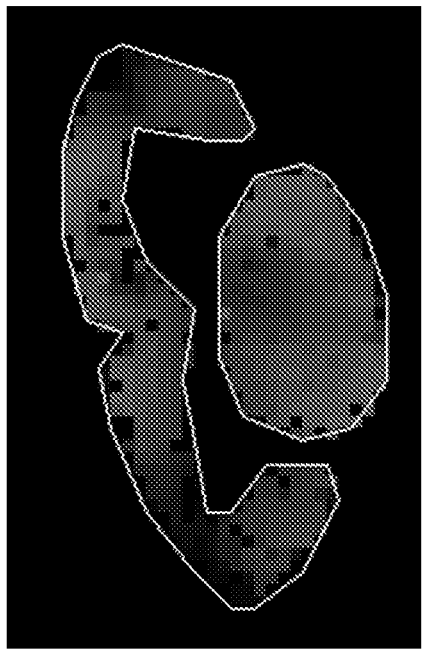
FIG. 24D  WATER
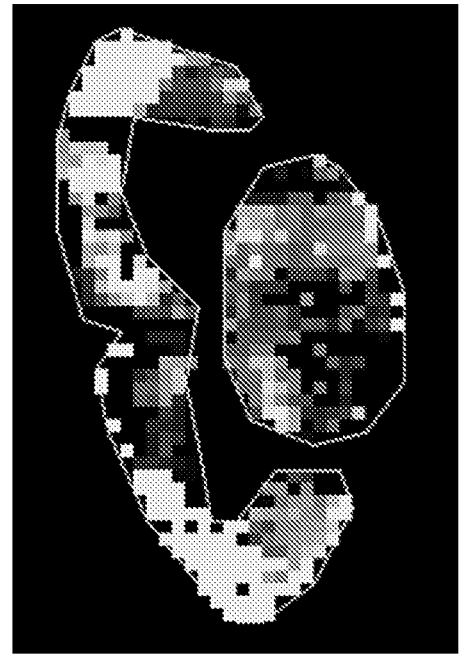

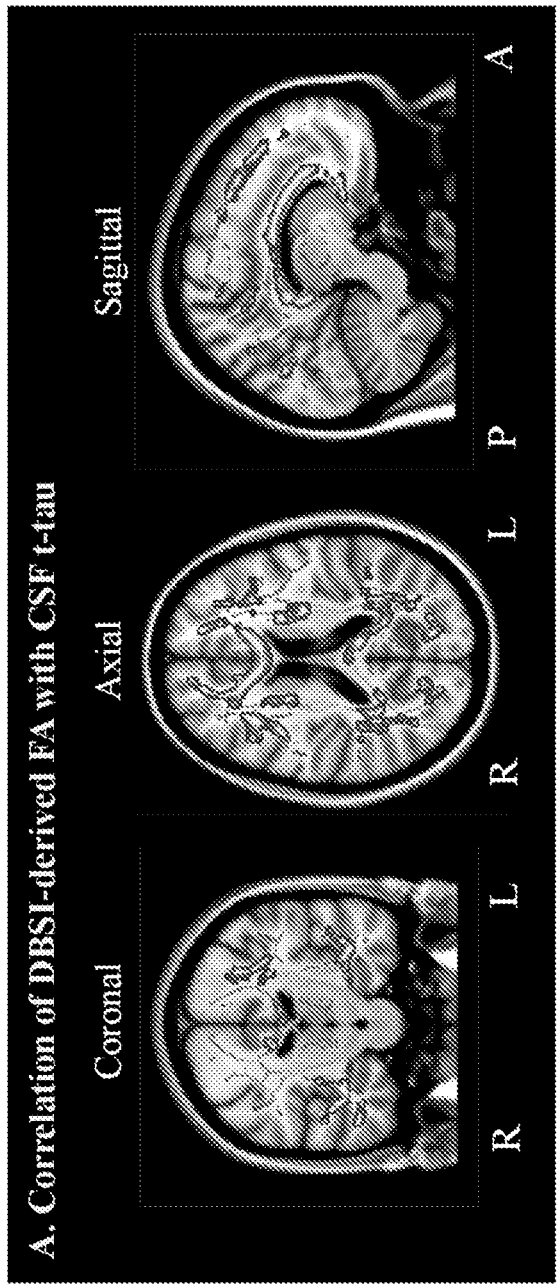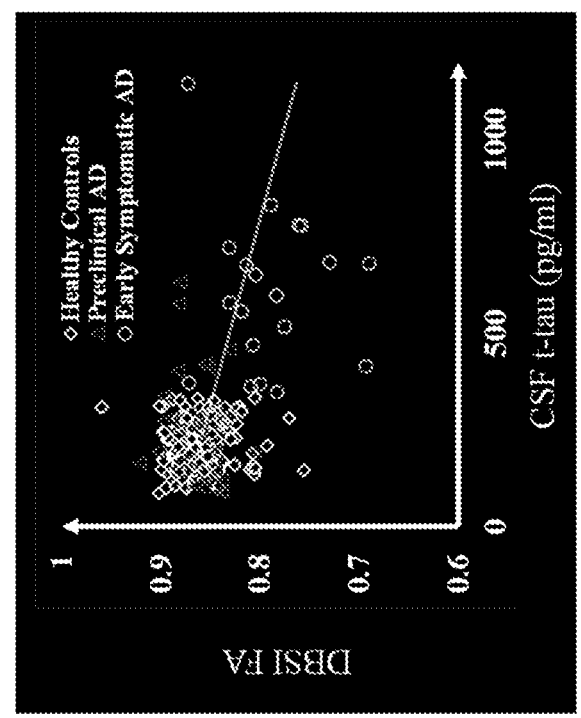
FIG. 77

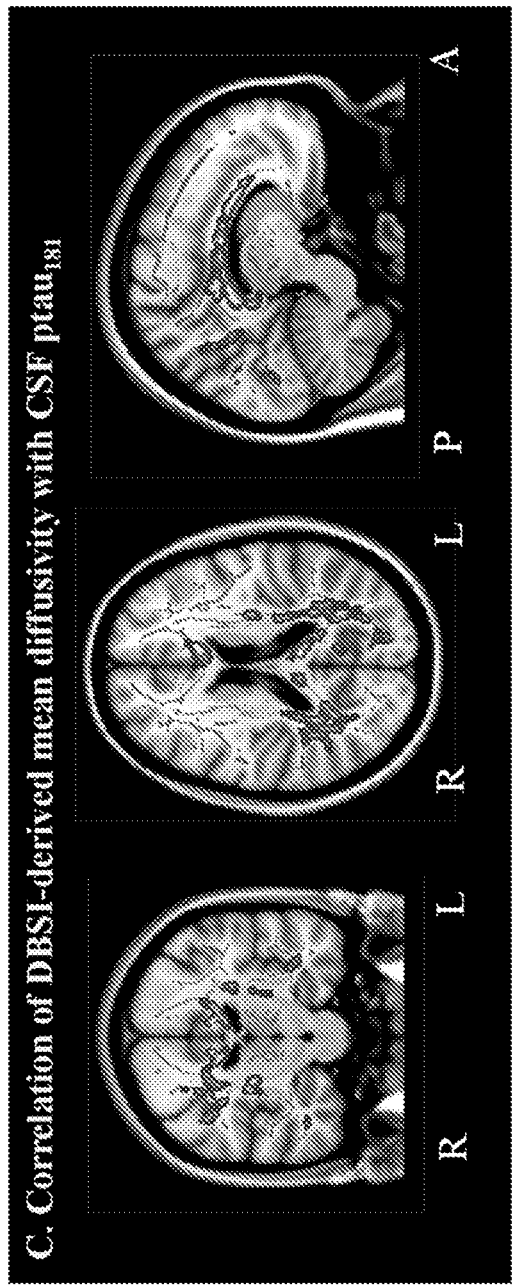
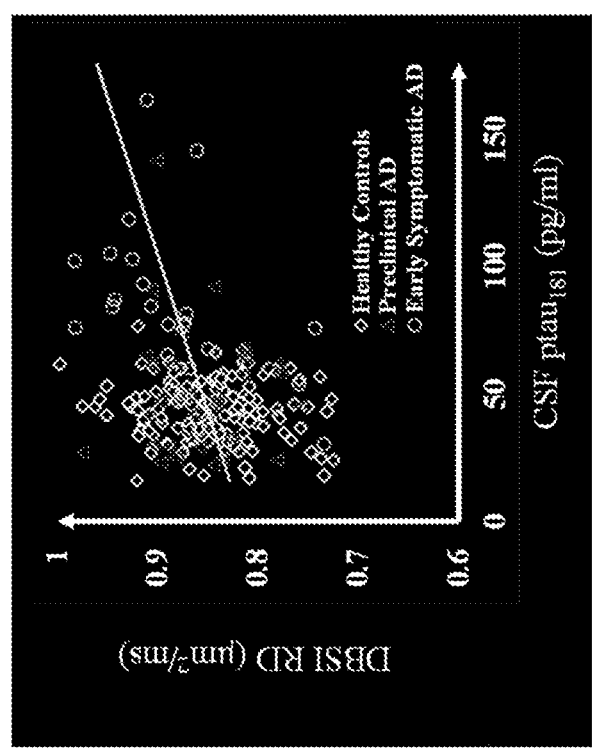
FIG. 77

SYSTEM AND METHOD FOR MULTI-MODALITY QUANTIFICATION OF NEUROINFLAMMATION IN CENTRAL NERVOUS SYSTEM DISEASES

CROSS-REFERENCE TO RELATED APPLICATIONS

This application is a U.S. National Phase Application of WO Application No. PCT/US2017/030161, filed Apr. 28, 2017, which claims benefit of priority to U.S. Provisional Application No. 62/329,633 filed on Apr. 29, 2016, the contents of which are incorporated herein by reference in their entirety. WO Application No. PCT/US2017/030161 further claims the benefit of priority to U.S. Provisional Application No. 62/353,159 filed on Jun. 22, 2016, the contents of which are incorporated herein by reference in their entirety.

STATEMENT REGARDING FEDERALLY SPONSORED RESEARCH & DEVELOPMENT

This invention was made with government support under AG026276 and AG003991 awarded by the National Institutes of Health. The government has certain rights in the invention.

BACKGROUND

Aspects of the disclosure relate generally to a medical test and a quantitative multi-modality platform to provide quantification of neuroinflammation for patients with central nervous system (CNS) diseases, such as Alzheimer's disease (AD), to facilitate early diagnosis and a new therapy efficacy evaluation in clinical trials. As described herein Non-Invasive Histology (NIH) can be used to detect, quantify and track complex neuropathological changes in human CNS diseases.

Abbreviations: Aβ, beta-amyloid; AD, Alzheimer's Disease; CNS, central nervous system; NIH, non-invasive histology; MRI, magnetic resonance imaging; DBSI, diffusion basis spectrum imaging; FA, fractional anisotropy; CSF, cerebrospinal fluid; dMRI, diffusion magnetic resonance imaging; DTI, diffusion tensor imaging; PET, positron emission tomography; TBSS, tract-based spatial statistics; WM, white matter; ADRC, Alzheimer's Disease research center.

CNS is composed by brain and spinal cord. Obtaining CNS tissue samples to study pathologies by conventional histology has the potential to cause serious harm to patients with various CNS disorders. These difficulties are further compounded, considering that CNS lesions usually vary spatially within/across patients and dynamically evolve over time, and may require serial biopsies of many affected patients. Therefore a safe and cheap imaging test that is capable of providing accurate measurements of the CNS histopathologies may enable a more complete (spatial wise) and dynamic (temporal wise) characterization of pathological progression and assessment of drug's disease modifying effects in patients with various CNS disorders. The major CNS disease to target at first is Alzheimer's disease.

Conventional histology technique is invasive and imposes significant risk to patients with CNS diseases, preventing it from being used in longitudinal and global studies. Contrast-enhancing MRI is invasive and the injected contrast agent may cause serious chronic health problems. PET imaging employs radio-active tracer, which is expensive and hazardous for multiple usages. Conventional relativity-based MRI techniques have also been used to study the pathology of CNS diseases, but they cannot separate the effects from multiple coexisting pathological components, leading to poor histopathology specificity.

NIH is a noninvasive, endogenous (without injecting contrast agents) and non-radiative medical test using clinical magnetic resonance imaging (MRI). In a signal test, NIH provides multiple parametric images corresponding to and correlated with conventional histology measures of CNS pathologies. NIH aims to provide critical pathological information when conventional histology cannot be applied, especially in human CNS disease where large and/or multiple biopsies can potentially harm patients. NIH may impact laboratory research, clinical practice, drug development and clinical trials.

Diffusion basis spectrum imaging MRI (DBSI-MRI) methods and systems are provided for detecting at least one DBSI biomarker to quantify neuroinflammation is disclosed herein. Compared to currently available methods of measuring neuroinflammation (lumbar puncture for CSF measure, or PET imaging), the methods disclosed herein are non-invasive and non-radioactive. The at least one DBSI biomarker obtained using DBSI-MRI has excellent test-retest stability, high sensitivity to disease progression and close correlation with currently available techniques. By integrating the at least one DBSI biomarker for neuroinflammation with other available CSF and/or PET measures, a more complete measure of a patient's inflammation can be provided to CNS patients/physicians. The DBSI-MRI systems and methods described can be used for efficient evaluation of new drugs targeting immunoresponse and neuroinflammation in CNS and related neurodegeneration diseases, such as Alzheimer's disease, and may facilitate early diagnosis and risk stratification for CNS patients.

BRIEF DESCRIPTION

In one aspect, a method for diagnosing a condition of a central nervous system in a patient is provided. The method comprises providing a DBSI-MRI data set obtained from the central nervous system of the subject, and transforming the DBSI-MRI data set to obtain at least one DBSI biomarker value. The method further comprises comparing each DBSI biomarker value to at least one corresponding threshold value from a diagnostic database to obtain a relation between each DBSI biomarker value and the at least one corresponding threshold value, and diagnosing the condition according to at least one diagnostic rule, wherein each diagnostic rule defines a candidate condition in terms of the relations between the at least one DBSI biomarker value and the at least one corresponding threshold value.

In another aspect, a central nervous system diagnosis computing device is provided. The central nervous system diagnosis computing device includes a processor in communication with a memory. The processor is programmed to retrieve a DBSI-MRI data set obtained from the central nervous system of the subject from the memory, transform the DBSI-MRI data set to obtain at least one DBSI biomarker value, and retrieve a diagnostic database comprising at least one corresponding threshold value from the memory. The processor is further programmed to compare each DBSI biomarker value to at least one corresponding threshold value from the retrieved diagnostic database to obtain a relation between each DBSI biomarker value and the at least one corresponding threshold value, and diagnose the condition according to at least one diagnostic rule, wherein each diagnostic rule defines a candidate condition in terms of the relations between the at least one DBSI biomarker value and the at least one corresponding threshold value.

In yet another aspect, at least one non-transitory computer-readable storage media for providing a diagnosis of a condition of a central nervous system in a patient is provided. The at least one non-transitory computer-readable storage media has computer-executable instructions embodied thereon, wherein, when executed by at least one processor, the computer-executable instructions cause the at least one processor to transform a DBSI-MRI data set to obtain at least one DBSI biomarker value, the DBSI-MRI data set obtained from the central nervous system of the subject, compare each DBSI biomarker value to at least one corresponding threshold value from a stored diagnostic database to obtain a relation between each DBSI biomarker value and the at least one corresponding threshold value, and diagnose the condition according to at least one diagnostic rule, wherein each diagnostic rule defines a candidate condition in terms of the relations between the at least one DBSI biomarker value and the at least one corresponding threshold value.

BRIEF DESCRIPTION OF THE DRAWINGS

FIG. 6 is an illustration of an exemplary optimization process of DBSI basis set.

FIG. 18 is an exemplary phantom of mouse trigeminal nerves embedded in gel with known in vivo DTI character.

FIG. 24A is a detailed view of the DBSI-derived MBP fraction of the scan of FIG. 22.

FIG. 24B is a detailed view of the DBSI-derived SMI-31 fraction of the scan of FIG. 22.

FIG. 24C is a detailed view of the DBSI-derived DAPI fraction of the scan of FIG. 22.

FIG. 24D is a detailed view of the DBSI-derived water fraction of the scan of FIG. 22.

DETAILED DESCRIPTION

Figure 1:
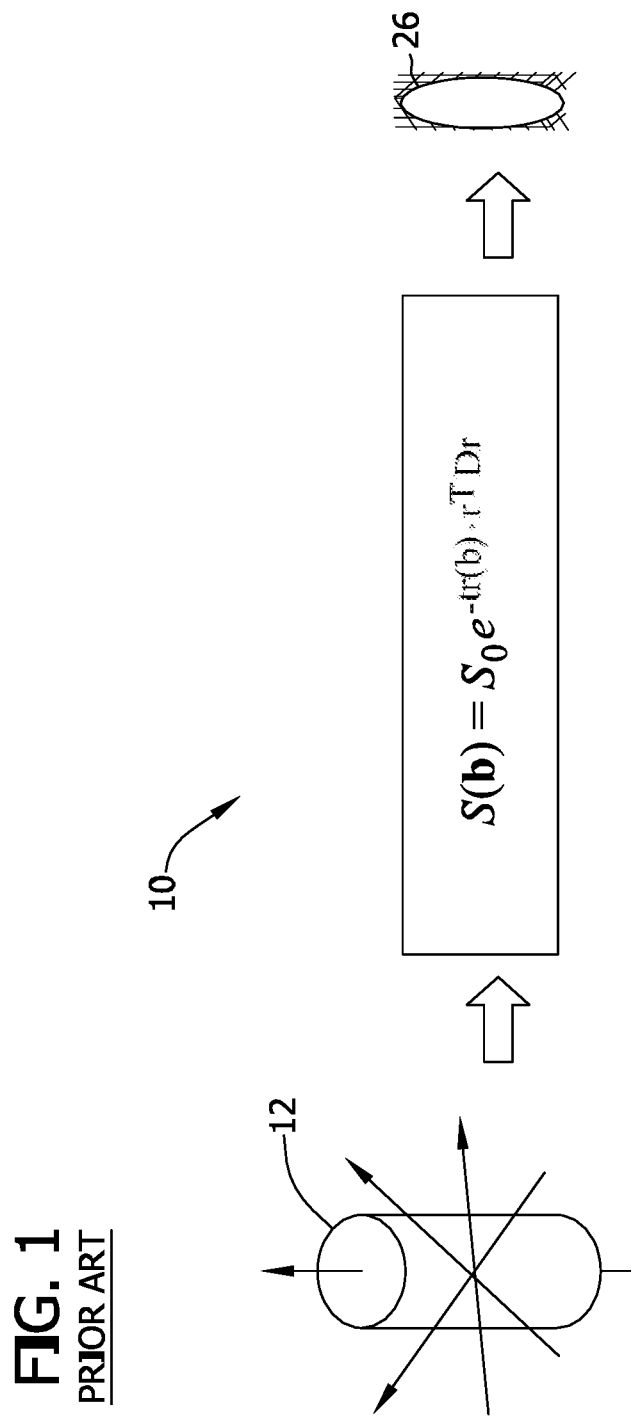
FIG. 1 is an illustration of diffusion magnetic resonance (MR) signal response when diffusion tensor imaging (DTI) is applied to a single white matter tract of coherent axonal fibers.

Methods and systems are disclosed herein for a component (MRI neuroinflammation biomarker) to quantify neuroinflammation. Compared to currently available methods of measuring neuroinflammation (lumbar puncture for CSF measure, or PET imaging), the methods discussed herein are non-invasive and non-radioactive. Preliminary data has shown that this MRI modality has excellent test-retest stability, high sensitivity to disease progression and close correlation with currently available techniques. By integrating this MRI neuroinflammation biomarker with other available CSF and/or PET measures, a more complete measure of a patient's inflammation can be provided to CNS patients/physicians. The methods and systems described herein can be used to efficient evaluation of new drug targeting immunoresponse and neuroinflammation in CNS and related neurodegeneration diseases, such as Alzheimer's disease. They may also facilitate early diagnosis and risk stratification for CNS patients.

For the context of the present disclosure, an in-depth discussion of diffusion MRI is first provided, following by a detailed description of multi-modality quantification of neuroinflammation in CNS diseases.

Diffusion MRI

The following discussion relates generally to magnetic resonance imaging (MRI) and, more particularly, to diffusion magnetic resonance data provided by an MRI scanner.

White matter injury is common in central nervous system (CNS) disorders and plays an important role in neurological dysfunctions in patients. Understanding the pathology of complex and heterogeneous central nervous system diseases such as multiple sclerosis (MS) has been greatly hampered by the dearth of histological specimens obtained serially during the disease. Clinicians are reluctant to perform invasive CNS biopsies on patients with white matter disorders, due to the potential injury to the patients.

The insight of CNS white matter neuropathology has been derived typically from occasional biopsies consisting of small tissue samples of unusual cases. These autopsies usually derive from patients with end-stage disease and often have long postmortem delay artifacts due tissue degradation. It is therefore advantageous to have a noninvasive imaging tool to accurately quantify and better understand the chronic and non-fatal injury in CNS disease during the whole course of the individual patient.

Diffusion tensor imaging (DTI) is a commonly used MRI modality in CNS disease/injury diagnosis. However, the current use of DTI technique is not capable of resolving the complex underlying pathologies correctly, despite being considered better than other techniques.

A diffusion MRI technique is discussed herein to noninvasively study and quantify complicated CNS diseases in a noninvasive fashion without the limitation of invasive histological examinations.

Such embodiments facilitate improved results compared to diffusion tensor imaging (DTI). The directional diffusivities derived from DTI measurements describe water movement parallel to ($\lambda_\parallel$, axial diffusivity) and perpendicular to ($\lambda_\perp$, radial diffusivity) axonal tracts. It was previously proposed and validated that decreased $\lambda_\parallel$ is associated with axonal injury and dysfunction, and increased $\lambda_\perp$ is associated with myelin injury in mouse models of white matter injury.

The presence of inflammation, edema, or gliosis during CNS white matter injury may impact the DTI measurement. One significant effect of inflammation is the resulting isotropic component of diffusion, due to the increased extracellular water and the infiltrating immune cells. This component complicates the DTI measurements and distorts the estimated directional diffusivity and anisotropy preventing its accurate interpretation of underlying pathologies. In addition to inflammation, similar isotropic diffusion tensor component may result from the loss of CNS tissues in the chronic MS lesions, spinal cord injury (SCI), or traumatic brain injury (TBI). The currently used DTI protocol is not able to resolve this isotropic component or differentiate inflammation from tissue loss. Only an averaged diffusion tensor reflecting the overall effect can be obtained from existing DTI methods.

DTI fails to (1) correctly describe axonal fiber directions in crossing white matter tracts, or (2) accurately reflect the complex white matter pathologies such as vasogenic edema, inflammation, and tissue loss commonly coexisting with axonal and myelin damages. Even recently developed existing systems are not capable of resolving white matter pathologies in complex tissue scenarios.

A noninvasive process based on diffusion MRI technique is described herein to facilitate accurately quantifying the complex human CNS white matter pathology where the current DTI and its relevant improvements have failed. As an exemplary embodiment, diffusion basis spectrum imaging (DBSI) is implemented and provided herein to demonstrate the feasibility and detailed operation of the process. The quantity and primary direction of diffusion tensor components within a tissue volume resulting from white matter pathology is determined using diffusion MRI before constructing the multi-tensor model. After the identification of each diffusion tensor component corresponding to individual pathology, the diffusivity and volume ratio of each component can be derived accordingly.

In some embodiments, the quantity of candidate fibers and their associated primary directions are calculated first by DBSI based on a combination of diffusion basis set best describing the measured diffusion magnetic resonance data. An isotropic diffusion component is also considered to improve the computation accuracy. Based on all candidate fibers' primary directions, DBSI is used to compute the axial diffusivity, indicating water diffusion parallel to the fiber, and radial diffusivity, indicating water diffusion perpendicular to the fiber. A diffusivity spectrum of isotropic diffusion components, such as those resulting from inflammation or tissue loss, as well as associated volume ratios of all candidate fibers and isotropic components may be calculated.

An exemplary embodiment employs diffusion basis spectrum imaging (DBSI) to facilitate an accurate diagnosis of CNS white matter pathology. Each diffusion tensor's directional diffusivity as well as its primary orientation is derived using the less stringent diffusion tensor acquisition schemes retaining DTI's applicability in clinical settings. Preliminary data in mouse corpus callosum, spinal cord injury, and phantoms demonstrates that DBSI is capable of identifying different underlying pathologies accurately estimating the extent of cell infiltration, axonal fiber density in corpus callosum of cuprizone treatment, as well as estimating tissue loss in chronic mouse spinal cord injury. Diffusion phantoms have also been designed and fabricated for a quantitative evaluation of DBSI and existing DTI methods.

The exemplary embodiment of diffusion MRI described herein resolves the multi-tensor complication resulting from diverse pathologies in CNS white matter to quantitatively derive diffusion parameters of crossing fibers as well as reflecting the actual pathologies. This unique capability of the proposed process and the exemplary DBSI method has the potential to differentiate acute inflammation from chronic tissue loss in patients. Such capability can estimate the extent of acute inflammation guiding the use of anti-inflammatory treatment and chronic tissue damage guiding the effort in axonal/neuronal preservation. There are many potential clinical applications of the proposed process. For example, it can document the efficacy of stem cell treatment in axonal regeneration by clearly estimating the isotropic component of the implanted cells while reflecting the axonal regeneration by quantifying the anisotropic component changes after cell transplantation. It could also be used to estimate the degree of CNS tumor growth by accurately estimating the isotropic tensor component representing the tumor cells. Methods described further facilitate evaluating the effectiveness of a drug in treating one or more medical conditions. For example, DBSI could be applied in clinical drug trial treating CNS diseases, tumors, and injury by accurately reflecting the progression of clinical and preclinical pathologies.

One important characteristic of DTI is its ability to measure diffusion anisotropy of CNS tissues for a detailed description of the underlying tissue injury based on the changed diffusion character. However, such measurement is not always obtainable in diseased tissues due to the complicated cellular responses to the pathology or the presence of crossing fibers.

The fundamental operation of DTI 10 can be explained by examining an MRI signal 12 under the influence of diffusion weighting gradients 14. When applying DTI to measure the single white matter tract of coherent axonal fibers, the MRI signal response can be expressed as shown in FIG. 1.

DTI assumes that there is only a pure coherent axonal fiber tract in the measured tissue and the signal response to diffusion weighting gradients is well described by the diffusion weighted (DW) profile. The insufficiency of DTI can be demonstrated by examining the diffusion ellipsoid responding to the different tissue components that typically seen in CNS tissues with and without pathology, as shown in FIG. 2.

Figure 2:
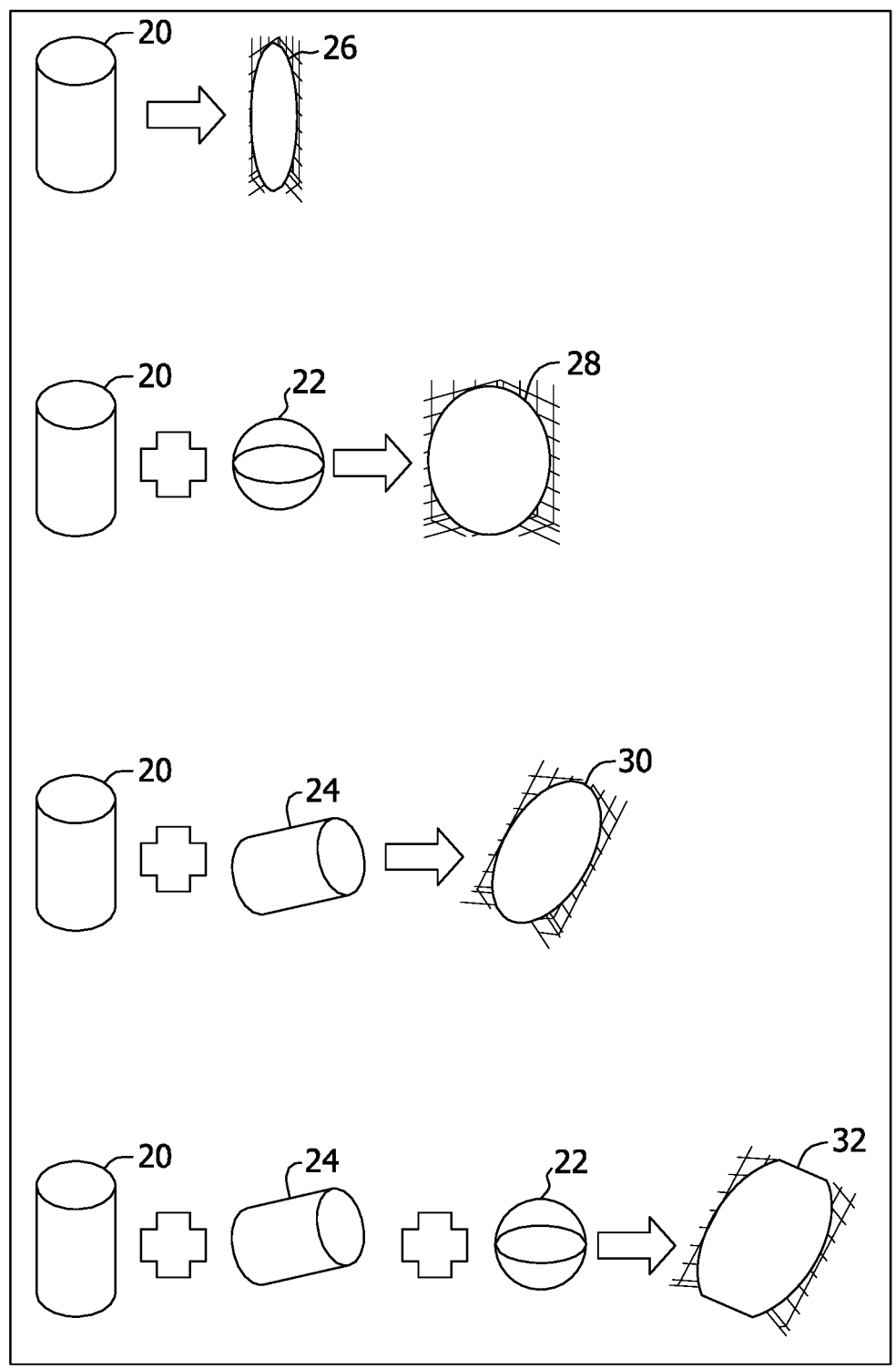
FIG. 2 is an illustration of exemplary DTI results corresponding to scenarios in which different tissue components are included within a scanned volume.

FIG. 2 illustrates exemplary DTI results corresponding to scenarios with the different tissue components (objects), including (A) ideal coherent single fiber 20 (spinal cord white matter or optic nerves), (B) fiber 20 plus an isotropic component 22 (tissue loss, inflammation, or edema), (C) two crossing fibers 24, and (D) two crossing fibers 24 with an isotropic component 22. If fiber 20 of (A) is of interest and the target for a DTI measurement as demonstrated, the correct DTI result for the ideal fiber result 26. Nevertheless, the various mixed conditions result in misrepresentations 28, 30, and 32 of the targeted fiber, which is the major shortcoming of DTI.

To definitively resolve the issue regarding the utility of directional diffusivity in detecting white matter injury in MS and/or other CNS white matter disorders, a careful evaluation was performed on the mouse model of cuprizone intoxication that is widely employed to examine the mechanisms of CNS white matter de- and re-myelination. It has been demonstrated that axonal injury, inflammation, and demyelination co-exist at 4 weeks of continuous cuprizone feeding. Previous DTI studies showed that decreased $\lambda_\parallel$ correlated with histology-confirmed axonal injury, while no significant increase of $\lambda_\perp$ was seen, thus failing to reflect the concurrent demyelination. A Monte Carlo simulation modeling the three underlying pathologies was performed. Preliminary results suggested that the presence of infiltrating inflammatory cells exerted significant effect on the derived directional diffusivity reducing both $\lambda_\parallel$ and $\lambda_\perp$, exaggerating the effect of axonal injury while diminishing the sensitivity to demyelination. This finding suggests that the current DTI analysis is suboptimal to accurately depict the underlying pathology in diseases with inflammation, such as MS.

Figure 3A:
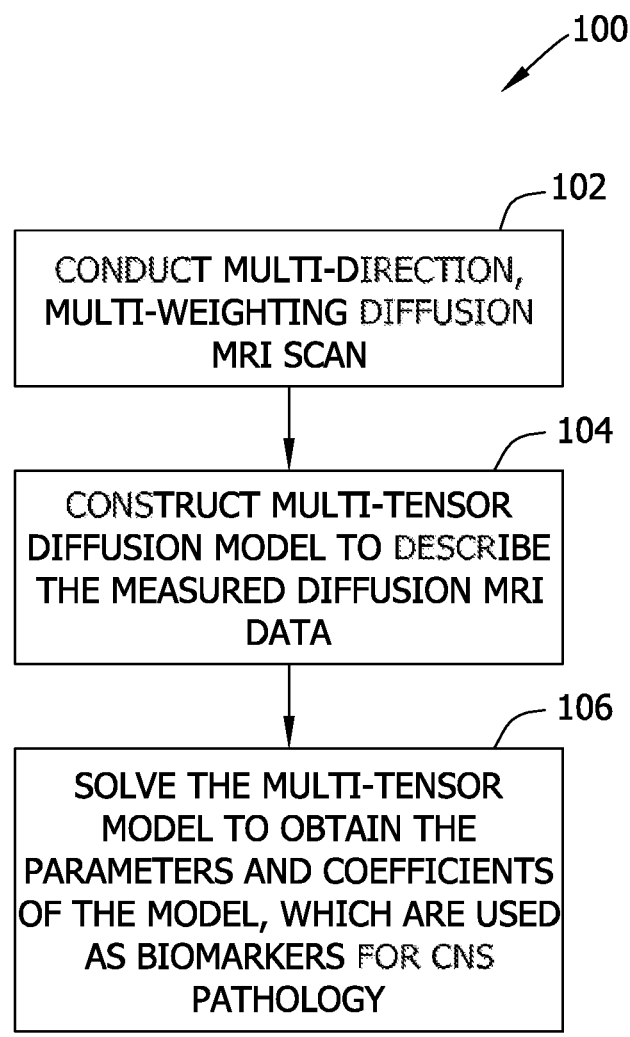
FIG. 3A is a flowchart of an exemplary noninvasive process to quantify complex CNS white matter pathology.

To address this shortcoming of DTI, a process allowing an accurate description of the underlying tissue pathology is described herein. FIG. 3A is a flow chart 100 illustrating the basic steps contemplated to detect and differentiate the underlying CNS white matter pathologies. First, a multi-direction, multi-weighting diffusion MRI scan is conducted 102 utilizing a signal acquisition and processing component. A multi-tensor diffusion model is constructed 104, and the multi-tensor model is solved 106 to obtain the parameters and coefficients of the model.

Figure 3B:
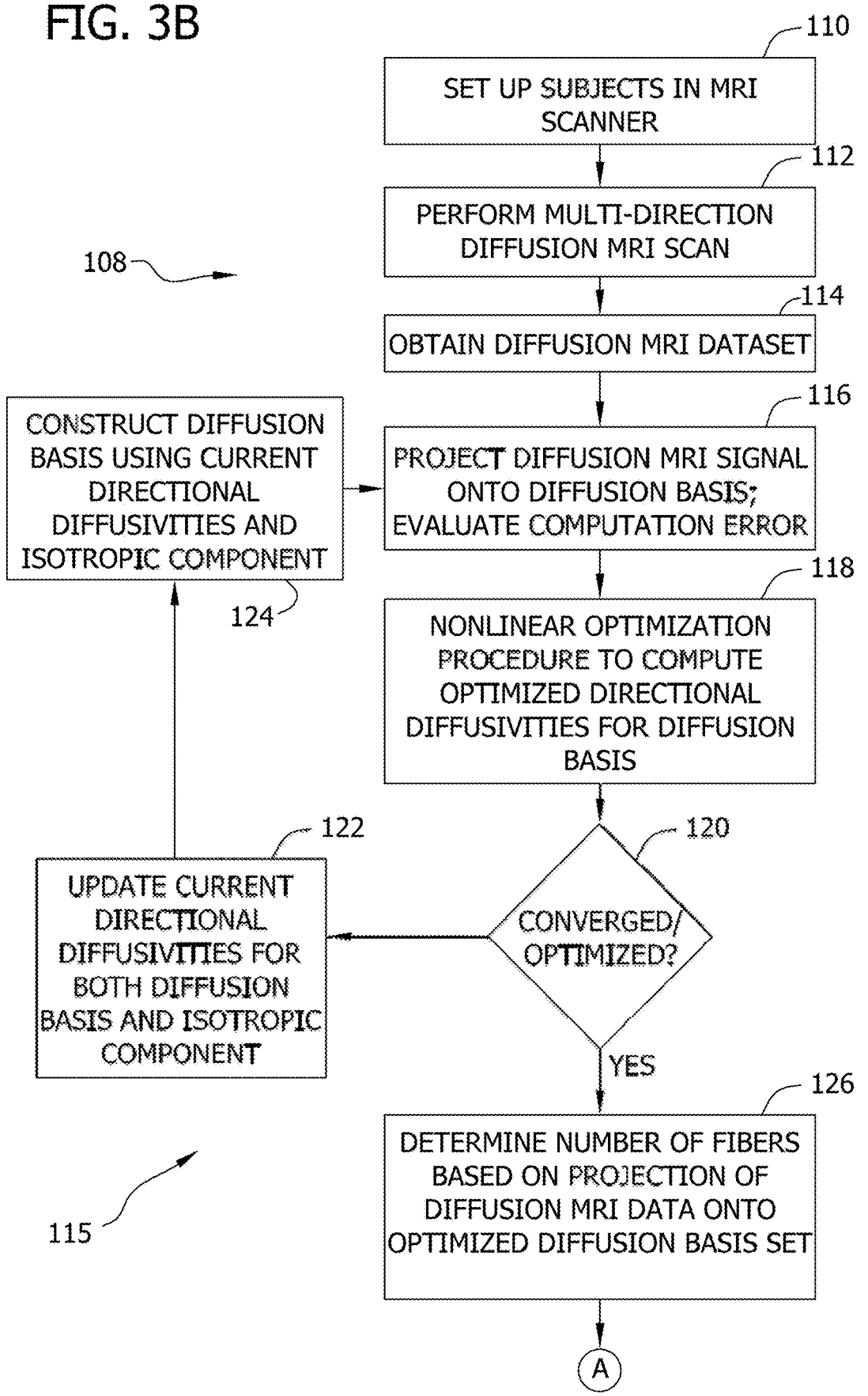
FIGS. 3B and 3C are a flowchart of an exemplary method for determining diffusivities of fibers and isotropic components within a tissue.
Figure 3C:
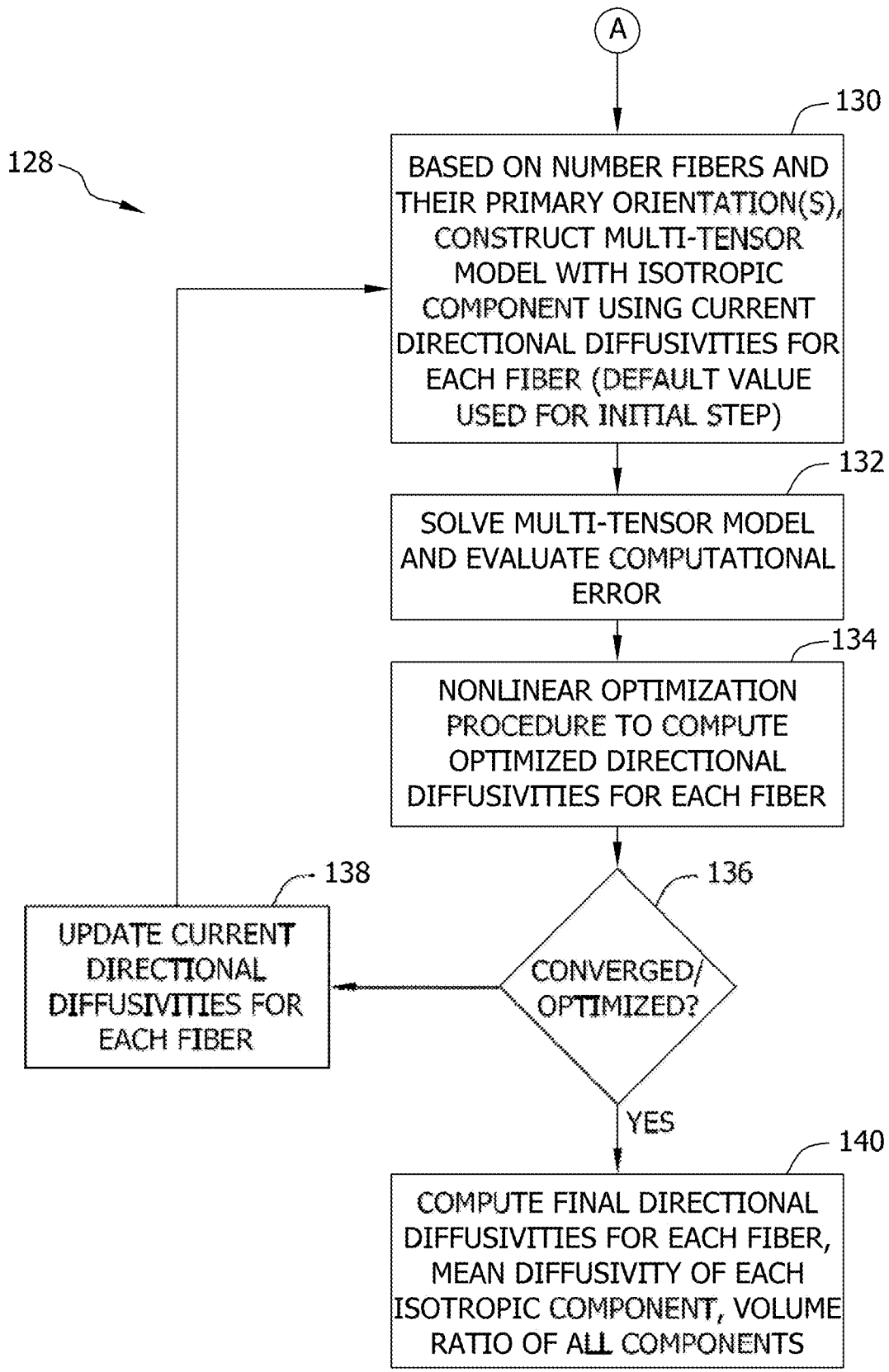

In the exemplary embodiment, a multiple-tensor based DBSI, or diffusivity component, is provided (FIGS. 3B and 3C). The method illustrated may be used to determine diffusivity of each diffusion tensor component within a tissue. In the multiple-tensor based DBSI, an MRI scan is performed 108. In performing the MRI scan, subjects are set up 110 in MRI scanner and a multi-direction diffusion MRI scan is performed 112. From the performed 112 MRI scan, a diffusion MRI dataset is obtained 114.

After an MRI scan is performed 108, number of fibers and their primary orientation is determined 115. In determining 115 the number of fibers and their primary orientation a diffusion MRI signal is projected 116 onto diffusion a basis and a computation error is evaluated. Next, a nonlinear optimization procedure is performed 118 to compute optimized directional diffusivities for diffusion basis. It is determined 120 whether the fibers are converged and optimized.

If the fibers are determined 120 not to have been converged and optimized, the current directional diffusivities for both diffusion basis and isotropic components are updated 122. After update 122, a diffusion basis using current directional diffusivities and isotropic component is constructed 124 and projected 116 is performed again. If the fibers are determined 120 to have been converged and optimized, the number of fibers based on projection of diffusion MRI data onto optimized diffusion basis set is determined 126.

After the number of fibers and their primary orientation is determined 115, diffusivities of each fiber and isotropic components are determined 128. In determining 128 the diffusivities of each fiber and isotropic components, a multi-tensor model with isotropic component using current directional diffusivities for each fiber is constructed 130. A multi-tensor model is solved 132 and evaluated for computational error. Next, a nonlinear optimization procedure is performed 134 to compute optimized directional diffusivities for each fiber. It is determined 136 whether the fibers are converged and optimized. If the fibers are determined 136 not to have been converged and optimized, the current directional diffusivities for each fiber are updated 138 and the multi-tensor model is constructed 130 again. If the fibers are determined 136 to have been converged and optimized, a final directional diffusivity for each fiber is computed 140. Additionally, a mean diffusivity of each isotropic component, and a volume ratio of all components is computed 140.

Figure 4A:
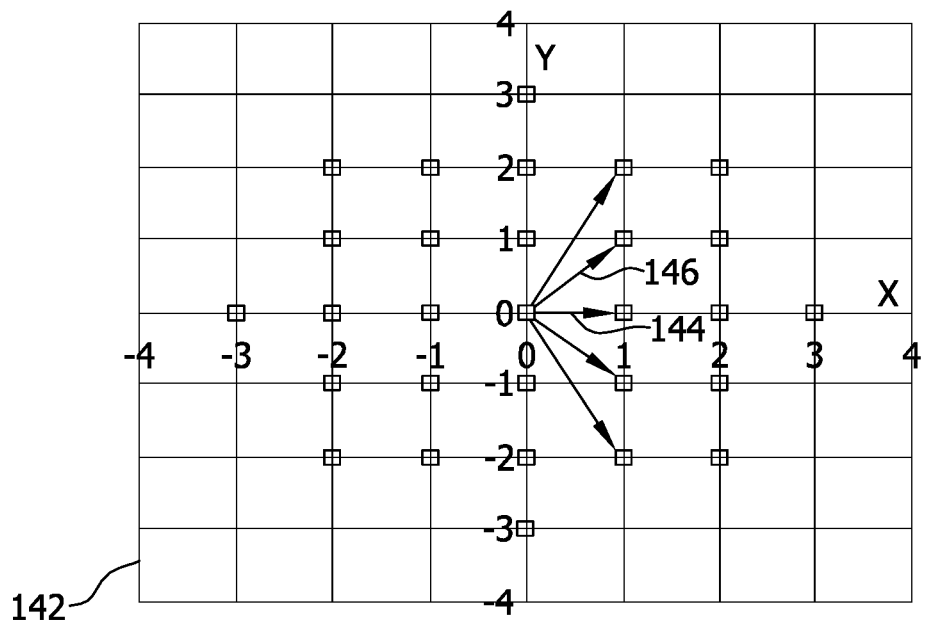
FIG. 4 is an illustration of the design of an exemplary 99-direction diffusion-weighting scheme.
Figure 4B:
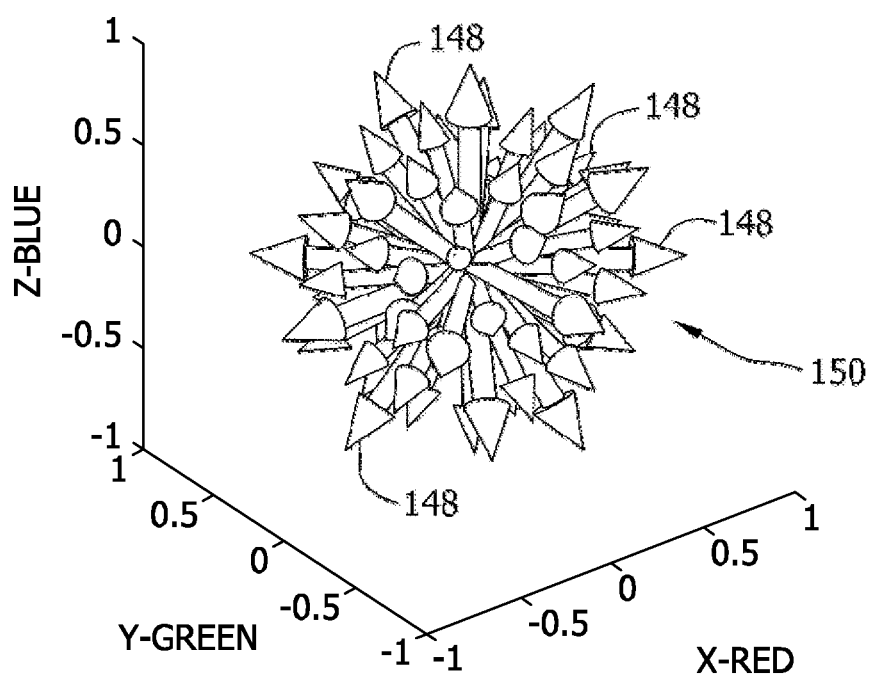

FIG. 4 is an illustration of the design of an exemplary 99-direction diffusion-weighting scheme. As shown in the 2D schematic 142, each diffusion-weighting direction is selected based on the grid point location. For example, the first diffusion weighting direction 144 is from origin (0,0) to grid point (1,0), the second diffusion weighting direction 146 is from (0,0) to (1,1), and so on. In the exemplary embodiment, 99 diffusion directions are selected based on the 3D grid locations 148 shown by 3D model 150.

An advantage of designing the 99-direction diffusion weighting gradients 148 based on regular grid locations is that the directions are uniformly sampled in the 3D space. No matter which direction the real axonal fiber orients, the scheme has no bias to it. Another advantage is that the weighting of diffusion gradients is naturally set as different values in this grid-based design, which is favorable in terms of determining multiple isotropic diffusion components.

However, embodiments described herein are not limited to this particular design. Any diffusion-weighting scheme that samples the whole 3D space uniformly and provides multiple weighting factors may work well resolving multi-tensor reflecting the CNS white matter pathology.

Similar to diffusion basis function decomposition (DBFD), DBSI employs the following multi-tensor model as the first-step analysis:

$$S_k = \sum_{i=1}^{N} S_i \exp\left(-\vec{b}_k \cdot \lambda_\perp\right) \exp\left(-\vec{b}_k \cdot (\lambda_\parallel - \lambda_\perp) * \cos^2(\theta_1)\right), \quad \text{(Equation 1)}$$

$$k = 1, 2, \ldots, 99$$

In Equation 1, $\vec{b}_k$ is $k^{th}$ diffusion gradient (k=1, 2, . . . , 99); $\lambda_\parallel$ is the axial diffusivity and $\lambda_\perp$ is the radial diffusivity; $S_k$ is the measured diffusion weighted signal at direction $\vec{b}_k$; $\theta_i$ is the angle between the diffusion gradient $\vec{b}_k$ and the primary direction of $i^{th}$ diffusion basis; N is the number of diffusion basis components uniformly distributed in 3D space.

Figure 5:
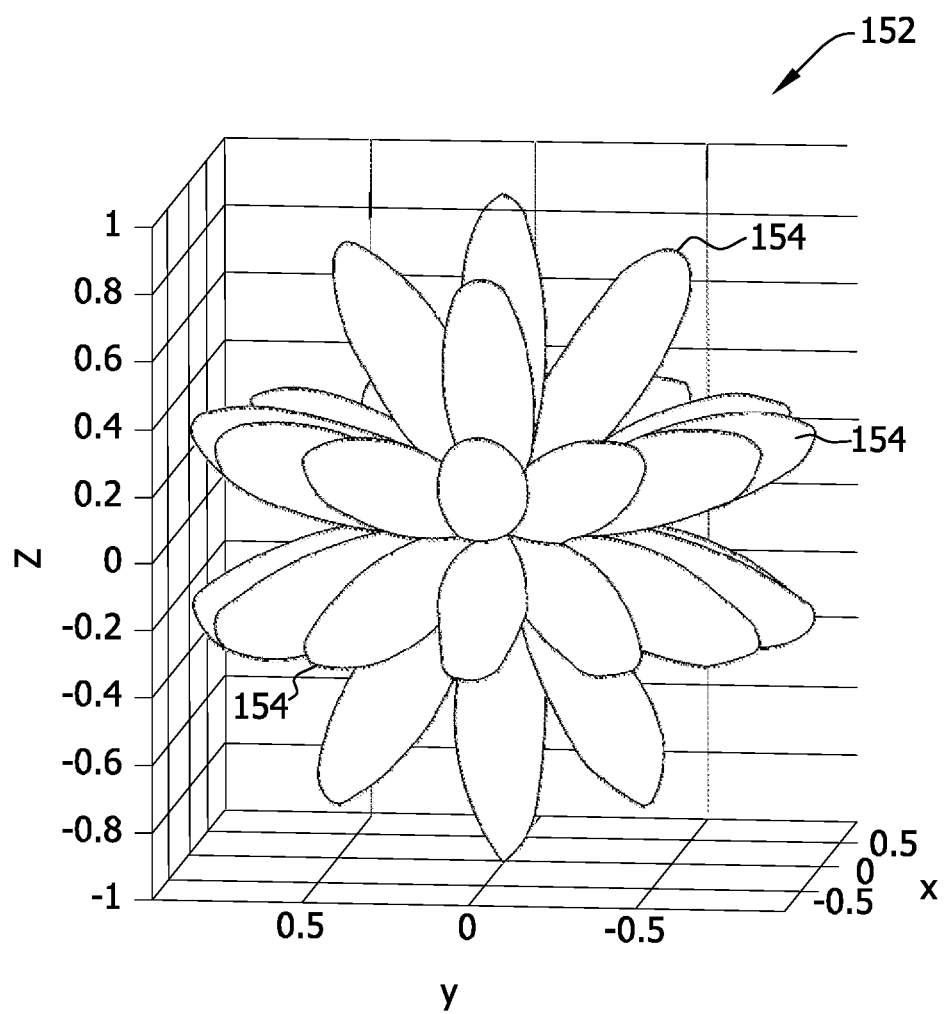
FIG. 5 is an illustration of an exemplary diffusion basis set for DBSI.

FIG. 5 illustrates a diffusion basis set 152 with 40 diffusion bases 154. As shown in FIG. 5, each diffusion basis 154 represents a candidate fiber orientation, and the diffusion basis 154 set is uniformly distributed in the 3D space. As described by Equation 1, the real fiber is treated as the linear combination of the entire diffusion basis set.

Instead of presetting $\lambda_{s1}$ and $\lambda_\perp$ at fixed values for the entire diffusion basis in DBFD, DBSI performs a nonlinear searching to estimate the optimal values of $\lambda_{s1}$ and $\lambda_\perp$ best fitting the acquired diffusion weighted data. Isotropic tensor component is uniquely incorporated in DBSI to improve the accuracy, as shown in Equation 2.

$$f(\lambda_\|, \lambda_\perp, d) = \min \left\| \sum_{k=1}^{99} \left\{ S_k - \sum_{i=1}^{N} S_i \exp(-\vec{b}_k \cdot \lambda_\perp) \exp(-\vec{b}_k \cdot (\lambda_\| - \lambda_\perp) \cos^2(\theta_1)) - S_{N+1} \cdot \exp(\vec{b}_k \cdot d) \right\}^2 \right\|$$

(Equation 2)

In Equation 2, $S_i$ (i=1, 2 . . . N+1)≥0, $\lambda_\|$ and $\lambda_\perp$ are directional diffusivities, and d is the diffusivity of isotropic diffusion component with d, $\lambda\|$, and $\lambda\perp$ selected as the optimization variables. Unknown coefficients $S_i$ (i=1, 2 . . . N+1) are not optimization variables because $S_i$ are not independent to $\lambda\|$ or $\lambda\perp$. Each $S_i$ is computed using the least square estimation under the nonnegative constraint ($S_i$≥0) and the basic principle of sparsity as employed in DBFD during the nonlinear optimization procedure. After the optimization, the number of fibers and their primary axis directions are estimated similar to DBFD.

A unique feature of this disclosure is that the shape of each diffusion basis is not prefixed as in DBFD method. Instead, the basis shape is optimized during the optimization process to estimate both $\lambda\|$ and $\lambda\perp$. This optimization process is demonstrated in FIG. 6 using a single axonal fiber 156 as the example. In the exemplary embodiment, experimental data is fitted by the linear combination of a diffusion basis set 154 with fitting error improved through iterations 158, 160, 162, and 164 until the optimal coefficients of linear combination of diffusion basis are estimated 166. In the exemplar embodiment, iteration 158 has a fitting error of 0.6, iteration 160 has a fitting error of 0.4, iteration 162 has a fitting error of 0.2, and iteration 164 has a fitting error of 0.04. Isotropic component is also considered according to Equation 2 in this process (not shown) to improve the optimization accuracy.

Figure 7A:
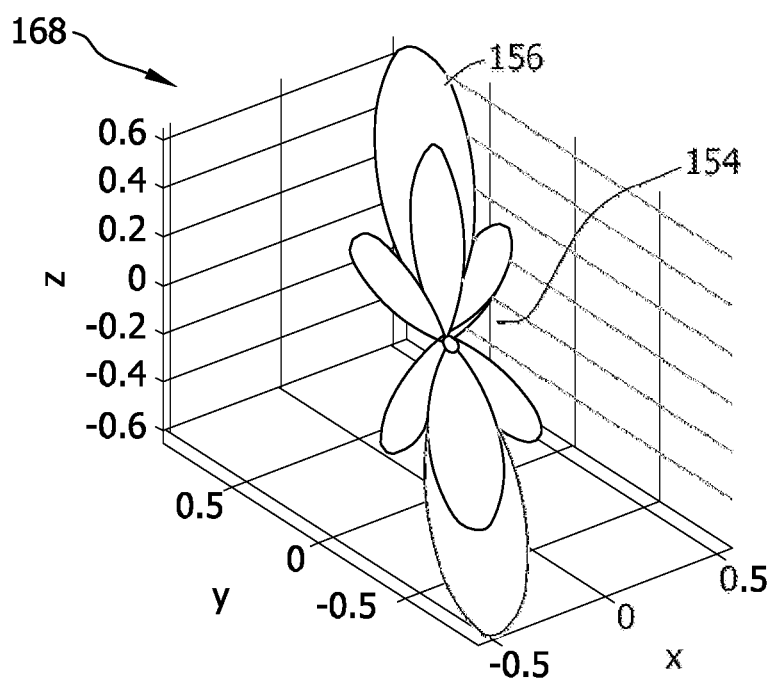
FIG. 7 is an illustration of determining the number of fibers and primary directions of candidate fibers using DBSI.
Figure 7B:
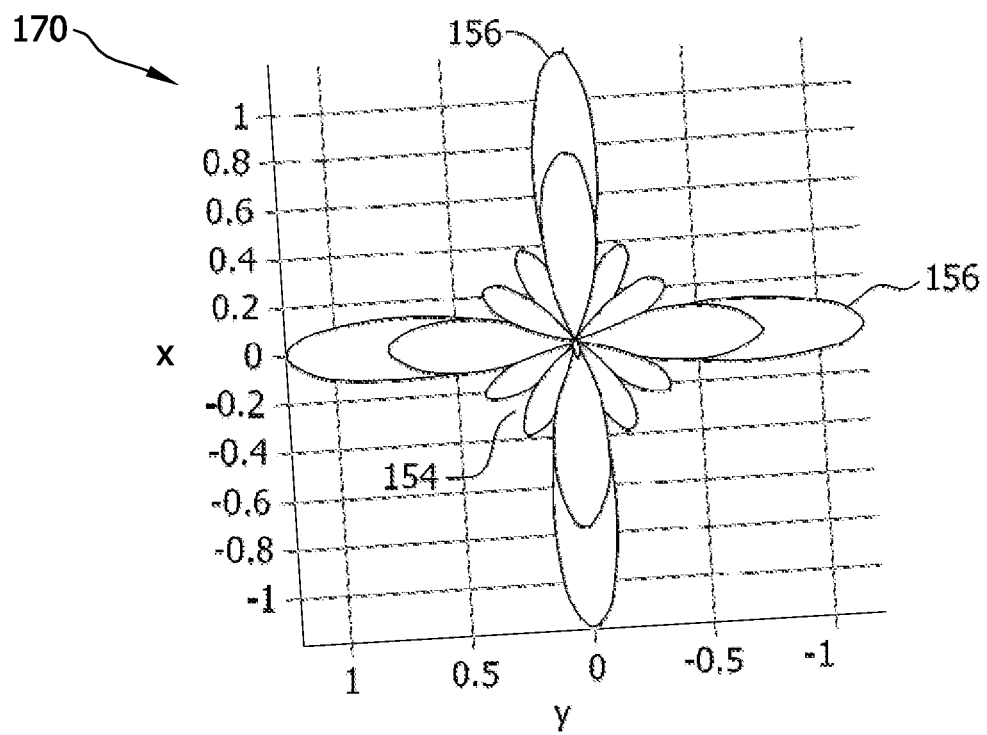

As shown in FIG. 7, the diffusion basis 154 with direction close to that of the axonal fiber 156 contributes more significantly to the linear combination with higher magnitude of the coefficients Si. The diffusion basis 154 with direction away from that of the axonal fiber 156 has limited contribution to the coefficient of linear combination of the basis set fitting the experimental data. Both single 168 and two-fiber 170 tracts are demonstrated.

DBSI determines the number and primary direction of fibers according to the description of Equation 1. Each coefficient is associated with one diffusion tensor basis at a particular direction. These preliminary coefficients are grouped based on the magnitude and the closeness in orientations of the associated basis diffusion tensor. Coefficients smaller than a threshold determined by raw signal SNR are ignored. Significant coefficients with closely oriented (within 15 degrees) diffusion basis tensors are grouped as one fiber. The threshold of 15 degrees is set based on the desired angular resolution. Once the grouping process is complete, the averaged direction of the grouped diffusion basis is defined as the primary direction of the fiber.

Based on the number of fiber (anisotropic tensor) components and associated primary directions, DBSI constructs another multi-tensor model with the assumption of axial symmetry. A set of isotropic tensor components are included in the model:

$$h(\lambda_{\|\_i}, \lambda_{\perp\_i}, i = 1 \ldots L) = \min \left\| \sum_{k=1}^{99} \left\{ S_k - \sum_{i=1}^{L} S_i \exp(-\vec{b}_k \cdot \lambda_{\perp\_i}) \exp(-\vec{b}_k \cdot (\lambda_{\|\_i} - \lambda_{\perp\_i}) \cos^2(\varphi_i)) - \sum_{j=1}^{M} S_{L+j} \cdot \exp(\vec{b}_k \cdot d_j) \right\}^2 \right\|$$

(Equation 3)

In Equation 3, $S_k$ is the measured diffusion weighted signal at diffusion gradient direction $\vec{b}_k$. L is the number of estimated fibers in the imaging voxel. $\lambda_{\|\_i}$ and $\lambda_{\perp\_i}$ (i=1, 2 . . . L) are the axial and radial diffusivity of the ith fiber. $\varphi_i$ is the angle between the diffusion gradient $\vec{b}_k$ and the primary direction of ith estimated fiber. $d_j$ (j=1 . . . M) are the diffusivities of M isotropic diffusion components. $S_i$ (i=1, 2 . . . L) are fiber volume ratios and $S_i$ (i=L+1, L+2 . . . L+M) are the volume ratio of isotropic components.

Based on this multi-tensor model, a nonlinear optimization search is constructed as following:

$$h(\lambda_{\|\_i}, \lambda_{\perp\_i}, i = 1, \ldots, L) = \min \left\| \sum_{k=1}^{99} \left\{ S_k - \sum_{i=1}^{L} S_i \exp(-\vec{b}_k \cdot \lambda_{\perp\_i}) \exp(-\vec{b}_k \cdot (\lambda_{\|\_i} - \lambda_{\perp\_i}) \cos^2(\varphi_i)) - \sum_{j=1}^{M} S_{L+j} \cdot \exp(\vec{b}_k \cdot d_j) \right\}^2 \right\|$$

(Equation 4)

Equation 4 is subject to $S_i$ (i=1, 2, . . . , L+M)≥0. In this optimization procedure, isotropic diffusivity $d_j$ (j=1 . . . M) are not selected as optimization variables to reduce the total number of the free variables. Instead, isotropic diffusivities are uniformly preset within the physiological range. Directional diffusivities, $\lambda_{\|\_i}$ and $\lambda_{\perp\_i}$ (i=1 . . . L) of each anisotropic component are the only free variables to be optimized based on the experimental data and Equation 4 with the nonnegative constraint ($S_i$≥0). All diffusion tensor's volume ratios $S_i$ (i=1, 2 . . . L+M) based on T2-weighted (i.e., non-diffusion weighted) image intensity are computed with least square fitting during the nonlinear optimization procedure.

Figure 8:
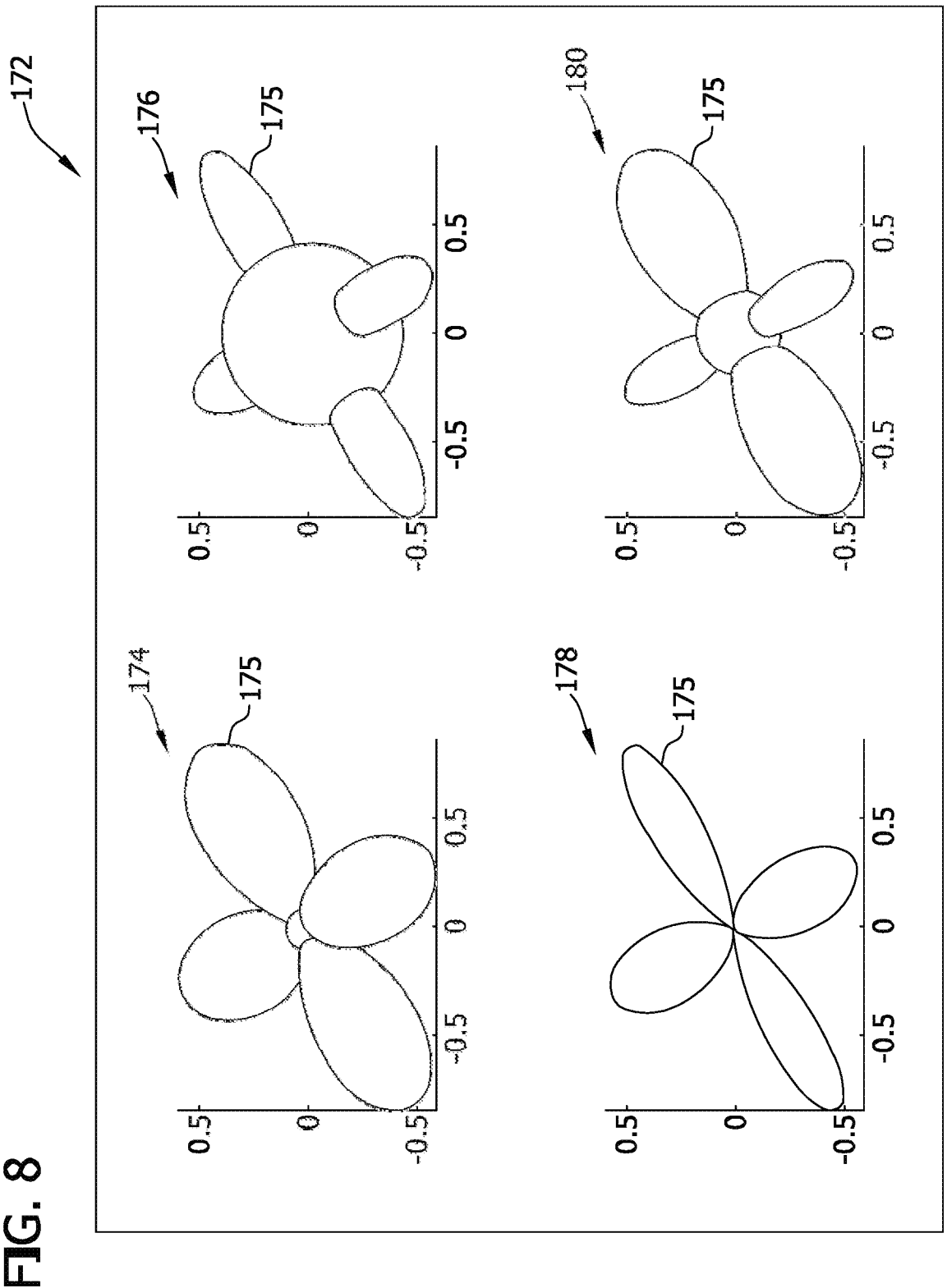
FIG. 8 is an illustration of an exemplar optimization process for determining the directional diffusivity of each candidate fiber, isotropic components and corresponding volume ratios using DBSI.

In one embodiment, an optimization process 170, as shown in FIG. 8, is used to search the best directional diffusivities for each candidate fiber and compute all the volume ratios of each diffusion component. Process 170 demonstrates two crossing fibers (L=2). In such an embodiment, a first optimization 174 includes candidate fibers 175 with a fitting error of 0.4. Likewise, a second optimization 176 includes candidate fibers 175 with a fitting error of 0.2, a third optimization 178 includes candidate fibers 175 with a fitting error of 0.1, and a fourth optimization 180 includes candidate fibers 175 with a fitting error of 0.02

After the fourth optimization 180, the fitting error is smaller than 2%, which falls within the acceptable range. Therefore, the directional diffusivity of each candidate fiber 175, and corresponding volume ratios computed after the optimization 180 are determined as the final DBSI results. In the DBSI algorithm, the nonlinear optimization procedure is executed based on criteria including maximal iteration numbers, tolerance of mesh size, tolerance of variable, tolerance of function, accepted accuracy, and many other criteria set according to the need. Once some or all of these criteria are met according to the preset level, the optimization procedure is considered satisfactorily fit the data and the optimization stops.

Figure 10:
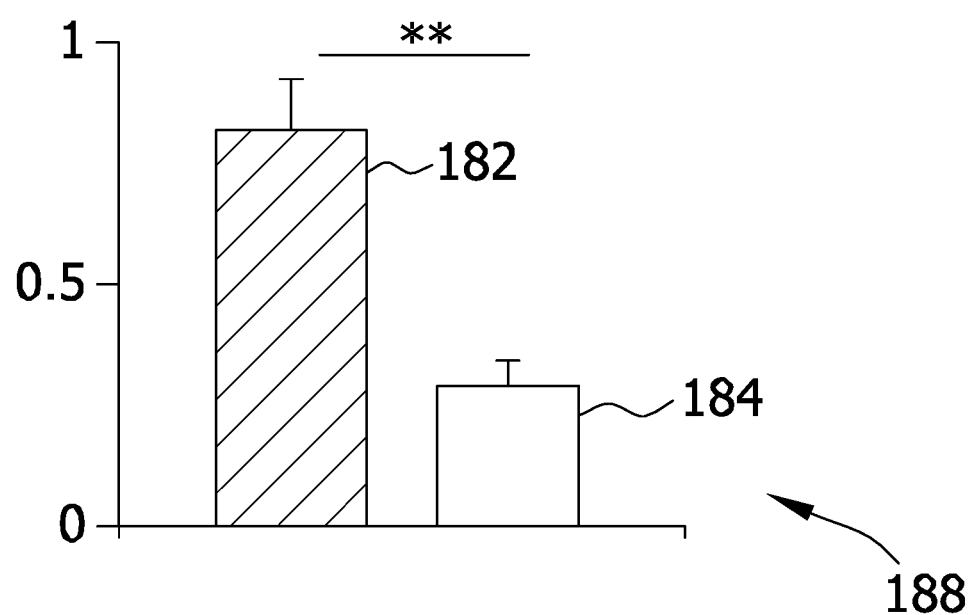
FIG. 10 is a graph of myelin basic protein in a MBP-positive area derived from DBSI of FIG. 9.
Figure 11:
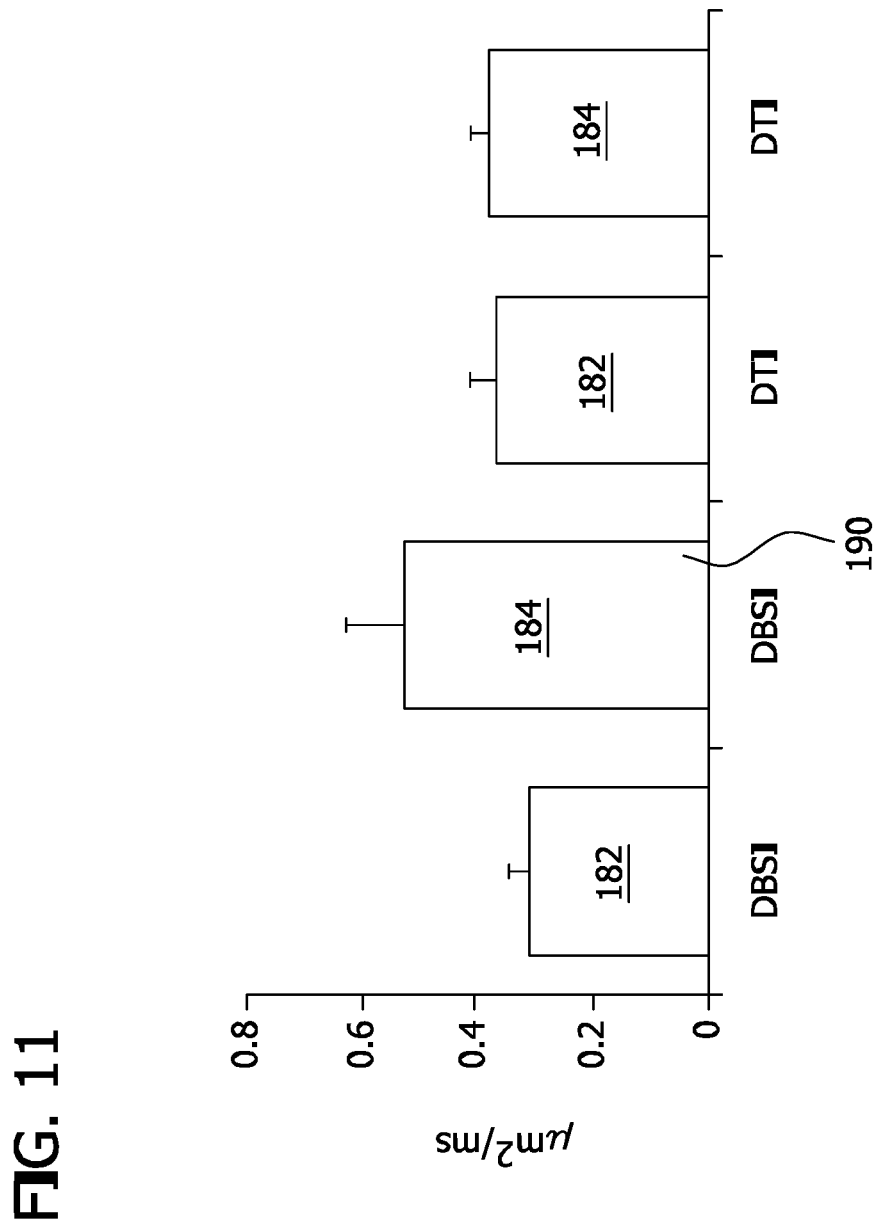
FIG. 11 is a graph of the radial diffusivity derived using DBSI of FIG. 9.

To determine the capability of the newly developed DBSI approach in detecting and differentiating the underlying co-existing pathology, the cuprizone model was again employed to compare conventional DTI with the new DBSI analysis. Striking contrast between DTI and DBSI was observed at the corpus callosum from C57BL/6 mice treated with cuprizone for 4 weeks. DTI failed to detect demyelination and overestimated axonal injury even with 99-direction diffusion weighting, while offering no information on inflammation. However, DBSI correctly reflected the presence of demyelination (FIG. 9), axonal injury (FIG. 10), and inflammation (FIG. 11).

Figure 9:
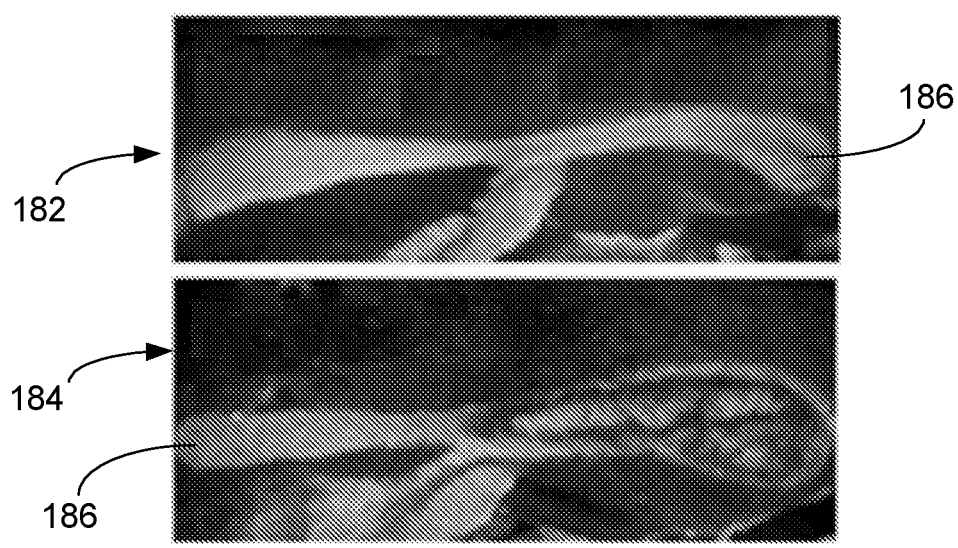
FIG. 9 is an illustration of diffusion basis spectrum imaging (DBSI) results reflecting demyelination as increased radial diffusivity in the presence of axonal injury, and inflammation in contrast to the failure of DTI to detect the pathology.

FIG. 9 is an illustration of a sagittal view of corpus callosum from a control 182 and a 4-week cuprizone fed male C57BL/6 mice (n=5) 184 examined using DBSI and DTI. As shown by myelin basic protein 186 immunostaining, significant demyelination in the caudal corpus callosum is seen by reduced MBP-positive area 188 (FIG. 10) and increased radial diffusivity 190 (FIG. 11) derived using DBSI. Consistent with previous reports, lack of increase in DTI derived radial diffusivity failed to reflect the histological finding of demyelination (FIG. 12).

Figure 12:
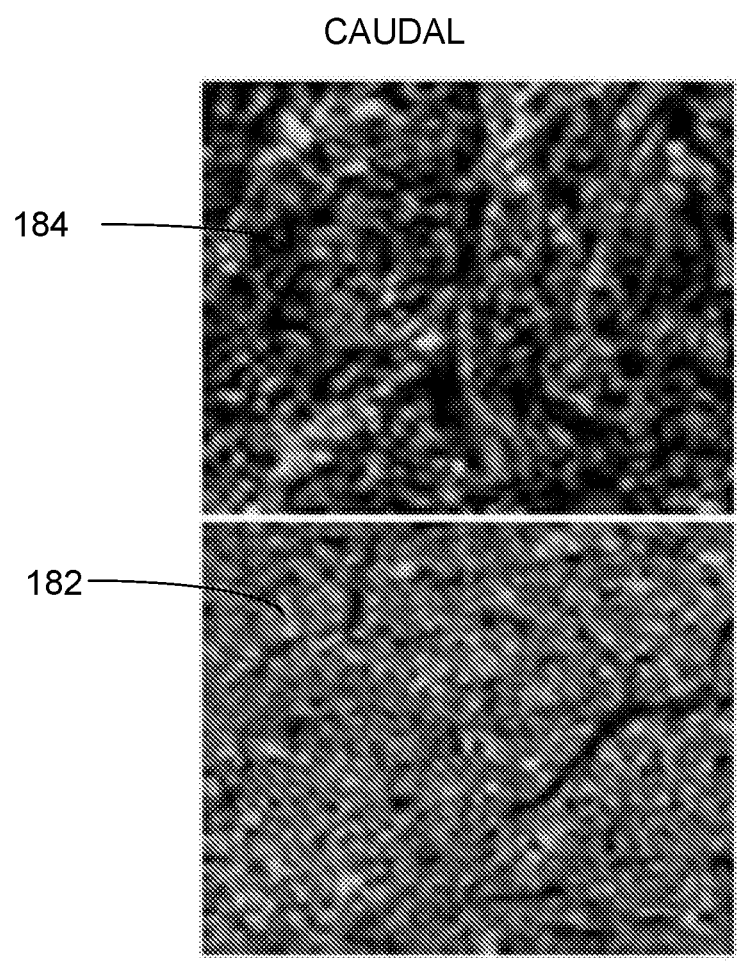
FIG. 12 is an illustration of DBSI results detecting axonal injury in the presence of demyelination and inflammation.
Figure 13:
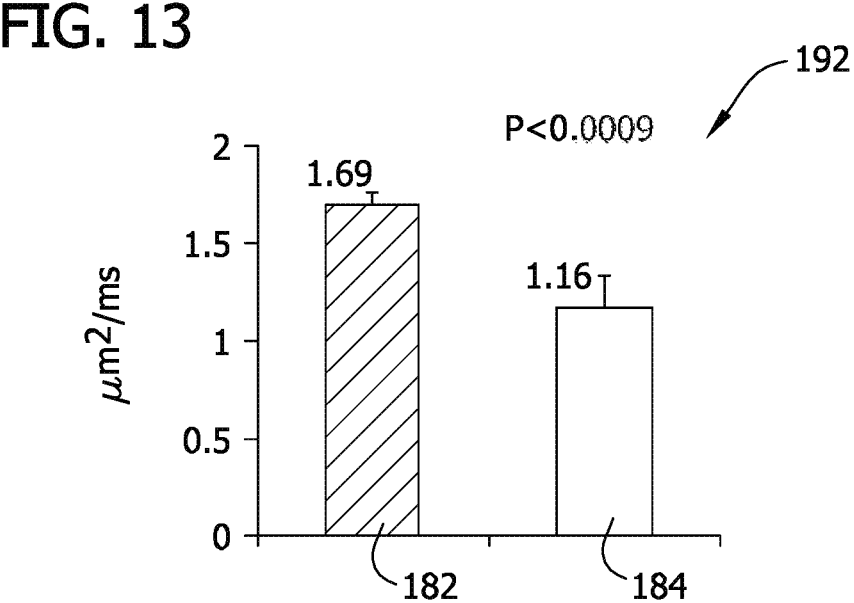
FIG. 13 is a graph of the axial diffusivity of the DBSI of FIG. 12.
Figure 14:
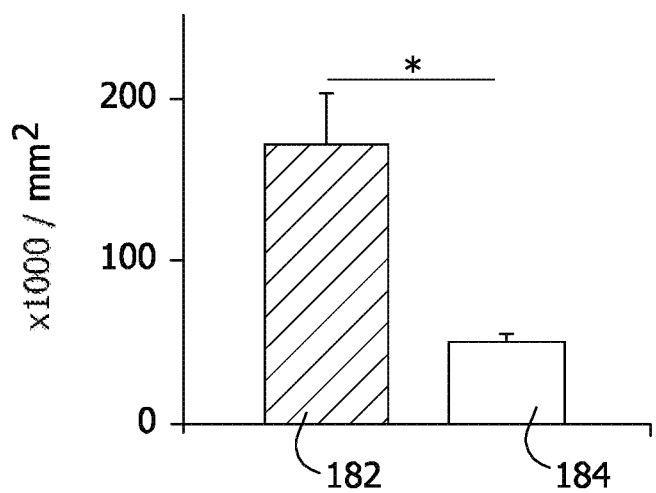
FIG. 14 is a graph of the SMI-31 stain of the DBSI of FIG. 12.
Figure 15:
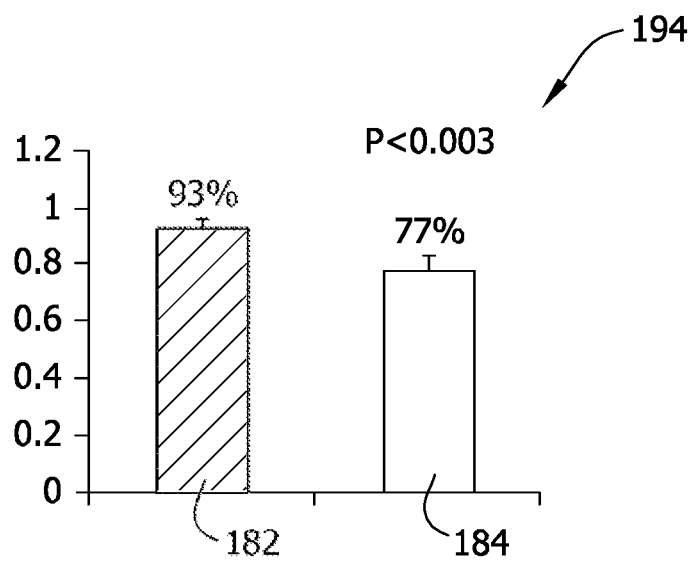
FIG. 15 is a graph of axonal fiber tract density was also derived using DBSI expressing as volume ratio of the DBSI of FIG. 12.

FIG. 12 illustrates that similar to previous findings that decreased DTI derived axial diffusivity was seen in corpus callosum from 4-week treated mice 184 (n=5, −43%) from control 182, DBSI derived axial diffusivity 192 (FIG. 13) decreased (−31% from the control 182) to reflect the histology proved axonal injury (FIG. 14). The axonal fiber tract density 194 (FIG. 15) was also derived using DBSI expressing as volume ratio. Due to the infiltrating inflammatory cells, the density of axonal fiber tracts was reduced from 93% to 77%, a finding not available for conventional DTI.

Figure 16:
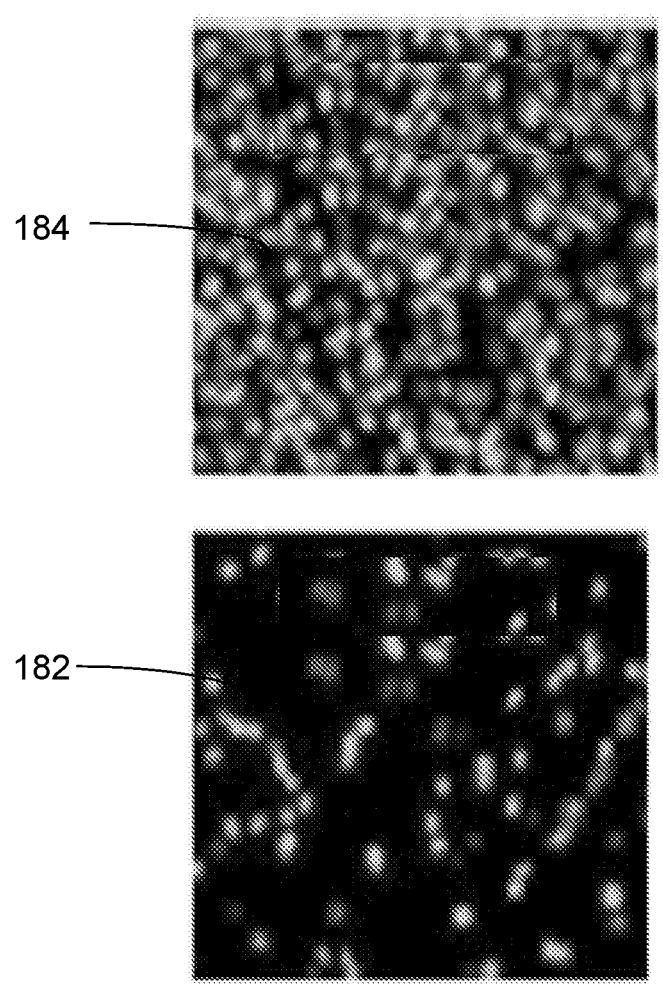
FIG. 16 is an illustration of DBSI results quantifying inflammation in the presence of axonal injury and demyelination.
Figure 17:
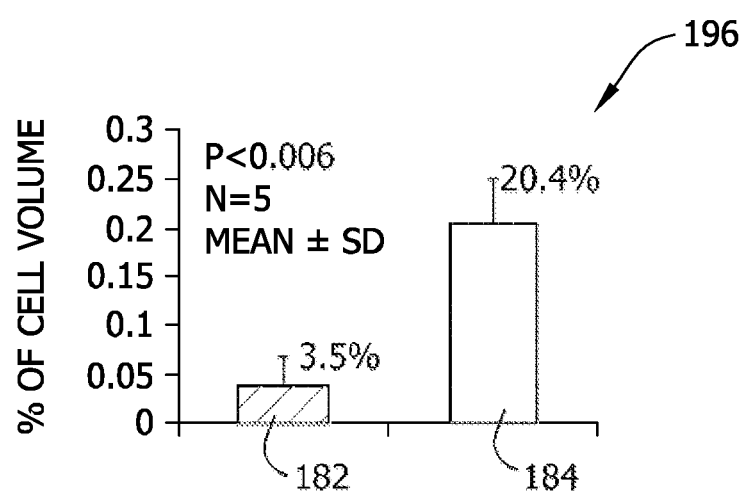
FIG. 17 is a graph of the percentage of inflammatory cell infiltration thought to be in the cells of the illustration of FIG. 16.

FIG. 16 illustrates inflammatory cell infiltration 196 derived using DBSI. In such an embodiment, the inflammatory cell infiltration 196 is to be 16.9% (20.4−3.5) of total volume in 4-week cuprizone treated corpus callosum 184, above the baseline 3.5% cellular content. This is consistent with the significantly increased DAPI positive stains in the same region; information has not been available using DTI.

In another embodiment, 99-direction diffusion weighted images are analyzed following one or more operations described above to determine the number of intravoxel fibers and isotropic components on a laboratory fabricated phantom containing mouse trigeminal nerves with known in vivo DTI character and isotropic gel as shown in FIG. 18.

Diffusion weighted MRI was performed on the phantom using 99 distinct diffusion weighting gradients for both DTI 200 and DBSI 202 analysis. For the pure gel, DTI 200 and DBSI 202 estimated the isotropic apparent diffusion coefficient to be identical at 1.91 $\mu m^2/ms$ suggesting both methods are accurate for simple medium. When examining the mixture of fiber/gel in this phantom using DTI 202, the isotropic gel component was not identified. In addition, the true fiber diffusion anisotropy (FA=0.82±0.005) determined previously using an in vivo high resolution DTI was not obtained. In contrast, using the newly proposed DBSI identified a fiber ratio 204 of 21%, a gel ratio 206 of 74%, and a cell ratio of 5% with correct fiber diffusion anisotropy of FA=0.83. The anisotropy was compared because it was previously observed that diffusion anisotropy is preserved in vivo and ex vivo in mouse nerve fibers.

Another fiber phantom 210 was built to contain two mouse trigeminal nerves crossing each other at 90° with isotropic gel. As expected that DTI failed to identify the two crossing fibers or the gel. In contrast, DBSI was able to identify the presence of two fibers crossing at 90° estimating fiber orientations of (1,0,0) and (0,0,1). The diffusion anisotropy of the two fibers was estimated to be 0.81 and 0.83 respectively. Correct volume ratio was also estimated by DBSI to report 19% of (1,0,0) fiber, 19% of (0,0,1) fiber, 52% of gel, and 10% of cell component.

In the chronic CNS injury, tissue loss is common. Current DTI techniques have not been able to correctly reflect the status of chronic tissue injury. In a mouse spinal cord injury model, the non-injured and moderately injured cord tissues were examined. In the non-injured white matter of the mouse spinal cord, the DTI derived diffusion parameters were ADC=0.29 $\mu m^2/ms$, axial diffusivity=0.69 $\mu m^2/ms$, radial diffusivity=0.12 $\mu m^2/ms$, and FA=0.85. These are comparable with those obtained using DBSI where ADC=0.29 $\mu m^2/ms$, axial diffusivity=0.69 $\mu m^2/ms$, radial diffusivity=0.10 $\mu m^2/ms$, and FA=0.85. Both DTI and DBSI were successful in describing the non-injured white matter characteristics. However, when the moderately injured spinal cord tissues were examined, the DTI failed to capture the underlying pathology, i.e., the extent of tissue loss, resulting in overestimating axial diffusivities thus underestimating the severity of the injury. In contrast, DBSI was able to estimate that there is a 10% tissue loss in the injured white matter.

Methods described herein facilitate determination of an axial diffusivity, a radial diffusivity, and/or a volume ratio of a scanned volume of tissue with increased accuracy relative to known methods, which are distinguishable at least as follows.

Figure 19:
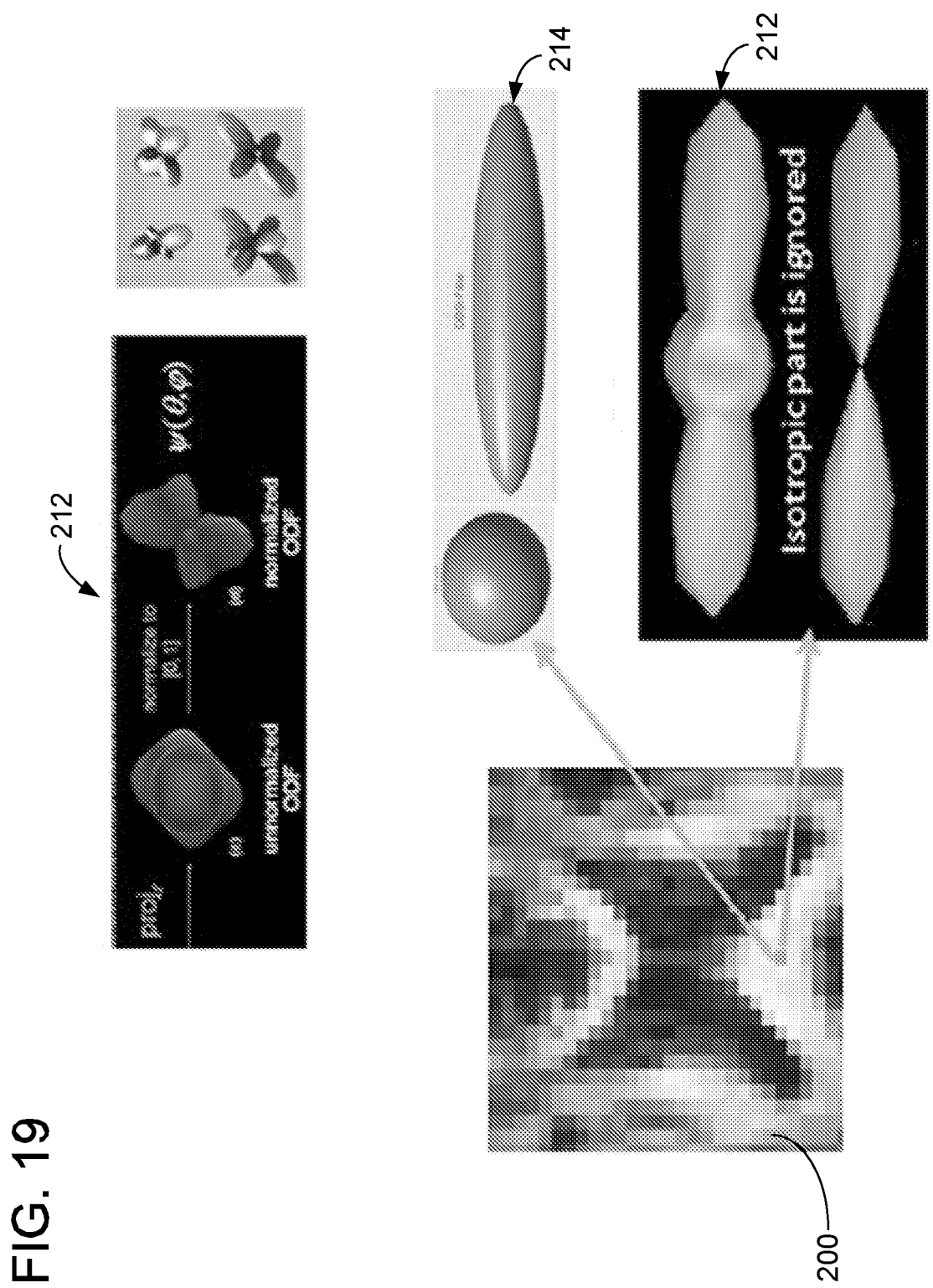
FIG. 19 is a comparison of diffusion spectrum imaging (DSI) and DBSI from a human subject.

FIG. 19 is a comparison of diffusion spectrum imaging (DSI) 212 and DBSI 214 from human subjects 216. DSI 212 is a method that attempts to directly measure the probability distribution function of the displacement of water molecules without an assumption of tissue structure or the shape of probability distribution function. It was proposed to identify multiple fibers within an image voxel. The use of orientation distribution function (ODF) by DSI effectively estimates angles of crossing fibers. However, its ODF based analysis does not offer other crucial quantitative information of water diffusion relevant to tissue physiology and pathology such as the apparent diffusion coefficients, diffusion anisotropy, or the volume ratio of different components. Therefore, DSI's applications are limited to fiber tracking.

The presence of an isotropic component within the image voxel is an important biomarker for cell infiltration, edema, and tissue loss. As shown in FIG. 19, the isotropic diffusion component is ignored in DSI 212 operation for the better estimation of the fiber orientation. In contrast, DBSI 214 quantitatively separates the isotropic from fiber component with accurate isotropic diffusivity assessment.

Operationally, DSI requires high diffusion weighting gradients of various magnitudes and directions to accurately estimate the ODF, a typically impractical challenge on regular clinical MR scanners. In contrast, DBSI facilitates operation with the clinically used diffusion weighting gradient strength and smaller number of directions. Thus, DBSI may be performed on clinical MR scanners with typical hardware resources.

Figure 20:
FIG. 20 is a diffusion tensor imaging (DTI) for mouse trigeminal nerve embedded in gel.
Figure 21:
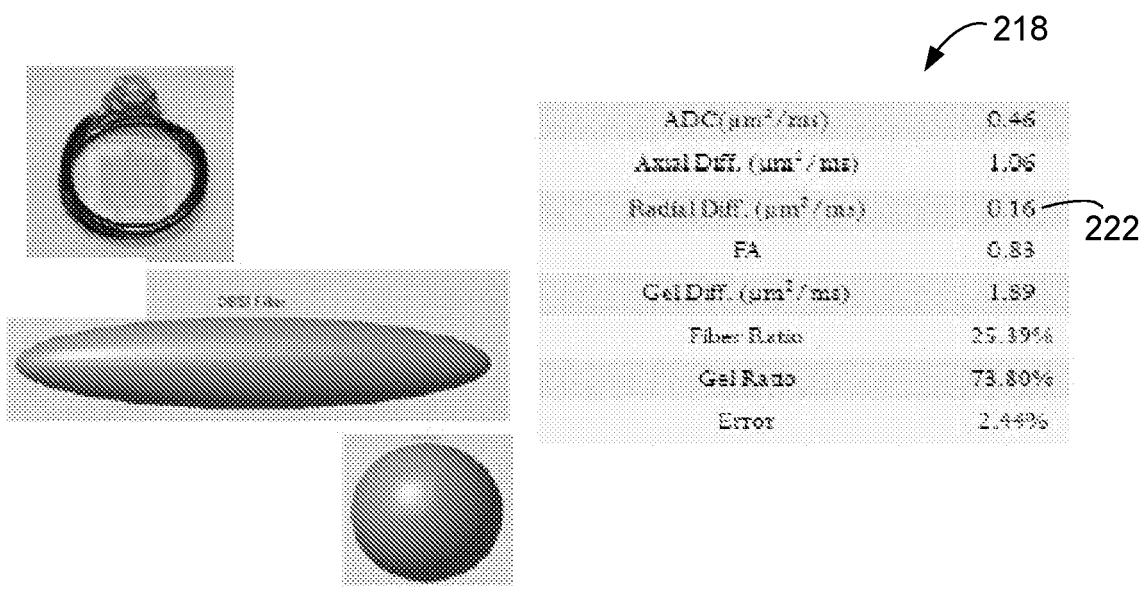
FIG. 21 is a DBSI for mouse trigeminal nerve embedded in gel.

FIG. 20 is a diffusion tensor imaging (DTI) 216 for mouse trigeminal nerve embedded in gel, and FIG. 21 is a DBSI 218 for mouse trigeminal nerve embedded in gel. DTI 216 derived radial diffusivity is very dependent on the tissue environment, and inaccurate assessment is common due to both the intra- and inter-voxel partial volume effect as demonstrated in FIG. 20. Using a simple yet realistic phantom constructed from fixed mouse trigeminal nerves and gel, as described above and as shown in FIG. 21, DTI 216 significantly over estimated the radial diffusivity 220, while DBSI 218 correctly quantified diffusivities 222, anisotropy, and volume ratios of all components.

This phantom study demonstrates the superior results enabled by DBSI in quantifying the overwhelming isotropic component within the image voxel and reporting correct diffusion properties of both the fiber and its environment. Embodiments described herein facilitate correctly estimating the extent of axonal loss noninvasively (e.g., in a clinical setting).

In one embodiment, eight trigeminal nerves from 4 normal male C57BL/6 mice were isolated after fixation. Diffusion MR spectroscopy was performed at 19° C. using a custom-built surface coil with the following parameters (common to all nerve fiber measurements): max b=3200 (s/mm2), repetition time (TR) 2 s, echo time (TE) 49 ms, time between application of gradient pulses ($\Delta$) 20 ms, duration of diffusion gradient on time ($\delta$) 8 ms, number of averages 4, 99-direction diffusion weighting gradients 44. Three diffusion tensor components were observed: anisotropic diffusion (75.9±2.6%: axon fibers), restricted isotropic diffusion (12.1±0.99%: cells), and non-restricted isotropic diffusion (12.1±2.5%: extra-axonal and extracellular water). The assignment of cell and water components was based on the DBSI-derived spectrum of isotropic diffusion.

Figure 22:
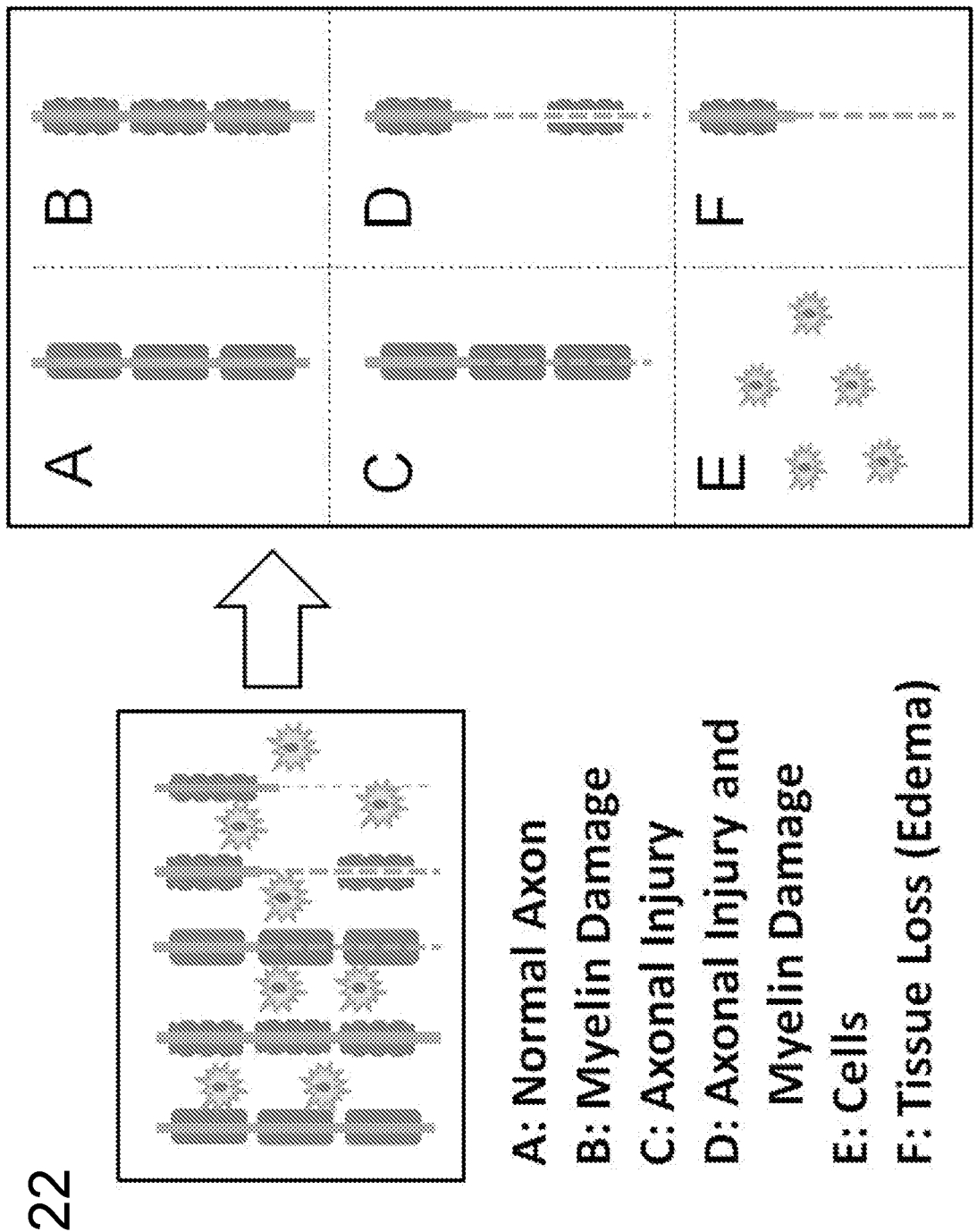
FIG. 22 is an illustration of heterogeneous pathology within one image voxel of interested white matter lesion.
Figure 23:
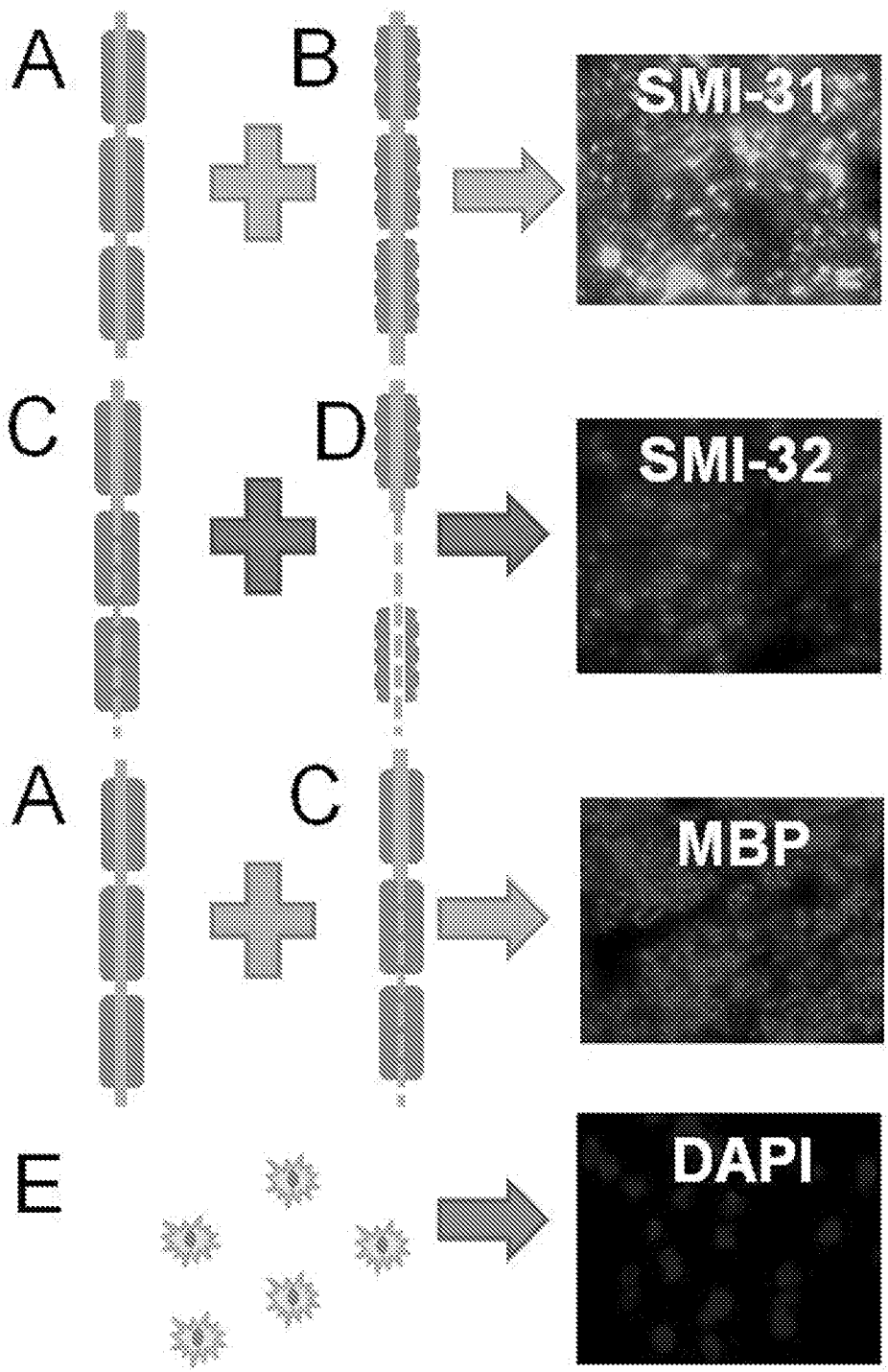
FIG. 23 is an illustration of conventional invasive histology.
Figure 25:
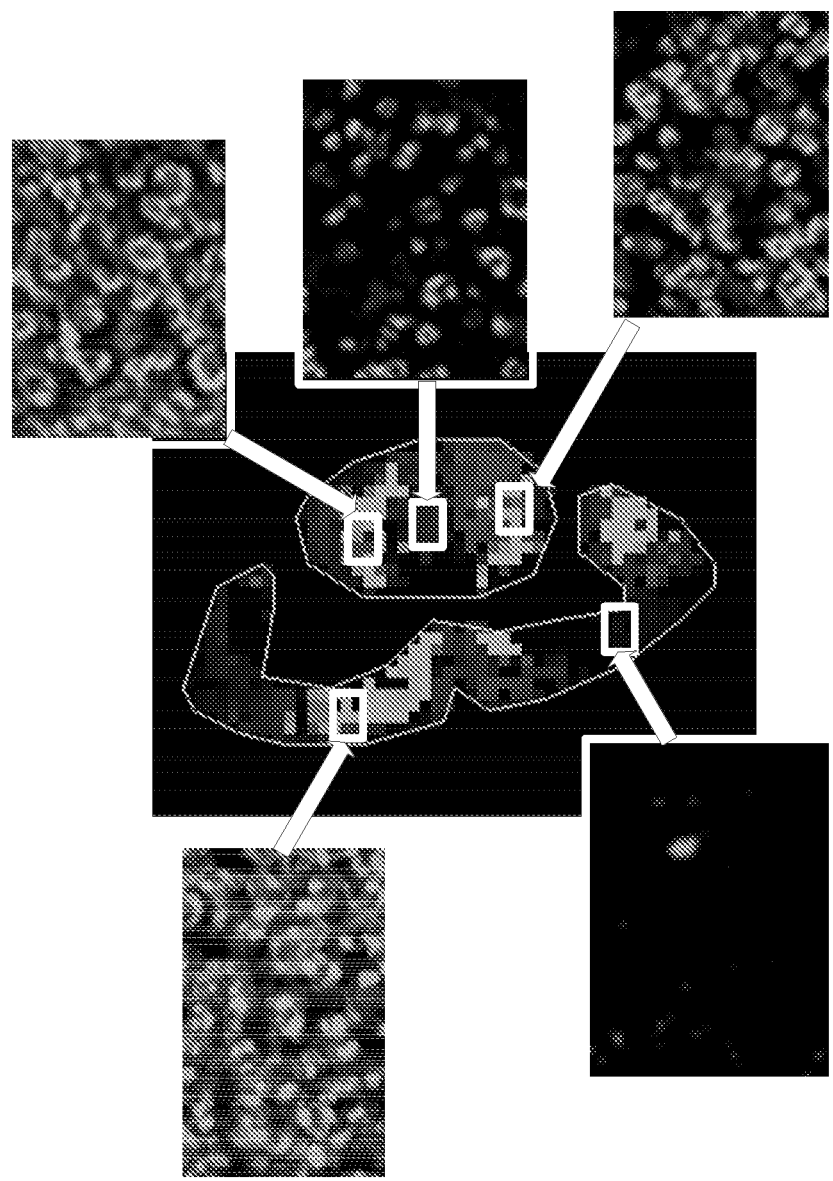
FIG. 25 is a detailed view of the DBSI-derived MBP fraction of the scan of FIG. 22 in the center surrounded by conventional invasive histology images from five selected regions.
Figure 26:
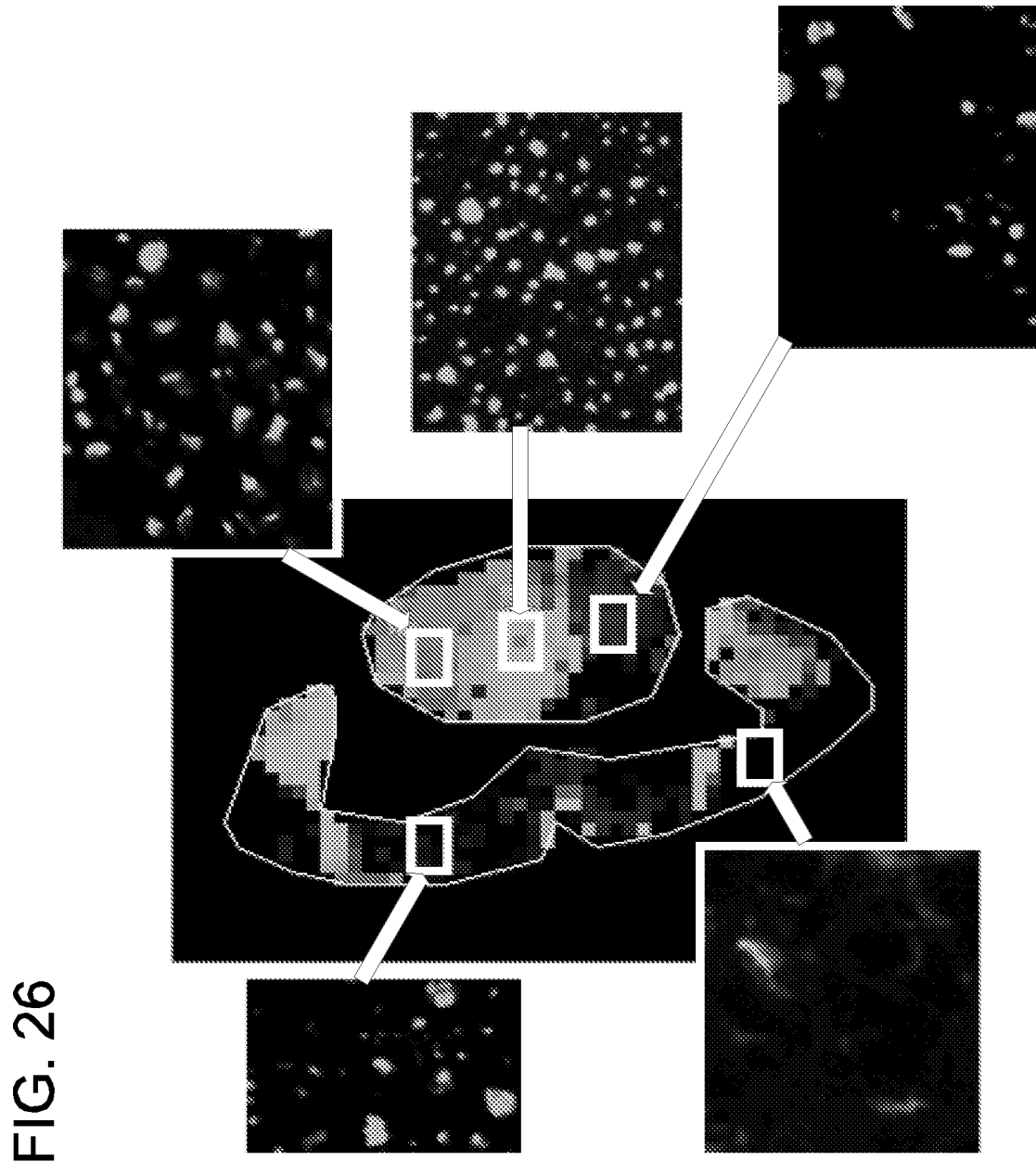
FIG. 26 is a detailed view of the DBSI-derived SMI-31 intensity of the scan of FIG. 22 in the center surrounded by conventional invasive histology images from five selected regions.
Figure 27:
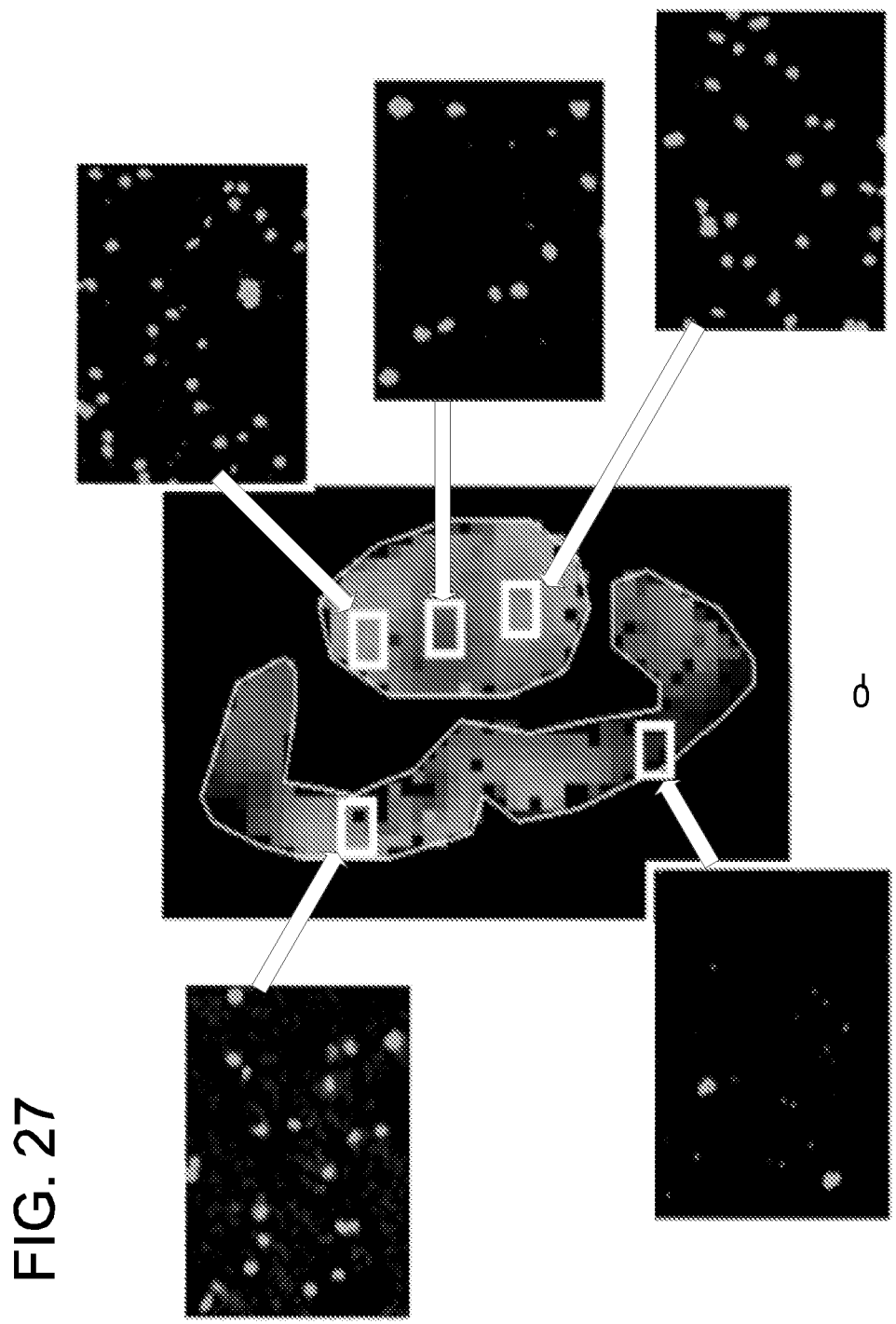
FIG. 27 is a detailed view of the DBSI-derived DAPI intensity of the scan of FIG. 22 in the center surrounded by conventional invasive histology images from five selected regions.
Figure 28A:
FIG. 28 is an illustration of a DAPI and SMI-31 staining of a fixed mouse trigeminal nerve and a comparison of isotropic diffusion spectra with gel.
Figure 28B:
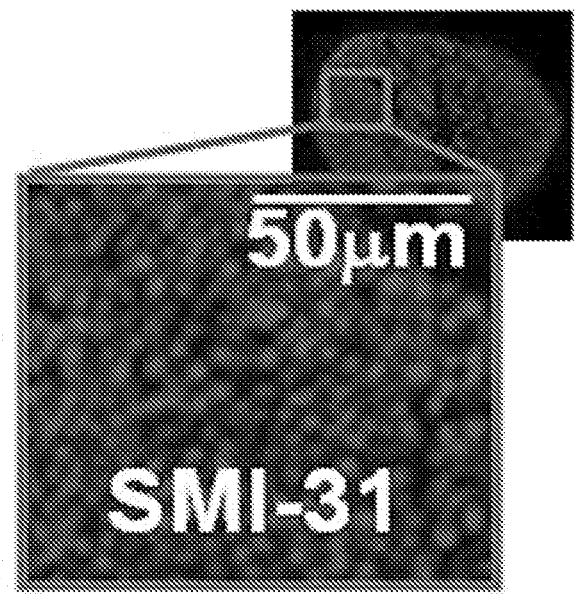

FIGS. 24A, 24B, 24C, and 24D are detailed views of the intensities of the scan of FIG. 22. In these figures, the 24A represents intact myelin, 24B represents intact axons, 24C represents cell nucleus and 24D represents tissue loss.

Figure 40:
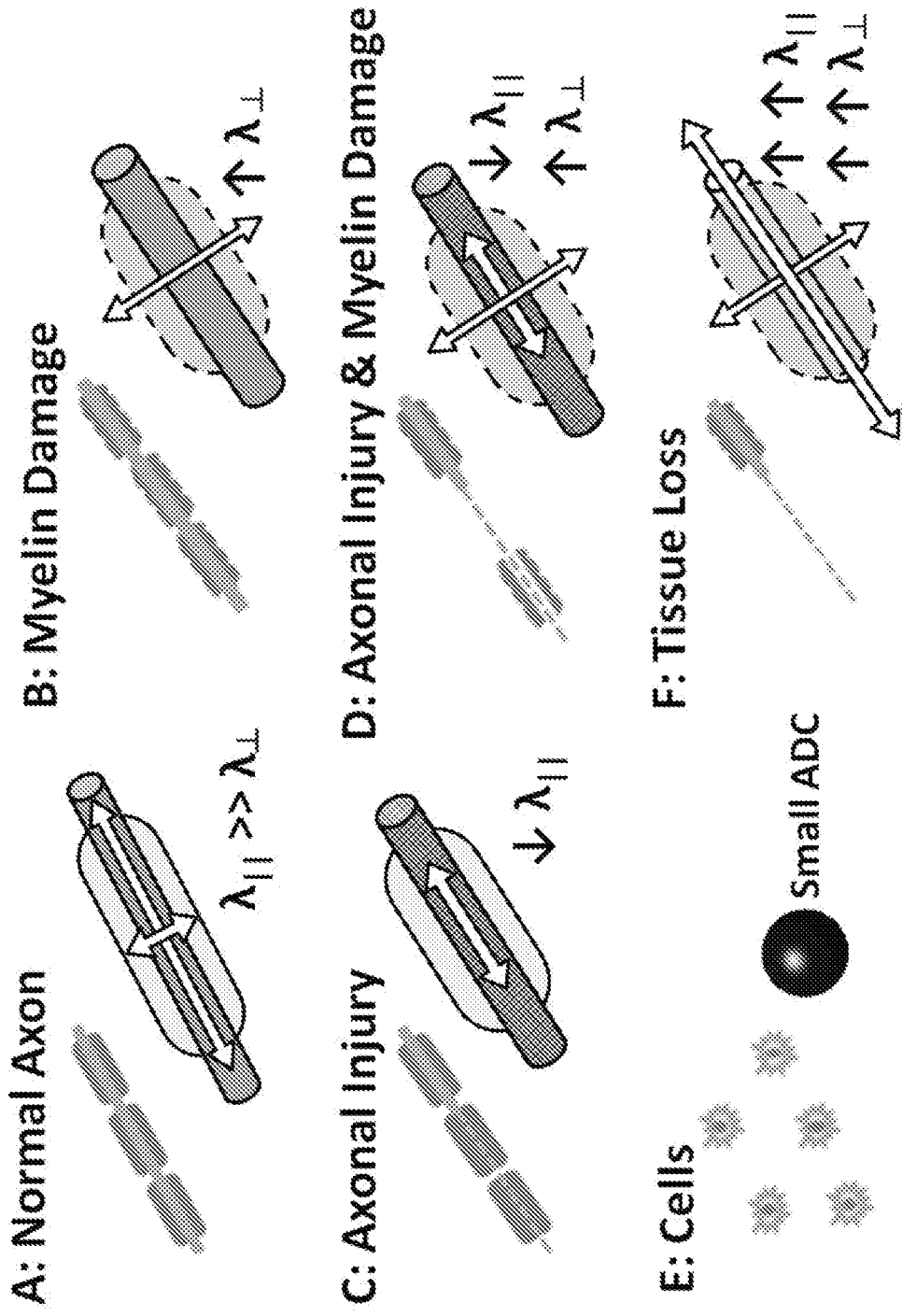
FIG. 40 is an illustration of the DTI signature of homogeneous pathologies.
Figure 41:
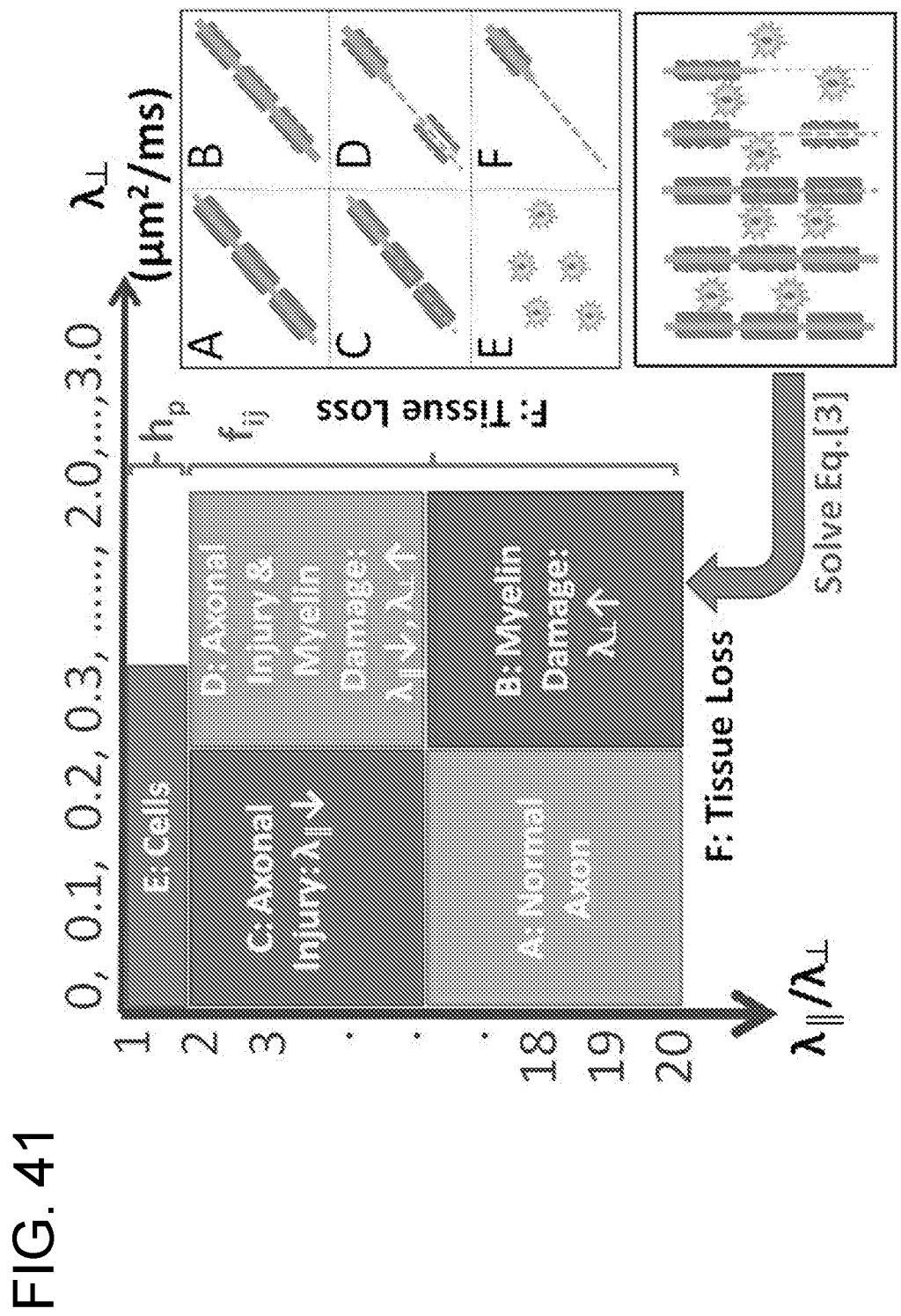
FIG. 41 is an illustration of the procedure to calculate individual pathology maps.

Based on DBSI-derived number fibers and the associated fiber principle orientations (Eq. [2]), the detailed composition of each nerve bundle can be further estimated and classified according to the structure and/or pathology (FIG. 40). Homogenous pathological change in a coherent white matter tract bundle exhibits a unique signature of DTI-derived directional diffusivities (FIG. 41A). To demonstrate the effect of complex pathologies, spinal cord white matter, a simple nerve bundle without fiber crossing, was examined. To properly model spinal cord white matter lesions containing heterogeneous and co-existing pathologies (FIG. 40), diffusion weighted MR signal was modeled as a linear combination of a series of anisotropic diffusion tensors (representing heterogeneous axon fibers with different pathology) plus a spectrum of isotropic diffusion components (representing inflammation associated cell infiltration and edema, or tissue loss), Eq. [5]:

$$S_k = \sum_{i=1}^{M}\sum_{j=1}^{N} f_{ij} e^{-|\vec{b}_k|\lambda_{\perp\_i}} e^{-|\vec{b}_k|(\lambda_{\parallel\_j}-\lambda_{\perp\_i})\cos^2\theta_k} + \sum_{p=1}^{H} h_p e^{-|\vec{b}_k|\lambda_p} \quad \text{(Equation 5)}$$

$f_{ij}$ is the non-diffusion weighted signal intensity fraction of the anisotropic tensor delineated by ($\lambda_{\perp\_i}$, $\lambda_{\parallel\_j}$). As demonstrated by the schematic plot in FIG. 41B, $\lambda_{\perp\_i}$ are the $i^{th}$ (i=1, 2, . . . , M) radial diffusivity uniformly distributed within the limits of [0,2] (μm²/ms); $\lambda_{\parallel\_j}$ are the $j^{th}$ (i=1, 2, . . . , N) axial diffusivity uniformly discretized within the limits of [1.1, 20]×$\lambda_{\perp\_i}$. M×N is the total number of possible anisotropic tensor types distributed within physiological and pathological ranges, which can be classified into five groups: (A) normal axon; (B) demyelinated axon (increased $\lambda_{\perp\_i}$, and unchanged $\lambda_{\parallel\_j}$); (C) injured axon (unchanged $\lambda_{\perp\_i}$, and decreased $\lambda_{\parallel\_j}$); (D) injured axon with demyelination (increased $\lambda_{\perp\_i}$, and decreased $\lambda_{\parallel\_j}$), and (F) tissue loss (significantly increased $\lambda_{\parallel\_j}$ or $\lambda_{\perp\_j}$). Mean−2×STD of DBSI-derived $\lambda_\parallel$ on normal spinal cord white matter is used as threshold to define the decreased $\lambda_{\parallel\_j}$; $\lambda_{\parallel\_j}$>Mean−6×STD indicates significant $\lambda_{\parallel\_j}$ increase. Similarly, Mean+2×STD of DBSI-derived $\lambda_\perp$ is used as threshold to define the increased $\lambda_{\perp\_j}$. $h_p$ is the non-diffusion weighted signal intensity fraction of the $p^{th}$ (p=1, 2 . . . H) isotropic tensor with mean diffusivity $\lambda_p$ uniformly distributed within the range of [0,3] (μm²/ms). In the present pilot study, a diffusion-weighting scheme with K=100 distinct b-values and directions uniformly distributed on 3D Cartesian grid was employed. The detailed composition of the spinal cord white matter described by $f_{ij}$ together with the isotropic diffusion spectrum described by $h_p$ is determined by solving Equation [5] through a regularized nonnegative least-squares (NNLS) analysis (FIG. 41B). The a priori information of nonnegative signal intensity and smooth signal intensity distribution is incorporated as penalty terms to effectively prevent the NNLS from over-fitting the measured noisy data while retaining the numerical accuracy of the solution. Based on the results of the second step, the non-diffusion weighted signal intensity fraction ($f_{ij}$) of the anisotropic tensors belonging to each group were summed up to compute individual pathology component map (FIG. 41B): (Map A) the normal axon density; (Map B) demyelinated axon density; (Map C) injured axon density; (Map D) injured and demyelinated axon density; and (Map F) density map of tissue loss. Isotropic diffusion component (Map E) was computed as the summation of fractions from all the isotropic components ($h_p$). The classic immunohistochemical SMI-31+ staining for the intact axons was approximated by the summation of maps A and B; SMI-32+ map (staining for injured axons) by the summation of maps C and D; MBP+ map (staining for axons with intact myelin) by the summation of maps A and C; DAPI+ map (staining for cell nucleus) by map F. Examples are shown in FIGS. 24-27.

Figure 29:
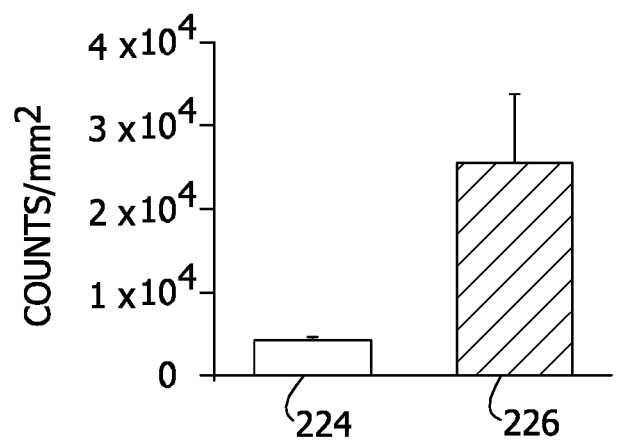
FIG. 29 is a graph of the nucleus and axon counts by IHC of FIG. 29.
Figure 30:
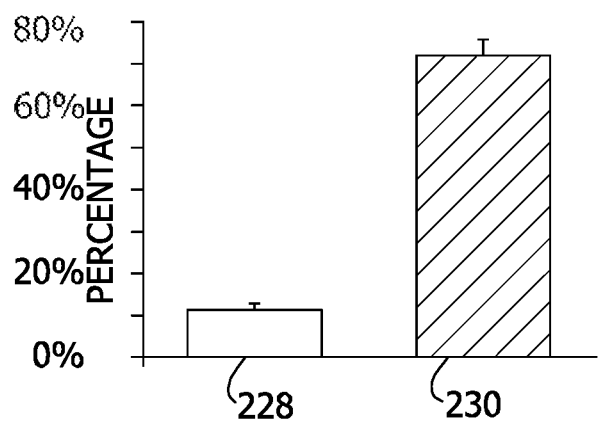
FIG. 30 is a graph of the DBSI derived cell percentage and fiber percentage of FIG. 29.

FIG. 29 illustrates a DAPI 224 and SMI-31 226 staining of a fixed mouse trigeminal nerve and a comparison of isotropic diffusion spectra with gel. In such an embodiment, nucleus and axon staining was performed using 4′,6′-diamidino-2-phenylindole (DAPI) and phosphorylated neurofilament (SMI-31) to count cells (4109±629/mm2) and axons (25434±8505/mm2). The powder-average effect of the 25% (FIG. 30) isotropic diffusion component in the fixed trigeminal nerve is apparent when comparing $\lambda_\parallel$ and $\lambda^\perp$ derived using DBSI ($\lambda_\parallel$=1.07±0.05 μm2/ms; $\lambda^\perp$=0.12±0.01 μm2/ms) vs. DTI ($\lambda_\parallel$=0.77±0.03 μm2/ms; $\lambda^\perp$=0.17±0.02 μm2/ms). Compared to DBSI, DTI underestimated $\lambda_\parallel$ by 28%, while overestimating $\lambda^\perp$ by 42%. Five fiber-gel samples were examined at 19° C. using DBSI to quantify anisotropic and isotropic diffusion, and T2 W MRI to quantify total gel signal intensity.

Figure 31:
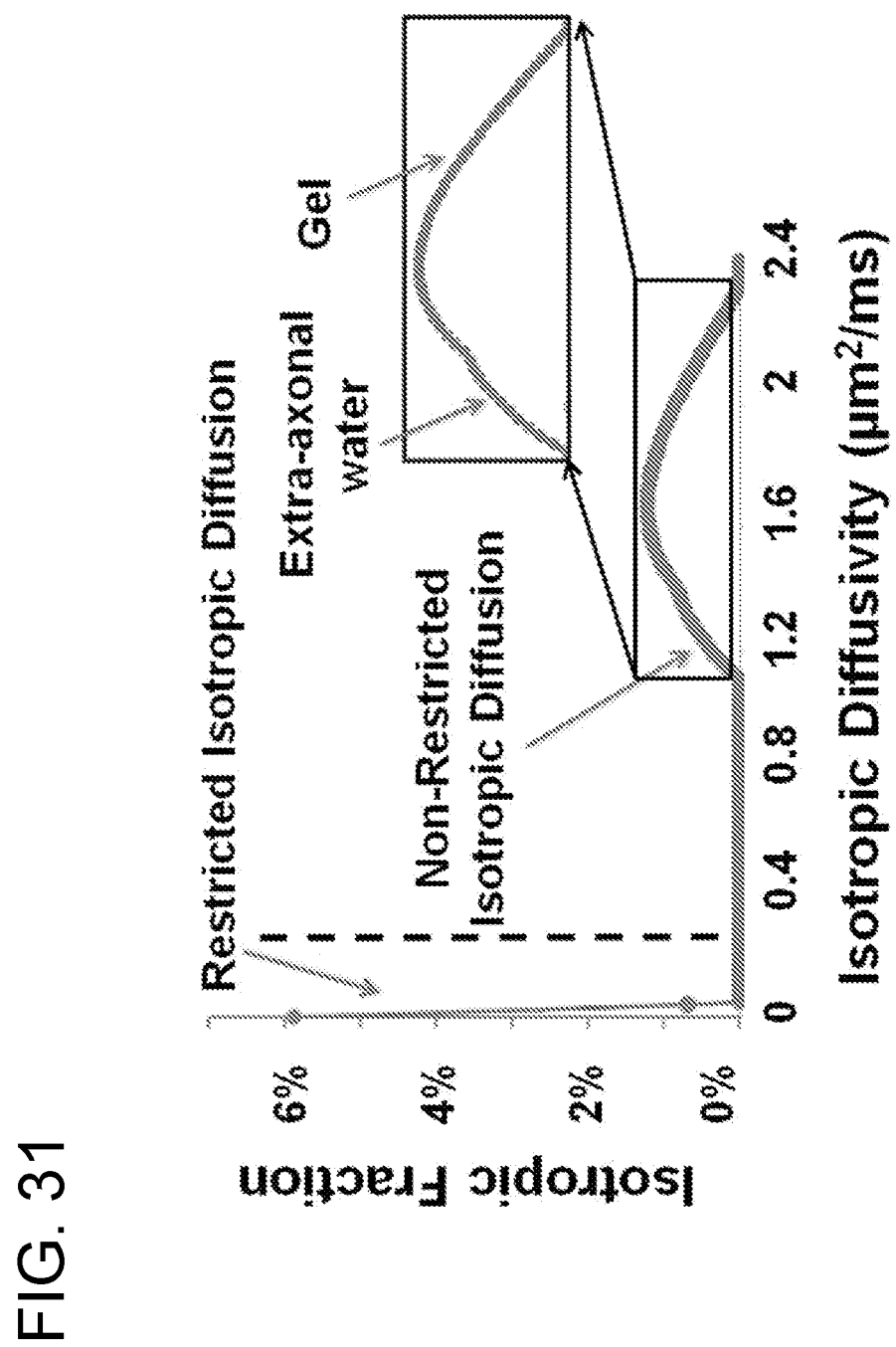
FIG. 31 is an illustration of a typical DBSI-derived spectrum of isotropic diffusivity from a fixed mouse trigeminal nerve juxtaposed with gel.
Figure 32:
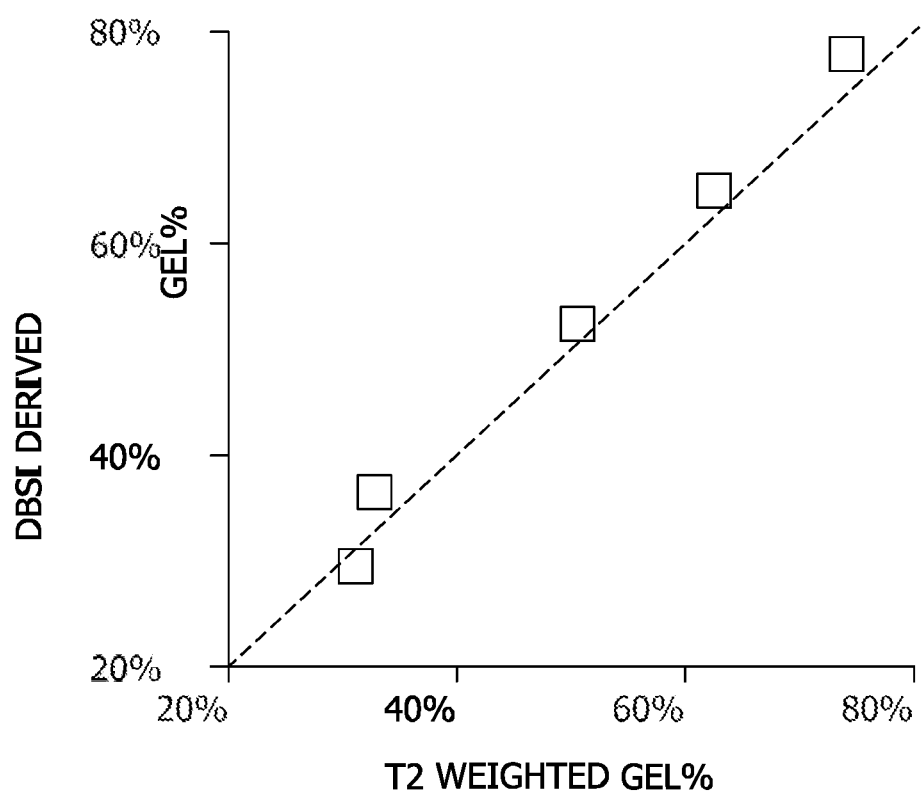
FIG. 32 is a comparison of DBSI-derived gel fractions to those measured by T2 W MRI signal intensity.
Figure 33:
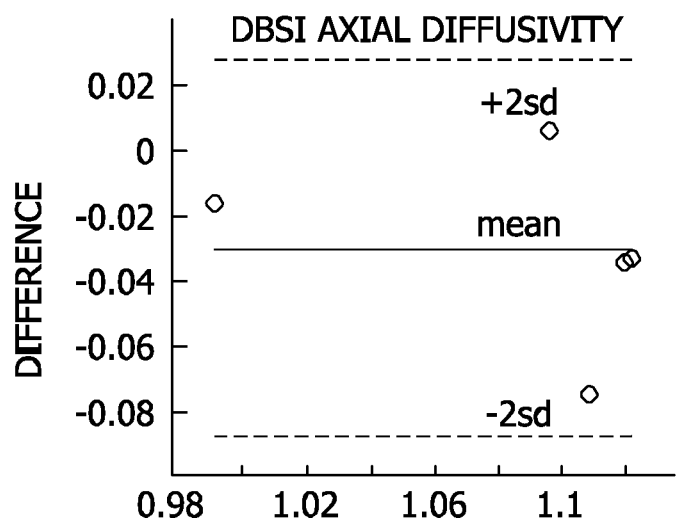
FIG. 33 is a graph of $\lambda_{\parallel}$ derived from trigeminal nerves with and without gel.
Figure 34:
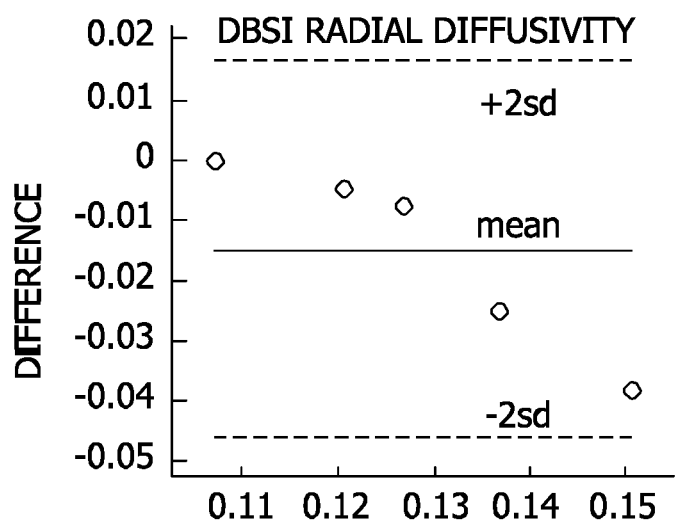
FIG. 34 is a graph of $\lambda_{\perp}$ derived from trigeminal nerves with and without gel.

The DBSI-determined gel water fraction closely matches that determined using T2 W MRI as shown in FIG. 31-32, suggesting the potential of DBSI to estimate edematous water from more freely diffusing water in regions of tissue loss. The derived fiber directional diffusivities with and without gel are comparable as shown in FIGS. 33 and 34, indicating that DBSI can correctly assess fiber diffusion properties in the presence of edema or tissue loss.

Figure 35:
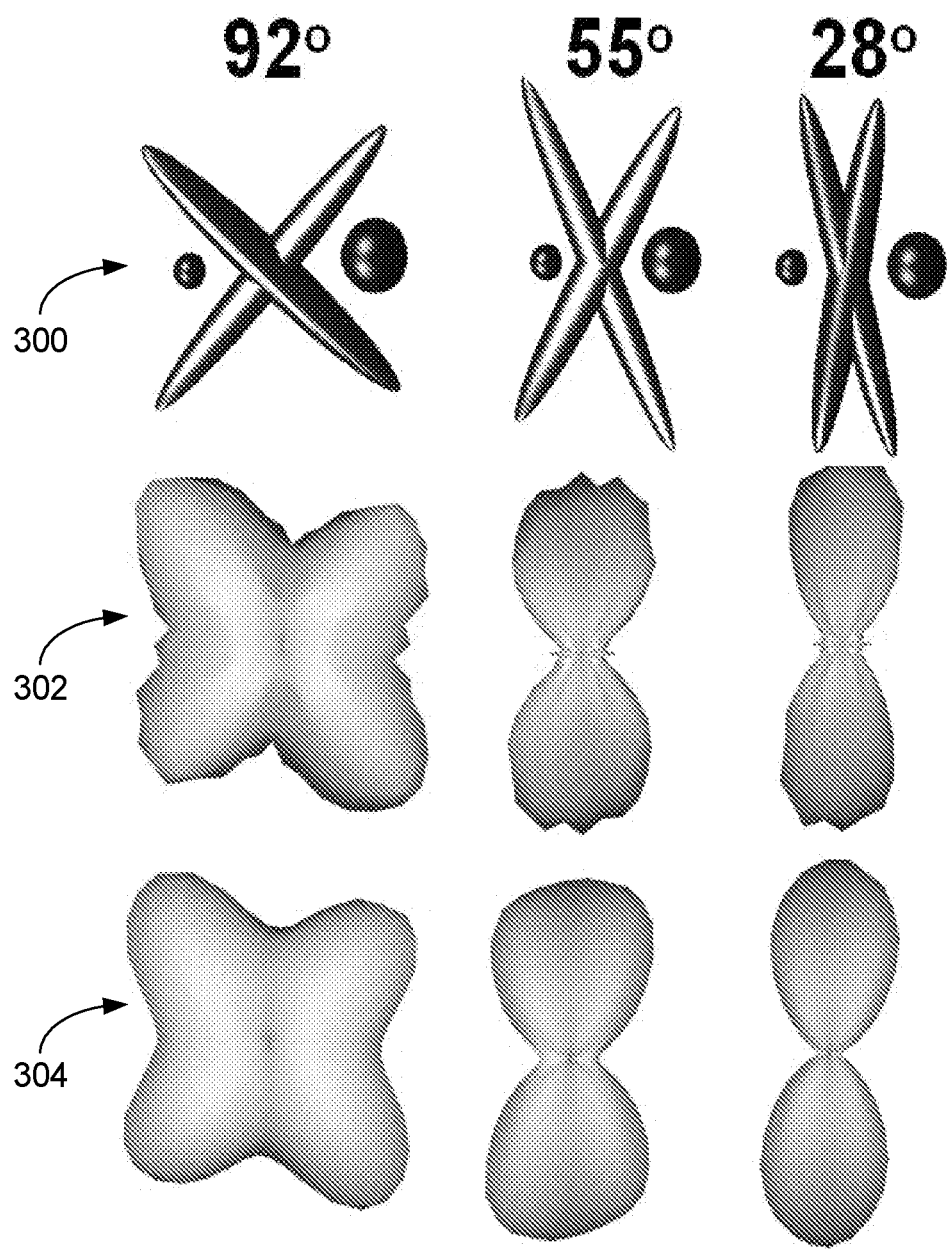
FIG. 35 is an illustration of six fixed trigeminal nerves grouped into three pairs of crossing fibers at 32°, 58°, and 91° juxtaposed with 2% agarose gel.

FIG. 35 is an illustration of six fixed trigeminal nerves grouped into three pairs of crossing fibers at 32°, 58°, and 91° juxtaposed with 2% agarose gel. DBSI-estimated crossing fiber angles 300 compare favorably with those derived using an orientation distribution function (ODF) by DSI 302 and general q-sampling imaging (GQI) 304. DBSI-quantified mean fiber 300 $\lambda\|=1.14\pm0.06$ μm2/ms, $\lambda^{\perp}=0.12\pm0.02$ μm2/ms agreed well with measured values for a single fiber without gel $\lambda\|=1.07\pm0.05$ μm2/ms, $\lambda^{\perp}=0.14\pm0.02$ μm2/ms. For 91°, 58°, 32° phantoms, DBSI-derived gel percentages were 15%, 14%, and 50%, in close agreement with T2 W MRI determined 18%, 13%, and 45%. DSI 302 and GQI 304 failed to resolve crossing FIGS. 33 and 34 comparable $\lambda\|$(A), $\lambda^{\perp}$(B) derived from trigeminal nerves with and without gel was confirmed by Bland-Altman plots.

Figure 36:
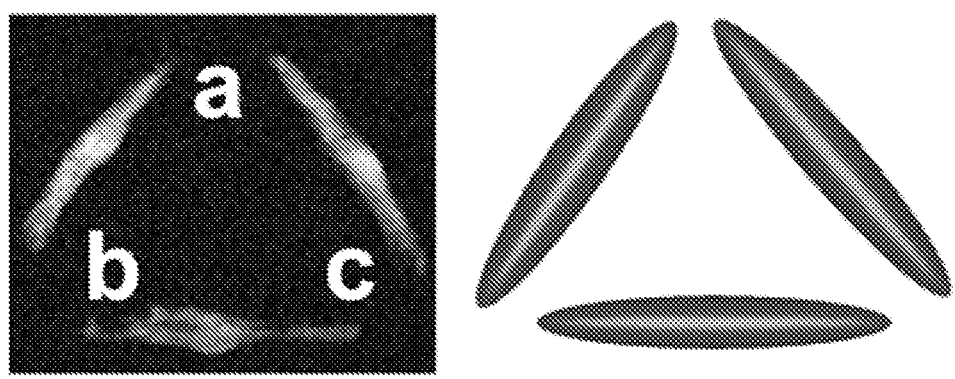
FIG. 36 is an illustration of a three-fiber crossing phantom forming a triangle.
Figure 37A:
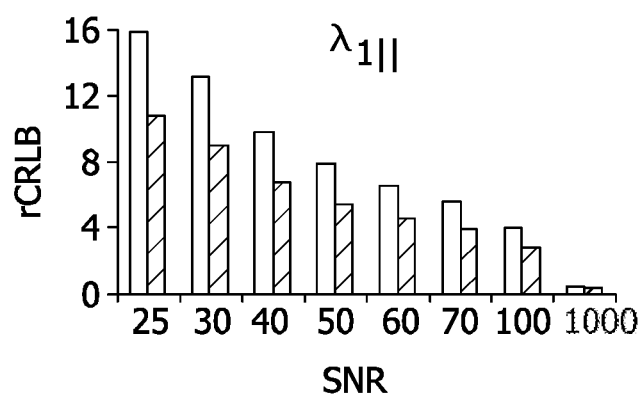
FIG. 37A is a graph of an axial diffusivity $\lambda_{1\parallel}$ of a first fiber.
Figure 37B:
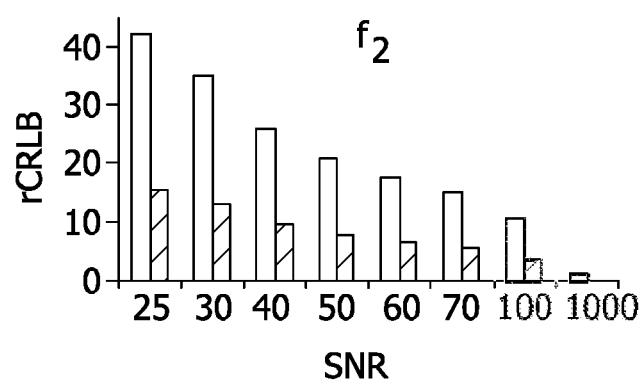
FIG. 37B is a graph of a volume ratio $f_2$ of a second fiber.
Figure 37C:
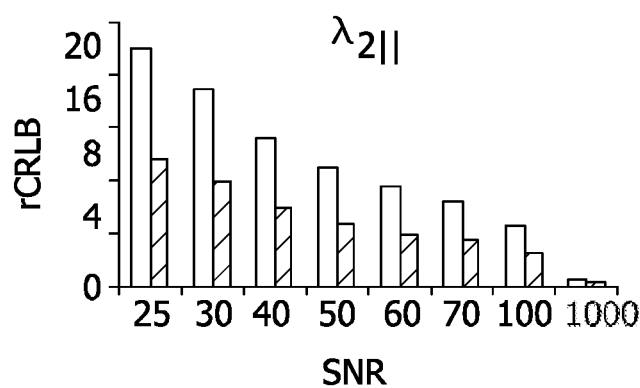
FIG. 37C is a graph of axial diffusivity $\lambda_{2\parallel}$ of the second fiber.
Figure 37D:
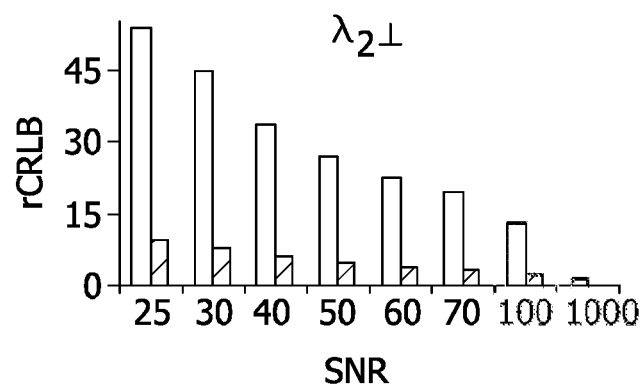
FIG. 37D is a graph of radial diffusivity $\lambda_{2\perp}$ of the second fiber.

To further demonstrate the capability of DBSI to resolve multiple crossing fibers, a 3-fiber crossing phantom was built using fixed mouse trigeminal nerves arranged in an approximate equilateral triangle with inner angles of (a/b/c)=(75°/55°/50°), as is shown in FIG. 36.

A SNR dependent Monte Carlo simulation and a Cramér-Rao Lower Bound (CRLB) analysis on a model (two crossing fibers with one non-restricted isotropic component) and diffusion scheme (three-fold tessellated icosahedric gradient directions, 184 total directions, on two shells: b1/b2=1000, 3500 s/mm2) was performed. FIGS. 37A, 37B, 37C, and 37D illustrate the relative CRLB (rCRLB for axial diffusivities ($\lambda1\|$, $\lambda2\|$) of both fibers, and the volume ratio (f2) and radial diffusivity ($\lambda2^{\perp}$) of the second fiber as a function of SNR.

Figure 38A:
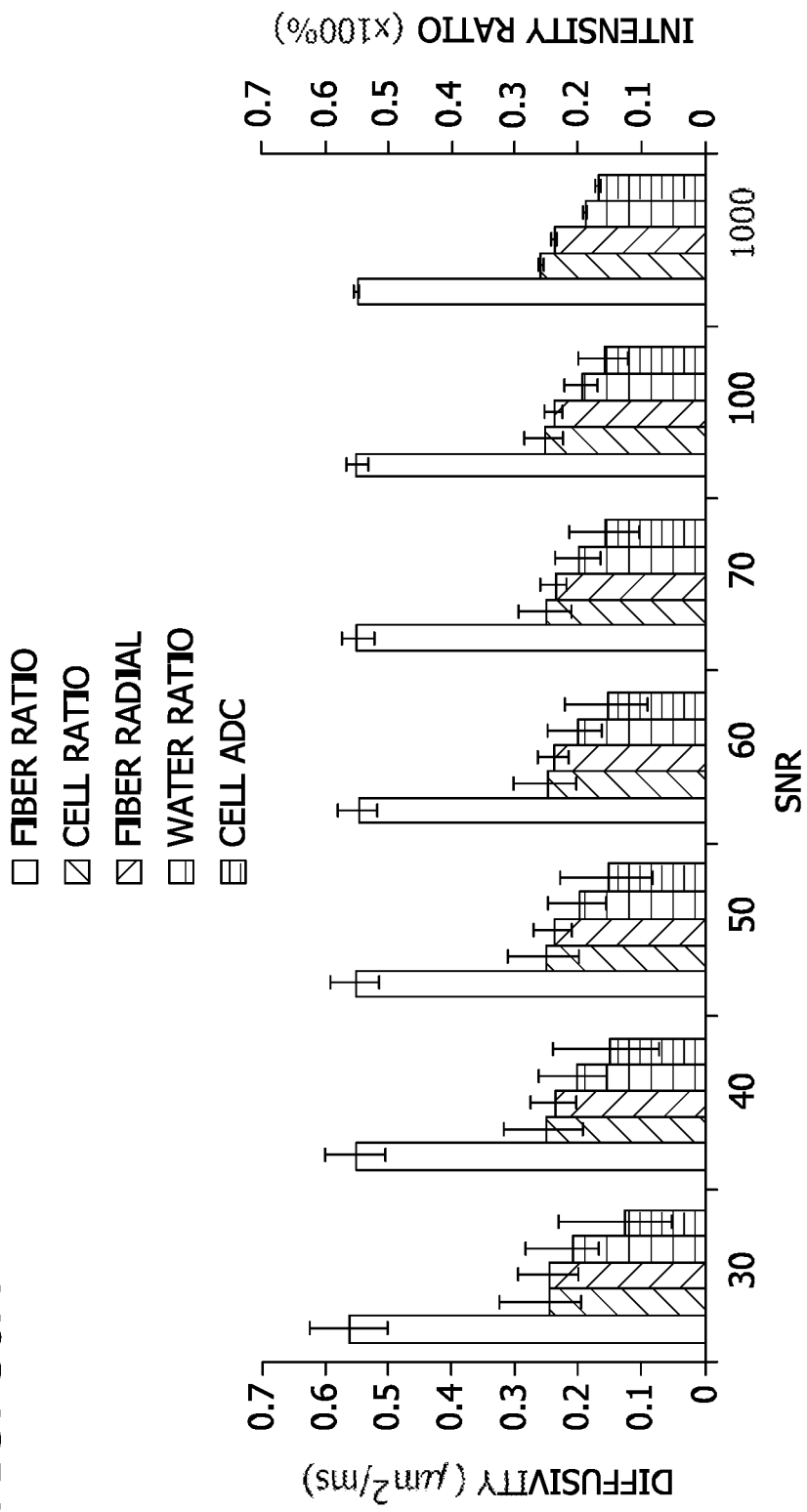
FIG. 38A is an MC-simulation-derived graph displaying fiber ratio, water ratio, cell ratio, cell ADC, and fiber radial diffusivity of diffusion MRI data generated in silico.
Figure 38B:
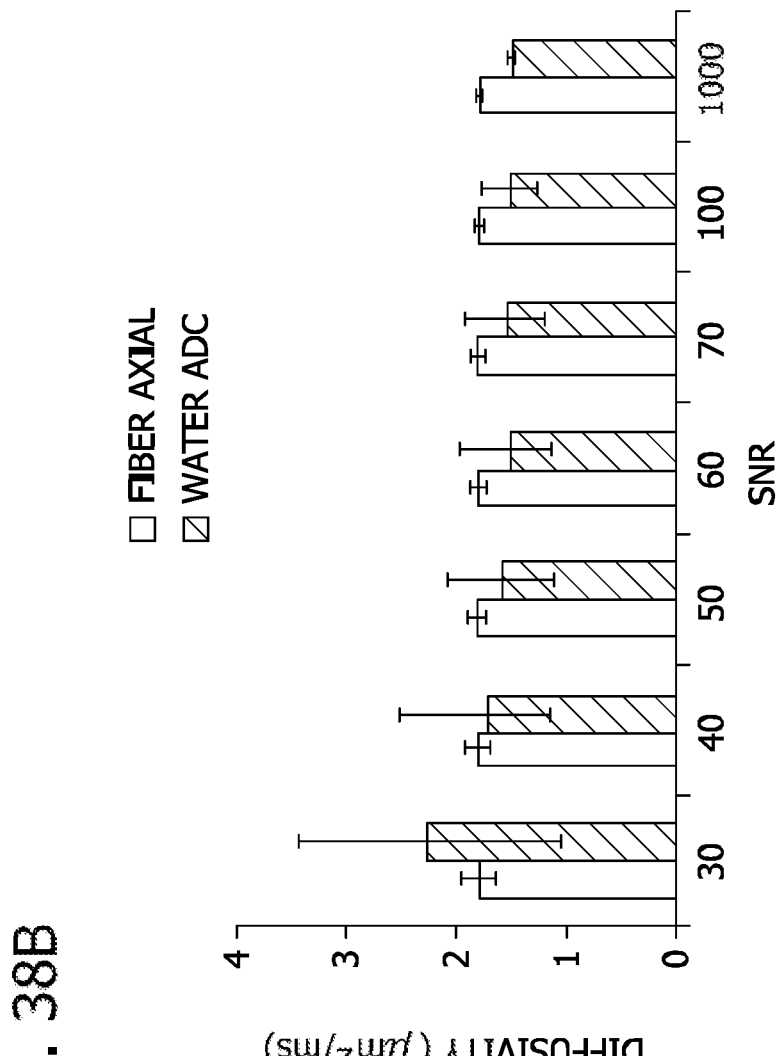
FIG. 38B is an MC-simulation-derived graph displaying fiber axial diffusivity, water ADC of diffusion MRI data generated in silico.
Figure 39:
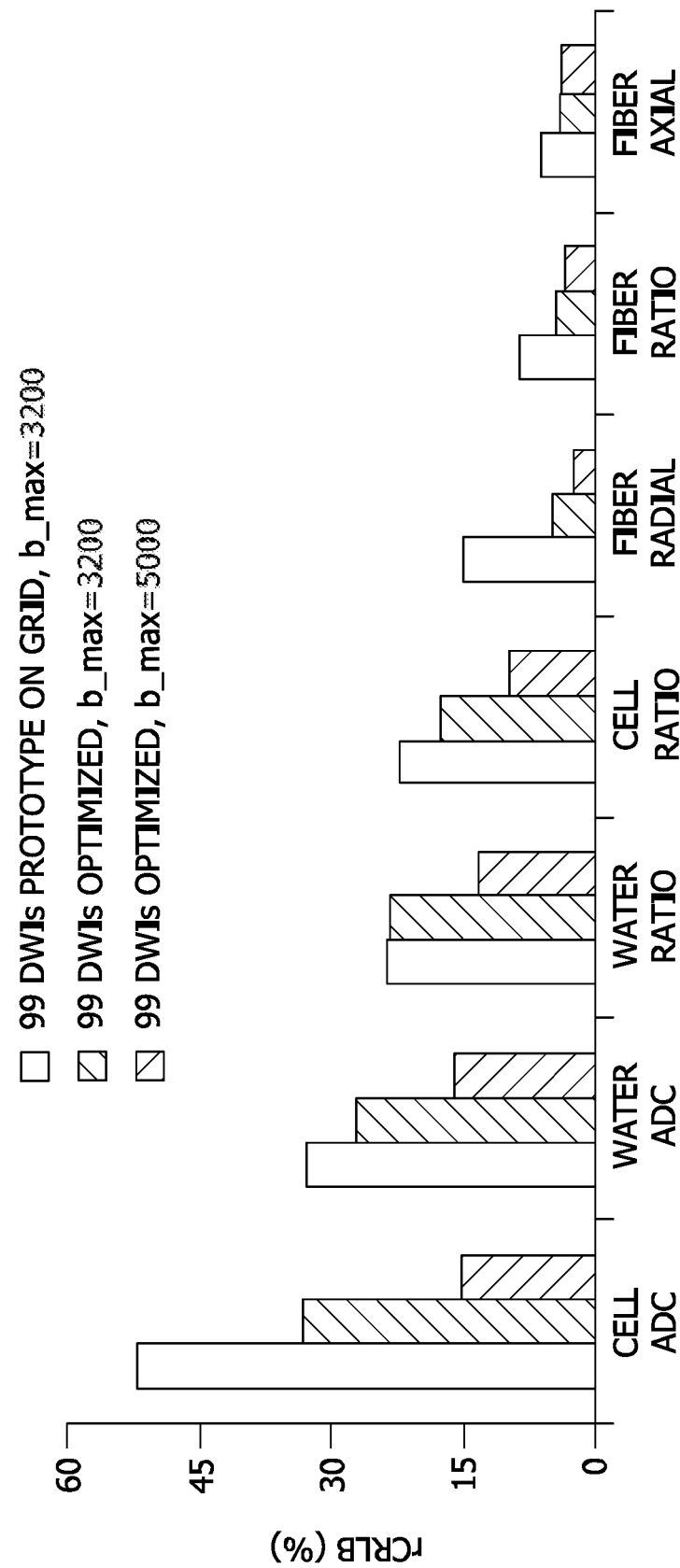
FIG. 39 is a CRLB based optimization of a one-fiber and a two-isotropic compartments diffusion model.

FIGS. 38A and 38B are graphs pertaining to diffusion MRI data representative of a single-fiber with restricted isotropic diffusion and nonrestricted isotropic diffusion were generated in silico via Monte Carlo simulations. The in silico generated data mimicked in vivo mouse spinal cord white-matter diffusion properties at the peak of EAE: single fiber (white-matter tract, $\lambda\|=1.8$ μm2/ms, $\lambda^{\perp}=0.24$ μm$^2$/ms, along z direction, fiber fraction 55%), restricted isotropic component (infiltrating cells, ADC=0.17 μm$^2$/ms, cell fraction 26%), and nonrestricted isotropic component (edema, ADC=1.8 μm$^2$/ms, 19%). All model parameters were estimated accurately at SNR=40, typical of the in vivo mouse spinal-cord measurements, with bias<15% (FIG. 10). MC simulation and CRLB derived variances agreed with each other, and improved with SNR. These results confirm that DBSI-derived diffusion parameters have sufficient precision to permit meaningful estimates of fiber ratio, water ratio, cell ratio, cell ADC, and fiber diffusivities in mice in vivo. Results suggest that with CRLB optimization at the same max b-value the precision can be improved by optimizing diffusion directions (~40% improvement vs. the prototype DBSI). The optimized directions with increased max b-value (=5000) yielded ~140% improvement over the prototype DBSI (b-value in s/mm2), as is shown in FIG. 39.

Figure 42:
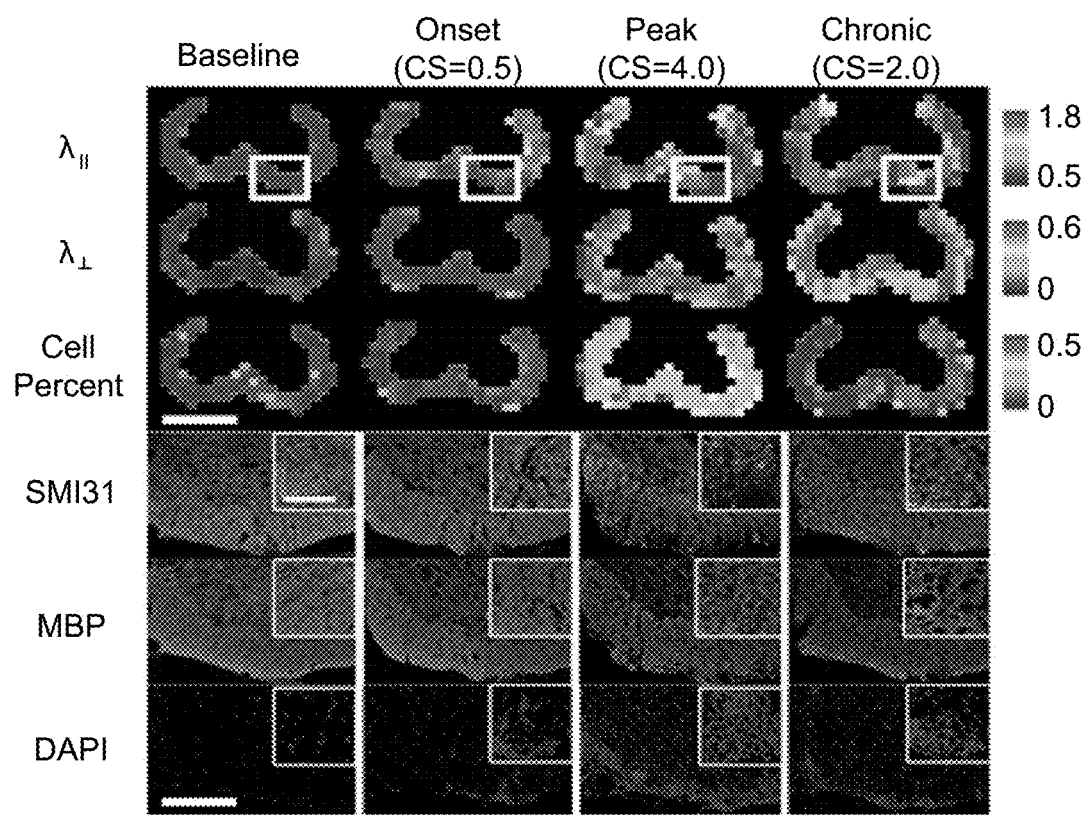
FIG. 42 is an illustration of in vivo DBSI derived $\lambda_\parallel$, $\lambda_\perp$, and cell fraction maps of mice from each time point are displayed with the corresponding axon (SMI-31), myelin (MBP), and nucleus (DAPI) staining.
Figure 43:
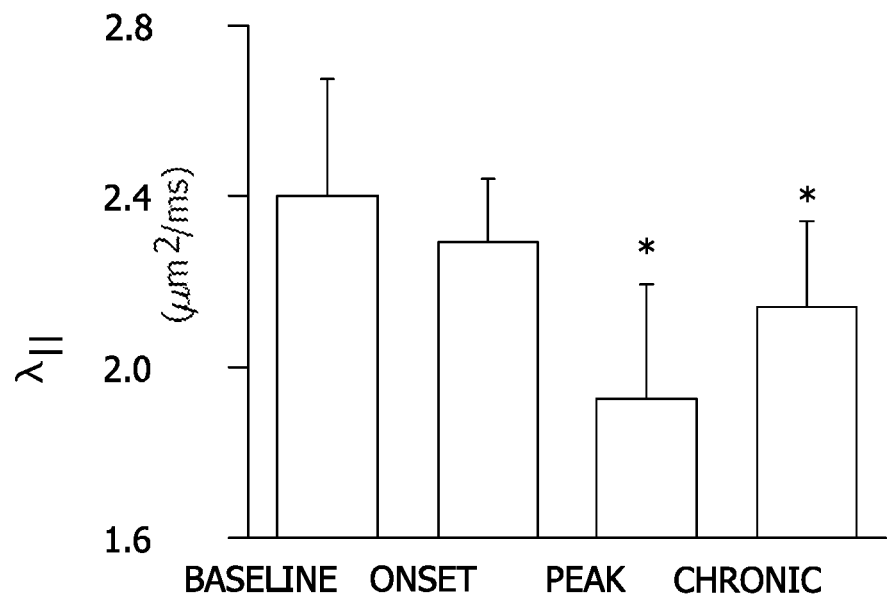
FIG. 43 is a cross-sectional time course of in vivo DBSI derived $\lambda_\parallel$ from B6-EAE mice at baseline (control), onset, peak, and chronic disease states.
Figure 44:
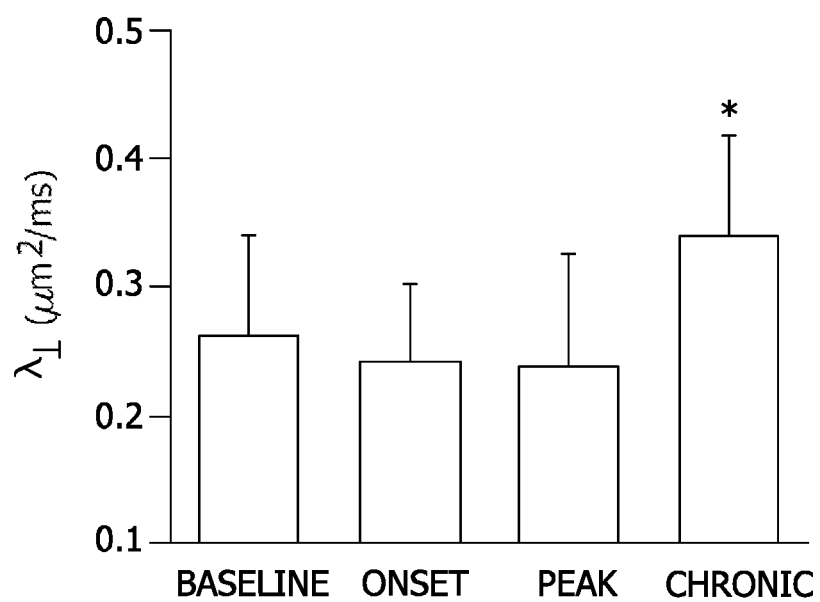
FIG. 44 is a cross-sectional time course of in vivo DBSI derived $\lambda_\perp$ from B6-EAE mice at baseline (control), onset, peak, and chronic disease states.

A cross-sectional study was performed on 12 B6-EAE mice spinal cords at baseline (control), onset, peak, and chronic states, followed by IHC (N=5 for each time point). In the representative mouse, $\lambda\|$ decreased at the peak and recovered slightly at the chronic EAE stage, consistent with decreased SMI-31 staining followed by the recovery of the staining as is shown by FIGS. 42 and 43. Increased $\lambda^{\perp}$ was seen at EAE peak and continued to increase to the chronic EAE stage, consistent with the MBP staining gradually losing its intensity FIGS. 42, and 44.

Figure 45:
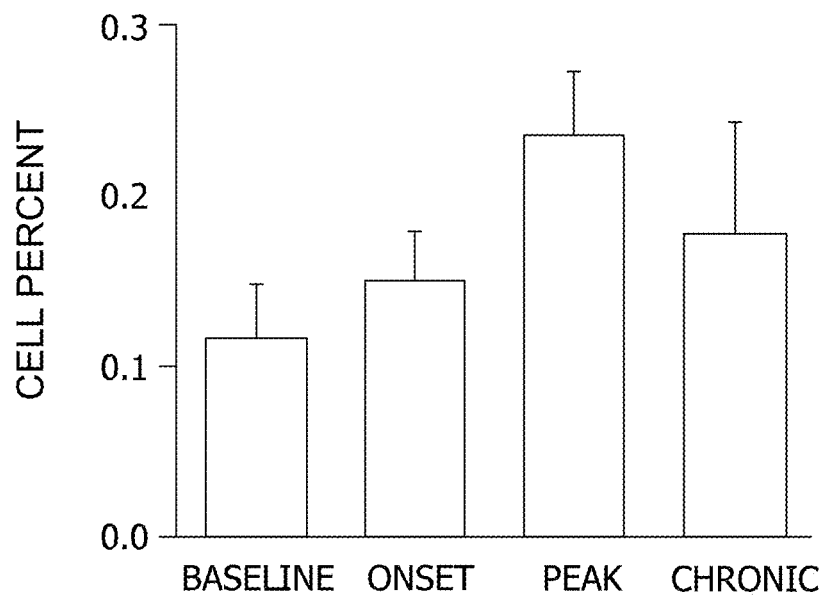
FIG. 45 is a cross-sectional time course of in vivo DBSI derived cell intensity percentage from B6-EAE mice at baseline (control), onset, peak, and chronic disease states.
Figure 46:
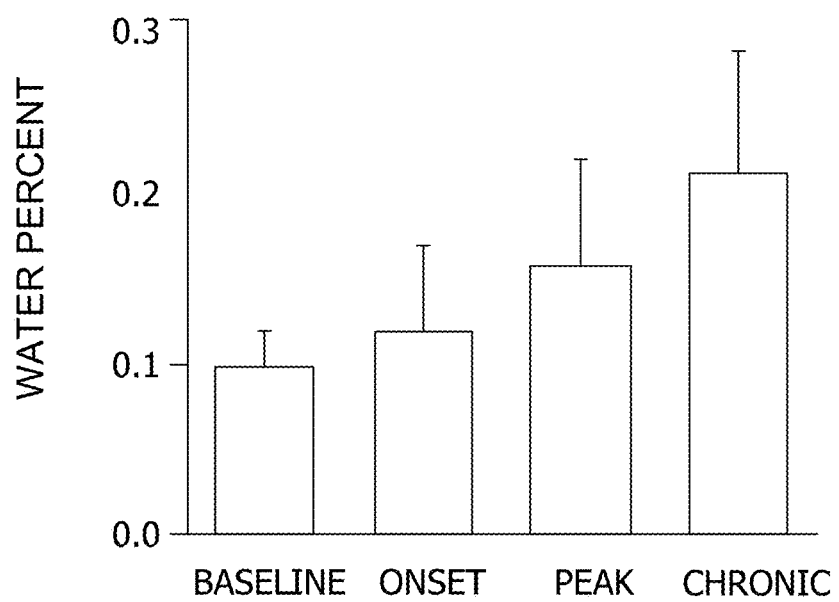
FIG. 46 is a cross-sectional time course of in vivo DBSI derived water intensity percentage from B6-EAE mice at baseline (control), onset, peak, and chronic disease states.

DBSI revealed cell infiltration at peak EAE, consistent with DAPI staining and clearly indicating the presence of inflammation (FIGS. 42 and 45). Quantitative analysis of the ventrolateral white matter DBSI parameters closely reflects the same pathology profile suggested by IHC shown in FIGS. 43-46. DBSI reflects axon and myelin injury more accurately than that previously determined by DTI, and correctly depicts inflammatory pathological features of the spinal cord white matter from EAE mice in terms of both cell infiltration and vasogenic edema as shown in FIGS. 45 and 46.

A segment of autopsy cervical spinal cord, fixed in 10% formalin, from 54 years old Caucasian female with 22-year disease duration was examined on a 4.7-T preclinical MR scanner: Varian DirectDrive™ console, 15-cm inner diameter, actively shielded Magnex gradient coil (60 G/cm, 270 μs rise time). Tissue contained in a 3-ml syringe with 10% formalin was placed in a custom-made solenoid coil for data acquisition using the following parameters: TR 2 s, TE 39 ms, Δ20 ms, δ8 ms, slice thickness 0.5 mm, number of slices 5, field-of-view 2.4×2.4 cm2, number of averages 1, data matrix 192×192.

Figure 47:
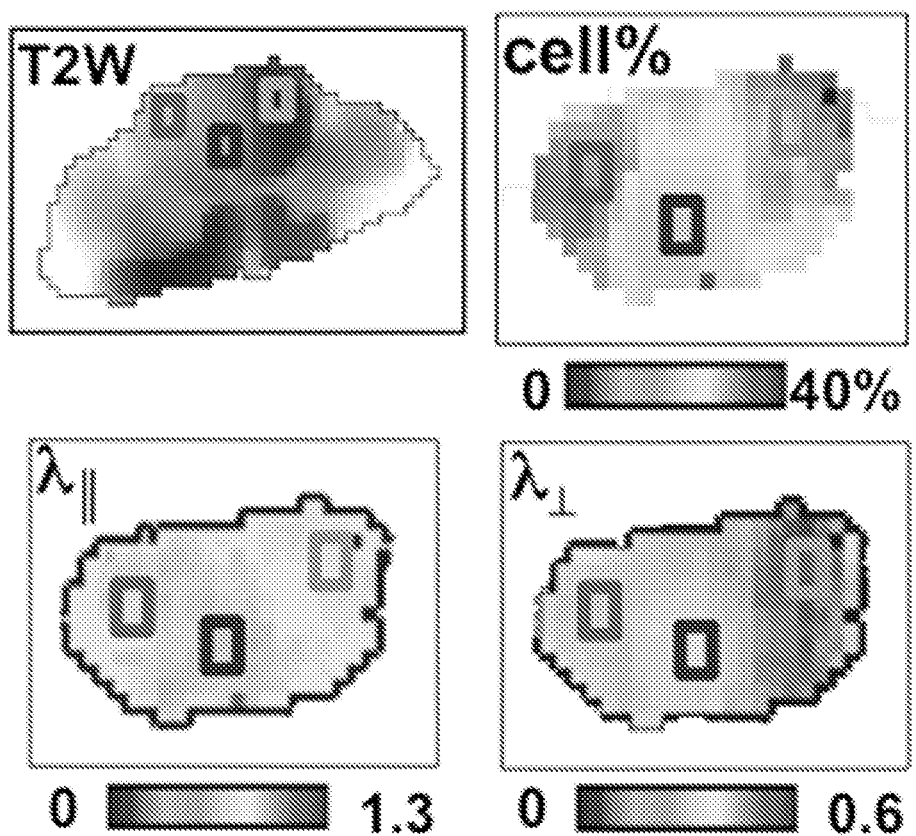
FIG. 47 is an ex vivo DBSI of a human MS autopsy spinal cord specimen.
Figure 48:
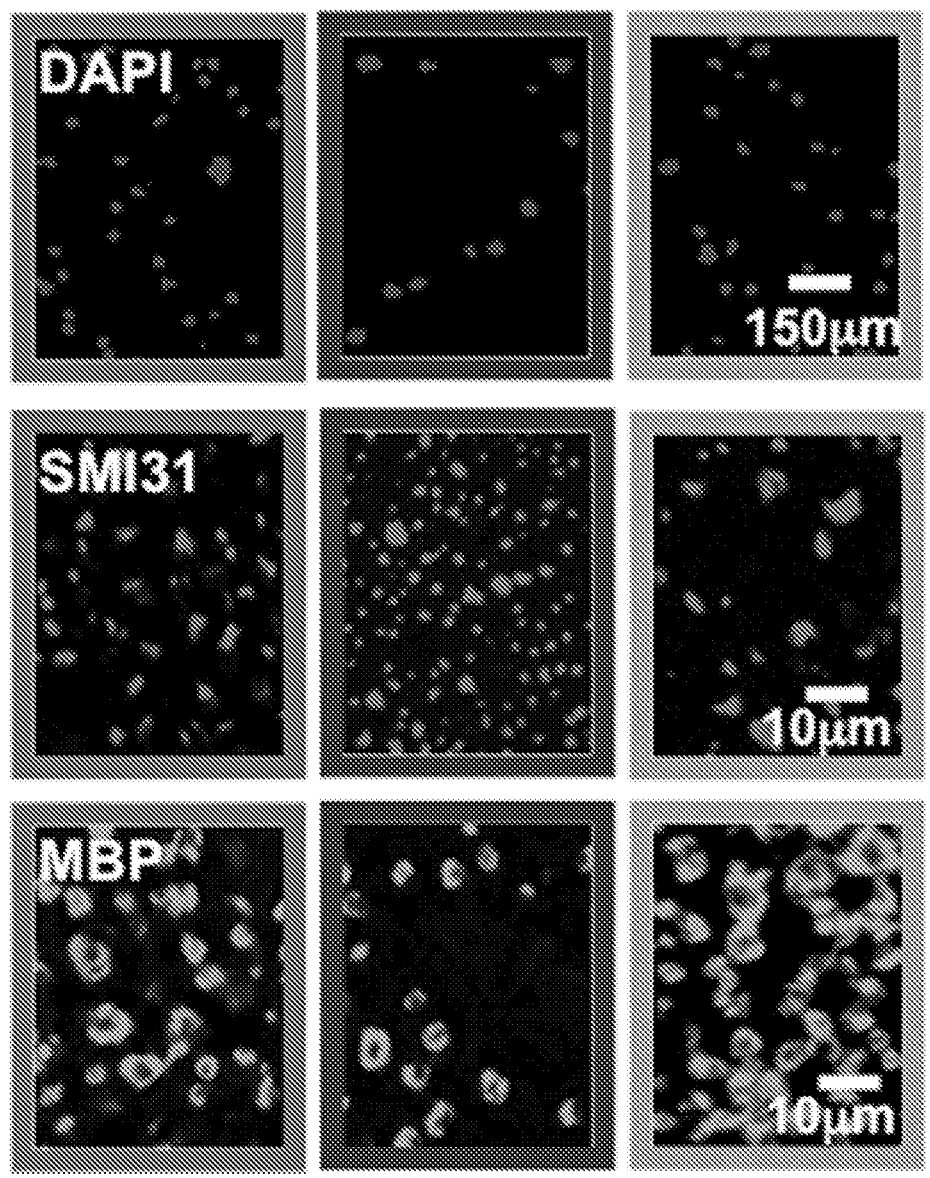
FIG. 48 is an ex vivo histology images of a human MS autopsy spinal cord specimen.
Figure 49:
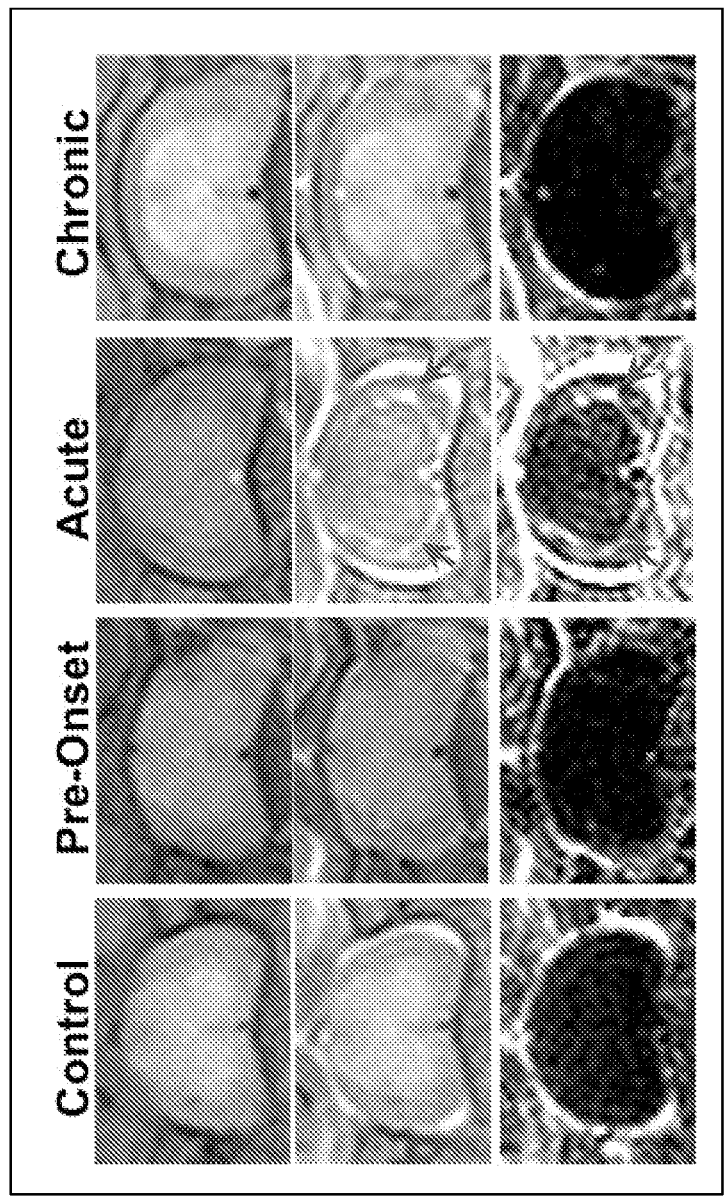
FIG. 49 is T1 W MRI of mouse spinal cords.
Figure 50:
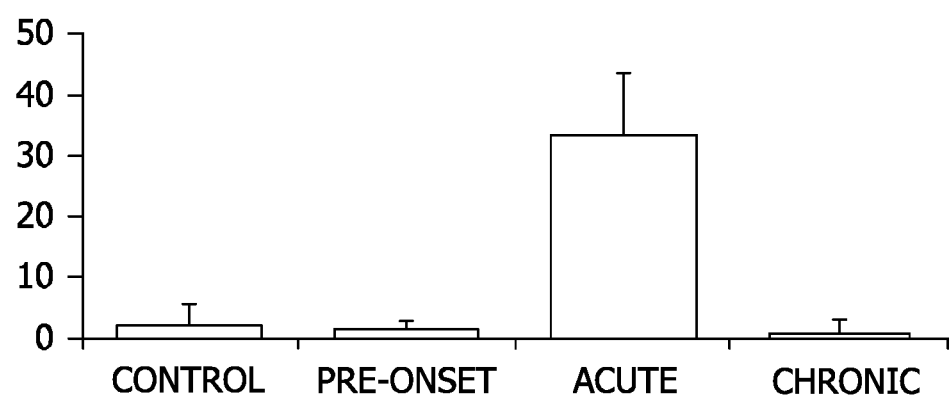
FIG. 50 is a quantitative analysis of percentage enhancement map of FIG. 49.

Diffusion sensitizing gradients were applied in 99 directions with max b-value=3200 s/mm$^2$. In plane resolution was 125×125 μm$^2$. DBSI/DTI maps were coregistered with IHC images and an ROI analysis was employed after co-registration of MRI and IHC images as shown in FIGS. 47 and 48. Diffuse white-matter injury was present in the dorsal column, consistent with the recorded upper extremity numbness of this patient. Significantly increased cell infiltration was seen in all three ROIs, consistent with DAPI staining. The effect of infiltrating cells on diffusion is evident by examining DTI-derived $\lambda\|$ at (0.36±0.02 μm$^2$/ms) and (0.31±0.01 μm$^2$/ms; total 16 image voxels, p=0.07) from the left and right ROI of the dorsal column, where more cell infiltration was noted. In contrast, DBSI-derived $\lambda\|$ at the left (0.81±0.03 μm2/ms) and right (0.74±0.03 μm2/ms; total 16 voxels, p=0.0005) ROI was significantly different, revealing more axonal injury at the right ROI, consistent with the SMI-31 staining. Similarly, DBSI-derived $\lambda^{\perp}$ reveals that the severity of demyelination is again consistent with the MBP staining. This co-registered ROI analysis confirms that DBSI is consistent with IHC findings (FIGS. 47 and 48).

Spherical Harmonic Decomposition (SHD) has been proposed as a method for classifying imaging voxels into isotropic, single-, and multi-fiber components based on SHD coefficients. However, SHD cannot accurately estimate the intra-voxel fiber numbers, fiber volume fractions, fiber anisotropy, or fiber orientations. Even in the simple case of two fibers, it is not possible to use SHD to uniquely determine the intra-voxel fiber numbers and orientation since both the volume fraction and relative fiber orientations interfere with the higher order SHD components in a similar fashion. Similar to DSI, SHD also requires high diffusion weighting gradients. In contrast, DBSI facilitates separating and quantifying the isotropic and individual anisotropic (fiber) components while maintaining the use of low diffusion weighting gradient magnitudes.

Q-ball imaging of the human brain is a method closely related to DSI. In DSI, the ODF is reconstructed by sampling the diffusion signal on a Cartesian grid, Fourier transformation, followed by the radial projection. Q-ball imaging acquires the diffusion signal spherically and reconstructs the ODF directly on the sphere. The spherical inversion is accomplished with the reciprocal space funk radon transform (FRT), a transformation of spherical functions that maps one function of the sphere to another. Q-ball and DSI are theoretically equivalent and generate similar ODF. However, q-ball methods are not capable of estimating fiber angles as well as quantifying multiple tensor parameters.

Independent Component Analysis (ICA) has been proposed for application in DTI tractography to recover multiple fibers within a voxel. Although the angle of crossing fibers within voxels can be estimated to within 20 degrees of accuracy, eigenvalues cannot be recovered to obtain the complete tensor information such as the Fractional Anisotropy (FA).

Moreover, it has been proposed to use a high angular resolution diffusion imaging (HARDI) data set as a method that is capable of determining the orientation of intra-voxel multiple fibers. For example, up to 2 fiber components and one isotropic component may be considered. Similar to DBSI, HARDI methods have employed a mixed Gaussian model incorporating the isotropic diffusion component. However, HARDI is very different in nature compared with DBSI. For example, (i) HARDI fails in voxels with more than 2 fibers; (ii) HARDI does not work in voxels with more than 1 isotropic component, which is commonly seen in pathological conditions with both cell infiltration and edema; (iii) HARDI fails to compute isotropic diffusivity, improving fiber orientation estimation at the expense of removing the isotropic diffusion component; (iv) HARDI cannot compute the absolute axial and radial diffusivities for each component fiber; (v) HARDI cannot compute the true volume fractions of each fiber or isotropic component. In contrast, DBSI facilitates achieving all the goals enumerated above because it may be used to solve for issues that HARDI ignores or simplifies. HARDI-based methods have aimed to enhance the tools available for fiber tracking but do not compute the directional diffusivities of fibers, the isotropic diffusivity, or true volume fractions.

In summary, diffusion MRI methods in the field currently focus on determining the primary orientation of crossing fibers within one voxel. To achieve this goal, most have to relax the condition needed for accurate estimation of diffusivity or the volume ratio of individual component. DBSI facilitates not only resolving the primary direction of each fiber component, but also identifying and quantifying one or more other physical properties available from the diffusion measurements.

With the quantified fraction, axial diffusivity, and radial diffusivity of each fiber as well as the fraction and mean diffusivity of each isotropic diffusion tensor, CNS white matter pathology maps corresponding to the classic immunohistochemistry staining of excised tissues may be generated. For example, based on the axial diffusivity distribution intact (or injured) axonal fiber tract fraction may be estimated and the fraction distribution map may be generated to reflect the classic phosphorylated neurofilament (SMI-31, for intact axons), or dephosphorylated neurofilament (SMI-32, for injured axons), staining. The restricted isotropic diffusion component estimated using DBSI constitutes a map of cell distribution corresponding to nucleus counting using DAPI staining on the fixed tissue allowing a direct estimate the extent of inflammation in patient CNS white matter.

In the preceding discussion, a method approach has been developed incorporating the diffusion profile of each component within the image voxel to perform the tissue classification based on the raw diffusion MRI data. The typical classification is performed using the generated parameters, not the source data. This approach generates realistic "non-invasive histology" maps of various CNS white matter pathologies directly related to the actual immunohistochemistry staining that is only available after tissue excision and fixation. Although an accurate assessment of the underlying white matter pathologies may or may not correctly reflect clinical symptoms during the early phase of the disease, it would likely predict the long-term patient disability. Such a quantitative assessment of CNS white matter that tracks integrity would enable a clinically-based intervention for the patient. For example, current MS treatments follow a standard dosing regimen, with limited opportunity to adjust management for individual patient responses. By quantitatively distinguishing and tracking inflammation, and axon and myelin injury, DBSI provides the opportunity for efficient assessment of disease-modifying interventions and allows treatment planning to reflect individual patient response.

Multi-Modality Quantification of Neuroinflammation in CNS Disease

The multi-modality quantification of neuroinflammation is generally directed to a non-invasive and non-radioactive approach to the characterization of Alzheimer's disease. By applying signal separation to dMRI using the DBSI model described herein, distinctions can be made between WM abnormalities and neuroinflammation. These distinctions further allow for detection and measurement of a DBSI neuroinflammation biomarker (e.g., an inflammatory cell fraction). Effective detection and accurate quantification of neuroinflammation as indicated by the DBSI biomarker may provide early diagnosis for Alzheimer's disease and other CNS diseases, as well as improved tracking of disease progression and improved treatment assessment.

Embodiments of this disclosure include methods and systems for detection and quantification of neuroinflammation using a DBSI biomarker. A system and method for characterizing the progression of CNS disease, such as Alzheimer's disease, by utilizing DBSI-MRI include capturing patient data using DBSI-MRI, identifying a DBSI biomarker in the captured data, detecting neuroinflammation based on the DBSI biomarker, and quantifying the detected neuroinflammation based on the DBSI biomarker. Some embodiments may include quantifying a patient's overall neuroinflammation using DBSI-MRI and applying a treatment plan based on said quantified neuroinflammation. Other embodiments may include quantifying a patient's overall neuroinflammation using DBSI-MRI and tracking said neuroinflammation over time and in response to various treatment measures.

More specifically, DBSI-MRI imaging is used to detect the various different diffusion components from which the DBSI biomarker is derived. The DBSI biomarker, a measure of inflammatory cellularity, can also be used in a DBSI total neuroinflammation index that is defined as the summation of inflammatory cell fractions across the entire brain including both white matter and gray matter. Also, by integrating this DBSI neuroinflammation biomarker with other available CSF and/or PET measures, a more complete measure of a patient's inflammation can be provided to CNS patients/physicians, tracked over time, and used to effectively evaluate applied treatments. Further, because DBSI-MRI modality has excellent test-retest stability and high sensitivity to disease progression, the systems and methods described herein can be used for efficient application and evaluation of new drugs targeting immunoresponse and neuroinflammation in CNS and related neurodegeneration diseases, such as Alzheimer's disease.

Despite intense research, there is a lack of effective therapies for Alzheimer's disease (AD). It is well known that AD affects 1 in 3 seniors and costs USA $226 Billion in 2015. Unfortunately, there are currently no effective treatments. This is, in part, due to the incomplete understanding of the pathological steps leading to dementia. In addition to Aβ and tau, researchers are beginning to recognize the role of neuroinflammation in AD pathogenesis and progression. However, because central nervous system tissue is inaccessible for longitudinal sampling, surrogate measures of neuroinflammation amenable to longitudinal sampling are desired to better understand AD pathophysiology and progression, and to develop and evaluate response to therapeutic interventions.

A challenge in human CNS disease is obtaining CNS tissue (e.g. brain, spinal cord, optic nerve) samples to study pathologies by histology, because there is the potential to cause serious harm to patients. Other challenges include: an incomplete understanding of the pathologic progression of CNS disease, inaccurate diagnosis and prognosis in patients, and imprecise evaluation of the treatment effects of new therapies in trials. These challenges are compounded by CNS legion spatial variation within/across patients and dynamic evolvement over time, which may require serial biopsies of many affected patients. In view of these challenges, effective therapies are still largely unavailable and needed. In particular, pathological quantification is desired that is both global and dynamic.

A non-invasive, non-radioactive clinical test that is equivalent to histology is desirable. The techniques disclosed herein describe a non-invasive histology (NIH) method using diffusion basis spectrum imaging (DBSI) that may meet at least some of the challenges listed above, defined herein as NIH-DBSI. NIH-DBSI uses FDA-approved clinically available MRI sequences to detangle multiple sub-voxel pathologies. For example, NIH-DBSI can mix white matter pathologies with neuroinflammation in one image voxel. This technique has been validated and produces non-invasive, non-radioactive NIH-DBSI scans by leveraging pattern separation.

NIH-DBSI related test products may include both NIH-DBSI software packages as well as NIH-DBSI cloud computing services and may be used to support clinical trials of new drugs for treatment of various CNS diseases. NIH-DBSI may be employed for drug discovery and clinical trials, as well as for research labs and clinical practice. Some of the major diseases amenable to NIH-DBSI systems and methods include Alzheimer's disease, Multiple Sclerosis, brain tumors, traumatic brain injuries, etc. NIH-DBSI is a valuable tool which may reduce the cost of scientific research by cost-effectively enabling re-analysis of previously collected MRI data. Medical imaging costs may be reduced by saving the cost of tracer and scanning time. For example, a PET scan with one tracer may cost $3000, a Gd-MRI scan may be $4000, and a CSF analysis may be $5300, while an NIH-DBSI scan may cost $800. In addition, a reduction of clinical treatment costs may be realized. For example, the one year cost of drug treatment for brain cancer is around $100-150K per patient. The potential cost savings are exponential with NIH-DBSI as it could expediently identify non-responders to treatment. Further, the cost of clinical trials and drug development may be reduced by the effective reduction of trial duration for true longitudinal trials.

DBSI is an approach to diffusion MRI and can detect one or more parameters that may serve as biomarkers both sensitive and specific to neuroinflammation in AD as part of the disclosed NIH-DBSI method. Unlike diffusion tensor imaging (DTI), which attempts to assess structural and pathological complexity in neurodegenerative diseases, DBSI can specifically quantify inflammatory cell infiltration and edema by separating diffusion effects from other coexisting pathologies such as axonal injury/loss and demyelination. In one aspect, the DBSI biomarker for neuroinflammation includes, but is not limited to, the DBSI cell fraction (an estimate of cellularity).

Development of accurate and robust DBSI biomarkers may significantly improve the understanding of the role of neuroinflammation in AD pathogenesis and provide attractive neuroimaging surrogates that are relevant for early diagnostics and testing of new disease-modifying therapies targeting the immune response.

In the central nervous system (CNS), microscopic barriers (e.g., cellular and nuclear membranes, myelination, and gliosis) constrain the free Brownian motion of water molecules, resulting in a reduced apparent diffusivity measurable by diffusion MRI. Within the diffusion time range achievable in most clinical MRI scanners, water molecules inside cellular structures (blue spheres in FIG. 58) experience highly restricted diffusion (solid lines in FIG. 58), leading to a small apparent diffusion coefficient (ADC). Extracellular water has faster, non-restricted diffusion (dashed lines in FIG. 58), leading to a relatively large ADC. Raw diffusion MRI signals are a mixture of different types of constrained water diffusion, carrying rich CNS microstructural information.

Figure 59:
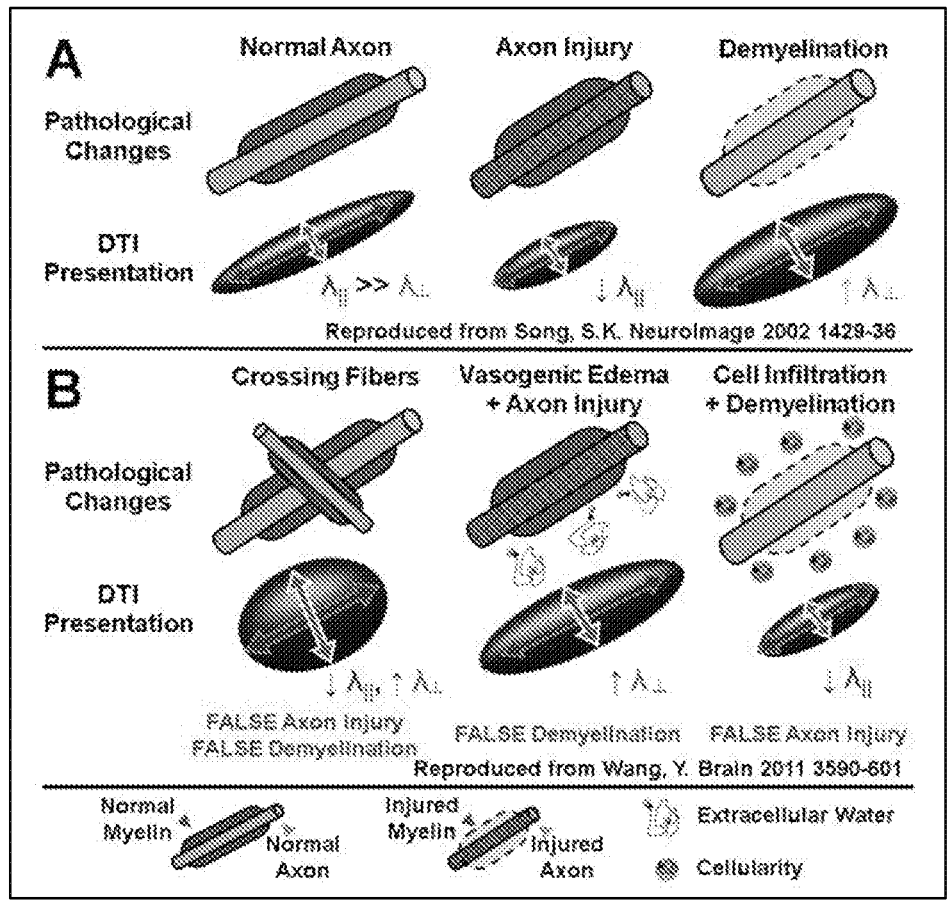
FIG. 59 shows a schematic of DTI limitations.

DTI is a widely used clinical and research MRI technique that detects CNS microstructural changes, yet has limitations. DTI has been used to identify neuronal injury, myelin damage, microglia activity, and reactive gliosis associated with AD (FIG. 59A). In FIG. 59A, DTI can separate axon injury from demyelination on the basis of directional diffusivity changes. In FIG. 59B, DTI fails to detect axon/myelin damage in the context of crossing fibers, vasogenic edema, or cell infiltration. However, the heterogeneity of human CNS pathology significantly reduces the specificity of DTI for measuring histopathological changes, largely because DTI only reflects the overall averaged diffusion profile and cannot tease apart neuroinflammation signals (inflammatory cell infiltration, and vasogenic edema) from the anatomical complexity (crossing/dispersing fibers, etc.) and coexisting neurodegeneration (neuronal injury, myelin damage, etc.) (FIG. 59B). To disentangle the heterogeneous pathological components mixed in one voxel, advanced diffusion MRI techniques are described herein with more diffusion-encoding gradient directions and diffusion weightings (b-values). Crossing fibers have been successfully resolved to allow more accurate fiber tractography. Fiber dispersion and intra-axonal water fraction have also been estimated by multi-compartment modeling. However, none of these advanced diffusion MRI approaches are designed to target the inflammatory cell infiltration and vasogenic edema commonly involved in human neurodegenerative diseases.

Figure 60:
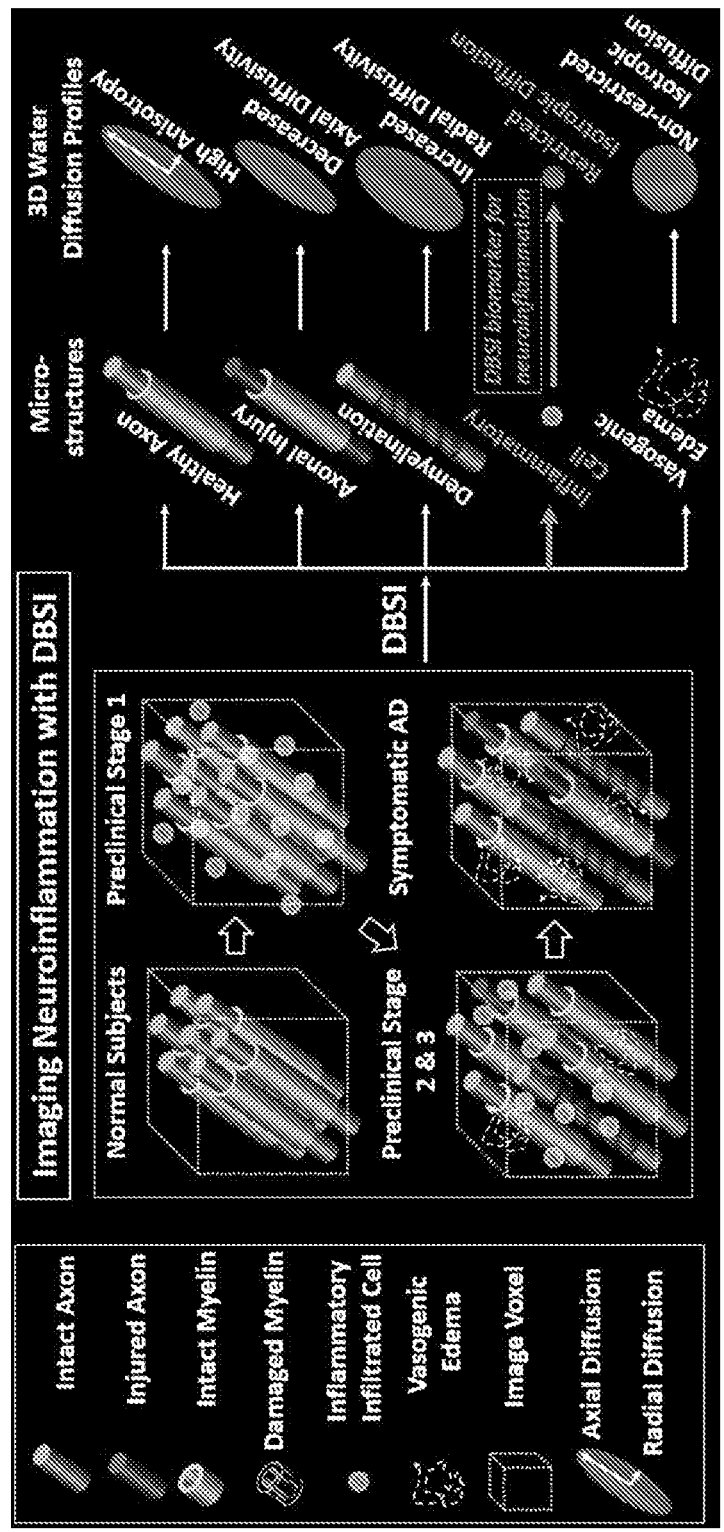
FIG. 60 is a DBSI model.

DBSI overcomes the previous MRI technique limitations. This new diffusion MRI analytic technique, DBSI simultaneously detects and quantifies neuroinflammation and neurodegeneration in MS. In DBSI (FIG. 60), each of the potential pathological components, including inflammatory cell infiltration, extracellular water/vasogenic edema, axonal injury/loss, and demyelination, within each voxel is modeled by a dedicated diffusion tensor. The weighted sum of all subvoxel pathological components describes the composition of pathological components. DBSI defines the isotropic diffusion components to represent restricted isotropic diffusion (associated with cell infiltration) and non-restricted isotropic diffusion (associated with vasogenic edema or tissue destruction) by using a threshold of isotropic diffusivity of 0.3 $\mu m^2/ms$, based on previous animal study findings. Unlike DTI and other advanced diffusion MRI approaches, DBSI can quantify inflammatory cell infiltration for white matter by excluding the confounding effects from the anatomical complexity and neurodegeneration. As described herein, DBSI may be used to obtain diagnostic parameters in both grey and white matter in the setting of preclinical and symptomatic AD. Diffusion measurements with multiple directions and weightings are used by DBSI to provide a unique solution. Regularized nonnegative least-squares analysis incorporating a priori information of non-negative signal intensities fraction and finite signal energy are employed to prevent over-fitting to the noisy data while retaining the accuracy of the DBSI solution. The inflammatory cell fraction, used as a DBSI neuroinflammation biomarker, as well as vasogenic edema fractions are accurately quantified by solving the DBSI model.

Figure 61:
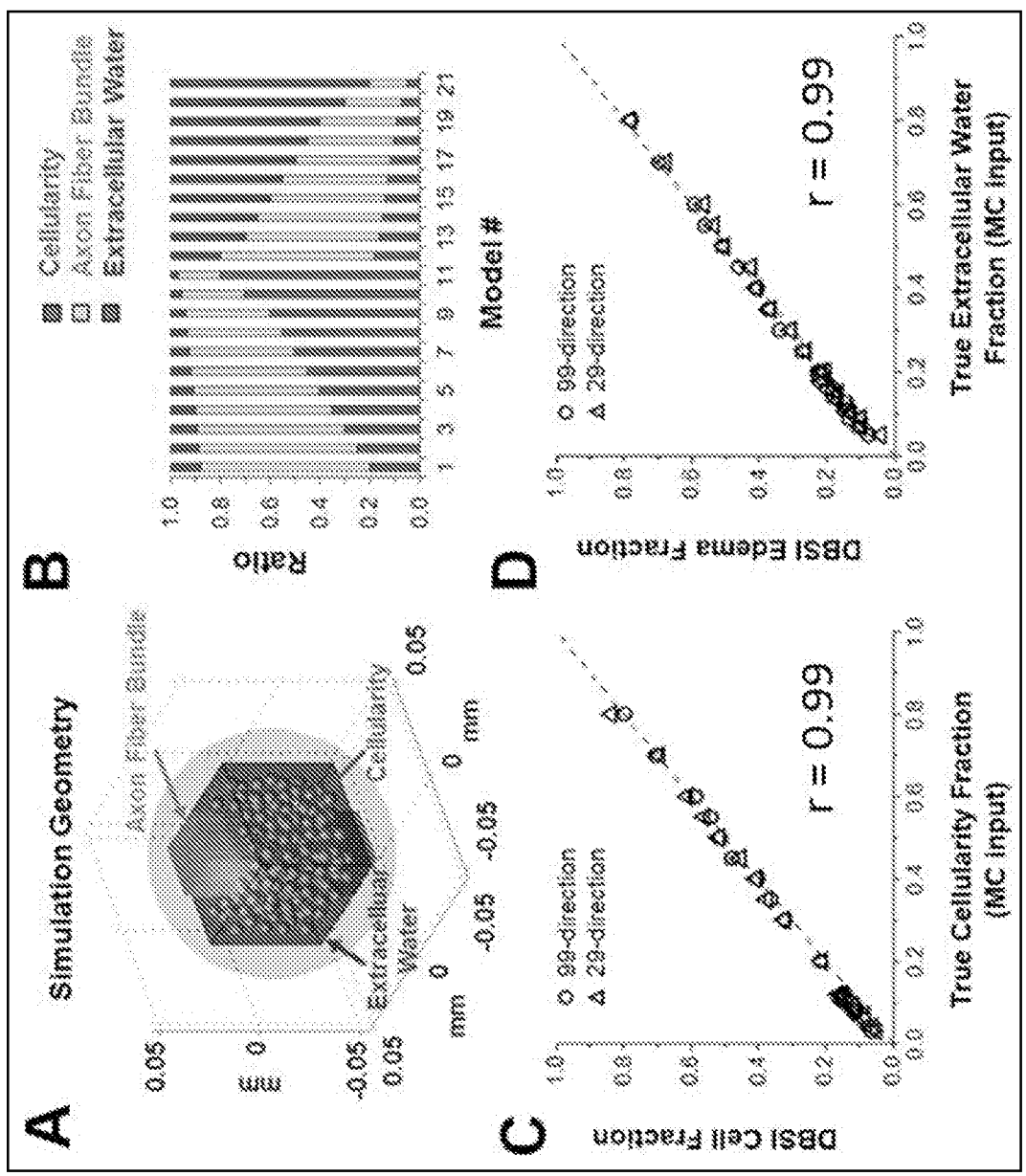
FIG. 61 is a computer model validation of DBSI.

DBSI computer simulation was performed to assess the accuracy of DBSI-derived cell and edema fractions. Monte-Carlo simulations were performed of three-dimensional computer-synthesized models with different amounts of inflammatory infiltrated cells and extracellular edema water. FIG. 61 shows computer model validation of DBSI. In FIG. 61(A) a 3D computer model was constructed for Monte-Carlo simulations. In FIG. 61(B) model configurations (21 total) were created to represent a wide range of cellularity (blue bars). FIGS. 61C and 61D show that DBSI cell fraction and DBSI edema fraction closely reflect the true values set in the simulation. The computer simulation models comprised (1) an axon fiber bundle modeled by uniformly oriented, tightly packed 2-µm diameter cylinders (green in FIG. 61A); (2) cellular components modeled as 6-µm isotropic spheres (blue in FIG. 61A) randomly placed surrounding the axonal fiber bundle; and (3) extra-axonal and extracellular space occupied by water molecules distributed outside of the axonal bundle and cellular components (pink in FIG. 61A). The imaging voxel (50×50×50 $\mu m^3$ cube in FIG. 61A) was placed in the center of a 90-µm diameter sphere (light blue outer sphere in FIG. 61A) in which $2.5 \times 10^5$ randomly distributed water molecules underwent random walks. By changing the relative composition of axon fibers, cellular components, and extracellular space, 21 three-dimensional models were generated in which the cell and edema fractions ranged from 5% to 80% (FIG. 61B). Maximum b-value=3200 s/mm$^2$, and 99-direction (circle) and 29-direction schemes were used. Rician noise was added to simulate diffusion MRI signals to mimic the typical achievable signal-to-noise ratio (SNR)=40. DBSI analysis was conducted on the 21 model configurations and found that, with the isotropic diffusivity threshold set at 0.3 $\mu m^2/ms$, the DBSI cell fraction positively correlated with the cellularity in the computer-synthesized models (R=0.99) (FIG. 61C). Additionally, the DBSI-derived edema faction closely reflected the extracellular water in the simulations (FIG. 61D).

The features of the NIH-DBSI systems and methods described herein expand the currently available tools for research related to AD and other CNS disorders described herein above. NIH-DBSI opens a new way to understand the role of inflammation in the pathogenesis and disease progression of AD. NIH-DBSI provides attractive neuroimaging biomarkers that are relevant for early AD diagnosis and effective treatment targeting neuroinflammation. One or more NIH-DBSI biomarkers of neuroinflammation can be obtained noninvasively and free from radioactivity or injection of a contrast agent. The diffusion MRI sequence required for DBSI analyses is FDA-approved and is standard on most clinical MRI systems. Thus, use of DBSI can readily be translated to the multicenter clinical trials and made accessible to the general clinical population. DBSI data can be acquired in conjunction with structural MRI during routine evaluation, significantly reducing burden and expense.

First addressed is the (I) utility of DBSI for probing white matter abnormalities and neuroinflammation in preclinical and early Alzheimer's disease. Subsequent sections more specifically address the utility of the DBSI biomarker with respect to (II) correlating in vivo DBSI with disease progression and cognition, (III) positron emission tomography (PET) and cerebrospinal fluid (CSF) measures of neuroinflammation, and (IV) correlating ex vivo DBSI-MRI with quantitative histopathology.

I. Utility of DBSI for Probing White Matter Abnormalities and Neuroinflammation in Preclinical and Early Alzheimer's Disease By probing white matter abnormalities and neuroinflammation in preclinical and early Alzheimer's disease, multimodality quantification was performed for neuroinflammation in Alzheimer's disease. Amyloid-β deposition begins decades before the onset of Alzheimer's disease symptoms. Both white matter changes and neuroinflammation are involved in the disease progression of Alzheimer's disease, but there is currently a lack of robust noninvasive methods to detect and quantify those early alterations in preclinical and early Alzheimer's disease. Although the magnetic resonance imaging technique, diffusion tensor imaging, has been used to detect white matter microstructure changes, it cannot differentiate between axon/myelin damage and neuroinflammation. Diffusion basis spectral imaging (DBSI) has recently been validated and applied in multiple sclerosis as a method to overcome diffusion tensor imaging's limitation. Diffusion basis spectral imaging employs multiple-tensor modelling of diffusion weighted magnetic resonance signals to separately characterize the neuronal compartments, inflammation-associated compartments (cellularity and vasogenic edema), and partial volume contamination effects from cerebrospinal fluid contamination. Previous studies have shown that diffusion basis spectral imaging-derived quantitative biomarkers are highly consistent with histology measures and can accurately characterize the heterogeneous white matter pathology in multiple sclerosis patients. In this study, the diffusion basis spectral imaging used to diagnose multiple sclerosis was used to diagnose and/or stage preclinical and early Alzheimer's disease participants with both diffusion basis spectral imaging and diffusion tensor imaging. In preclinical Alzheimer's disease patients who had Amyloid-β deposition but no tau pathology, diffusion basis spectral imaging detected increased restricted isotropic diffusion component without associated axon/myelin injury. This finding suggests that inflammatory cell infiltration, and potentially glia cell activation, occurs after Amyloid-β deposition but before tau pathology. In early Alzheimer's disease patients, who had both Amyloid-β and tau pathology, diffusion basis spectral imaging detected both demyelination and edema. These effects are consistent with the known white matter damage and blood-brain-barrier breakdown in early Alzheimer's disease patients. Diffusion basis spectral imaging-derived fractional anisotropy and radial diffusivity and diffusion tensor imaging-derived fractional anisotropy correlated with cerebrospinal fluid levels of neuronal injury markers. This study suggests that whereas diffusion tensor imaging is sensitive to early Alzheimer's disease pathology changes, diffusion basis spectral imaging is better able to separate and quantify white matter damage and neuroinflammation. Diffusion basis spectral imaging opens a new way to better understand the role of neurodegeneration and neuroinflammation in the pathogenesis of Alzheimer's disease, and potentially provides attractive surrogate measures that are relevant for longitudinal diagnostics and monitoring of treatments.

Alzheimer's disease (AD) pathology occurs early and evolves dynamically decades before the first symptoms are manifested. The understanding of AD pathology has significantly improved with the development of cerebrospinal fluid (CSF) biomarkers (such as beta-amyloid 42 [Aβ42], tau, phosphorylated tau 181 [ptau181], and visinin-like protein-1 [VILIP-1]) and positron emission tomography (PET) imaging of Aβ, tau pathology, and neuroinflammatory cell activation. Although AD has traditionally been considered a disease of gray matter, accumulating evidence from both human and animal studies have demonstrated that white matter (WM) alterations may also occur independently of gray matter degeneration. Additionally, WM alterations may precede and drive gray matter atrophy and WM disruption may occur as early as in the preclinical stage of AD. Moreover, disrupted WM may promote downstream formation of amyloid plaques and modulate the relationship between the pathological and clinical manifestations of AD. Thus, early detection and monitoring may help with understanding the mechanisms underlying WM alterations and contribute to development of therapeutic strategies to decelerate and halt development of AD symptoms.

In addition to axonal injury and demyelination, pathologies of AD include neuroinflammation, which is characterized by the presence of active microglia (the macrophages of the CNS), astroglia and blood-brain barrier breakdown. Although the exact role of neuroinflammation in AD pathogenesis is still unclear, neuronal damage and inflammation appear to reinforce one another: Aβ accumulation causes inflammation and also causes neurotoxicity, which induces upregulation of proinflammatory cytokines, leading to further neuronal damage.

One noninvasive method of imaging WM microstructure is diffusion magnetic resonance imaging (dMRI), in which the Brownian motion of water molecules within the CNS is measured. Formation and breakdown of CNS microscopic barriers (myelin, cell membrane, etc.) alters the Brownian motion and thus results in an altered dMRI image. For example, compared to water movement in normal axons, water movement in injured axons is disrupted, decreasing the apparent diffusivity parallel to an axonal fiber. Conversely, demyelination reduces the limitations on water movement perpendicular to an axonal fiber, thus increasing diffusivity in the radial direction. Inflammation can have two competing effects on diffusion: infiltration of microglia decreases mean diffusivity, whereas vasogenic edema increases mean diffusion.

Although one widely used type of dMRI, diffusion tensor imaging (DTI), is able to detect all of these changes, it only detects the overall averaged diffusion profile changes in AD and is incapable of separating the diffusion changes due to axonal injury and demyelination from those caused by neuroinflammation. Diffusion basis spectral imaging (DBSI) may be used to assess changes due to axonal injury and demyelination from those caused by neuroinflammation associated with CNS disorders such as multiple sclerosis and other CNS diseases. In this MRI method, a flexible multiple tensor model is used to identify and model heterogeneous CNS pathological processes. Thus, DBSI can separate the dMRI signals contributed by WM abnormalities from those resulting from neuroinflammation. The benefits of such dMRI signal separation are two-fold. First, because the contamination effects from neuroinflammation are excluded, WM abnormalities (axonal injury and demyelination) can be better detected and quantified by DBSI-derived axial diffusivity, radial diffusivity, mean diffusivity, and fractional anisotropy than by DTI counterparts. Second, DBSI provides neuroinflammation biomarkers to describe and track the severity of inflammatory cell infiltration and vasogenic edema in CNS diseases.

DBSI could be used to differentiate axonal injury and demyelination from inflammation in a cohort of healthy controls, preclinical AD patients, and early AD patients. Given its utility in examining WM injuries in multiple sclerosis, DBSI may overcome the limitations of DTI imaging by separately detecting and accurately quantifying complex early AD pathologies. Finally, the association between DBSI- and DTI-derived imaging biomarkers and invasive CSF neuronal injury markers was examined to track disease progression across preclinical and early AD stages.

Participants were enrolled in longitudinal studies of memory and aging, and cognitively normal (Clinical Dementia Rating [CDR]=0) participants were selected from the Adult Children Study (ACS), which enrolled 366 cognitively normal 43- to 76-year-old individuals in an extensive study of biomarkers for AD before the symptoms manifest. Inclusion criterion included full collection of CSF Aβ42, tau and ptau181 measures and diffusion weighted imaging acquisition. Participants who had very mild dementia (CDR=0.5) were selected from health aging and senile dementia (HASD) study which was designed to explore correlations of preclinical AD in persons 65 and older. Inclusion criterion included diagnosis with dementia of Alzheimer's type and diffusion weighted imaging acquisition. A positive family history for AD was defined and apolipoprotein E genotyping was performed. Demographics are presented in Table 1 below.

TABLE 1

Characteristics of study participants

| Characteristics | Stage $0^a$ (n = 144) | Stage $1^b$ (n = 31) | CDR $0.5^c$ (n = 82) |
|---|---|---|---|
| Age, years | 61.0 (8.1) $^\dagger$ | 62.4 (6.3) $^\dagger$ | 75.0 (5.8) *$^\ddagger$ |
| Male sex | 55 (38%) $^\dagger$ | 10 (32%) $^\dagger$ | 45 (55%) *$^\ddagger$ |
| Education, years | 16.0 (2.4) $^\dagger$ | 15.8 (2.2) | 15.3 (3.2) $^\ddagger$ |
| ApoE4+ | 18 (13%)* $^\dagger$ | 31 (100%) $^\dagger$ | 34 (72%) *$^\ddagger$ |
| FH+ | 80 (56%) | 16 (52%) | 45 (55%) |

Data are presented as mean (SD) or number (%).
$^a$Stage 0, participants with >500 pg/ml Aβ42, <339 pg/ml total tau, and <80 pg/ml phosphorylated tau (ptau181) in the CSF
$^b$Stage 1, participants with <500 pg/ml Aβ42, <339 pg/ml total tau, and <80 pg/ml phosphorylated tau (ptau181) in the CSF
$^c$CDR, clinical dementia rating; CDR 0.5, very mild cognitive impairment
ApoE4+, positive for apolipoprotein E ε4-allele
FH+, participants with a family history of late onset of AD
* $P < 0.05$ compared with the stage 1 group;
$^\dagger$ $P < 0.05$ compared with the CDR 0.5 group;
$^\ddagger$ $P < 0.05$ compared with the stage 0 group.

Cerebrospinal fluid (CSF) was collected within 24-months before or after the imaging session. CSF (20-30 mL) was collected by routine lumbar puncture using a 22-gauge atraumatic Sprotte spinal needle (Pajunk Medical Systems, Norcross, Ga., USA) after overnight fasting. Samples were gently inverted to avoid possible gradient effects, briefly centrifuged at low speed, and aliquoted (0.5 mL) into polypropylene tubes before being frozen at −84° C. Samples were analyzed by ELISA (Innotest; Innogenetics, Ghent, Belgium) after one freeze-thaw for beta amyloid 42 (Aβ42), total tau, and tau phosphorylated at threonine-181 (ptau181) and by ELISA (Quidel, San Diego, Calif.) after two freeze-thaw cycles for VILIP-1.

Cognitively normal participants were divided into preclinical stage 0 and stage 1 groups according to CSF measures and research criteria proposed by the National Institute on Aging and the Alzheimer's Association (NIA-AA). Amyloidosis was marked by Aβ42, and neuronal injury was marked by tau and ptau181. Participants were classified as preclinical stage 0 if they had neither amyloidosis nor neuronal injury (all biomarkers negative [Aβ42>500 pg/ml, tau<339 pg/ml, and ptau181<80 pg/ml]). Participants were classified as preclinical stage 1 if they had amyloidosis but no neuronal injury (Aβ42<500 pg/ml and either tau>339 pg/ml or ptau 181>80 pg/ml).

Diffusion weighted images (DWI) were collected on one of two 3T TIM Trio (Siemens, Erlangen, Germany) scanners with a 12-channel head coil equipped with parallel imaging. The imaging resolution was 2×2×2 mm. Repetition time (TR) and echo time (TE) were 145,000 ms and 112 ms, respectively. The 24-direction diffusion-encoding scheme (23 diffusion sensitized+1 unsensitized [$B_0$] volumes) was implemented for data acquisition. The maximal b-value was 1400 s/mm². Data were collected in two 6-minute runs using a single-shot diffusion weighted echo planar imaging sequence. Diffusion-weighted images were registered to T1-weighted magnetization prepared rapid acquisition gradient echo (MPRAGE) and T2-weighted fast spin echo (T2 W-FSE) scans. The acquisition parameters for MPRAGE were the following: TR, 2400 ms; TE, 3.16 ms; inversion time, 1000 ms; imaging resolution, 1×1×1 mm. T2 W-FSE was acquired with the following parameters: TR, 3200 ms; TE, 455 ms; imaging resolution, 1×1×1 mm.

DBSI models diffusion-weighted MRI signals as a linear combination of multiple tensors describing both the anisotropic axonal fiber and its surrounding environment, and a full range of isotropic components with varying diffusivities. The formula for the DBSI model is $$S_k = \sum_{i=1}^{N_{Aniso}} f_i e^{-e^{-|\vec{b_k}|\lambda_{\perp_i}} e^{-|\vec{b_k}|(\lambda_{\|i}-\lambda_{\perp i})\cos^2\psi_{ik}}} + \int_a^b f(D) e^{-|\vec{b_k}| \cdot D} dD \quad (k = 1, 2 \ldots K) \quad \text{(Equation 6)}$$

where $S_k$ and $|b_k|$ are the signal and b-value of the $k^{th}$ diffusion gradient, $N_{Aniso}$ is the number of anisotropic tensors, $\psi_{ik}$ is the angle between the $k^{th}$ diffusion gradient and the principal direction of the $i^{th}$ anisotropic tensor, $\lambda_{\|_i}$ and $\lambda_{\perp_i}$ are the axial diffusivity and radial diffusivity of the $i^{th}$ anisotropic tensor, $f_i$ is the signal intensity fraction for the $i^{th}$ anisotropic tensor, and a and b are the low and high diffusivity limits for the isotropic diffusion spectrum f(D). The anisotropic diffusion component represents the intra-axonal water molecules and those outside but adjacent to axon fibers, whether myelinated or non-myelinated. These anisotropic signal intensity fractions ($f_i$) were denoted as fiber ratios. DBSI-derived fiber fraction, axial diffusivity, and radial diffusivity reflected the integrity of anisotropic diffusion components of the WM fibers. The diffusion of water molecules inside and immediately outside of cells was isotropic and highly restricted—close to stationary under the typical diffusion measurement conditions. Thus, the DBSI-derived restricted isotropic diffusion component was assigned to reflect cellularity. Cellular and axonal packing plays a crucial role in extracellular and extra-axonal diffusion characteristics. Hindered (less restricted) isotropic diffusion components may represent those water molecules in less densely packed environments, such as areas of tissue disintegration or edema. The isotropic diffusion components were defined to represent restricted isotropic (associating with cells) and hindered isotropic diffusion (associating with vasogenic edema and tissue loss) using a threshold of isotropic diffusivity of 0.3 μm²/ms, based on previous animal study findings.

Twenty-four diffusion weighted images in one dataset were motion-corrected using an iterative procedure. The final resampling step output twenty-four volumes in spatial register with the $B_0$ volume of the first acquired DWI dataset, which was registered to a group-specific atlas. The two runs were averaged together to obtain better signal-to-noise ratio. The diffusion data were processed with locally written software using a log linear algorithm to obtain DTI parameter data using the commonly used tensor model. All datasets were also computed by a DBSI multi-tensor model analysis package developed using Matlab® software (MathWorks). Maps of DTI- and DBSI-derived fractional anisotropy, axial diffusivity, radial diffusivity, mean diffusivity were generated. DBSI-derived restricted isotropic component map which indicates the cellularity and hindered isotopic component map which indicated the edema were generated as well. One representative image voxel in the posterior limb of internal capsule in the middle part of the brain was chosen to demonstrate the quantitative assessment of DTI- and DBSI-derived indices in the preclinical stages and CDR0.5 participants.

The whole brain voxel-wise DBSI- and DTI-derived indices were analyzed by using Tract Based Spatial Statistics (TBSS) (available in FSL). Fractional anisotropy images were slightly eroded, so the boundary image slices were excluded to remove possible outliers caused by the poor diffusion tensor fitting at the edges. Participants' fractional anisotropy data were aligned into a common space by using the nonlinear registration tool FNIRT. A mean fractional anisotropy image was then created and thinned to create a mean fractional anisotropy skeleton that represents the centers of all tracts common to the group. Each participant's aligned fractional anisotropy data and other DBSI- and DTI-derived indices were projected onto this skeleton for statistical analyses. Nonparametric permutation tests were used for voxel-wise statistical analysis of the individual fractional anisotropy skeletons between preclinical stage 0 and stage1, and between preclinical stage 0 and CDR 0.5 groups. The significance threshold for group differences was set at $P<0.05$, corrected for multiple comparisons across voxels by using the threshold-free cluster-enhancement option in Randomise 2.0 in FSL. Identification of the abnormal WM tracts revealed by TBSS was based on the atlas formulated at Johns Hopkins University. The statistics performed by TBSS controlled for age, gender, education, ApoE4 genotype, and family history of AD.

Continuous and categorical variables in characteristics between any two groups were compared by a Kruskal-Wallis test and the Fisher's exact test, respectively. These variables included age, gender, education, ApoE4 genotype, and family history of AD. ANOVA using proc glm in SAS was considered in multivariate analyses for Aβ42, tau, ptau181, and VILIP-1. The model included group, age, gender, education, genotype, and family history if available. The least square means per group for each outcome were estimated. All statistical tests were two-sided using α=0.05. SAS version 9.3 (Cary, N.C.) was used to perform statistical analyses.

257 preclinical AD participants were classified according to the criteria proposed by the working group of the National Institute on Aging and Alzheimer's Association. The cohort included 144 preclinical stage 0 subjects (biomarker negative), 31 preclinical stage 1 subjects (Aβ positive), and 82 clinical dementia rating (CDR) 0.5 subjects (Table 1). Preclinical stage 0 subjects were defined as those subjects with no AD pathophysiology and who were negative for the CSF markers Aβ42, tau, and ptau181. Preclinical stage 1 subjects were positive for Aβ42 and negative for tau and ptau181. CDR 0.5 subjects were positive for Aβ42, tau, and ptau181. On average, the CDR 0.5 participants were significantly older than the preclinical stage 0 and stage 1 participants. There was no age difference between participants in the stage 0 and stage 1 groups. The CDR 0.5 group had more male participants than the other two groups, but no difference in gender frequency was observed between the preclinical stage 0 and stage 1 groups. The CDR 0.5 group had, on average, a significantly higher level of education than the stage 0 group. Only 13% of the stage 0 participants were positive for the apolipoprotein E ε4 allele, whereas 100% of the stage 1 and 72% of the CDR 0.5 participants carried this allele. The percentages of participants with a family history of AD were comparable between the three groups.

Figure 51:
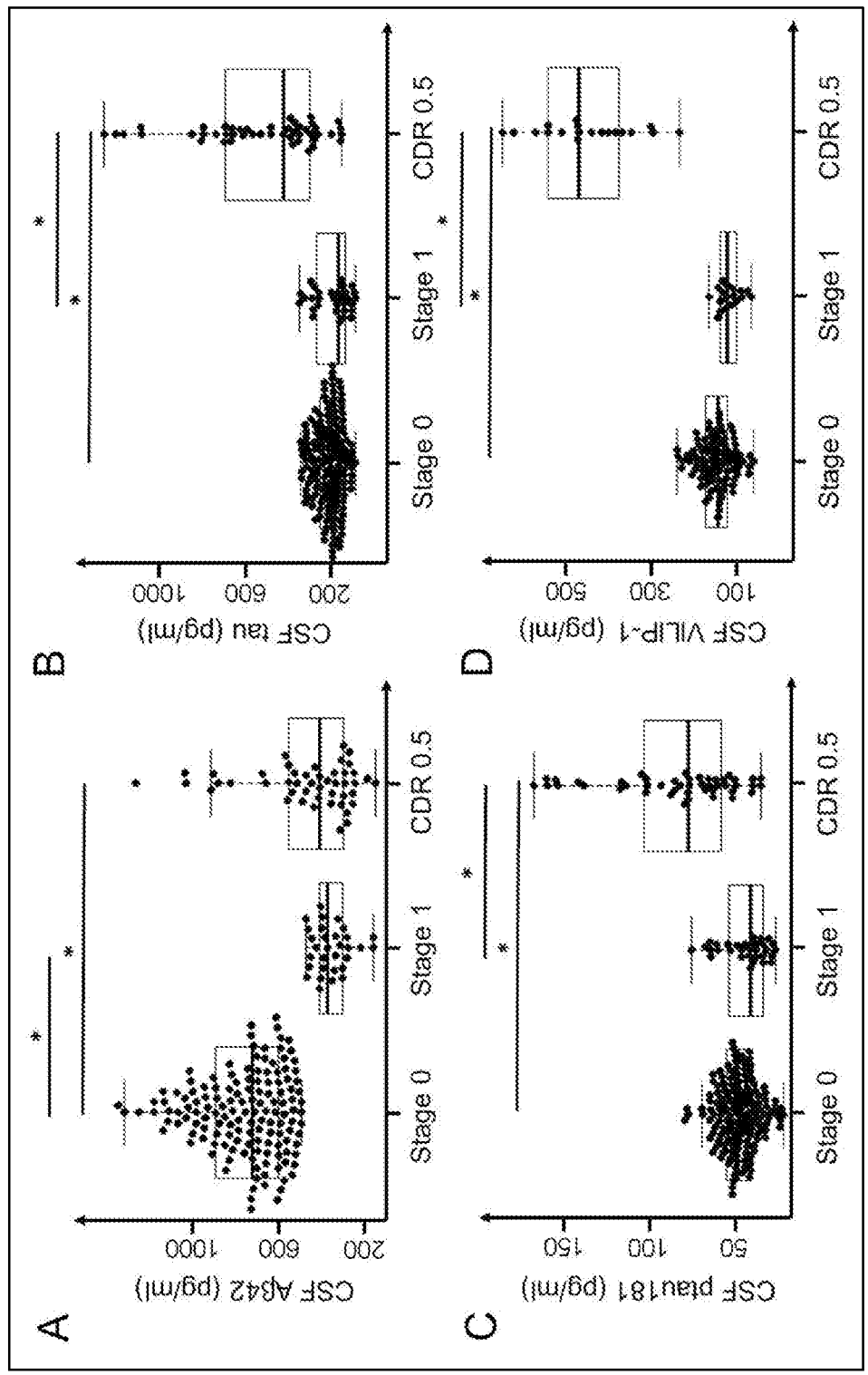
FIG. 51 shows levels of CSF markers in study participants.

With respect to CSF markers of amyloid burden and neuronal injury, levels of AD markers in CSF from the participants were compared. FIG. 51 shows levels of CSF markers in study participants. FIG. 51(A) shows that the mean CSF level of Aβ42 was significantly lower in the preclinical stage 1 (n=31) and CDR 0.5 groups (n=47) than in the preclinical stage 0 group (n=144). FIG. 51(B,C) shows that the mean CSF levels of tau and ptau181 in the stage 1 (n=31) and stage 0 groups (n=144) were comparable but significantly lower than those in the CDR 0.5 group (n=47). FIG. 51(D) shows that the CSF level of VILIP-1 was significantly higher in the CDR 0.5 group (n=20) than in the stage 0 (n=84) and stage 1 (n=18) groups. The age, gender, education, ApoE4 genotype, and family history of AD were controlled for in computing the statistical significance of differences. *P<0.05. As expected, Aβ42, an indicator of amyloid burden, was significantly higher in the preclinical stage 0 group than in the stage 1 and CDR 0.5 groups (FIG. 51A); having a high level of Aβ42 is categorized as being Aβ42-negative. No statistical difference was found in level of Aβ42 between the stage 1 and CDR 0.5 groups (FIG. 51A). There were no significant differences in CSF levels of tau, ptau181, or VILIP-1 between the preclinical stage 0 and stage 1 groups (FIG. 51B-D), suggesting that the preclinical stage 1 patients had no neuronal injuries. In contrast, CSF levels of tau, ptau181, and VILIP-1 were significantly higher in the CDR 0.5 group than in the preclinical stage 0 and stage 1 groups (FIG. 51B-D), indicating neuronal injury in the CDR 0.5 participants.

Figure 52:
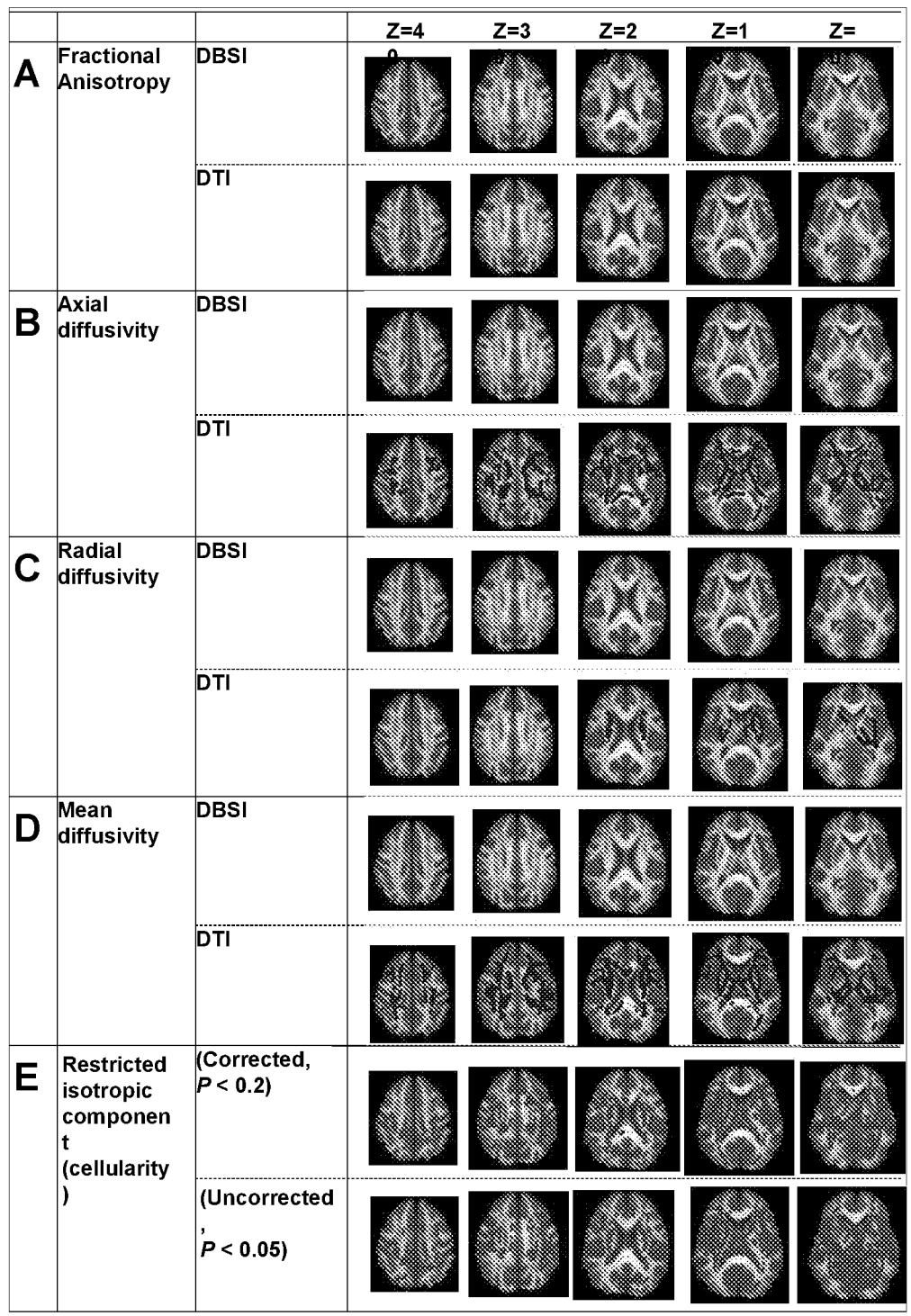
FIG. 52 shows tract-based spatial statistics comparison of the preclinical AD stage 1 and stage 0 groups.

Neuroinflammation was characterized for both DTI and DBSI in AD preclinical stage 1. To assess the ability of DTI and DBSI to detect preclinical AD pathologies, a first comparison was made for DTI of the stage 0 and stage 1 participants. FIG. 52 shows tract-based spatial statistics comparison of the preclinical AD stage 1 and stage 0 groups. The mean fractional anisotropy skeleton (green) representing the centers of all WM tracts common to both stage 1 (n=31) and stage 0 (n=144) participants is overlaid on the mean fractional anisotropy images of all those participants in axial view. In FIG. 52(A-D) the skeletal voxels in blue represent significantly (P<0.05) lower DBSI- or DTI-derived indices in stage 1 than in stage 0 participants. FIG. 52(E) shows the multiple comparison corrected non-significant skeletal voxels (red, P<0.2 to show the increase trend pattern) and multiple comparison uncorrected significant skeletal voxels (red, P<0.05) with higher DBSI-derived restricted isotropic components in stage 1 than in stage 0 participants. The age, gender, education, ApoE4 genotype, and family history of AD were controlled for in computing the statistical. Although DTI-derived fractional anisotropy was similar in stage 0 and stage 1 participants (FIG. 52A, Table 1), three other DTI-derived measures differed between the two groups of participants. First, DTI-derived axial diffusivity was significantly lower (FIG. 52B, Table 1) in 31 WM regions in stage 1 participants than in stage 0 participants. Those regions included the corpus callosum, fornix, cerebral peduncle, and cingulum (see Table 3 for a complete list). Second, DTI-derived radial diffusivity in 12 WM regions was significantly lower in stage 1 than in stage 0 participants (FIG. 52C, Table 1, Table 3). Third, DTI-derived mean diffusivity was significantly lower in 28 WM regions in stage 1 participants than in stage 0 participants (FIG. 52D, Table 1, and Table 3).

TABLE 2

Summary of changes in DBSI- and DTI-derived indices.

| | Fractional anisotropy | | Axial diffusivity | | Radial diffusivity | | Mean diffusivity | | Restricted isotropic component (cellularity)[a] | Hindered isotropic component (edema) |
|---|---|---|---|---|---|---|---|---|---|---|
| | DBSI | DTI | DBSI | DTI | DBSI | DTI | DBSI | DTI | DBSI | DBSI |
| Preclinical stage 1 vs. stage 0 | — | — | — | ↓ | — | ↓ | — | ↓ | ↑ | — |
| CDR 0.5 vs. Stage 0 | ↓ | ↓ | — | — | ↑ | ↑ | — | ↑ | — | ↑ |

NOTE:
Arrows indicate significantly (P < 0.05) higher (↑) or lower (↓) indices in preclinical stage 1 (top row) and CDR 0.5 (bottom row) than in the preclinical stage 0 group;
"—" indicates there was no significant difference between the stages.
[a]P < 0.07.

Next, DBSI of the same participants was examined. There were no significant differences observed between stage 0 and stage 1 groups in any of the four DBSI-derived measures: fractional anisotropy, axial diffusivity, radial diffusivity, or mean diffusivity (FIG. 52, Table 1). These findings suggested that WM in the stage 1 group had normal integrity, which was consistent with the detected levels of CSF markers (FIG. 51). To understand why DTI revealed apparently false differences between stage 0 and stage 1 participants, the DBSI-derived restricted isotropic component in the two groups of patients was examined. It was found that the restricted isotropic component was more prominent in stage 1 participants than in stage 0 (not statistically significant, P<0.07 corrected for multiple comparisons, Table 4). Importantly, the WM regions in which were observed this restricted isotropic component increase trend (P<0.2 is used to show the increase trend pattern in FIG. 52E top panel) largely overlapped with those regions, in which were observed decreased DTI-derived axial diffusivity and mean diffusivity (FIGS. 52 B, D and E, Table 3). It was also examined the WM regions with significant restricted isotropic component increase (P<0.05) before multiple comparison (FIG. 52E bottom panel) and found high similarity with the WM regions with increased trend after multiple comparison, confirming that the presence of infiltrated inflammatory cells, instead of white matter damages, caused the reduced DTI-derived axial and mean diffusivities in those preclinical stage 1 participants.

Figure 53:
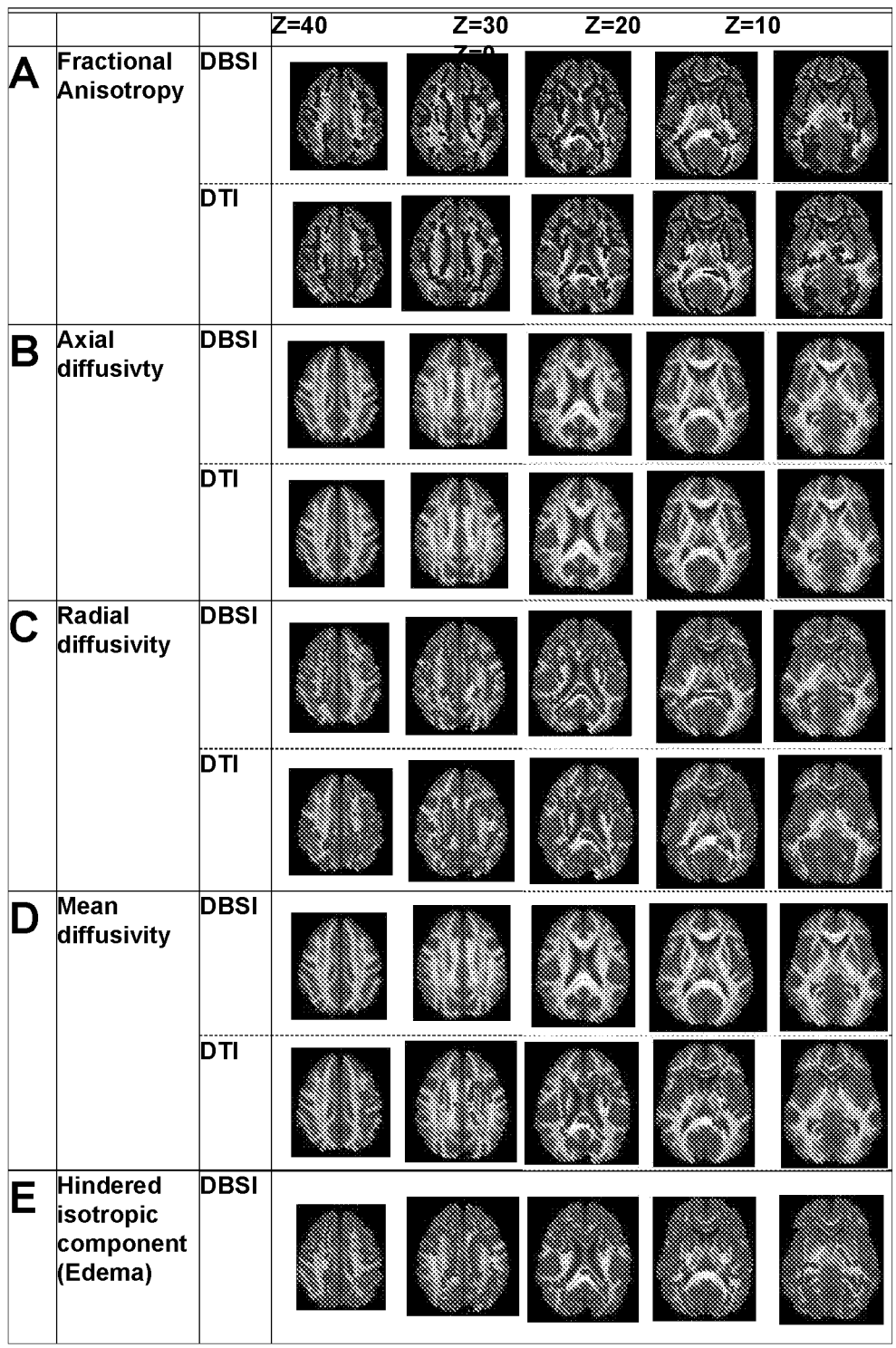
FIG. 53 shows tract-based spatial statistics comparison of the CDR 0.5 and preclinical stage 0 groups.

DTI and DBSI characterization was performed for white matter abnormalities in CDR 0.5 AD participants. FIG. 53 shows tract-based spatial statistics comparison of the CDR 0.5 and preclinical stage 0 groups. The mean fractional anisotropy skeleton (green) representing the centers of all WM tracts common to participants in both the CDR 0.5 (n=82) and stage 0 groups (n=144) is overlaid on the mean fractional anisotropy images of all those participants in axial view. The skeletal voxels in blue represent the DBSI- or DTI-derived indices that were significantly (P<0.05) lower in the CDR 0.5 group than in the stage 0 group. The skeletal voxels in red represent the DBSI- or DTI-derived indices that were significantly (P<0.05) higher in the CDR 0.5 group than in the stage 0 group. Cluster-based thresholding corrected for multiple comparisons. The age, gender, education, ApoE4 genotype, and family history of AD were controlled for in computing the statistical significance of differences. It was found that DTI-derived fractional anisotropy was significantly lower in 39 WM regions in the CDR 0.5 group than in the preclinical stage 0 group (FIG. 53A, Table 2, Table 4), but there was no significant difference in DTI-derived axial diffusivity between the two groups (FIG. 53B). However, DTI-derived radial and mean diffusivities were significantly higher in 33 and 14 WM regions, respectively, in the CDR 0.5 participants than in the stage 0 participants (FIGS. 53 C and D, Table 2, Table 4).

Three of the four DBSI-derived measures were similar to the DTI-derived measures. First, DBSI-derived fractional anisotropy in 35 WM regions was lower in the CDR 0.5 group than in the stage 0 group (FIG. 53A, Table 2, Table 4), reflecting WM integrity deterioration in the CDR 0.5 group. Second, no significant difference was observed in DBSI-derived axial diffusivity between the stage 0 and CDR 0.5 groups (FIG. 53B). Third, the DBSI-derived radial diffusivity in 31 WM regions was significantly higher, suggestive of demyelination, in the CDR 0.5 group than in the stage 0 group (FIG. 53C, Table 2, Table 5). However, unlike with DTI, no significant difference was observed in DBSI-derived mean diffusivity between the CDR 0.5 and stage 0 groups (FIG. 53D). Instead, it was found that the DBSI-derived hindered isotropic component in 32 WM regions was significantly higher in the CDR 0.5 group than in the stage 0 group (FIG. 53E, Table 5), suggesting the presence of vasogenic edema in the CDR 0.5 participants. Moreover, the affected regions overlapped with those in which there was an observed, significantly higher DTI-derived radial diffusivity and mean diffusivity and lower DTI-derived fractional anisotropy (FIG. 53).

Figure 54:
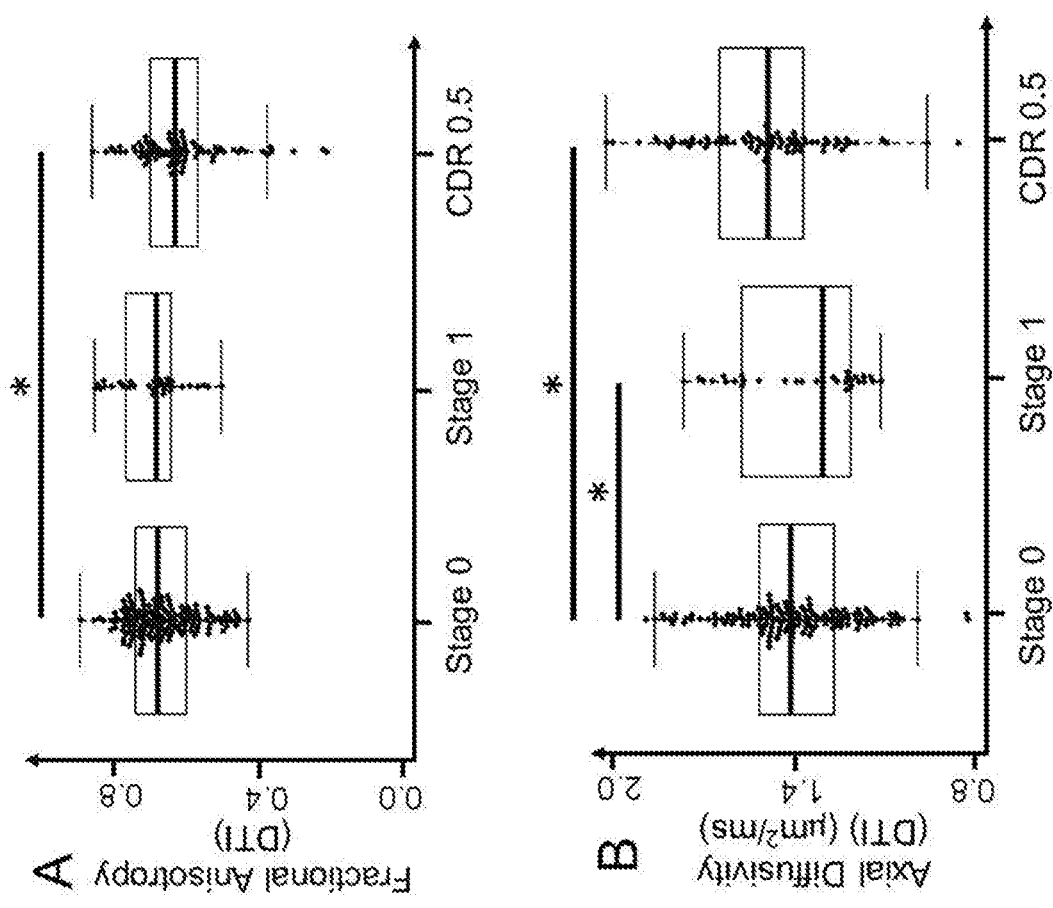
FIG. 54 shows quantitative assessment of DTI- and DBSI-derived indices in one representative voxel on the posterior limb of internal capsule in preclinical stage 0 and 1 and CDR 0.5 participants.
Figure 54:
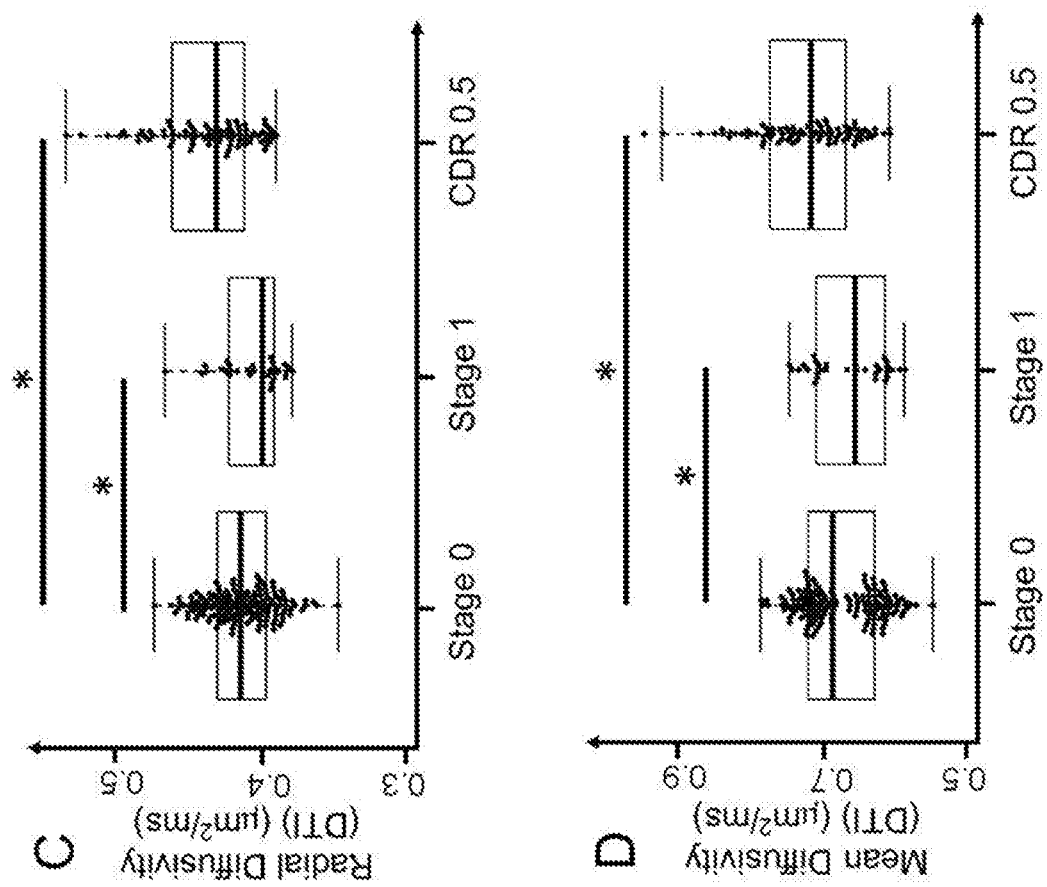
Figure 54:
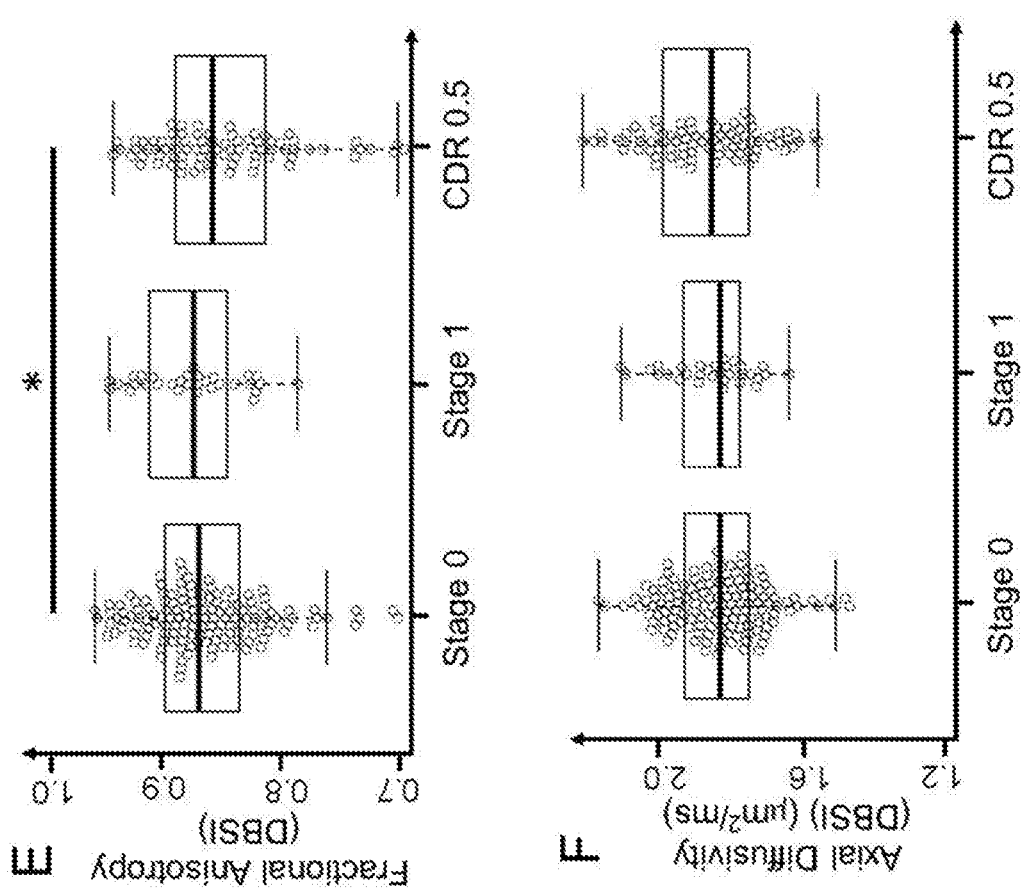
Figure 54:
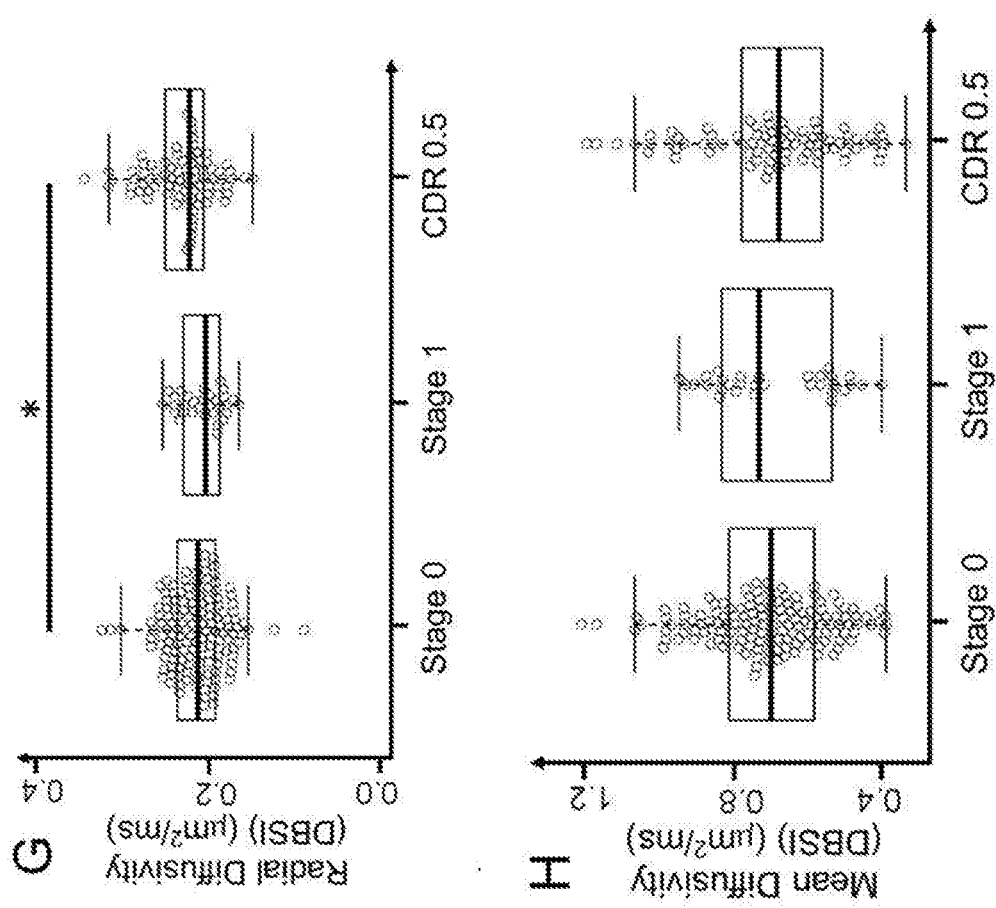
Figure 54:
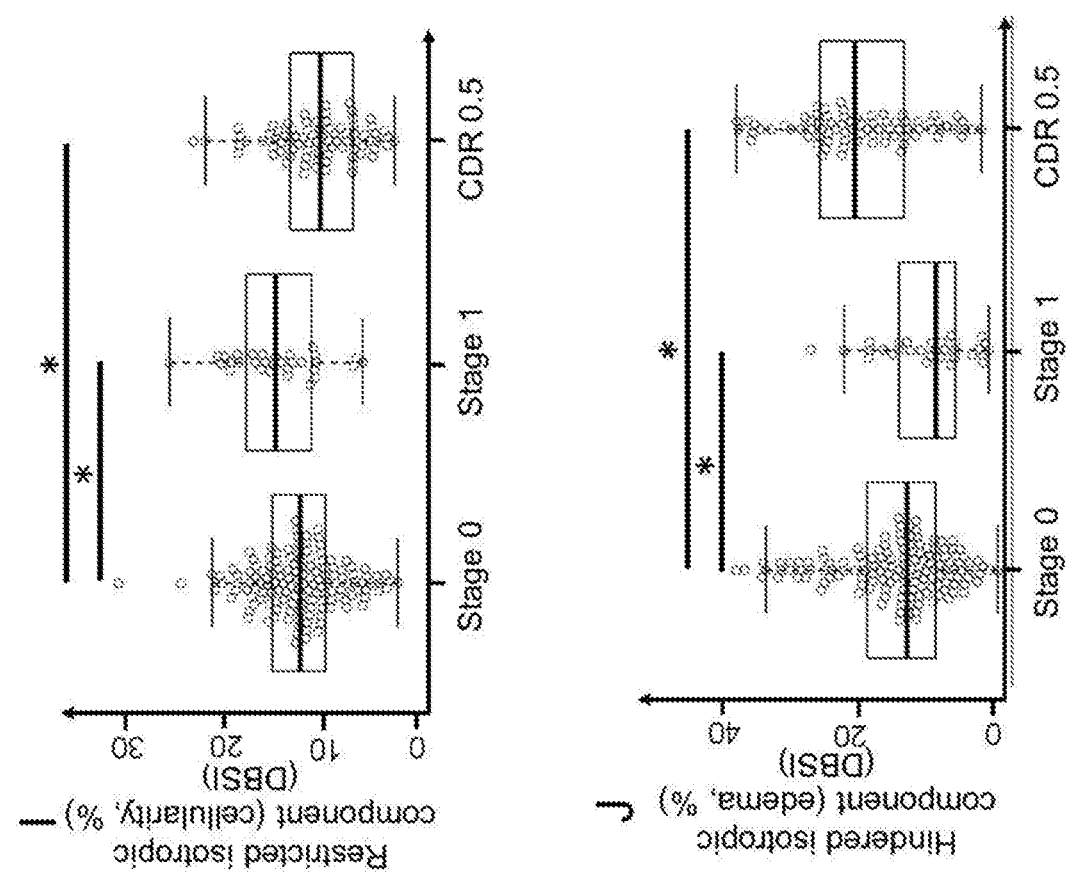

DTI and DBSI white matter pathology was compared in preclinical and CDR 0.5 AD participants. To quantitatively compare WM pathology in the two preclinical and one early Alzheimer's stage, a representative voxel was chosen from the posterior limb of internal capsule as a representative example. First, DTI-derived indices were compared in the three groups of participants. FIG. 54 shows quantitative assessment of DTI- and DBSI-derived indices in one representative voxel on the posterior limb of internal capsule in preclinical stage 0 and 1 and CDR 0.5 participants. FIG. 54(A-D) shows box and whisker plots of DTI-derived (A) fractional anisotropy, (B) axial diffusivity, (C) radial diffusivity, and (D) mean diffusivity in each group of patients. FIG. 54 (E-I) shows box and whisker plots of DBSI-derived (E) fractional anisotropy (F) axial diffusivity, (G) radial diffusivity, (H) mean diffusivity, (I) restricted isotropic diffusion component, and (J) hindered isotropic diffusion component in each group of patients. Thick lines indicate means, boxes 25th to 75th percentiles, and thin lines indicate 5th and 95th percentiles. *P<0.05. DTI-derived fractional anisotropy did not differ between preclinical stage 0 and 1 participants but was significantly lower in CDR 0.5 participants (FIG. 54A). DTI-derived axial diffusivity was significantly lower in preclinical stage 1 than in preclinical stage 0 participants, and significantly higher in CDR 0.5 than in preclinical stage 0 participants (FIG. 54B). DTI-derived radial diffusivity was slightly lower in preclinical stage 1 and dramatically higher in CDR 0.5 participants than in preclinical stage 0 participants (FIG. 54C). Finally, DTI-derived mean diffusivity was lower in preclinical stage 1 and higher in CDR 0.5 participants than in preclinical stage 0 participants (FIG. 54D).

A comparison was also made with the DBSI-derived indices in the representative voxel in the posterior limb of internal capsule in the three groups of participants. Similar to DTI-derived fractional anisotropy, DBSI-derived fractional anisotropy was similar in preclinical stage 1 and 0 participants and was moderately lower in CDR 0.5 participants (FIG. 54E). DBSI-derived axial diffusivity did not differ significantly between the three groups (FIG. 54F). DBSI-derived radial diffusivity did not differ between preclinical stage 1 and 0 participants but was higher in CDR 0.5 participants (FIG. 54G). Finally, DBSI-derived mean diffusivity did not differ between preclinical stage 1 and 0 participants but was moderately higher in CDR 0.5 participants (FIG. 54H).

In addition to providing diffusivity parameters to characterize WM damage, DBSI also provided markers of inflammatory cell infiltration (the restricted isotropic diffusion component) and vasogenic edema (the hindered isotropic diffusion component). The DBSI-derived restricted isotropic diffusion component was significantly higher in preclinical stage 1 than in stage 0 participants, but did not differ between CDR 0.5 participants and stage 0 participants (FIG. 54I). DBSI-derived hindered isotropic diffusion component was significantly lower in preclinical stage 1 and significantly higher in the CDR 0.5 participants than in the preclinical stage 0 participants (FIG. 54J). The increased restricted isotropic diffusion components and inflammatory cell's small apparent diffusivity (<0.3 μm²/ms) have led to the decrease of DTI-derived axial, radial and mean diffusivities, leading to DTI's false positive detection of white matter abnormality.

Figure 55:
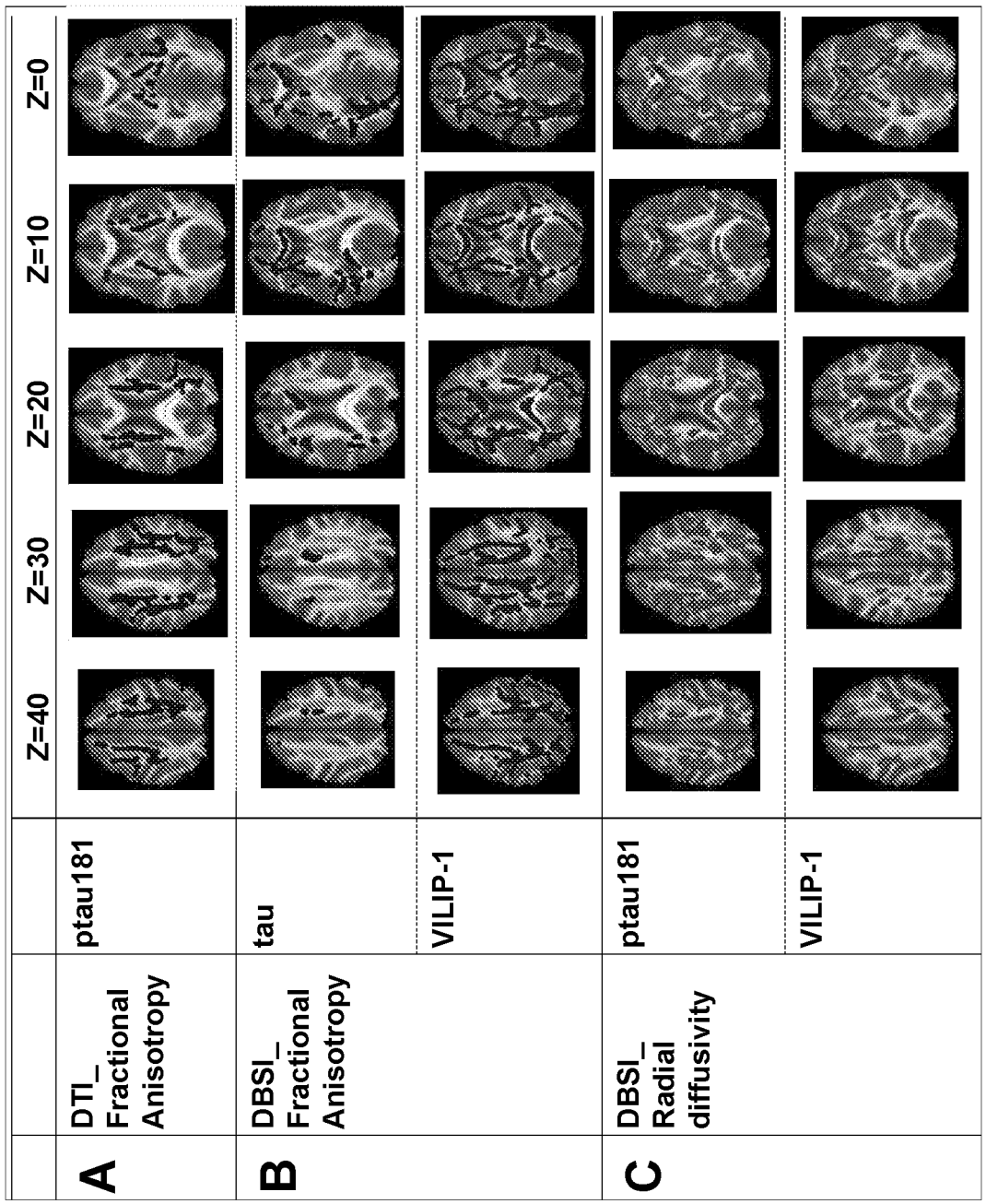
FIG. 55 shows correlations between CSF levels of neuronal injury markers and dMRI diffusivity indices.

In addition, correlation was made between dMRI and CSF markers of neuronal injury. DTI- or DBSI-derived indices were correlated with CSF levels of each of the neuronal injury markers (tau, ptau181, and VILIP-1) in preclinical stage 0, stage 1, and CDR 0.5 groups. FIG. 55 shows correlations between CSF levels of neuronal injury markers and dMRI diffusivity indices. The mean fractional anisotropy skeleton (green) representing the centers of all WM tracts common to participants in the preclinical stage 0 (for tau and ptau181, n=144; for VILIP-1, n=86), stage 1 (for tau and ptau181, n=31; for VILIP-1, n=16), and CDR 0.5 stage (for tau and ptau181, n=82; for VILIP-1, n=20) is overlaid on the mean fractional anisotropy images of all those participants in axial view. The skeletal voxels in blue and red represent the significantly (P<0.05) negative and positive, respectively, correlations between the indicated indices and levels of the indicated markers. Cluster-based thresholding corrected for multiple comparisons. The age, gender, education, ApoE4 genotype, and family history of AD were controlled for in computing the statistical significance of differences. The CSF level of ptau181 correlated with only one DTI measure, fractional anisotropy, in 25 WM regions (FIG. 55A, Supplemental Table 2). In contrast, the CSF levels of neuronal injury markers correlated with both DBSI-derived fractional anisotropy and radial diffusivity in many WM regions. For example, levels of tau negatively correlated with DBSI-derived fractional anisotropy in 14 WM regions (FIG. 55B, Table 5), and levels of ptau181 positively correlated with DBSI-derived radial diffusivity in 31 WM regions (FIG. 55C, Table 5). In addition, a significant correlation was observed between levels of VILIP-1 and DBSI-derived fractional anisotropy and radial diffusivity (FIGS. 55B and C, Table 5) in 36 and 28 WM regions, respectively.

In this study, dMRI revealed rich microstructural information about WM integrity and neuroinflammation in preclinical and early AD patients. Although DTI is very sensitive, it had limited accuracy and specificity in detecting early AD pathologies. In contrast, DBSI was able to differentiate between WM abnormalities and neuroinflammation in preclinical and early AD. Unlike assessment of CSF markers, which involves a lumbar puncture, and PET, which involves injection of a radioactive substance, DBSI is non-invasive. Moreover, the MRI sequence employed by DBSI is already approved by the US Food and Drug Administration and is standard on most clinical MRI systems; thus, use of DBSI can readily be translated to the clinical setting.

It was found that DTI-derived axial diffusivity, radial diffusivity, and mean diffusivity were all lower in the preclinical stage 1 participants and higher in the CDR 0.5 participants than in the preclinical stage 0 participants. This finding was consistent with previous WM studies and grey matter studies in presymptomatic AD subjects. However, the lower DTI-derived axial diffusivity suggested that preclinical stage 1 participants had axonal injury. This interpretation contradicts the findings from measurement of CSF markers, which indicated that there was no neuronal injury in this group (FIG. 51). It has been postulated that the reduced DTI-derived axial and mean diffusivity could be explained by an inflammatory response to molecular changes such as Aβ deposition, microglial activation and accumulation, and swelling of neurons and glia. The use of DBSI disclosed herein supports this idea. Consistent with the levels of CSF markers (FIG. 51), DBSI revealed no deterioration of WM integrity in the preclinical stage 1 group. Moreover, the WM regions with decreased DTI-derived axial and mean diffusivity largely overlapped with the regions with increased restricted DBSI-derived isotropic components (FIG. 52). Thus, these findings suggest that DTI falsely detected axonal injury in regions with inflammatory cell infiltration. Significantly decreased DTI-derived axial and mean diffusivity have been attributed tentatively to inflammatory microglial activation/accumulation, this study demonstrated that DBSI can provide a quantitative neuroimaging biomarker to reflect the severity of inflammatory cell infiltration.

Further, DTI-derived radial diffusivity was not as subject to false detection of WM injury as were axial and mean diffusivities. This is because DTI-derived radial diffusivity is much smaller than the other measures and thus is less sensitive to contamination from the restricted isotropic diffusion components (FIG. 52C). Furthermore, DTI-derived radial diffusivity decreased only between preclinical stage 0 and stage 1 participants in 12 WM regions. The DTI-derived radial diffusivity decrease has been attributed to increased intracellular and decreased extracellular space or increased oligodendritic activation. Herein, it is demonstrated that inflammatory cell infiltration is sufficient to reduce DTI-derived radial diffusivity.

Several indications point to the importance of neuroinflammation in AD progression. First, in preclinical AD, neuroinflammatory microglial activation may occur before cognitive decline. A previous study of autosomal dominant AD found astrocyte activation may occur in presymptomatic AD, suggesting inflammatory astrocytosis could be an early contributory driving force in AD pathology. Second, cognitively normal participants who chronically used non-steroidal anti-inflammatories had fewer activated microglia and lower risk of AD than those who did not. Third, fragments of Aβ can trigger and promote marked inflammatory response in the brain, and fibrillary Aβ stimulates a classical proinflammatory response in the microglia, which can be visualized in AD patients and may be present in preclinical AD stages. Currently, an optimal marker for neuroinflammation is the PET ligand [$^{11}$C] PK11195, which binds to activated microglia and has revealed significant increases of microglial activation in AD subjects. However, this radioligand has a high level of non-specific binding. Another PET ligand, [$^{11}$C] PBR28, has higher specific binding to activated microglia than [$^{11}$C] PK11195, but it has not yet been tested on large AD cohorts. Herein, the results suggest that neuroinflammation in the very early stages of preclinical AD, even before any WM disruption, could be noninvasively detected and quantified by DBSI-derived restricted isotropic diffusion components.

In the CDR 0.5 participants, increased (though not statistically significant) DTI axial diffusivity and significantly increased DTI radial diffusivity and mean diffusivity was observed, consistent with previous DTI studies. One study of stroke patients found that vasogenic edema caused by disruption of the blood-brain barrier (BBB) increased the DTI-measured diffusivities. Importantly, DBSI detected significantly increased hindered isotropic components (FIG. 53 E), suggesting the presence of vasogenic edema, probably resulting from BBB disruption in the CDR 0.5 participants. BBB dysfunction has been associated with AD neuropathology and cognitive impairment, is involved in the relationship between inflammation and AD neuropsychiatric symptoms, and occurs before cognitive decline in patients at risk for developing AD. Thus, the ability to use DBSI to noninvasively evaluate BBB integrity may contribute to studies of AD pathology progression. The WM regions with increased DBSI-derived hindered isotropic components largely overlapped with the regions with increased DBSI-derived radial diffusivity and decreased DBSI-derived fractional anisotropy, suggesting that WM demyelination and edema coexist in the CDR 0.5 participants. DTI-derived radial diffusivity and fractional anisotropy detected similar patterns of pathological changes as did DBSI-derived counterparts, but DTI was unable to separate the contributions from demyelination and vasogenic edema.

Comparing the WM pathological differences in the preclinical and early stage of AD can provide critical insights about disease progression and facilitate development of effective early therapies. Table 2 summarizes the differences in DBSI and DTI-derived indices between the groups of participants. DTI-derived axial diffusivity was contaminated by inflammatory cell infiltration, leading to false positive detection of axonal injury in preclinical stage 1 participants. Because it was not confounded by such effects, DBSI-derived axial diffusivity accurately reflected the absence of axonal injury (as indicated by the CSF levels of neuronal injury markers) at this early stage of the disease. DTI-derived radial diffusivity was reduced by the presence of inflammatory cell infiltration in preclinical stage 1 participants and dramatically increased due to the combination effects from both demyelination and edema in CDR 0.5 participants. In contrast, DBSI-derived radial diffusivity was not affected by neuroinflammation and could accurately reflect the intact myelin in preclinical stage 1 participants and moderate demyelination in CDR 0.5 participants. DTI-derived fractional anisotropy and mean diffusivity are very sensitive and prone to the presence of hindered isotropic components, reducing their accuracy and specificity and overestimating the severity of WM abnormalities. In comparison, DBSI counterparts can better reflect axonal injury and demyelination without the contamination effect from co-existing neuroinflammation. In addition to detecting WM abnormalities, the DBSI-detected and -quantified restricted isotropic diffusion components (reflecting inflammatory cell infiltration) and hindered isotropic diffusion components (reflecting vasogenic edema) can characterize the initial neuroinflammation in preclinical and early AD. The raw data from one representative voxel from the posterior limb of internal capsule demonstrated similar finding with the TBSS analysis (FIG. 54).

During neuroinflammation, activated microglia and astrocytes induce neuronal death, resulting in release of aggregated tau protein. CSF measures of tau protein and phosphorylated tau may reflect neurodegeneration and may be the biomarkers that are most relevant to microstructural WM changes in early AD. VILIP-1, a neuronal calcium-sensor protein, is a marker of neuronal injury, and CSF measures of VILIP-1 are useful for diagnosis and prognosis in early stages of AD. CSF levels of tau, patu181, and VILIP-1 are also closely associated with each other in AD pathology. Elevated CSF levels of tau, ptau181, and VILIP-1 were observed in the CDR 0.5 participants in this study, indicating that these participants had neuronal injury. It was found that DBSI-derived fractional anisotropy and radial diffusivity correlated significantly with CSF levels of tau, ptau181, and VILIP-1, whereas only DTI-derived fractional anisotropy correlated with ptau181 (FIG. 55). However, DTI-derived fractional anisotropy is sensitive to the mixed contribution from both WM damage and neuroinflammation, and DBSI metrics may reflect WM abnormalities more accurately and specifically than DTI indices do.

Figure 56:
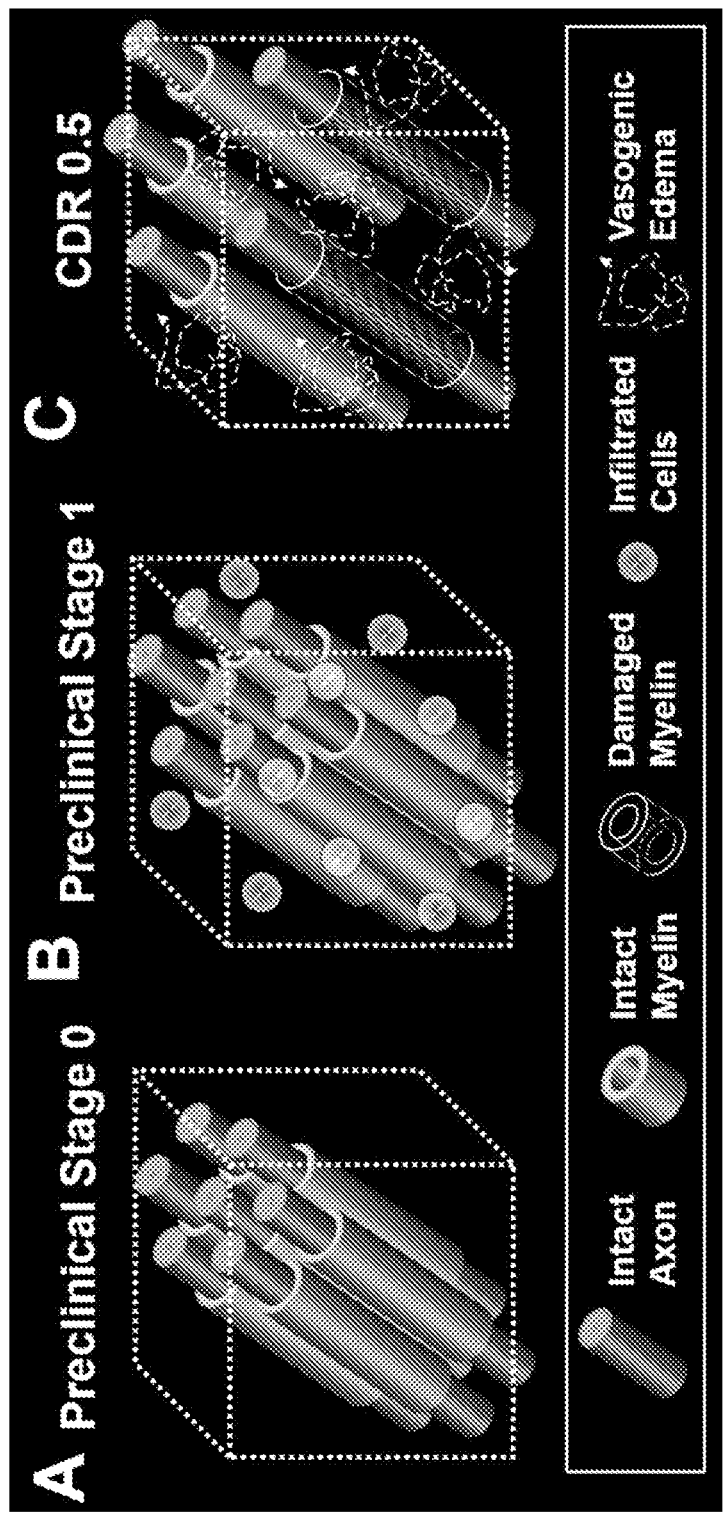
FIG. 56 is a schematic summary of the major DBSI findings in WM tracts in preclinical stage 1 and CDR 0.5 participants.

The findings of this study are summarized in a schematic (FIG. 56). FIG. 56(A) shows healthy axons and myelin in preclinical stage 0 (healthy) participants. FIG. 56(B) shows that, in preclinical stage 1 patients, no axon or myelin injury has occurred, but immune cells have infiltrated, suggesting that neuroinflammation is an early pathological event in preclinical AD. In FIG. 56(C) myelin damage and enlarged inter-axon space due to vasogenic edema are found in CDR 0.5 participants, suggesting dramatic disease progression from the preclinical stages. Dashed-line box indicates the MRI voxel. A particularly notable finding was that DBSI-detected neuroinflammation in preclinical stage 1 (FIGS. 56 A and B) occurred after Aβ deposition but before neurodegeneration (as detected by CSF levels of markers), suggesting the early involvement of neuroinflammation in early AD pathogenesis. Combining DBSI-derived inflammation markers with currently available Aβ and Tau markers provides a powerful way to characterize early AD pathologies. For example, recent histopathological study has shown that simultaneous presence of Aβ deposition and glia activation, instead of Aβ deposition without the accompaniment of glia activation, differentiates the AD patients from non-demented subjects with Aβ deposition. Compared to preclinical Stage 1, the most prominent pathological changes in CDR 0.5 participants were increased hindered isotropic diffusion and increased DBSI-derived radial diffusivity (FIGS. 56 A and C), suggesting that vasogenic edema and demyelination occur simultaneously in this stage of the disease.

Simulation study has found that smaller number of diffusion weighted images and lower diffusion weighting may reduce the accuracy and precision of DBSI-derived indices. In some embodiments, the clinical diffusion MRI protocols may be optimized by increasing maximal diffusion weighting (b value) and number of diffusion weighted gradients to improve the ability of DBSI to quantify restricted isotropic diffusion components. In some embodiments, longitudinal DBSI studies following subjects from the beginning of the preclinical stage to the symptomatic AD stage may advance the understanding of the pathogenesis of AD, establish the relationship between neuroinflammation and neurodegeneration, and facilitate the design of clinical trials to optimize timing of initiating treatment. Some embodiments include a DBSI method for image expansion and analysis of both white matter and gray matter microstructural changes in AD pathologies, and to combine DBSI with PET imaging of Aβ and tau pathology to simultaneously examine the molecular and microstructural aspects of AD pathologies.

TABLE 3

WM regions in which DTI- and DBSI-derived indices differed significantly ($P < 0.05$) between the preclinical stage 1 and stage 0 groups.

| | DTI_ radial diffusivity | DTI_ axial diffusivity | DTI_ mean diffusivity | DBSI_ restricted isotropic component [a] |
|---|---|---|---|---|
| Middle cerebellar peduncle | — | — | — | — |
| Pontine crossing tract | — | — | — | — |
| Genu of corpus callosum | — | ↓ | — | ↑ |
| Body of corpus callosum | — | ↓ | ↓ | ↑ |
| Splenium of corpus callosum | — | ↓ | ↓ | ↑ |
| Fornix (column and body of fornix) | — | ↓ | — | ↑ |

TABLE 3-continued

WM regions in which DTI- and DBSI-derived indices differed significantly (P < 0.05) between the preclinical stage 1 and stage 0 groups.

| | DTI_radial diffusivity | DTI_axial diffusivity | DTI_mean diffusivity | DBSI_restricted isotropic component [a] |
|---|---|---|---|---|
| Corticospinal tract | — | — | — | ↑ (R) |
| Medial lemniscus | — | — | — | — |
| Inferior cerebellar peduncle | — | — | — | — |
| Superior cerebellar peduncle | — | — | — | — |
| Cerebral peduncle | ↓ | ↓ | ↓ | ↑ |
| Anterior limb of internal capsule | ↓ (L) | ↓ | ↓ | ↑ |
| Posterior limb of internal capsule | ↓ (L) | ↓ | ↓ | ↑ |
| Retrolenticular part of internal capsule | ↓ (L) | ↓ | ↓ | ↑ |
| Anterior corona radiata | ↓ | ↓ | ↓ | ↑ |
| Superior corona radiata | ↓ (L) | ↓ | ↓ | ↑ |
| Posterior corona radiata | — | ↓ | ↓ | ↑ |
| Posterior thalamic radiation (include optic radiation) | — | ↓ | ↓ (L) | ↑ |
| Sagittal stratum (include inferior longitudinal fasciculus and inferior fronto-occipital fasciculus) | ↓ (L) | ↓ | ↓ | ↑ |
| External capsule | ↓ (L) | ↓ | ↓ | ↑ |
| Cingulum (cingulate gyrus) | — | ↓ (R) | — | ↑ (L) |
| Cingulum (hippocampus) | — | — | — | — |
| Fornix (cres)/Stria terminalis | ↓ (L) | ↓ | ↓ | ↑ |
| Superior longitudinal fasciculus | — | ↓ | ↓ (R) | ↑ |
| Superior fronto-occipital fasciculus | ↓ (L) | ↓ | ↓ | ↑ |
| Uncinate fasciculus | — | ↓ | ↓ | ↑ |
| Tapetum | — | ↓ | ↓ (L) | ↑ |

—, no significant difference;
↓, lower in stage 1 than stage 0 in both right and left hemispheres;
↑, higher in stage 1 than stage 0 in both right and left hemispheres;
R, difference only significant in right hemisphere;
L, difference only significant in left hemisphere;
[a] $P < 0.2$.

TABLE 4

WM regions in which DTI- and DBSI-derived indices differed significantly (P < 0.05) between the CDR 0.5 group and the preclinical stage 0 group.

| | Fractional anisotropy | | Radial diffusivity | | Mean diffusivity | | Hindered isotropic component |
|---|---|---|---|---|---|---|---|
| | DTI | DBSI | DTI | DBSI | DTI | DBSI | DBSI |
| Middle cerebellar peduncle | ↓ | — | — | — | — | — | — |
| Pontine crossing tract | ↓ | — | — | ↑ | — | — | — |
| Genu of corpus callosum | ↓ | ↓ | ↑ | ↑ | ↑ | — | ↑ |
| Body of corpus callosum | ↓ | ↓ | ↑ | ↑ | ↑ | — | ↑ |
| Splenium of corpus callosum | ↓ | ↓ | ↑ | ↑ | ↑ | — | ↑ |
| Fornix (column and body of fornix) | — | — | — | — | — | — | — |
| Corticospinal tract | ↓ | — | — | — | — | — | — |
| Medial lemniscus | ↓ | — | — | — | — | — | — |
| Inferior cerebellar peduncle | — | — | — | — | — | — | — |
| Superior cerebellar peduncle | ↓ | — | — | ↑(L) | — | — | — |
| Cerebral peduncle | ↓ | ↓(L) | — | ↑(L) | — | — | ↑(L) |
| Anterior limb of internal capsule | ↓ | ↓ | ↑ | ↑ | ↑ | — | ↑ |
| Posterior limb of internal capsule | ↓ | ↓ | ↑ | ↑ | ↑ | — | ↑ |
| Retrolenticular part of internal capsule | ↓ | ↓ | ↑ | ↑ | ↑ | — | ↑ |
| Anterior corona radiata | ↓ | ↓ | ↑ | ↑ | ↑ | — | ↑ |
| Superior corona radiata | ↓ | ↓ | ↑ | ↑ | ↑ | — | ↑ |
| Posterior corona radiata | ↓ | ↓ | ↑ | ↑ | ↑ | — | ↑ |
| Posterior thalamic radiation (include optic radiation) | ↓ | ↓ | ↑ | ↑ | — | — | ↑ |
| Sagittal stratum (include inferior longitudinal fasciculus and inferior fronto-occipital fasciculus) | ↓ | ↓ | ↑ | ↑ | — | — | ↑ |
| External capsule | ↓ | ↓ | ↑ | ↑ | ↑ | — | ↑ |
| Cingulum (cingulate gyrus) | ↓ | ↓ | ↑ | ↑ | — | — | ↑ |
| Cingulum (hippocampus) | | ↓ | ↑ | | — | — | |

TABLE 4-continued

WM regions in which DTI- and DBSI-derived indices differed significantly (P < 0.05) between the CDR 0.5 group and the preclinical stage 0 group.

| | Fractional anisotropy | | Radial diffusivity | | Mean diffusivity | | Hindered isotropic component |
|---|---|---|---|---|---|---|---|
| | DTI | DBSI | DTI | DBSI | DTI | DBSI | DBSI |
| Fornix (cres)/Stria terminalis | ↓ | ↓ | ↑ | ↑ | — | — | ↑ |
| Superior longitudinal fasciculus | ↓ | ↓ | ↑ | ↑ | ↑(L) | — | ↑ |
| Superior fronto-occipital fasciculus | ↓ | ↓ | ↑ | ↑ | ↑ | — | ↑ |
| Uncinate fasciculus | ↓ | ↓ | ↑ | ↑(L) | ↑(R) | — | ↑(L) |
| Tapetum | ↓(L) | ↓(R) | ↑(R) | ↑ | — | — | ↑ |

—, no significance;
↓, lower in CDR 0.5 than in stage 0 in both right and left hemispheres;
↑, higher in CDR 0.5 than in stage 0 in both right and left hemispheres;
R, difference only significant in right hemisphere;
L, difference only significant in left hemisphere.

TABLE 5

WM regions in which the DTI- and DBSI-derived indices correlated significantly (P < 0.05) with the CSF levels of neuronal injury markers.

| | Fractional anisotropy | | | Radial diffusivity | |
|---|---|---|---|---|---|
| | tau DBSI | ptau181 DTI | VILIP-1 DBSI | ptau181 DBSI | VILIP-1 DBSI |
| Middle cerebellar peduncle | — | — | Neg | — | — |
| Pontine crossing tract | — | — | — | — | — |
| Genu of corpus callosum | — | — | Neg | Pos | — |
| Body of corpus callosum | — | Neg | Neg | Pos | — |
| Splenium of corpus callosum | Neg | Neg | — | Pos | — |
| Fornix (column and body of fornix) | — | — | — | — | — |
| Corticospinal tract | — | — | — | — | — |
| Medial lemniscus | — | — | — | — | — |
| Inferior cerebellar peduncle | — | — | — | — | — |
| Superior cerebellar peduncle | — | — | — | — | — |
| Cerebral peduncle | — | Neg | Neg | Pos (R) | Pos |
| Anterior limb of internal capsule | Neg (R) | Neg | Neg | Pos | Pos |
| Posterior limb of internal capsule | — | Neg | Neg | Pos (R) | Pos |
| Retrolenticular part of internal capsule | Neg (R) | Neg | Neg | Pos | Pos |
| Anterior corona radiata | Neg | Neg | Neg | Pos | Pos |
| Superior corona radiata | Neg | Neg | Neg | Pos | Pos |
| Posterior corona radiata | Neg (R) | Neg | Neg | Pos | Pos |
| Posterior thalamic radiation (include optic radiation) | Neg (R) | Neg (L) | Neg | Pos | Pos |
| Sagittal stratum (include inferior longitudinal fasciculus and inferior fronto-occipital fasciculus) | Neg (R) | Neg (L) | Neg | Pos | Pos |
| External capsule | — | Neg | Neg | Pos | Pos |
| Cingulum (cingulate gyrus) | — | — | Neg | Pos | Pos |
| Cingulum (hippocampus) | — | — | Neg | — | — |
| Fornix (cres)/Stria terminalis | Neg (R) | Neg (L) | Neg | Pos | — |
| Superior longitudinal fasciculus | Neg (R) | Neg | Neg | Pos | Pos |
| Superior fronto-occipital fasciculus | — | Neg (R) | Neg | — | Pos |
| Uncinate fasciculus | Neg (R) | Neg (L) | Neg | Pos | Pos (L) |
| Tapetum | Neg (R) | — | Neg (R) | Pos | Pos (R) |

—, no correlation;
Neg, negative correlation in both right and left hemispheres;
Pos, positive correlation in both right and left hemispheres;
R, correlation only significant in right hemisphere;
L, correlation only significant in left hemisphere.

Figure 57:
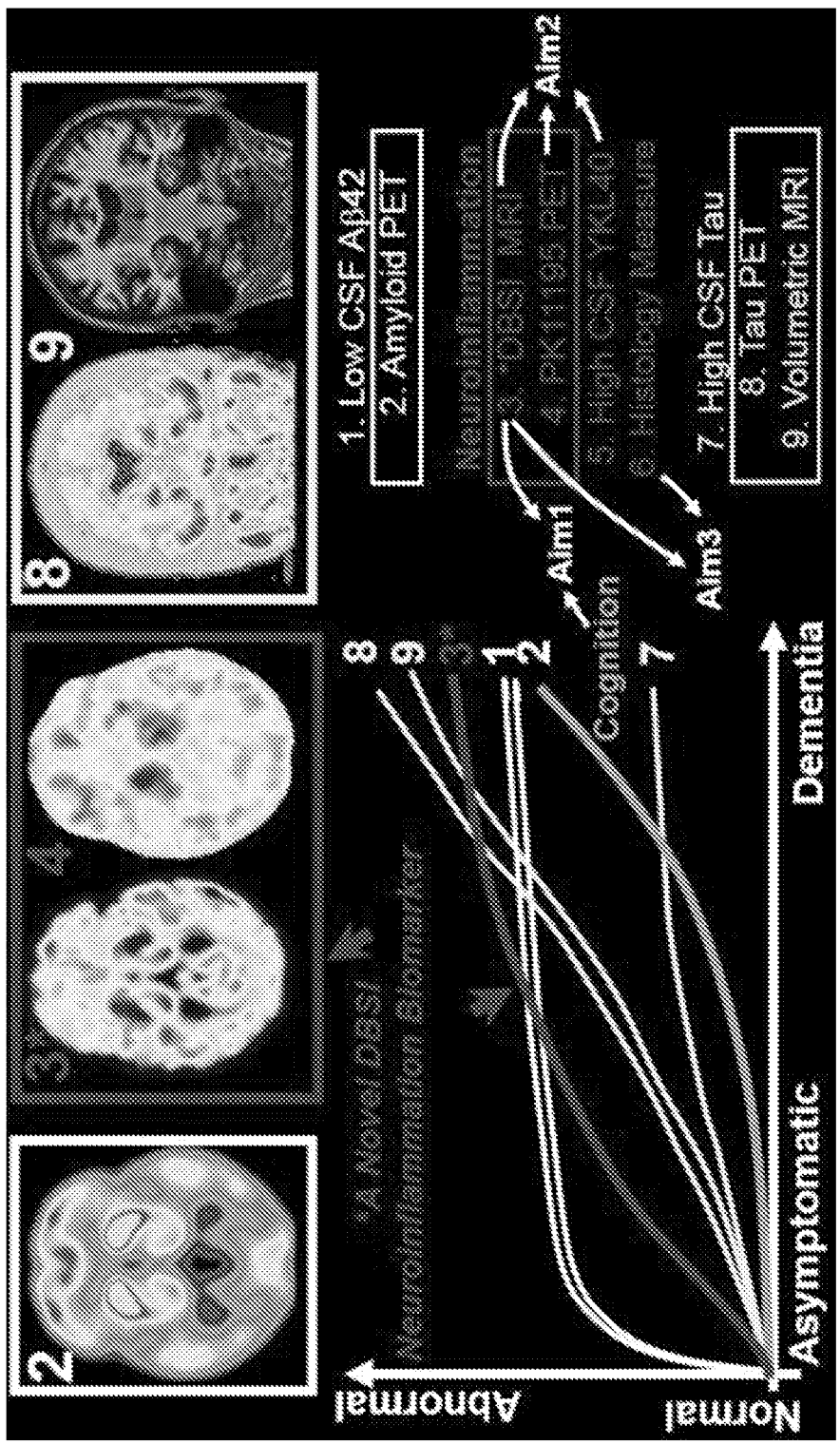
FIG. 57 is an overview of a DBSI neuroinflammation biomarker.

II. Utility of the DBSI Biomarker with Respect to Correlating In Vivo DBSI with Disease Progression and Cognition A DBSI-MRI acquisition and analysis platform may be used to quantify neuroinflammation in preclinical and symptomatic stages of AD. DBSI can be performed both cross-sectionally and longitudinally for individuals with the following characteristics: (1) cognitively normal with no biomarker evidence of preclinical AD, (2) cognitively normal with positive CSF Aβ, (3) cognitively normal with positive CSF Aβ and Tau, and (4) symptomatic AD. It is described herein that AD neuroinflammation can be robustly detected and quantified with DBSI and that longitudinal increases in neuroinflammation measured by DBSI (#3 in FIG. 57) associate with disease progression and cognitive decline (blue in FIG. 57).

Because AD leads to impaired memory and cognition, and ultimately, to dementia with associated loss of independence, causing a heavy personal toll on patients and families, there is a desire for a prognostic inflammation marker for Alzheimer's disease (AD). AD is currently estimated to afflict 5 million people in the United States, with an expected increase to 13 million by the year 2050. The annual cost of care for patients with AD in 2014 was over $214 billion and is predicted to reach $1 trillion by 2050 unless disease-modifying treatments are developed. A large body of evidence has supported the "amyloid beta (Aβ) hypothesis", which predicts that Aβ aggregates lead to synaptic dysfunction and neuronal death. Thus, numerous therapies targeting Aβ have been tested in the past two decades. However, more than 100 candidate treatment compounds have failed, leading to increasing interest in other contributors, such as accumulation of intracellular tau fibrils or neuroinflammation. Recent histopathological research has found that a major difference between Aβ-positive individuals with dementia and those who were cognitively normal (CN) at the time of death is inflammatory glia activation in the population with dementia. These findings have led to a search for accurate and robust biomarkers specific for neuroinflammation in AD that could both be used for prognosis and incorporated into clinical trials.

The DBSI-MRI acquisition and analysis platform described herein can quantify neuroinflammation in preclinical and symptomatic stages of AD with. AD neuroinflammation can be robustly detected and quantified with DBSI and longitudinal increases in neuroinflammation measured by DBSI associate with disease progression and cognitive decline.

The Knight Alzheimer's Disease Research Center (ADRC) has been recruiting participants into National Institutes of Health-funded longitudinal studies of memory and aging for over 30 years, and provides access to AD patients and data. As disclosed herein, focus is given to the clinical, cognitive, and biomedical correlates of AD in comparison with cognitively healthy aging, and in particular, on the transition between normal cognition (CN) and symptomatic AD. Early clinicopathologic correlations in this cohort established that spread of neurofibrillary tangles from medial temporal lobe structures such as entorhinal cortex and the hippocampus to the temporal neocortex is associated with the transition to abnormal cognition. The Total Registry (TR) of the Knight ADRC consists of an active cohort maintained at ~600 participants. Participant data includes longitudinal studies with structural and functional MRI (which includes a basic diffusion protocol that is not optimized for DBSI), Aβ PET using $^{18}$F-florbetapir (also known as AV45), CSF biomarker analyses, as well as clinical and cognitive measures. Three indications support the premise that DBSI can be used to detect and quantify neuroinflammation in AD.

The first indication supporting the premise that DBSI can be used to detect and quantify neuroinflammation in AD is that DBSI-derived cell fractions have detected neuroinflammation in preclinical AD patients. DBSI analysis was applied to baseline DTI MRI scans from 175 participants from the Knight ADRC (Table 6).

TABLE 6

Characteristics of participants.

| Characteristics | Stage 0 (n = 144) | Stage 1 (n = 31) |
|---|---|---|
| Age, years | 61.0 (±8.1) | 62.4 (±6.3) |
| Male sex | 55 (±38%) | 10 (±32%) |
| Education years | 16.0 (±2.4) | 15.8 (±2.2) |
| ApoE4+ | 18 (±13%) | 31 (±100%) |
| Family history+ | 80 (±56%) | 16 (±52%) |
| CSF Aβ42 | >500 pg/ml | >500 pg/ml |
| CSF total tau | <339 pg/ml | <339 pg/ml |
| CSF ptau1 181 | <80 pg/ml | <80 pg/ml |

Figure 62:
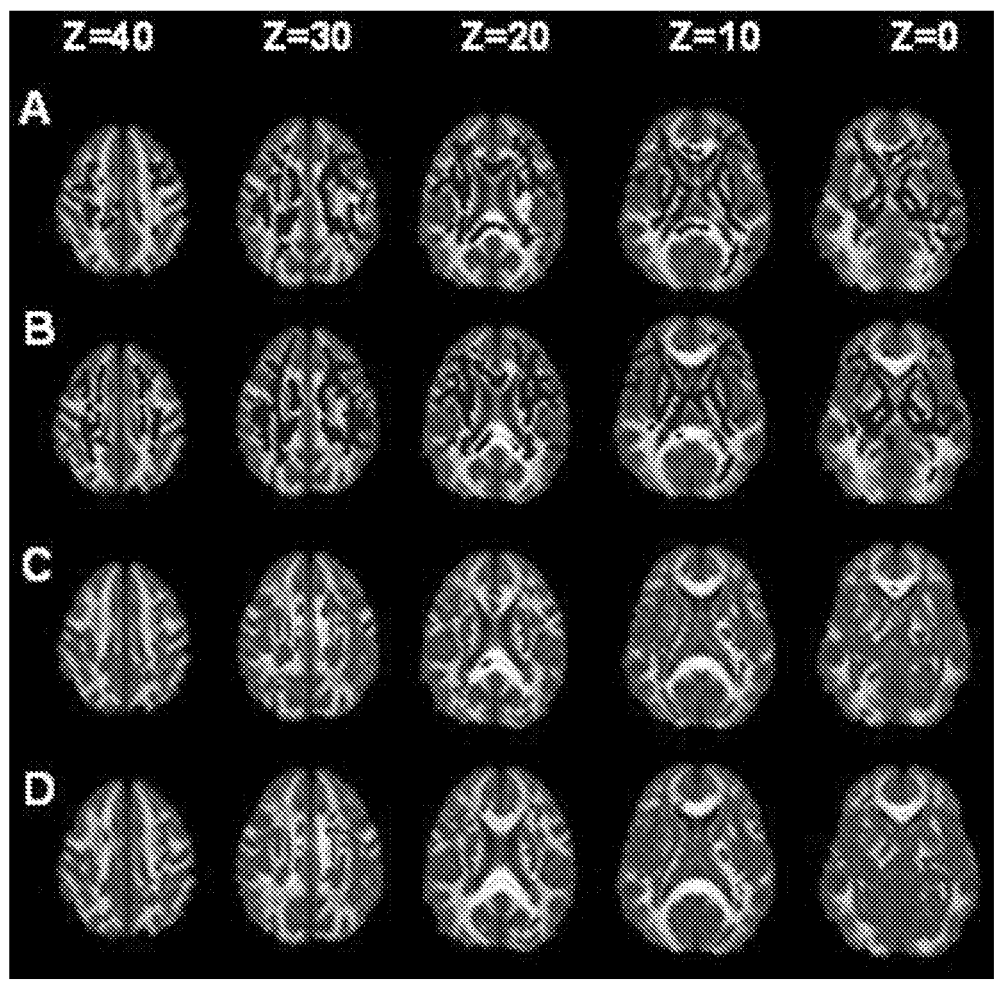
FIG. 62 shows DBSI detection of neuroinflammation in preclinical AD.

Participants were classified as normal controls (National Institute on Aging-Alzheimer's Association [NIA-AA] Stage 0) or amyloid positive/tau negative by CSF (NIA-AA Stage 1). The imaging resolution was 2×2×2 mm3 with 24-direction diffusion-encoding scheme. The maximal b-value was 1400 s/mm2. FIG. 62 shows DBSI detection of neuroinflammation in preclinical AD. FIGS. 62(A&B) shows that DTI axial and mean diffusivity was lower in stage 1 than in stage 0 (blue, P<0.05). FIGS. 62(C&D) shows that DBSI cell fraction was higher (red) in stage 1 than in stage 0 with (C, P<0.07) and without (D, P<0.05) multiple comparison correction. It was found that DTI-derived axial and mean diffusivity was significantly lower (FIGS. 62A&B) in the NIA-AA Stage 1 group than in the Stage 0 group. Classically, DTI with low axial and mean diffusivity would suggest the presence of neuronal injury (FIG. 59A), which is surprising given that these patients were negative for CSF tau and ptau, which have been considered as markers of progression to neuronal injury (NIA-AA Stage 2). However, when the data was analyzed with DBSI, it was found that DBSI-derived axial diffusivity did not differ between groups, whereas DBSI-derived cell fraction (DBSI neuroinflammation biomarker) was higher in Stage 1 than in Stage 0 participants. Importantly, the white matter (WM) regions with the increased cell fraction (FIGS. 62C&D) overlapped with the regions showing decreased DTI-derived axial and mean diffusivity (FIGS. 62A&B). These DBSI results are consistent with a recent report of inflammatory microglial activation/accumulation in preclinical AD.

Figure 63:
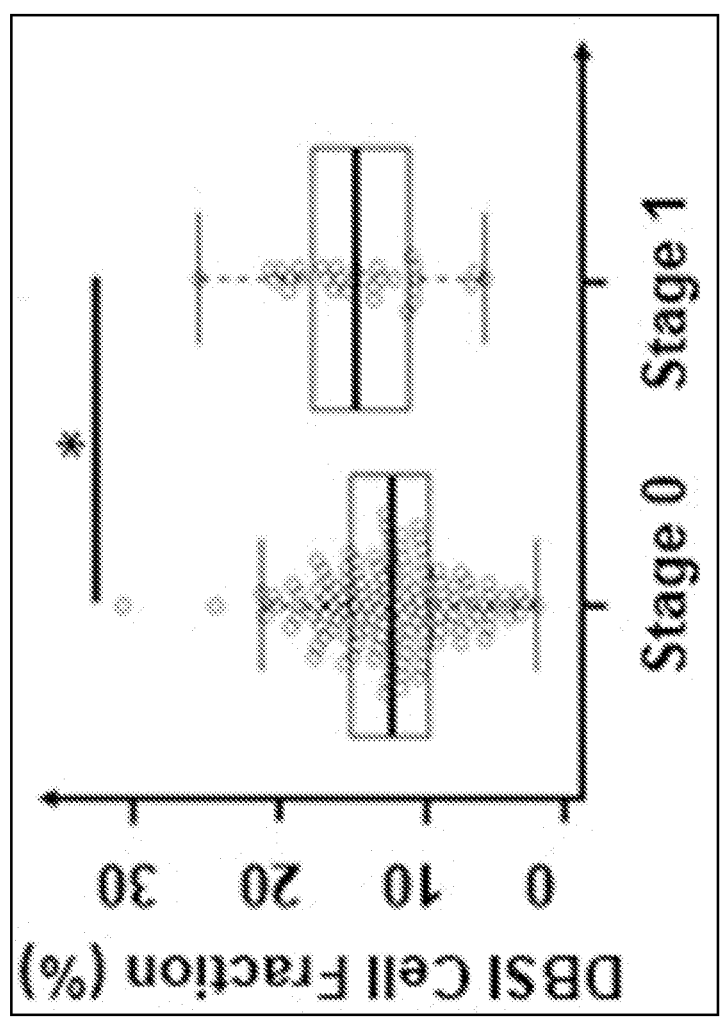
FIG. 63 shows DBSI cell fraction is higher in stage 1 than stage 0, suggesting neuroinflammation *P<0.05.

These findings were quantitated by comparing regions of interest (ROIs) from the posterior limb of internal capsule in stage 0 and 1 participants. Analyses were controlled for age, gender, education, ApoE4 genotype, and family history of AD. It was found that the DBSI-detected cell fraction, indicating neuroinflammation, was significantly higher in Stage 1 than in Stage 0 participants (FIG. 63). This suggests that in very early preclinical AD, neuroinflammation associated with microglial activation is present with Aβ deposition but precedes detectable CSF tau pathology in the cohort. This finding supports the idea that the DBSI cell fraction can serve as a neuroinflammation biomarker in the context of AD but also underscores the need for specific neuropathology correlations, which will be the focus in Aim 3.

Figure 64:
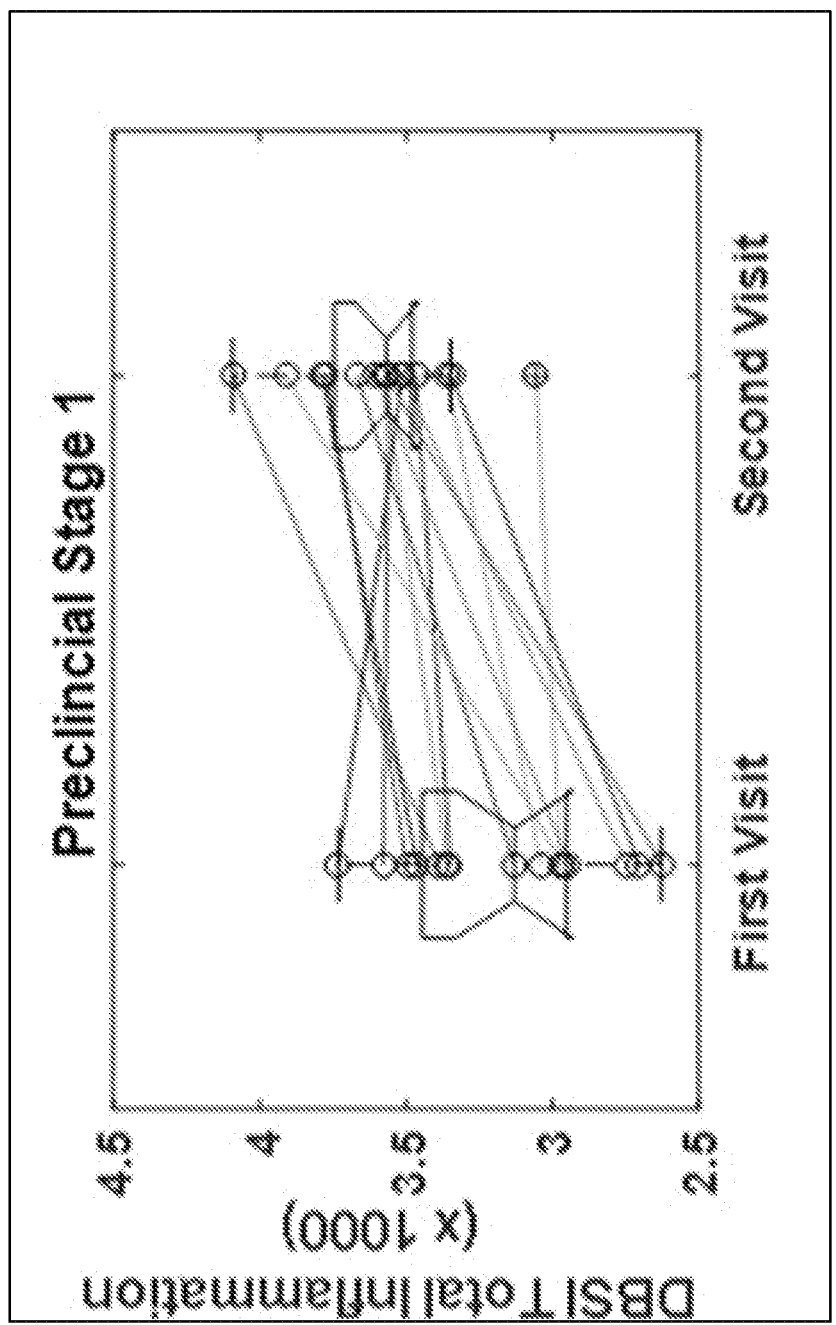
FIG. 64 shows inflammation detected by DBSI increases longitudinally in preclinical stage 1.

The second indication supporting the premise that DBSI can be used to detect and quantify neuroinflammation in AD is that DBSI-derived total neuroinflammation index was found to reflect inflammation progression in preclinical AD. DBSI was used to analyze baseline and follow-up (3±1 years) diffusion MRI data for 21 preclinical stage 0 participants and 15 preclinical stage 1 participants from the cohort. The DBSI total neuroinflammation index was defined as the summation of inflammatory cell fractions across the entire brain including both white matter and gray matter. A longitudinal increase was observed in the DBSI neuroinflammation biomarker in the preclinical Stage 1 participants (FIG. 64) but not in the Stage 0 participants (not shown), suggesting that neuroinflammation is abnormally accelerated in the context of Aβ deposition in preclinical Stage 1.

Figure 65:
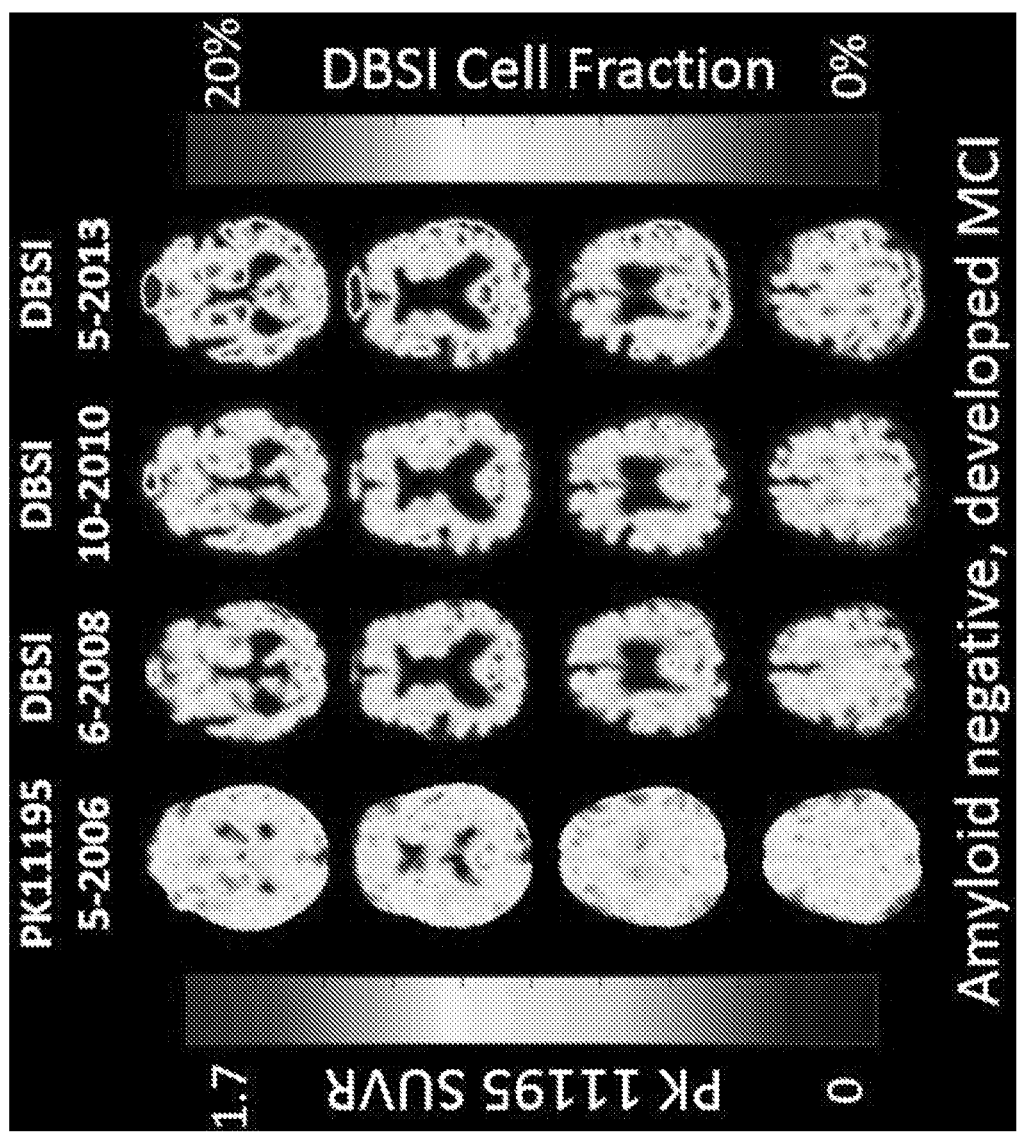
FIG. 65 shows DBSI neuroinflammation increased in an amyloid-positive, CN participant who developed MCI.
Figure 66:
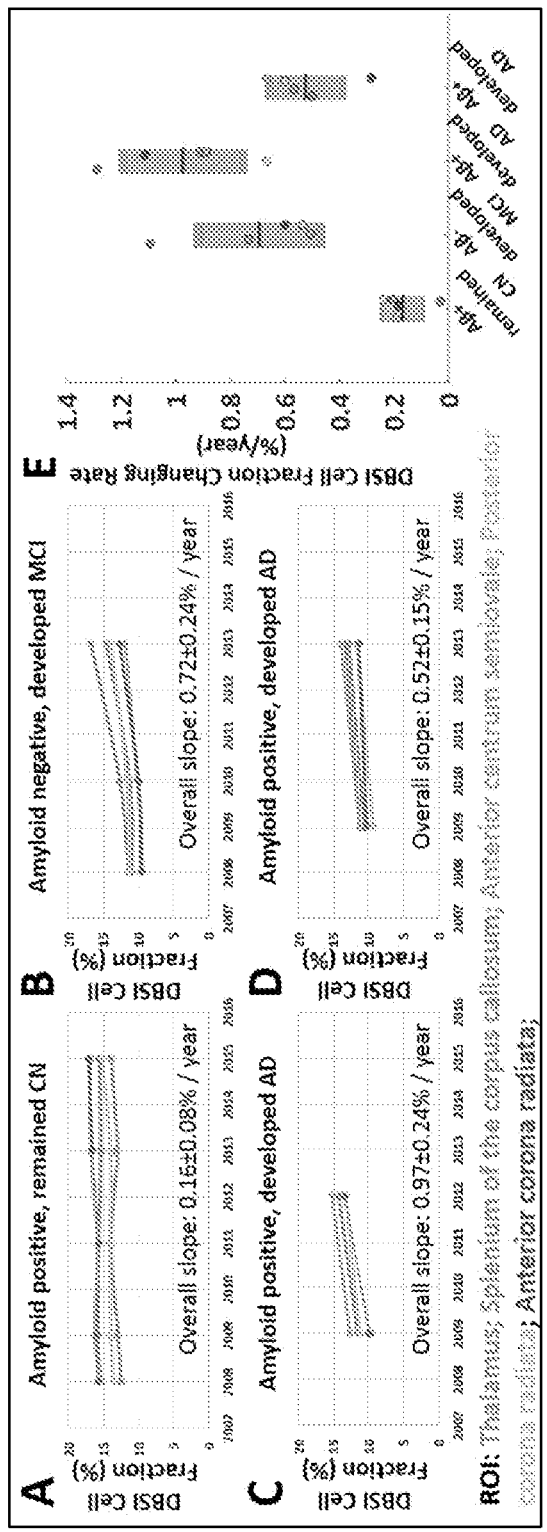
FIG. 66 shows DBSI inflammation (cell %) change rates predict AD progression.
Figure 67:
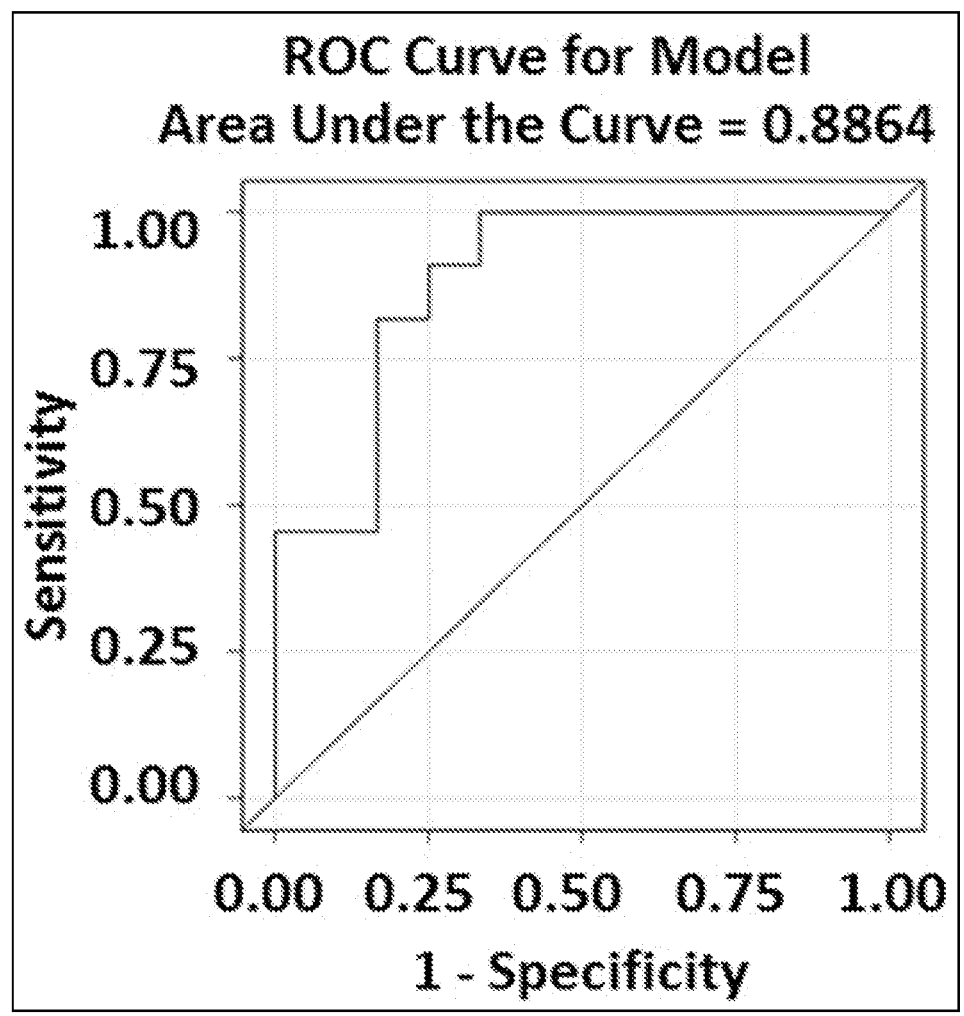
FIG. 67 shows PK11195 PET progression predictions.

The third indication supporting the premise that DBSI can be used to detect and quantify neuroinflammation in AD is that DBSI neuroinflammation images predicted disease progression. To evaluate inflammation associated with AD, longitudinal diffusion MRI data was used from 24 participants who underwent longitudinal PK11195 scans. The diffusion MRI scan was as described above. Diffusion MRI data was analyzed with DBSI and generated DBSI neuroinflammation images (cell fraction). The T1 image, which was registered to the PK11195 image, was then registered to the DBSI neuroinflammation images to transform the DBSI images into PK11195 space. The PK11195 images were normalized to a whole brain mean value to compute standardized uptake value ratio (SUVR). DBSI analysis was performed in an amyloid-negative CN participant who developed mild cognitive impairment (MCI) during the follow-up. Close matches were found between PK11195 PET images and DBSI neuroinflammation images (FIG. 65 Left). More strikingly, DBSI neuroinflammation increased over the course of the three follow-up visits (FIG. 65 Right), consistent with this participant's clinical outcome measure. DBSI was next used to examine an amyloid-positive participant who remained CN from 2008 through 2015. DBSI neuroinflammation images revealed that the distribution and severity of inflammation did not change across five follow-up visits from 2008 to 2015, suggesting that neuroinflammation progressed slowly. Also examined were two amyloid-positive CN participants who converted to_AD during the period of follow-up visits. Increased levels of DBSI neuroinflammation were observed in their follow-up examination. Five ROIs, including both grey and white matter regions, were selected for these four participants to assess the temporal change of DBSI neuroinflammation. FIG. 66 shows DBSI inflammation (cell %) change rates predict AD progression. FIG. 60(A) shows Aβ+ participant who remained CN. FIG. 66(B) shows participant in FIG. 65. FIGS. 66(C and D) shows Aβ+ participants who developed AD. FIG. 66(E) gives a summary of DBSI cell fraction change rates for the four participants. Whereas the level of DBSI neuroinflammation remained stable in the participant who remained CN, DBSI neuroinflammation levels dramatically increased in other participants who developed symptoms in follow-up visits, as suggested by the overall change in slope (FIG. 66). Additionally, it was noticed that the longitudinal neuroinflammation change rate, but not the baseline DBSI neuroinflammation strength, related strongly to disease progression.

Together, these data support the premise that DBSI can detect changes in neuroinflammation during AD progression. Additionally, they demonstrate that a 3T MRI scanner running FDA-approved diffusion sequences can reproducibly produce excellent DBSI data.

In some embodiments, patients may undergo both cross-sectional imaging and longitudinal imaging with DBSI, and may be followed longitudinally for clinical and psychometric evaluations and undergo biomarker analysis with lumbar puncture for CSF, conventional MRI and florbetapir amyloid imaging. In some embodiments, patients may be classified on the basis of clinical and biomarker status, and divided into four groups: (1) Cognitively normal with no CSF biomarker evidence of preclinical AD; (2) Cognitively normal with positive CSF Aβ marker; (3) Cognitively normal with positive CSF Aβ and Tau markers; and (4) Symptomatic AD.

Figure 72:
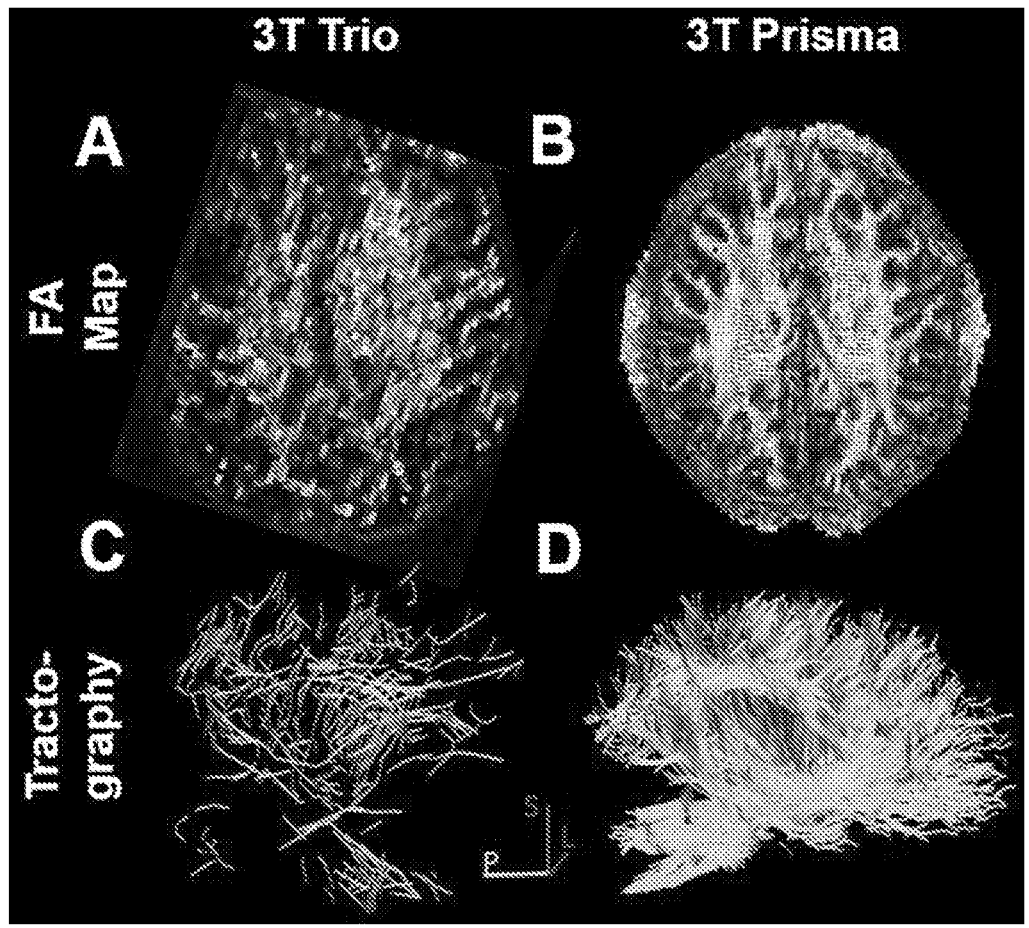
FIG. 72 shows autopsied brains imaged with a Siemens 3T Prisma MRI scanner.

With respect to DBSI Imaging Protocol, FIG. 72 shows autopsied brains imaged with a Siemens 3T Prisma MRI scanner. Although the 3T Trio scanner generated excellent DBSI data, a PRISMA scanner provided much improved SNR for diffusion MRI data (see FIG. 72). FIG. 72(A) is a DTI FA map obtained from 3T TIM Trio scanner. FIG. 72(B) is a DTI FA map obtained from 3T MAGNETOM Prisma scanner. FIGS. 72C and 72D show whole-brain tracking based on data in Panel A (FIG. 72C) and Panel B (FIG. 72D). Thus, in some preferred embodiments, DBSI imaging will be performed on a Siemens PRISMA 3 Tesla MRI. The volumetric MRI scan may consist of a 6 min three-dimensional (3D) T1-weighted image (MPRAGE) with 1.0×1.0× 1.2 mm resolution, using the Alzheimer's disease Neuroimaging Initiative protocol (see http://www.adni-info.org).

Diffusion-weighted MRI data may be collected at 2×2×2 mm$^3$ resolution in the axial plane covering the whole brain with TR/TE=7500/55 ms. The 99-direction diffusion encoding scheme was selected as prescribed in diffusion spectrum imaging where the position vectors are the entire grid points (qx, qy, qz) over the 3-D q-space under the relationship that $(qx^2+qy^2+qz^2) \leq r^2$, where r=3 for DBSI. A preferred maximum b-value is 2000 s/mm$^2$. The total acquisition time for DBSI using a single-shot diffusion-weighted echo planar imaging (EPI) sequence is 15 minutes. Phase maps may be collected after diffusion data acquisition to correct susceptibility artifacts.

Figure 58:
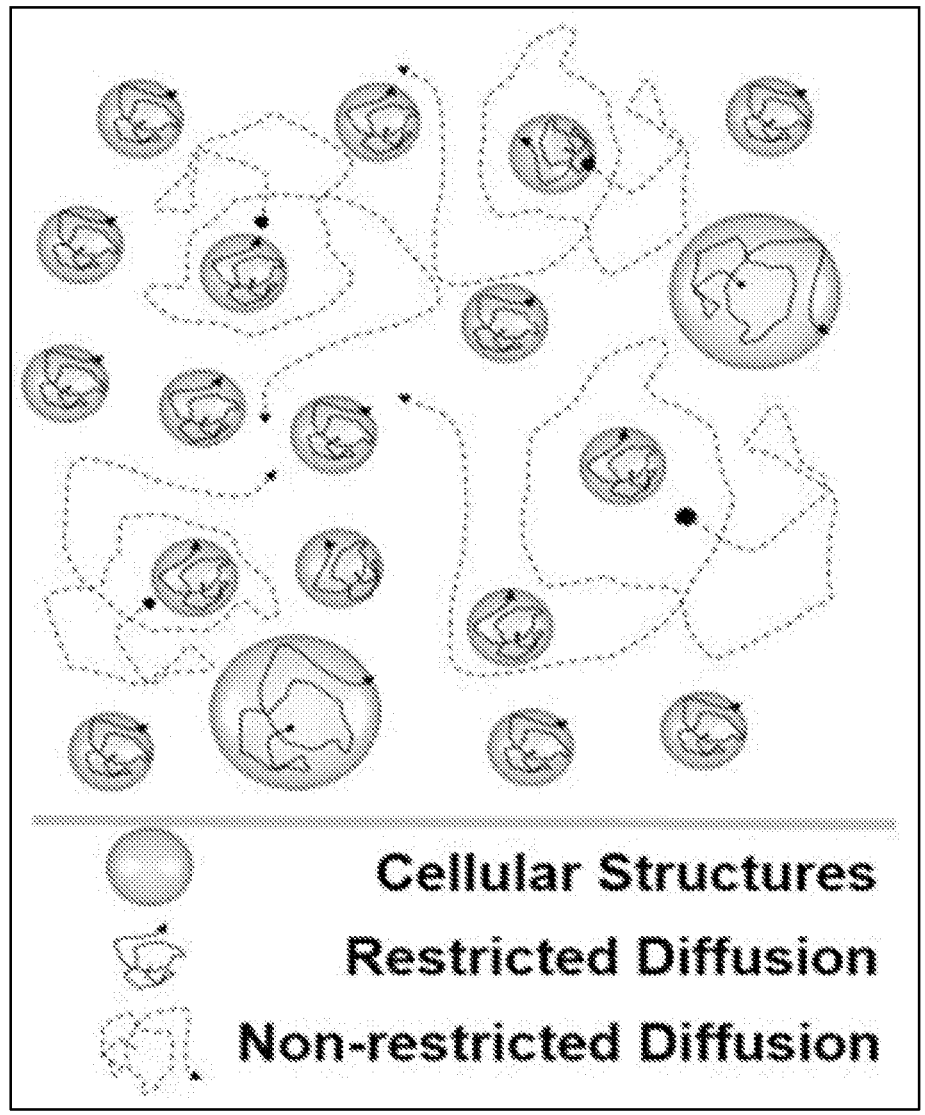
FIG. 58 shows different types of water molecular diffusion.

In some embodiments, a DBSI processing pipeline may be used. MRI data may be transferred from the scanner to, for example, the Neuroimaging Laboratories, where it may undergo software fusion with MRI anatomic imaging and post-processing. All images undergo quality control inspection before processing. The T1-weighted MRI scans may be processed through the FreeSurfer image analysis suite version 5.3 using Dell PowerEdge 1950 servers with Intel Xeon processors running CentOS 5.5 Linux. DBSI models diffusion-weighted MRI signals with a linear combination of multiple tensors describing both the anisotropic axonal fiber and its surrounding environment, and a full range of isotropic components with varying diffusivities (FIG. 58).

In some embodiments, two summary measures for DBSI (neuroinflammation index and edema index) may be compared with these among the four groups described above. Baseline data may first be used to compare the distribution of these measures across the four groups, and then choose the cutoffs that maximize the sensitivity and specificity of the symptomatic AD patients (group 4) (i.e., the Youden index). To compare baseline measures of DBSI index across preclinical groups (group 1, 2, and 3) and the symptomatic group (group 4), the distributions of DBSI indices within all participants can be examined. If the distributions are not normal, the data can be transformed appropriately (e.g., Box-Cox transformations) so that the transformed values approximate normality. The subsequent analyses may be conducted on the transformed values. Each measure across the four groups may be compared through the group means or adjusted means from either the original or transformed scale by using analysis of covariance (ANOCOVA) models. In addition to groups, the ANOCOVA models may also include the relevant covariates. For example, age, education, gender, APOE4 genotype, hypertension, and diabetic status, as well as possible interactions between these factors and groups. The interaction terms may be tested first. Depending on the outcome of these tests, the differences across the groups can be tested either by the main effect of groups or through the adjusted least square means. These analyses can be implemented by PROC GLM/SAS.

In some embodiments, the longitudinal rates of change of DBSI neuroinflammation and edema index as a function of preclinical and clinical groups at baseline may be examined. General linear mixed models can be used to analyze the rate of change of DBSI index as a function of baseline clinical and preclinical stages. More specifically, a random intercept and random slope longitudinal model can be employed to assess the rate of change of DBSI index over time. Other covariates can also be incorporated in these analyses to assess their potential effects on the rate of change. These analyses can be implemented by PROC MIXED/SAS.

In some embodiments, correlating in vivo DBSI with disease progression and cognition may be powered by testing for the difference of DBSI index in the four participant groups both cross-sectionally (n=120, 30 in each group assuming equal sample size at baseline) and longitudinally on the rate of change (n=80). For example, a proposed sample size of N=120 will provide at least 80% statistical power to detect an effect size of 0.31 (the mean difference/SD) at baseline (same SD assumed across the four subject groups), based upon the preliminary data with the non-optimized DBSI protocol. This power was based on an F-test on the main effect of subject groups with a one-way ANOVA model at a significance level of 5%. Similar power analysis on the annual rate of change on 80 subjects with two repeated measures on DBSI revealed that an effect size of 0.381 (on the rate of change) between two adjacent subject groups can be detected with 80% power. Based on an initial experience, the results from the optimized Prisma MRI protocol are anticipated to result in even larger power.

In other embodiments, contraindications to PET or MR may be screened before imaging. Use of CSF biomarker staging may be planned rather than imaging to make the analyses as independent as possible. However, imaging staging using a combination of florbetapir PET and hippocampal volumes may also be performed and analyzed as an alternative approach. It is noted that some patients may exhibit initial biomarkers or clinical assessments that suggest a non-Alzheimer pathology (SNAP), and also that these pathologies may develop over time. In some embodiments, patients who develop SNAP or infarcts may be analyzed as a separate, $5^{th}$ group. It is described herein that the DBSI neuroinflammation biomarker may be independent of other white matter findings, most notably, of periventricular white matter hyperintensities (WMH) commonly found in elderly people. WMH volumes as generated by the Knight ADRC Imaging Core may be quantitatively segmented to generate both volumes, which may be used as a regression in statistical analyses, and ROIs, and the DBSI neuroinflammation and edema biomarker measures may be assessed both inside and outside the areas of WMH. If differences are found, then analyses for each of the aims may be adjusted to incorporate this result. As described above, a maximum b-value=2000 s/mm$^2$ is preferred, however, if the SNR is insufficient to conduct DBSI analysis, the maximum b-value may be decreased to 1500 s/mm$^2$.

III. Utility of the DBSI Biomarker with Respect to Positron Emission Tomography (PET) and Cerebrospinal Fluid (CSF) Measures of Neuroinflammation DBSI was compared to alternative biomarkers of neuroinflammation in AD with respect to cerebrospinal fluid (CSF) YKL40 and PK11195 PET. The DBSI total inflammation index (#3 in FIG. 57, defined as the summation of DBSI cell fraction across the entire brain) correlates with CSF YKL-40 (#5 in FIG. 57), and the inflammatory cell fraction in DBSI neuroinflammation images corresponds to grey and white matter regions of $^{11}$C-PK11195 uptake in PET images (#4 in FIG. 57).

Currently available neuroinflammation biomarkers are suboptimal. Three major classes of biomarkers of neuroinflammation in AD have been tested. First, the CSF level of YKL-40 and other proteins are current markers of neuroinflammation. However, inter-laboratory measurements of CSF biomarkers are confounded by large bias and random variation, CSF collection requires an invasive procedure, and CSF marker levels provide no information about the anatomic location of pathology. Second, PET is used for high-resolution molecular imaging of neuroinflammation by detecting ligands of the microglial protein 18 kDa translocator protein (TSPO), which is upregulated with inflammation. PK11195, $^{11}$C-PBR28, and other ligands have been used to detect neuroinflammation in AD animal models and patients. However, these PET approaches are limited by issues including genetic heterogeneity, poor signal-to-noise ratio, and difficulty interpreting results. Additionally, PET can only be performed at academic centers in proximity to a research cyclotron facility. Third, magnetic resonance imaging (MRI) is a widely available tool that is less expensive and has higher spatial resolution than PET. A distinct advantage of MRI is that it does not require exposure to radiation. Gadolinium-based MRI contrast agents in conjunction with T1-Weighted MRI have been proposed to detect inflammation through the detection of blood-brain barrier leakage in multiple sclerosis (MS) and AD. However, the long-term safety of gadolinium-based MRI contrast agents remains unknown and new Food and Drug Administration (FDA) warnings were issued in 2015. Diffusion tensor imaging (DTI), a widely used MR approach to model CNS microstructure, cannot separate the signals from free water (vasogenic edema), inflammatory cell infiltration, and neuronal injury. Thus, the currently available biomarkers for neuroinflammation are far from ideal, hindering the understanding of the role of neuroinflammation in AD pathogenesis.

Comparison of DBSI-MRI to alternative biomarkers of neuroinflammation in AD (including CSF YKL40 and PK11195 PET) showed that DBSI total inflammation index (defined as the summation of DBSI cell fraction across the entire brain) correlates with CSF YKL-40, and the inflammatory cell fraction in DBSI neuroinflammation images corresponds to grey and white matter regions of $^{11}$C-PK11195 uptake in PET images. Two indications are given to support DBSI-MRI use for biomarkers.

The first indication supporting the premise that DBSI can be used as for biomarkers is that PK11195 PET predicts AD progression. To evaluate inflammation associated with AD, longitudinal PK11195 scans were examined from 24 patients described above. Initial review of the data indicated that PK11195 binding did not co-localize or correlate with [$^{11}$C] Pittsburgh Compound B (PiB) amyloid PET, nor did it correlate with baseline clinical symptoms. Longitudinal MRI and clinical and cognitive follow-up over 7 years was obtained, allowing analysis of the link between baseline PK11195 and longitudinal changes in cognition. PK11195 data was processed with software designed in-house. PK11195 PET scans were motion-corrected and coregistered to concurrent MRI scans, which were used to generate ROIs with FreeSurfer (Martinos Center, Boston, Mass.). FIG. 61 shows a logistic regression model based on PET imaging of the entorhinal cortical white matter for all subjects. This region has a large area under the curve (AUC) (0.8864), suggesting that white matter uptake of PK11195 is a predictor of progression to dementia. Several additional white matter regions were predictive of dementia progression. Early investigations with PK11195 were focused on gray matter uptake, which was not predictive. It is only with modern processing techniques and longitudinal outcome data that the importance of white matter neuroinflammation was able to be identified. These preliminary data suggest that neuroinflammation is an important early biomarker for assessing risk of developing dementia in CN participants. Furthermore, these data show that PK11195 data can be used as a marker of neuroinflammation.

Figure 68:
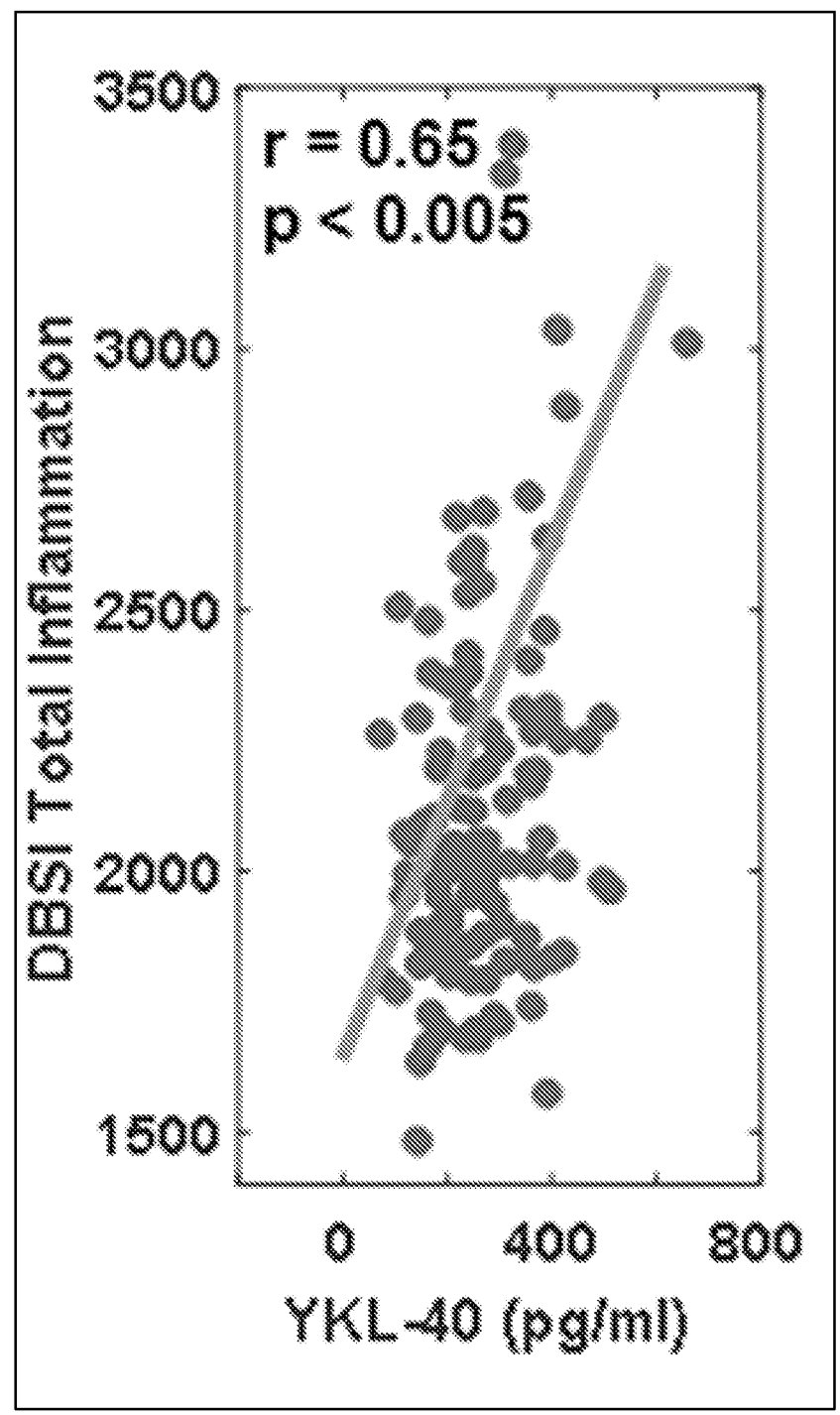
FIG. 68 shows a DBSI-derived total neuroinflammation index correlated with CSF level of YLK-40.

The second indication supporting the premise that DBSI can be used as for biomarkers is that correlation was found between CSF YKL-40 and DBSI total neuroinflammation index. A group of 120 participants (86 preclinical stage 0 participants, 16 preclinical stage 1 participants, 18 Clinical Dementia Rating 0.5 participants) from the Knight ADRC had MRI DTI analyzed with DBSI (even though the MRI protocol was not optimized for DBSI). The statistical analysis controlled for age, gender, education, ApoE4 genotype, and family history of AD. It was found that the CSF level of YKL-40, a measure of neuroinflammation, correlated with the DBSI total neuroinflammation index, defined as the summation of inflammatory cell fractions across the entire brain including both white and gray matter (FIG. 68). This finding suggested that the DBSI neuroinflammation biomarker reflects the CSF measure of inflammation.

In some embodiments, PET imaging sessions may be executed on a Siemens Biograph 40 PET/CT scanner. Each imaging session may consist of a PET scan for characterization of PK11195 uptake. PK11195 synthesis may be performed according to known methods. Each participant may be given an antecubital intravenous catheter placed for tracer injection. Each participant may then be positioned in the scanner followed by i.v. injection of approximately 15 mCi of PK11195 and a 60 minute 3-D dynamic PET scan reconstructed (12×10 sec frames; 9×20 sec frames; 10×1 min frames; 9×5 min frames) using an OSEM algorithm with standard normalization, dead time, randoms, scatter, and decay correction. In some embodiments, PK11195 scans may be collected over a three year period, with participants undergoing lumbar puncture every three years. These data may be used to classify the participants into NIA-AA Preclinical AD Stages.

For image analysis, in some embodiments a PET Unified Pipeline (PUP) may be used to automate PET data analysis. Inter-frame motion correction for the dynamic PET images may be performed by using standard image registration techniques. PET-MRI registration may be performed by using a vector-gradient algorithm in a symmetric fashion (i.e., average transformation for PET→MRI and inverse of MRI→PET will be used as the final transformation matrix). Regional analysis may be performed on the basis of ROIs defined by FreeSurfer (Martinos Center for Biomedical Imaging, Charlestown, Mass., USA). Regional time-activity curves for each ROI may be extracted by resampling the PET data to patient MRI space. Logan graphical analysis may be used to estimate regional binding potentials ($BP_{ND}$). Cerebellum may be used as the default reference region, and clustering-based automatic extraction of the reference region may also be explored for optimal quantification of PK11195 uptake. Partial volume correction (PVC) may also be performed by using a regional spread function technique implemented in PUP. Regional SUVR and $BP_{ND}$ may be estimated with and without PVC.

In some embodiments, correlation between DBSI total neuroinflammation index (the summation of inflammatory cell fractions across the entire brain) and CSF YKL40 may be determined for each of the four groups (see above), and all participants may be assessed by Pearson correlation or rank-based correlations such as Spearman, depending on whether the bivariate distribution is normal. These analyses can be implemented by PROC CORR/SAS.

In some embodiments, correlation between DBSI and PK11195, DBSI neuroinflammation images may be compared with PET images in both voxel wise and ROI manners. Similar analytic approaches as described above may be implemented for either voxel- or ROI-wise comparisons.

Regarding power analyses, support of DBSI-MRI use as biomarkers was powered by testing for correlations between DBSI and CSF YKL40. A sample size of 120 individuals provided at least 80% statistical power to detect a Pearson correlation of as small as 0.255. The power analyses were based on two-sided Pearson correlation test at a significance level of 5%.

In some embodiments, correlations between CSF markers and imaging may involve close coordination of lumbar puncture and DBSI imaging. In other embodiments, processing methods for PK11195 PET imaging may be refined as appropriate, including exploration of the impact of alternative reference regions and partial volume correction, an approach that has been established for other tracers. As part of the standard MRI, a magnetic resonance angiogram may also be obtained, which may be used as an alternative processing of the PET scans by using an arterial input function, which may be helpful for instances when a good reference region is difficult to identify. To more rigorously evaluate regional tracer uptake, alternative approaches such as the supervised clustering method for automated reference region extraction, which has been applied to PiB studies, may be explored. In addition to regional analysis, voxel-wise quantification may also be performed. To improve SNR in the obtained parametric image maps, a wavelet-based algorithm and/or an adaptive sampling scheme may be explored to improve voxel-wise quantification of tracer uptake. Although PK11195 is the most widely used TSPO PET imaging tracer, it suffers from high non-specific binding and low SNR. A number of second-generation TSPO PET tracers have been developed with higher affinity and/or lower non-specific binding. One of these newer TSPO tracers, $^{11}$C-PBR28, has been successfully synthesized and tested for PET imaging. However, TSPO from human tissue samples binds second-generation TSPO radioligands with either high affinity (high affinity binders, HABs), or low affinity (LABs) or expresses both HAB and LAB binding sites (mixed affinity binders). The expression of these different TSPO binding sites in humans is encoded by the rs6971 polymorphism in the TSPO gene. If switching to PBR28 as the tracer for inflammation PET imaging is decided upon, then genotyping of the rs6971 polymorphism may be included for each participant, and the image analysis may be performed by taking this polymorphism into consideration. (4) The DBSI metrics may be strongly non-Gaussian, in which case generalized linear models can be used to analyze the metrics in quantiles.

IV. Utility of the DBSI Biomarker with Respect to Correlating Ex Vivo DBSI-MRI with Quantitative Histopathology DBSI biomarkers of neuroinflammation in AD were validated using quantitative neuropathology. In some embodiments, DBSI-MRI may be used to scan 50 whole brain specimens obtained at autopsy. Regions of interest for histopathology can be chosen on the basis of both a standard template and the DBSI results. To detect inflammatory cells (microglia, astrocyte, etc.), staining may be performed for ionized calcium binding adaptor molecule 1 (IBA-1) and glial fibrillary acidic protein (GFAP). Quantitative histopathology may be aligned to the DBSI images. It is described herein that the DBSI inflammation biomarker (#3 in FIG. 57) correlates with histologic quantification of inflammatory cell infiltration (#6 in FIG. 57). Additionally, the cell type(s) responsible for the DBSI biomarker can be identified.

Development and evaluation of the diffusion MRI technique, Diffusion Basis Spectrum Imaging (DBSI), can be performed to identify neuroinflammation in preclinical and symptomatic AD. The result of which may be a safe, noninvasive tool to specifically image, detect, quantify, and track neuroinflammation in AD patients. A surrogate measure for disease progression and outcome may be generated, and accordingly the DBSI neuroinflammation biomarker may be readily incorporated into clinical trials. FDA Part 11-compliant pipelines for processing MRI and PET data have been established and may be similarly established for DBSI-MRI detection of neuroinflammation.

Validation of DBSI as a biomarker of neuroinflammation in AD can be performed by using quantitative neuropathology. DBSI inflammation biomarker correlates well with histologic quantification of inflammatory cell infiltration. Four indications are given to support the premise that the DBSI neuroinflammation biomarker will correlate with histological findings.

Figure 69:
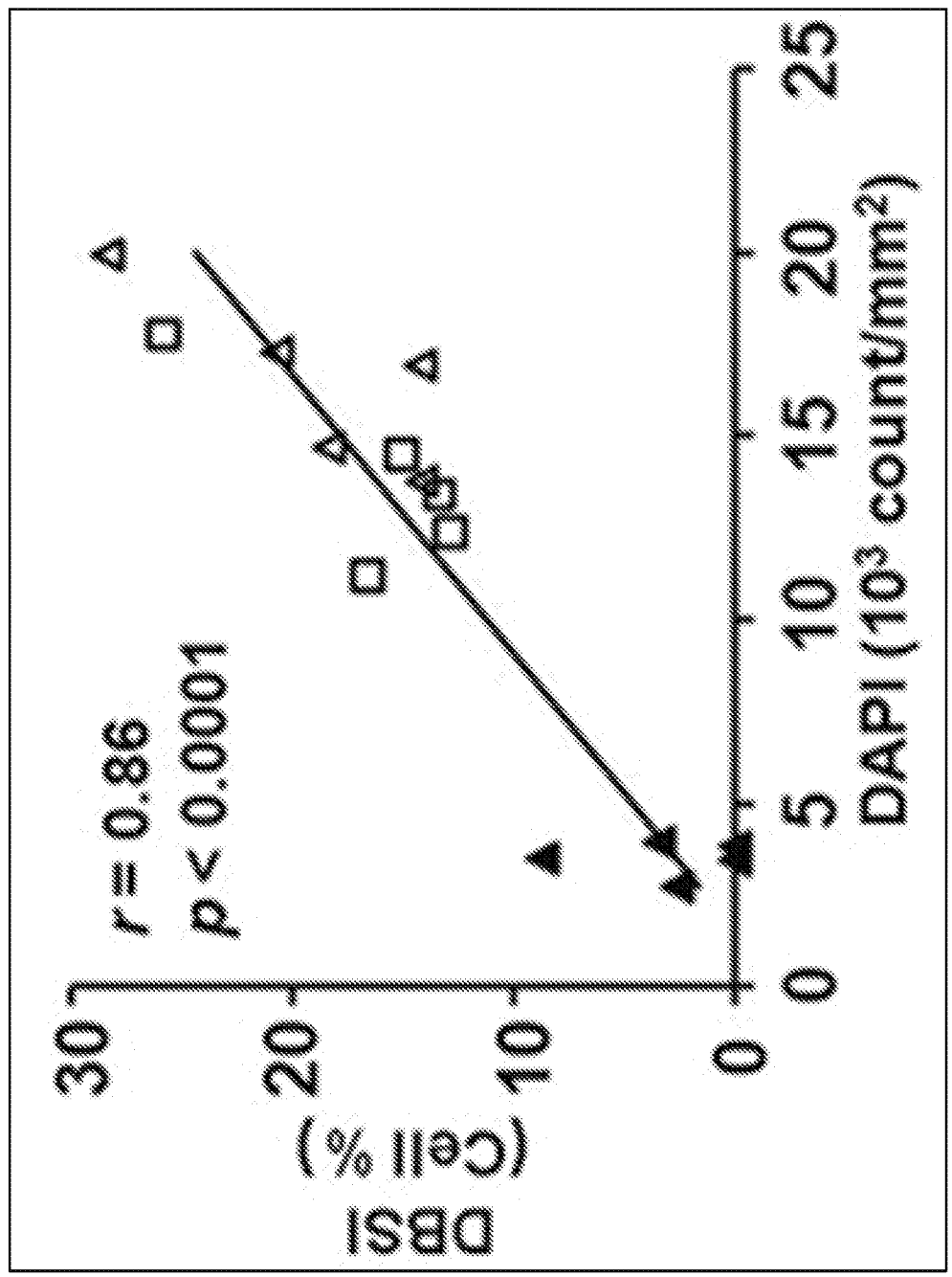
FIG. 69 shows DBSI-derived cell fraction correlates with numbers of microglia and astrocytes.

The first indication supporting DBSI neuroinflammation biomarker correlation with histological findings is that DBSI-derived cell fractions are consistent with histopathology in a mouse model of neuroinflammation. To assess correlation between the DBSI neuroinflammation biomarker and histopathology in an in vivo model, age-matched male mice were fed either control diet or a diet containing 0.2% cuprizone for four weeks beginning at eight weeks of age. This treatment resulted in infiltration of the brain with microglia and astrocytes, the same cell types as are involved in neuroinflammation in AD. MRI scans were performed on a 4.7T Varian DirectDrive spectrometer (Varian, Inc.) with the following parameters: maximal diffusion weighting factor, 1000 s/mm$^2$, TR=1.5 s, TE=36 ms, $\Delta$=20 ms, $\delta$=8 ms, 0.75 mm slice thickness, and 128×128 data matrix. After performing DBSI-MRI scans on these mice, their brains were sectioned in three regions of the corpus callosum and stained the sections with a nuclear dye to measure cellularity. FIG. 69 shows DBSI-derived cell fraction correlates with numbers of microglia and astrocytes. Data were collected from the control caudal (filled triangle), cuprizone-treated caudal (open triangle), and cuprizone-treated middle corpus callosum (open square). DBSI-derived cell fraction was then compared with the nuclear dye staining and found that they strongly correlated (FIG. 69), suggesting that the DBSI neuroinflammation biomarker (DBSI cell fraction) can accurately detect and quantify microglia and astrocytes. Additionally, these data suggest that DBSI neuroinflammation is representative of histologically determined neuroinflammation.

Figure 70:
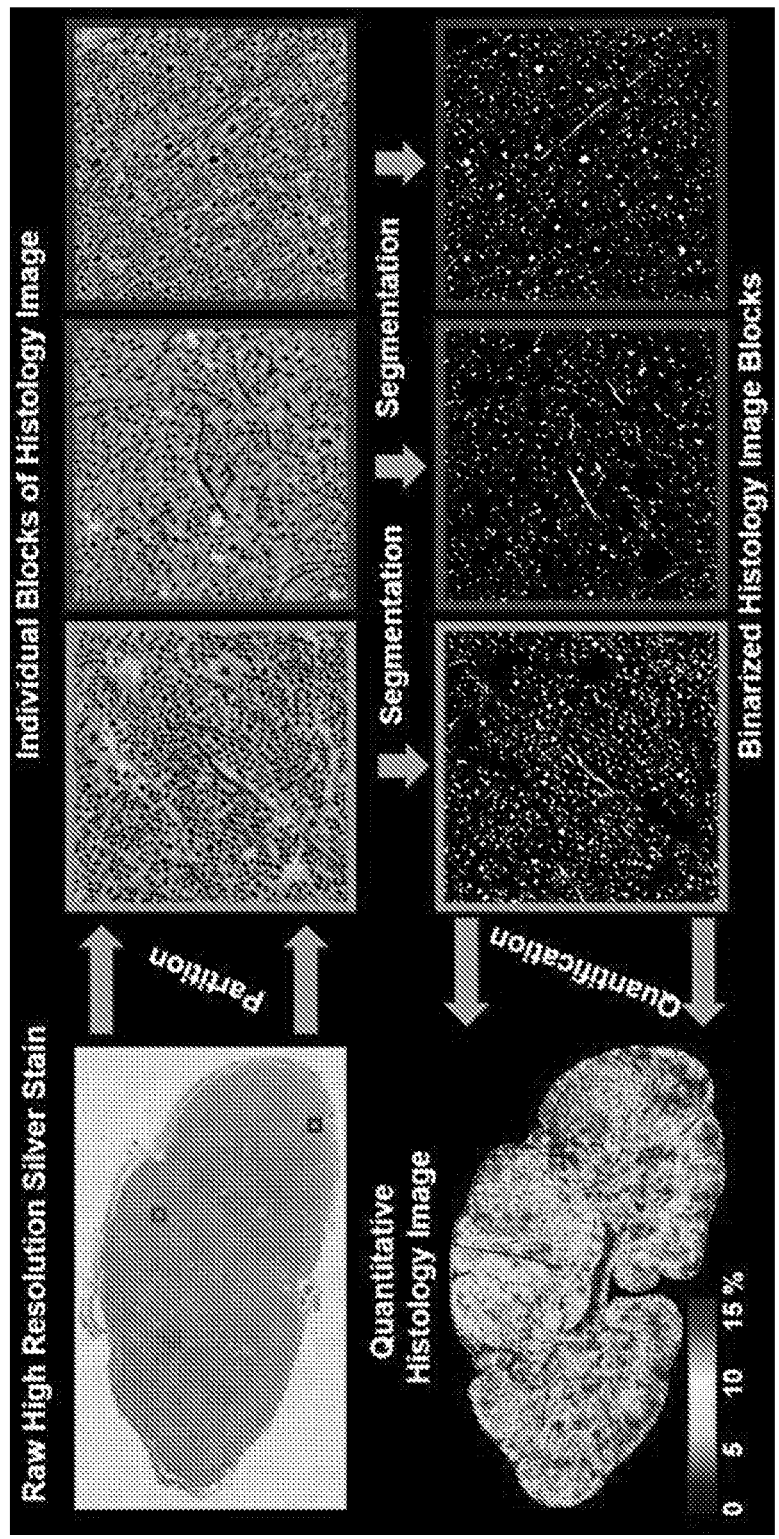
FIG. 70 shows an automatic processing pipeline developed to quantify whole-slide histological images.

The second indication that the DBSI neuroinflammation biomarker correlates with histological findings is that automatic image processing pipeline was able to analyze whole-slide histology images, quantify the positive stains, and characterize pathology severity and distribution. An automatic histology image processing software package was developed to quantify positive stains in human autopsy tissues. The raw histology images (human autopsy spinal cord) were down-sampled to MR image resolution (in plane 250 μm$^2$) (FIG. 70 top panels). Each down-sampled histology image block contained 1087×1087 pixels (in plane 0.23 μm$^2$) in the raw high-resolution image, and the positive stain areas were segmented on the basis of the color feature of the positive staining. The fraction of positively stained areas was computed as the ratio between the number of positive staining pixels and the total number of pixels (1087×1087) within the down-sampled histology block. With all blocks of histology images segmented and quantified, the software then generated a quantitative histology image (FIG. 70 bottom left). Application of this well-developed histology image processing pipeline to autopsy MS spinal cords was successful. In some embodiments, this pipeline may be adopted to detect and quantify microglia (IBA-1-positive) and astrocytes (GFAP-positive).

Figure 71:
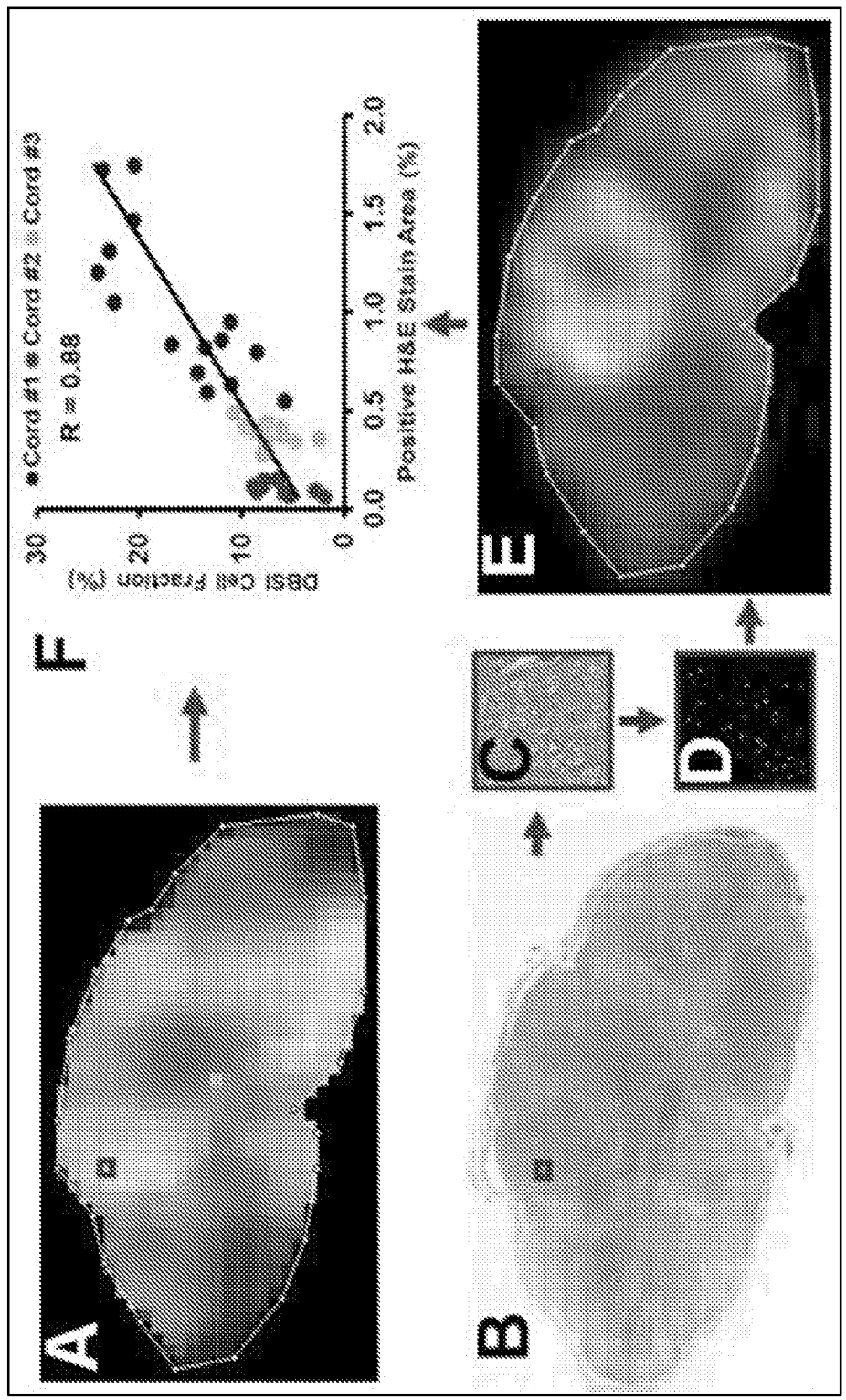
FIG. 71 shows DBSI-derived cell fraction mirrors histopathology in autopsy spinal cords.

The third indication that the DBSI neuroinflammation biomarker correlates with histological findings is that the DBSI-derived cell fraction from MS-affected spinal cords was consistent with histopathology. Three cervical cord specimens were obtained from deceased MS patients after autopsy and, within 10 hours, fixed them in 10% formalin in PBS at room temperature. FIG. 71 shows DBSI-derived cell fraction mirrors histopathology in autopsy spinal cords. FIG. 71(A) is a DBSI cell fraction image. FIG. 71(B) is an H&E staining image. FIG. 71(C) is a down-sampled H&E image block. FIG. 71(D) is a segmented positive stain area. FIG. 71(E) is a quantitative positive H&E stain area image. FIG. 71(F) shows strong correlation between DBSI cell fraction and positive H&E stain. A segment of formalin-fixed cervical spinal cord was imaged and analyzed by DBSI to generate cell fraction images (FIG. 71A). Diffusion sensitizing gradients were applied in 99 directions as employed in human brain DBSI with the following parameters: max b-value=3200 s/mm$^2$, in-plane resolution, 125×125 μm$^2$. After DBSI, haematoxylin and eosin (H&E) staining was performed to detect cellularity (FIG. 71B) and then down-sampled the H&E images to DBSI spatial resolution (FIG. 71C). Positive stain was segmented (FIG. 71D), and the positive stain area was quantified to form a quantitative positive H&E stain area image (FIG. 71E). Image co-registration was performed to align DBSI cell fraction image (DBSI neuroinflammation image) and quantitative H&E image to allow voxel-wise correlation (FIG. 71F). 10-15 voxels in each spinal cord were selected to validate the accuracy of the DBSI cell fraction, which were found to be strongly correlated with area of nuclei detected by H&E stain (r=0.88). This result supports the premise that DBSI cell fraction correlates with histopathology in autopsied human CNS tissue.

The fourth indication that the DBSI neuroinflammation biomarker correlates with histological findings is that a Siemens Prisma 3T scanner provided high signal-to-noise ratio (SNR) diffusion MRI signals sufficient for DBSI analysis of autopsied brains. Because autopsy tissue has dramatically reduced T$_2$, obtaining high quality diffusion weighted images of human autopsy brain has been a challenge. Siemens 3T MAGNETOM Prisma scanners have stronger gradients (80 mT/m) and faster slew rate (200 T/m/s) than the previous generation of 3T MRI scanners, effectively reducing echo time and dramatically increasing the SNR of diffusion MRI images. Compared to the noisy DTI-derived fractional anisotropy (FA) map obtained on an older Siemens 3T TIM Trio scanner (shortest TE 120 ms, TR 9200 ms, 15 minutes scan, 2×2×2 mm$^3$ resolution, max b-value 3500 s/mm$^2$, 55 diffusion directions) (FIG. 72A), the SNR was dramatically improved in the DTI-derived FA map obtained from the new Prisma scanner (shortest TE 72 ms, TR 7800 ms, 13 minutes scan, 2×2×2 mm$^3$ resolution, max b-value 3500 s/mm$^2$, 55 diffusion directions) (FIG. 72B). The significantly improved signal quality not only enables more accurate whole brain tractography (FIGS. 72 C&D), but more importantly, allows for accurate DBSI neuroinflammation quantification as described herein.

Given current estimates of autopsy participation and expiration rates in the TR, it is estimated that 50 human brains will come to autopsy each year (250 over 5 years). In some embodiments, both imaging and histopathology may be performed on an independent sample of 10 autopsy specimens selected per year over a five year period (50 total) to undergo DBSI-MRI (after formalin fixation but before sectioning). Brain specimens may be selected on the basis of time to autopsy and quality of the specimen by neuropathologist assessment and will be equally split between the four diagnostic categories described above.

Figure 73:
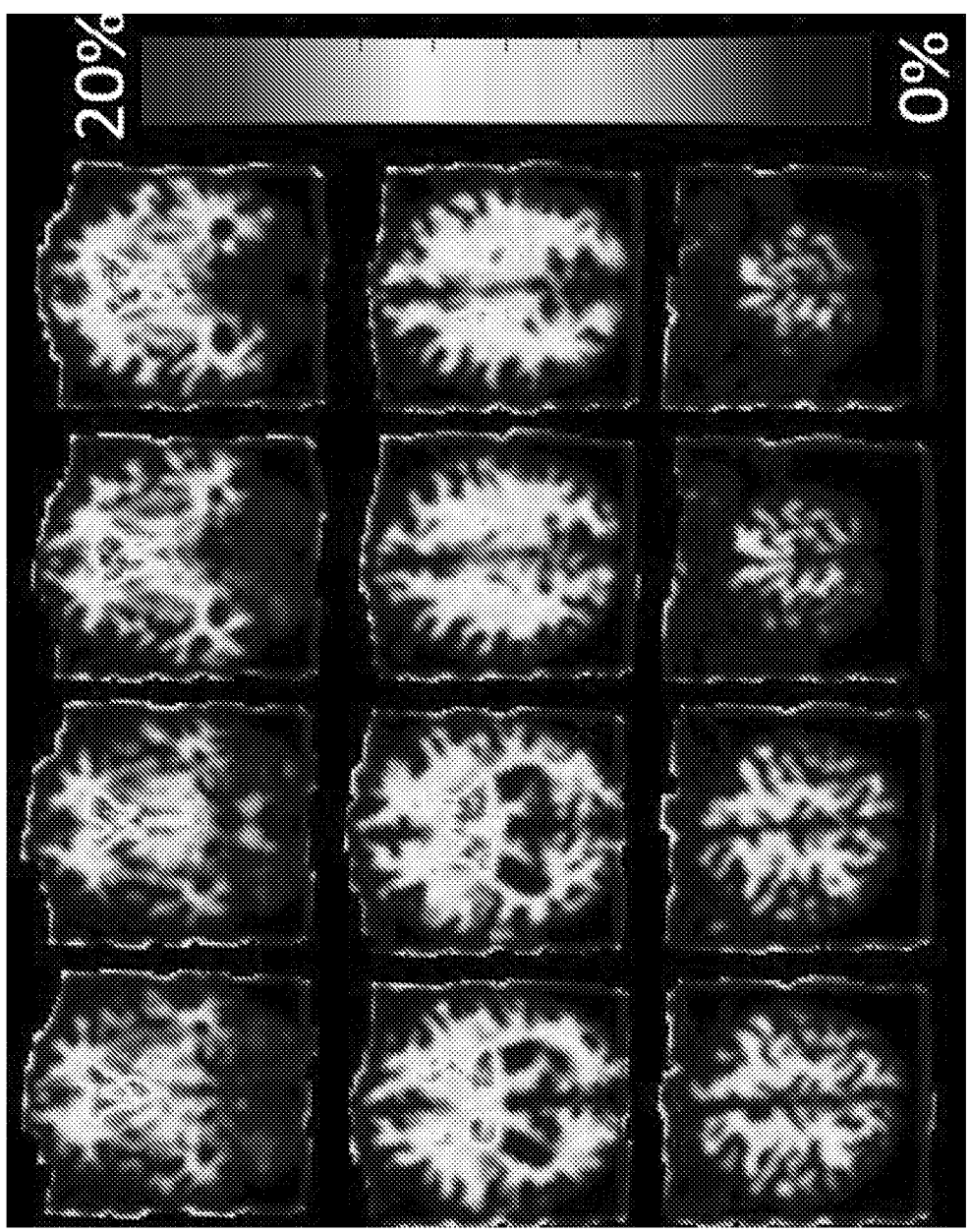
FIG. 73 shows DBSI neuroinflammation (cell fraction) images of autopsy AD brain (CDR=2).

Regarding ex vivo DBSI, in some embodiments the autopsy brains may be examined on the Siemens Prisma 3T MRI. Whole brain specimens fixed with 10% formalin may be placed in a plastic container and scanned at room temperature using a 32 channel head coil (as in FIG. 73). Acquisition parameters for autopsy brain DBSI-MRI include: TR 7800 ms, TE 72 ms, slice thickness 1 mm, number of slices 60, field-of-view 25.6×25.6 cm$^2$, number of average 10, data matrix 256×256, resulting in 1×1×1 mm$^3$ resolution. Diffusion sensitizing gradients may be applied in 99 directions as employed in human brain DBSI with max b-value=3200 s/mm$^2$. Scans may be repeated overnight for up to 10 hours of total imaging time to acquire sufficient SNR for DBSI analysis.

In some embodiments, sectioning and staining protocol for autopsy AD brain specimens may include embedding and sectioning the formalin-fixed brain after diffusion MRI. Grey and white matter ROIs may be generated from the ex vivo DBSI-MRI imaging and applied to pathology. In addition, all standard sections assessed by the Neuropathology Core of the Knight ADRC (Core Leader Nigel Cairns) may be aligned to the DSBI MRI and reverse ROIs may be generated. Thus, ROIs may be generated independently by imaging and by histology and matched for analysis, as described above and shown in FIG. 70. Neuroinflammation in tissue sections may be individually assessed by using immunohistochemistry to detect activated astrocytes and microglia: GFAP and IBA-1 immunohistochemistry. This can be assessed by area fraction measures. In some embodiments, images may be acquired, for example, with a Hamamatsu NanoZoomer 2.0-HT System (Hamamatsu).

In some embodiments, histology images of each tissue section may be loaded and analyzed with MatLab® and image J (http://rsbweb.nih.gov/ij/) for the purpose of validation of DBSI-detected neuroinflammation by immunohistochemistry. In addition to the pipeline described above, particle analysis plugin may be used to quantify positive stains in histology images. Histology images and DBSI maps may be co-registered with ImageJ as previously described. Voxel-based correlation within all tissue sections may be conducted to compare/correlate positive immunohistochemistry staining with DBSI cell fraction to examine inflammation severity.

In some embodiments, exploratory analyses may be performed to determine the correlation of DBSI (neuroinflammation index and edema index) with IBA-1 and GFAP staining conducted to stain inflammatory cells (microglia, astrocytes, etc.) using the ex vivo imaging protocol. Similar analytic approaches as described above may be implemented. Power analyses may or may not be performed.

In instances when there are insufficient numbers of brains to autopsy to correlate actual in vivo and postmortem correlations, some embodiments may involve repeating the DBSI-MRI on post-mortem samples. In some embodiments, the larger number of existing autopsy specimens may be used as an alternative. Should any of the participants from the in vivo DBSI study come to autopsy, additional analysis maybe performed comparing the in vivo DBSI to the ex vivo DBSI. In some embodiments, exact co-registration between MRI and histology images may be challenging due to introduction of tissue deformation and breakage by the staining procedure that may not be present in MRI images. In these embodiments, ROIs may be manually selected based on clear anatomical landmarks on both MRI and histological images. Additionally, in some embodiments potential errors may stem from a large difference in spatial resolution of the whole brain DBSI-MRI for the autopsy specimens and histology. In these embodiments, where the imaging-histology correlations are more difficult than anticipated, repeat DBSI-MRI scans may be performed on small sections using the high field small animal scanners (as shown in FIG. 71). DBSI metrics may be strongly non-Gaussian, in which case generalized linear models can be used to analyze the metrics in quantiles.

In summary, DBSI neuroinflammation biomarker (cell fraction) (1) can be robustly reproduced and can detect early pathological changes in AD, (2) correlates with in vivo markers of neuroinflammation, including CSF YKL-40 and PK11195 PET, (3) increases longitudinally in participants who convert from CN to dementia, and (4) corresponds to regional inflammatory cell infiltrates at autopsy. Development of accurate and robust DBSI biomarkers specific to neuroinflammation can significantly improve the understanding of the role of neuroinflammation in AD pathogenesis and provide attractive neuroimaging surrogates that are relevant for early diagnostics and testing of new disease-modifying therapies targeting the immune response.

V. Utility of the DBSI Biomarker with Respect to White Matter Cellularity Change and Damage Correlation with CSF Biomarkers in Preclinical and Early Symptomatic AD Both white matter (WM) inflammation and damage are known to occur early and jointly contribute to Alzheimer disease (AD) progression. However, the imaging techniques capable to noninvasively and simultaneously detect WM inflammatory cellularity changes and damage are still lacking. A novel diffusion magnetic resonance imaging (MRI) technique, diffusion basis spectrum imaging (DBSI), is disclosed herein to image and quantify the severity and spatial distribution of WM inflammation and degeneration in Multiple Sclerosis patients and animal models without using contrast agents or radioactive tracer. DBSI and Cerebrospinal fluid biomarkers were assessed for three groups of preclinical and early symptomatic AD patients: 140 cognitively normal healthy controls with negative cerebrospinal fluid (CSF) markers of AD pathologies, 34 cognitively normal preclinical AD participants with positive CSF marker of amyloid plaque, and 26 cognitively impaired participants in the early symptomatic AD with positive CSF markers of AD pathologies. Among the three groups, DBSI found significant WM cellularity changes, predominately manifested as increased cellularity diffusivity and unchanged cellularity fraction, suggesting the early immune cell activation without infiltration. The increased cellularity diffusivity detected by DBSI correlated with CSF measure of amyloid plaque severity, consistent with previous findings that amyloid deposition may induce immune cell activation. WM damage was also detected by DBSI and correlated with CSF measure of tau pathology. Interestingly, the significant change of WM cellularity was observed in both preclinical group and early symptomatic AD group, while WM damage was only observed in the early symptomatic AD group. The beneficial, protective effect of WM inflammation to clean abnormal amyloid deposition in preclinical AD stage is disclosed herein, as is the toxin/damage effect when the WM inflammation lasts and becomes chronic in early symptomatic phase of the disease. WM inflammation and damage can be simultaneously detected by DBSI in the preclinical and early symptomatic phase of AD, and provides a novel tool to study the individual and composite roles of inflammation and WM damage in early disease progression, and to quantify the efficacy of treatments targeting immune response or neuroprotection.

Alzheimer disease (AD) leads to impaired memory and cognition, and ultimately, to dementia with associated loss of independence, causing a heavy personal toll on patients and families. AD is currently estimated to afflict 5 million people in the United States, with an expected increase to 13 million by the year 205. The annual cost of care for patients with AD in 2014 was over $214 billion and is predicted to reach $1 trillion by 2050 unless disease-modifying treatments are developed. Understanding AD pathology has significantly improved with the development of cerebrospinal fluid (CSF) biomarkers (such as beta-amyloid 42 [$A\beta_{42}$], total tau [t-tau] and phosphorylated tau 181 [$ptau_{181}$]), and positron emission tomography (PET) imaging of $A\beta$ and tau pathology. A large body of evidence has supported the "Amyloid hypothesis" that dysregulation of $A\beta$ metabolism and the associated aggregation of $A\beta$ into amyloid plaque leads to synaptic dysfunction and neuronal death. Thus, numerous therapies specifically targeting $A\beta$ have been tested in the past two decades. However, more than 100 candidate treatment compounds have failed to meet their clinical endpoints, leading to increasing interest in other contributors, such as accumulation of inflammation or intracellular tau fibrils.

Several lines of evidence point to the involvement of inflammation and white matter (WM) damage in early AD and disease progression. First, cognitively normal individuals who chronically use non-steroidal anti-inflammatories have fewer activated microglia and lower risk of AD than non-users. Second, fibrillary $A\beta$ stimulates a classical proinflammatory response in microglia, which can be visualized in AD patients and may be present in preclinical AD. Third, $A\beta$ fragments can trigger and promote marked inflammatory responses in the brain. Fourth, a recent study of autosomal dominant AD suggested that astrocyte activation occurs in presymptomatic AD, indicating that inflammatory astrocytosis may contribute to early symptomatic AD pathology. Finally, histopathological analysis has shown that $A\beta$-positive individuals with dementia have higher levels of inflammatory glia activation than cognitively normal individuals at the time of death. Accordingly, accurate and robust markers specific for inflammation in AD are needed.

Disclosed herein is a novel multi-parametric diffusion MRI technique, diffusion basis spectrum imaging (DBSI), to simultaneously detect and quantify WM inflammation and damage in the central nervous system. DBSI-derived cellularity fraction has been demonstrated to be closely correlated with inflammatory cell infiltration in multiple sclerosis. Cellularity diffusivity has also been associated with cell size changes; therefore it can be potentially employed as a marker for immune cell activation. Moreover, the DBSI derived FA, axial, radial and mean diffusivities are more specific and accurate in reflecting WM pathologies than DTI counterparts according to those studies.

In order to better understand the role of WM inflammation and degeneration in the pathogenesis and disease progression of AD, DBSI was applied to a clinical 24-direction, multiple b values diffusion MRI dataset from healthy controls (w/negative CSF markers of AD pathologies and normal cognition), participants with preclinical (asymptomatic) AD (w/positive CSF marker of amyloid plaque and normal cognition), and participants with early symptomatic AD (w/positive CSF marker of AD pathologies and impaired cognition). DBSI simultaneously quantified WM cellularity change and damage in all participants. The correlations between DBSI-derived indices and CSF markers of AD pathologies were examined to assess the relationship between WM inflammation, degeneration and AD amyloid and tau pathologies.

Two hundred participants were enrolled in longitudinal studies of memory and aging at the Knight Alzheimer disease Research Center at Washington University School of Medicine (St Louis, Mo., USA). Details of recruitment and assessment have been published elsewhere. The Human Research Protection Office at Washington University approved all studies, and written informed consent was obtained from all participants. All individuals were evaluated by experienced clinicians using a semi-structured interview with a knowledgeable collateral source. Detailed neurological examinations of the participants were performed in accordance with the Uniform Data Set protocol of the National Alzheimer's Coordinating Center. A clinical diagnosis of symptomatic AD, where appropriate, was made in accordance with criteria developed by working groups from the National Institute on Aging and the Alzheimer's Association. Dementia was staged according to the global Clinical Dementia Rating (CDR). Healthy controls and preclinical AD participants were selected from the Adult Children Study, which is a longitudinal study of early stage AD biomarkers. The inclusion criteria were the following: participants were 45-74 years of age and had to be cognitively normal, defined as a CDR=0, and the participants had CSF measures of amyloid ($A\beta_{42}$), tau-related neuronal injury (total tau [t-tau]), and DBSI acquisition. The time between CSF measures and DBSI scab had to be within two years. Participants were classified as the healthy controls (n=140) if they were AD biomarker negative (CSF $A\beta_{42}$>459 pg/ml and t-tau<339 pg/ml) as defined in a previous study. Participants were classified as preclinical AD (n=34) according to NIA-AA criteria if they had positive CSF $A\beta_{42}$ (CSF $A\beta_{42}$<459 pg/ml) with normal cognition. Early symptomatic AD participants (n=26) were selected from the cohorts enrolled in the Healthy Aging and Senile Dementia study, which is designed to explore AD biomarker correlations in persons 65 years of age and older and had matched clinical and biomarker assessments comparable to the younger Adult Children Study cohort. The inclusion criteria were: participants had very mild dementia (CDR=0.5) and DBSI acquisition within two years of CSF collection, and the participants were diagnosed with dementia thought to be due to AD without other disease contribution (e.g., depression, cerebrovascular disease, etc.).

DNA was extracted from peripheral blood samples by standard procedures. Apolipoprotein E genotyping was performed as previously described. CSF (20-30 mL) was collected within 24 months of the imaging session by routine lumbar puncture using a 22-gauge atraumatic Sprotte spinal needle (Pajunk Medical Systems, Norcross, Ga., USA) after overnight fasting as previously described. Samples were gently inverted to avoid possible gradient effects, briefly centrifuged at low speed, aliquoted (0.5 mL) into polypropylene tubes, and frozen at −84° C. Samples were analyzed by ELISA for $A\beta_{42}$ t-tau and $ptau_{181}$ (INNOTEST; Fujirebio, formerly Innogenetics, Ghent, Belgium).

Diffusion MRIs were collected on 3T TIM Trio (Siemens, Erlangen, Germany) scanners with a 12-channel head coil equipped with parallel imaging. The imaging resolution was 2×2×2 mm. Repetition time (TR) and echo time (TE) were 14,500 ms and 112 ms, respectively. The 24-direction diffusion-encoding scheme (23 diffusion sensitized+1 unsensitized [$B_0$] volumes) was implemented for data acquisition. The maximal b-value was 1400 s/mm². Data were collected in two 6-minute runs using a single-shot diffusion-weighted echo planar imaging sequence. Diffusion-weighted images were registered to T1-weighted magnetization prepared rapid acquisition gradient echo (MPRAGE) and T2-weighted fast spin echo (T2 W-FSE) scans. The acquisition parameters for MPRAGE were the following: TR, 2400 ms; TE, 3.16 ms; inversion time, 1000 ms; imaging resolution, 1×1×1 mm. T2 W-FSE was acquired with the following parameters: TR, 3200 ms; TE, 455 ms; imaging resolution, 1×1×1 mm.

Figure 78:
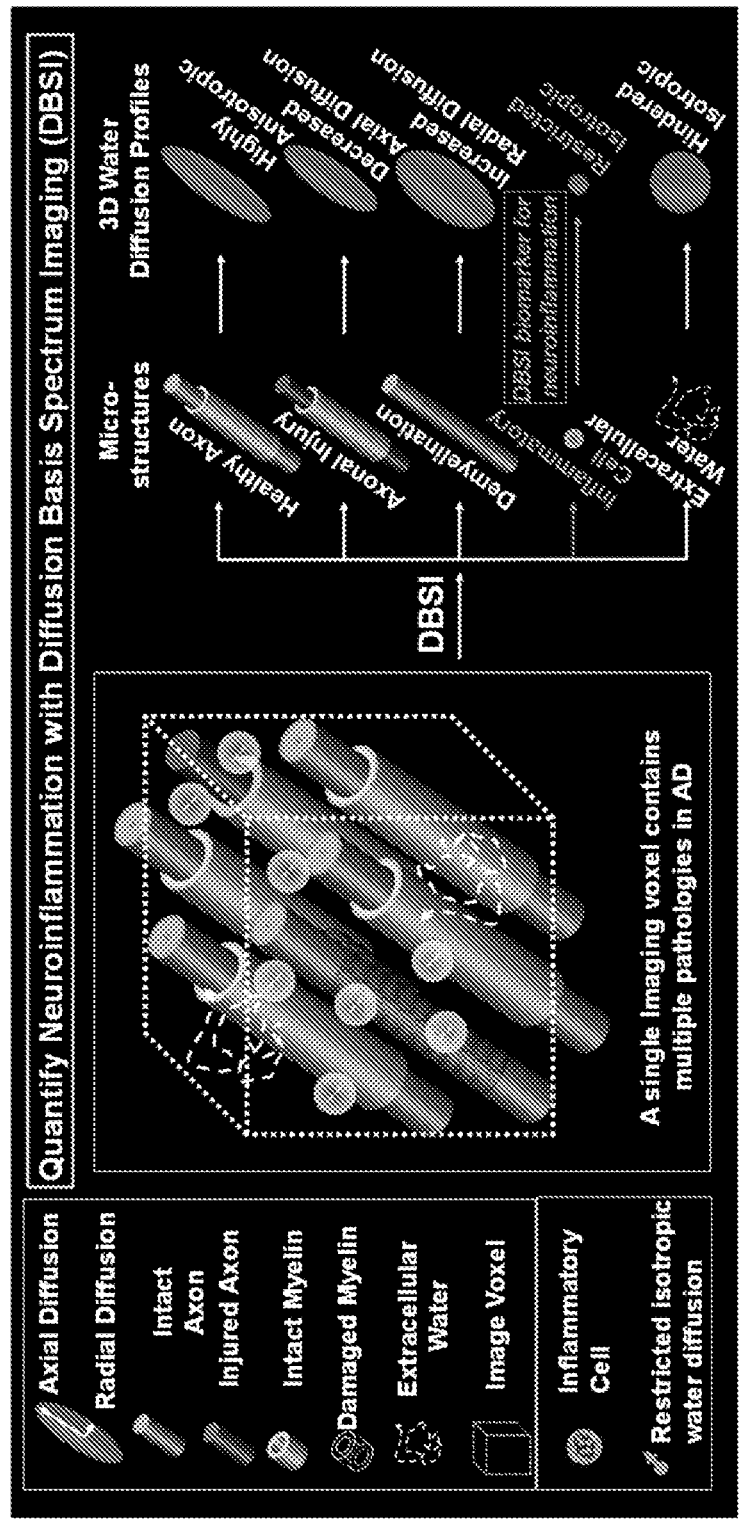
FIG. 78 shows a schematic illustration of DBSI differentiation between and quantification of potential pathological components.

Diffusion basis spectrum imaging (DBSI) has been developed to simultaneously detect and quantify WM inflammation and degeneration. In DBSI, each of the potential pathological components, including inflammatory cell components, extracellular water/vasogenic edema, neuronal injury/loss, and demyelination, within each voxel is modeled by a dedicated diffusion tensor (FIG. 78). FIG. 78 shows a schematic illustration of DBSI differentiation between and simultaneous quantification of potential pathological components (left) by modeling each with a dedicated diffusion tensor (blue ellipsoids at right). The restricted isotropic component derived by DBSI is the marker of inflammation (orange). The weighted sum of all sub-voxel pathological components describes the composition of pathological components. The isotropic diffusion components are defined to represent restricted isotropic diffusion (associated with cell components) by using a tentative threshold of isotropic diffusivity of 0.3 $\mu m^2/ms$, based on previous animal study findings. Unlike DTI and other advanced diffusion MRI approaches, DBSI can detect and quantify the unique restricted isotropic signal signature reflecting inflammatory cells by excluding the confounding effects from the anatomical complexity and WM degeneration. Diffusion measurements with multiple directions and weightings are required for DBSI to provide unique solution. Regularized nonnegative least-squares analysis incorporating a priori information of nonnegative signal intensities fraction and finite signal energy are employed to prevent over-fitting to the noisy data while retaining the accuracy of the DBSI solution. By solving the DBSI model, the infiltrated inflammatory cellularity fractions described by DBSI-derived cellularity fraction, the inflammatory cell activation (might be microglia/astrocytes activation in AD) described by DBSI-derived cellularity diffusivity and WM integrity described by DBSI-derived FA, axial, radial and mean diffusivities are accurately quantified.

The 24 diffusion-weighted images in one dataset were motion-corrected by using an iterative procedure. The final resampling step output 24 volumes registered with the $B_0$ volume of the first acquired diffusion-weighted imaging dataset. The two runs were averaged together to obtain a better signal-to-noise ratio. All datasets were also computed by a DBSI multi-tensor model analysis package developed in-house with Matlab (MathWorks). Maps of DBSI-derived cellularity fraction, cellularity diffusivity, FA, axial, radial and mean diffusivities were generated as well.

The whole-brain voxel-wise DBSI-derived indices were analyzed by using Tract Based Spatial Statistics (TBSS) (available in FSL, http://www.fmrib.ox.ac.uk/fs1). DBSI-derived FA images were slightly eroded, so the boundary image slices were excluded to remove possible outliers caused by the poor diffusion tensor fitting at the edges. Participants' FA data was aligned into a common space by using the nonlinear registration tool FNIRT. A mean FA image was then created and thinned to create a mean FA skeleton that represents the centers of all tracts common to the group. Each participant's aligned FA data and other DBSI-derived indices were projected onto this skeleton for statistical analyses. Nonparametric permutation tests were used for voxel-wise statistical analysis of the individual FA skeletons among the healthy controls, the preclinical AD and the early symptomatic AD cohorts. The voxel-wise correlations between DBSI-derived indices and CSF markers of AD pathologies (CSF $A\beta_{42}$ and t-tau) were generated through TBSS. The significance threshold for group differences and correlations was set at $P<0.05$, corrected for multiple comparisons by using a family-wise error correction across voxels by using the threshold-free cluster-enhancement option in Randomise 2.0 in FSL. Identification of the abnormal WM tracts revealed by TBSS was based on the atlas formulated at Johns Hopkins University (JHU). The statistical analyses performed by TBSS controlled for age, gender, and the presence of an APOE ε4 allele.

Continuous and categorical variables in characteristics between any two cohorts were compared by a Kruskal-Wallis test and the Fisher's Exact test, respectively. The least square means per group for each outcome were estimated after controlling for age, gender and APOE ε4 genotype. The partial correlation was also considered to measure the strength of a relationship between CSF measures and imaging metrics while controlling the effect of other variables. All statistical tests were two-sided with $\alpha=0.05$. SAS version 9.4 (Cary, N.C.) was used to perform all statistical analyses.

Demographic data is summarized in Table 7. The retrospective cohort included 140 cognitively normal healthy control participants (CSF biomarker negative), 34 cognitively normal individuals with preclinical AD (CSF $A\beta_{42}$ positive), and 26 participants with early symptomatic AD (clinical dementia rating 0.5) (CSF $A\beta_{42}$ positive, CSF t-tau positive). On average, the early symptomatic AD individuals were significantly older than the healthy controls and preclinical AD individuals, and the early symptomatic AD group included more male participants than the other two cohorts. Only 12.9% of the healthy controls carried at least one APOE ε4 allele, whereas 76.5% of the preclinical AD and 88.5% of the early symptomatic AD participants carried this allele. The CSF level of $A\beta_{42}$ in the healthy controls is significantly higher than that in the preclinical and early symptomatic AD. The CSF levels of t-tau and $ptau_{181}$ are significantly elevated in the early symptomatic AD, while no difference between the healthy controls and the preclinical AD participants.

TABLE 7

Characteristics of study participants.

| Characteristics | Healthy controls | Preclinical AD | Early symptomatic AD | P-value |
|---|---|---|---|---|
| n | 140 | 34 | 26 | |
| Clinical dementia rating (CDR) | 0 | 0 | 0.5 | |
| Age, years | 61.1 ± 8.1 | 62.6 ± 7.0 | 75.0 ± 5.7 | <0.001 |
| Male sex | 53 (37.9%) | 11 (32.4%) | 16 (61.5%) | <0.05 |
| ApoE e4+ | 18 (12.9%) | 26 (76.5%) | 23 (88.5%) | <0.001 |
| CSF $A\beta_{42}$ (pg/ml) | 786.1 ± 200.7 | 375.3 ± 76.1 | 325.1 ± 71.9 | <0.001 |
| CSF t-tau (pg/ml) | 206.9 ± 61.2 | 228.8 ± 101.8 | 507.4 ± 240.6 | <0.001 |
| CSF $ptau_{181}$ (pg/ml) | 45.2 ± 17.8 | 50.1 ± 24.7 | 86.4 ± 44.3 | <0.001 |

Data are presented as mean (SD) or number (%).
Healthy controls: participants with >459 pg/ml Aβ42 and <339 pg/ml total tau in the cerebrospinal fluid (CSF) and with normal cognition (CDR = 0).
Preclinical AD: participants with <459 pg/ml Aβ42 in the CSF and with normal cognition (CDR = 0).
Early symptomatic AD: participants with <459 pg/ml Aβ42 in the CSF and with very mild AD dementia (CDR = 0.5).
ApoE ε4+, positive for at least one apolipoprotein E ε4-allele.

No voxel-wise statistic differences of the DBSI-derived cellularity fraction were found among the healthy controls, the preclinical and early symptomatic AD cohorts. As an example, the averaged DBSI-derived cellularity fraction in the region of genu of corpus callosum is 4.5% (±1.1%) for the healthy controls, 4.5% (±0.8%) for the preclinical AD and 4.4% (±1.3%) for the early symptomatic AD.

Figure 74:
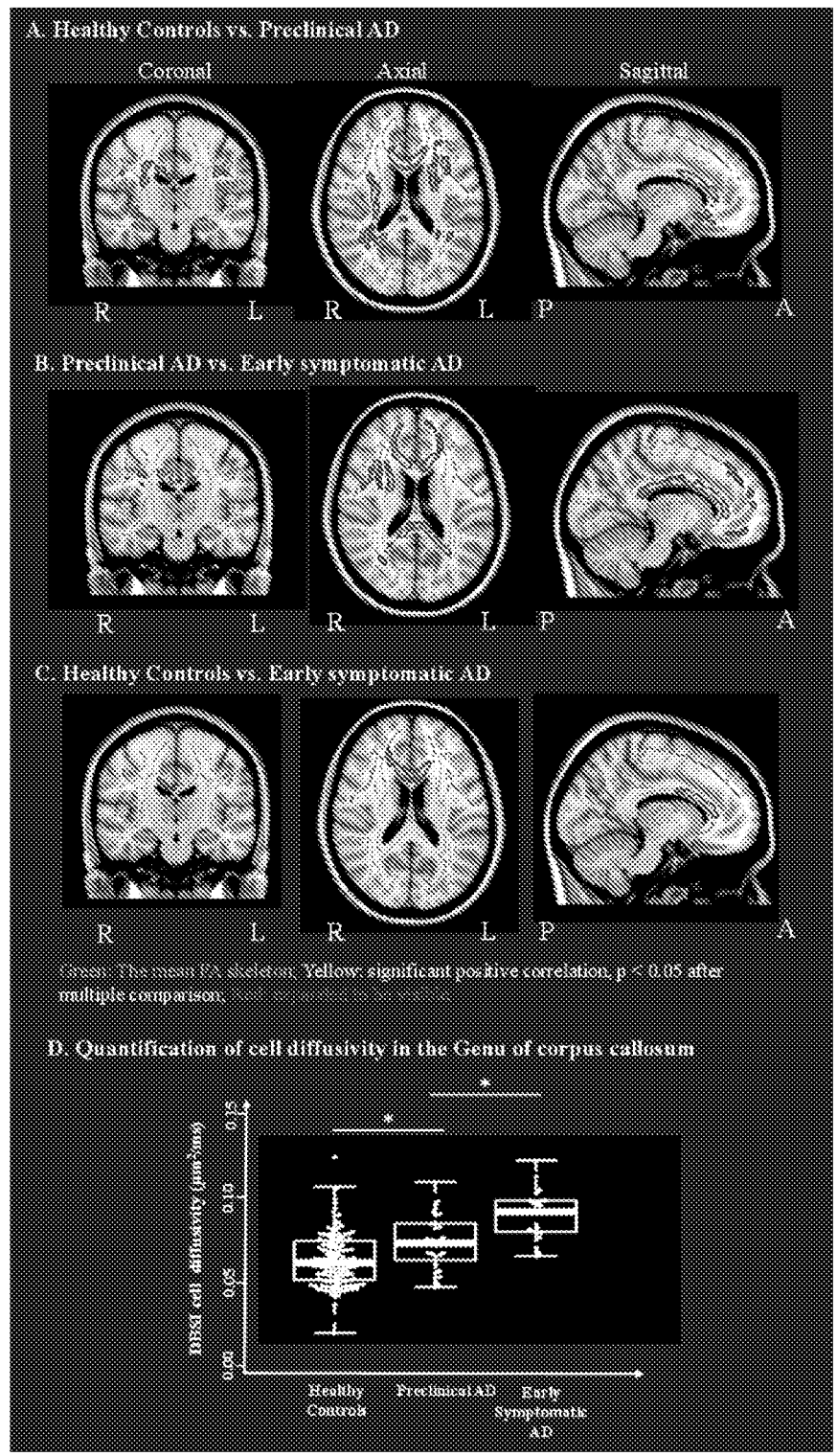
FIG. 74 shows DBSI-detected cellularity diffusivity in brain images for preclinical AD, early symptomatic AD, and healthy control participants.

Elevated DBSI-derived cellularity diffusivity was found in the preclinical AD cohort when compared to the healthy controls in the major WM tracts such as corpus callosum, internal capsule, corona radiata and cingulum etc. (FIG. 74 and Table 8). FIG. 74 shows diffusion basis spectrum imaging (DBSI) detects increased cellularity diffusivity in the preclinical AD and in the early symptomatic AD when compared to the healthy control participants. Coronal, axial and sagittal views show the voxels (red/yellow clusters, expanded to be visible) in which DBSI-derived cellularity diffusivity significantly (P<0.05) increased (1) in the preclinical AD after multiple comparison when compared to the healthy controls cohort (A), (2) in the early symptomatic AD cohort when compared to the preclinical AD cohorts (B) and (3) in the early symptomatic AD cohort when compared to the healthy controls cohort (C). The mean FA skeleton (green) representing the centers of all WM tracts common to participants was overlaid on the Montreal Neurological Institute standard space brain T1-weighted image. (D) Boxplot demonstrates that the DBSI-derived cellularity diffusivity in the region of genu of corpus callosum is significantly increased in the preclinical AD and further significantly increased in the early symptomatic AD when compared to that in the healthy controls cohort. Thick lines indicate means, boxes indicate $25^{th}$ to $75^{th}$ percentiles, and thin lines indicate $5^{th}$ and $95^{th}$ percentiles. The age, gender, and ApoE ε4 genotype were controlled for in computing the statistical significance of differences. L, left hemisphere; R, right hemisphere; P, posterior; A, anterior; *P<0.05.DBSI-derived cellularity diffusivity was significantly increased in the early symptomatic AD cohort when compared to those in the preclinical AD and healthy controls in some major WM tracts (FIG. 74 and Table 8). In the corpus callosum and corona radiata tracts, the gradient increasing of the DBSI-derived diffusivity was found among the three cohorts. The significant voxels common to all participants in the genu of corpus callosum were extracted to demonstrate there was a significantly increasing DBSI-derived cellularity diffusivity in the preclinical AD when compared to the healthy controls, and the further increasing of this index in the early symptomatic AD cohort (P<0.05) (FIG. 74).

TABLE 8

| WM Tracts | DBSI cellularity diffusivity | | | DBSI FA | | | DBSI radial diffusivity | | |
|---|---|---|---|---|---|---|---|---|---|
| | HC vs. PC | PC vs. EAD | HC vs. EAD | HC vs. PC | PC vs. EAD | HC vs. EAD | HC vs. PC | PC vs. EAD | HC vs. EAD |
| Middle cerebellar peduncle | — | — | — | — | ↓ | — | — | — | — |
| Pontine crossing tract | — | — | — | — | ↓ | — | — | — | — |
| Genu of corpus callosum | ↑ | ↑ | ↑ | — | ↓ | ↓ | — | ↑ | ↑ |
| Body of corpus callosum | ↑ | ↑ | ↑ | — | ↓ | ↓ | — | ↑ | ↑ |
| Splenium of corpus callosum | ↑ | ↑ | ↑ | — | ↓ | ↓ | — | ↑ | ↑ |

TABLE 8-continued

| WM Tracts | DBSI cellularity diffusivity | | | DBSI FA | | | DBSI radial diffusivity | | |
|---|---|---|---|---|---|---|---|---|---|
| | HC vs. PC | PC vs. EAD | HC vs. EAD | HC vs. PC | PC vs. EAD | HC vs. EAD | HC vs. PC | PC vs. EAD | HC vs. EAD |
| Fornix (column and body of fornix) | — | — | — | — | — | — | — | — | — |
| Corticospinal tract | — | — | — | — | ↓ | — | — | — | — |
| Medial lemniscus | — | — | — | — | ↓ | — | — | — | — |
| Inferior cerebellar peduncle | — | — | — | — | ↓ | — | — | — | — |
| Superior cerebellar peduncle | — | — | — | — | ↓ | — | — | — | — |
| Cerebral peduncle | — | — | — | — | ↓ | ↓ (L) | — | ↑ (L) | — |
| Anterior limb of internal capsule | ↑ (L) | ↑ (R) | — | — | ↓ | ↓ | — | ↑ | — |
| Posterior limb of internal capsule | ↑ | — | — | — | ↓ | ↓ | — | ↑ | ↑ (L) |
| Retrolenticular part of internal capsule | ↑ (R) | — | — | — | ↓ | ↓ | — | ↑ | ↑ (R) |
| Anterior corona radiata | ↑ | ↑ | ↑ | — | ↓ | ↓ | — | ↑ | ↑ |
| Superior corona radiata | ↑ | ↑ (R) | ↑ (R) | — | ↓ | ↓ | — | ↑ | ↑ |
| Posterior corona radiata | ↑ | ↑ | — | — | ↓ | ↓ | — | ↑ | ↑ |
| Posterior thalamic radiation | ↑ (R) | ↑ | — | — | ↓ | ↓ | — | ↑ | ↑ |
| Sagittal stratum | ↑ (R) | — | — | — | ↓ | ↓ | — | ↑ | ↑ (R) |
| External capsule | ↑ | ↑ (R) | — | — | ↓ | ↓ | — | ↑ | ↑ |
| Cingulum (cingulate gyrus) | — | ↑ | — | — | ↓ | ↓ | — | ↑ | ↑ |
| Cingulum (hippocampus) | — | — | — | — | ↓ | ↓ | — | ↑ (R) | ↑ (R) |
| Fornix (cres)/Stria terminalis | ↑ (R) | — | — | — | ↓ | ↓ | — | ↑ | ↑ (R) |
| Superior longitudinal fasciculus | ↑ | ↑ (R) | — | — | ↓ | ↓ | — | ↑ | ↑ |
| Superior fronto-occipital fasciculus | ↑- (L) | ↑ (R) | — | — | ↓ | ↓ | — | ↑ | ↑ |
| Uncinate fasciculus | — | — | — | — | ↓ | — | — | ↑ | ↑ (R) |
| Tapetum | ↑ | — | — | — | ↓ | ↓ | — | ↑ (R) | ↑ |

Significant negative correlation was found between CSF levels of Aβ$_{42}$ and DBSI-derived cellularity diffusivity in major WM tracts (FIG. 74 and Table 9). Partial correlations were also examined between DBSI imaging markers and CSF Aβ$_{42}$ in those voxels that were significant in the genu of corpus callosum. When controlling with age, gender and ApoE ε4 genotype, the partial correlation with CSF Aβ$_{42}$ was $r_{partial}$=−0.39 (P<0.001) for DBSI-derived cellularity diffusivity.

TABLE 9

| WM Tracts | CSF Aβ42 DBSI-derived cellularity diffusivity | CSF Aβ42 DBSI-derived FA | CSF t-tau DBSI-derived FA | CSF ptau181 DBSI-derived radial diffusivity | CSF ptau181 DBSI-derived mean diffusivity |
|---|---|---|---|---|---|
| Middle cerebellar peduncle | N/A | N/A | N/A | N/A | N/A |
| Pontine crossing tract | N/A | N/A | N/A | N/A | N/A |
| Genu of corpus callosum | − | + | − | N/A | + |
| Body of corpus callosum | − | + | − | + | + |
| Splenium of corpus callosum | − | + | − | + | + |
| Fornix (column and body of fornix) | N/A | N/A | N/A | N/A | N/A |
| Corticospinal tract | N/A | N/A | N/A | N/A | N/A |
| Medial lemniscus | N/A | N/A | N/A | N/A | N/A |
| Inferior cerebellar peduncle | N/A | N/A | N/A | N/A | N/A |
| Superior cerebellar peduncle | N/A | N/A | N/A | N/A | N/A |
| Cerebral peduncle | − | N/A | N/A | N/A | N/A |
| Anterior limb of internal capsule | − | + | − | + | N/A |
| Posterior limb of internal capsule | − | + | − (L) | + | + |
| Retrolenticular part of internal capsule | − | + (L) | − | + | + |
| Anterior corona radiata | − | + | − | + (R) | N/A |
| Superior corona radiata | − | + | − | + | + |
| Posterior corona radiata | − | + | − | + | + |
| Posterior thalamic radiation | − | + (L) | − | + | + |
| Sagittal stratum | − | + (L) | − | + | + |
| External capsule | − | + | − | + | + |
| Cingulum (cingulate gyrus) | − | + (L) | − (R) | + | + |
| Cingulum (hippocampus) | N/A | − | − | N/A | N/A |
| Fornix (cres)/ Stria terminalis | − | (L) | − | + | + (L) |
| Superior longitudinal fasciculus | − | + | − | + | + |
| Superior fronto-occipital fasciculus | − | + | − | + (R) | N/A |
| Uncinate fasciculus | − | N/A | − | + | N/A |
| Tapetum | − | N/A | − | + | + |

Figure 76:
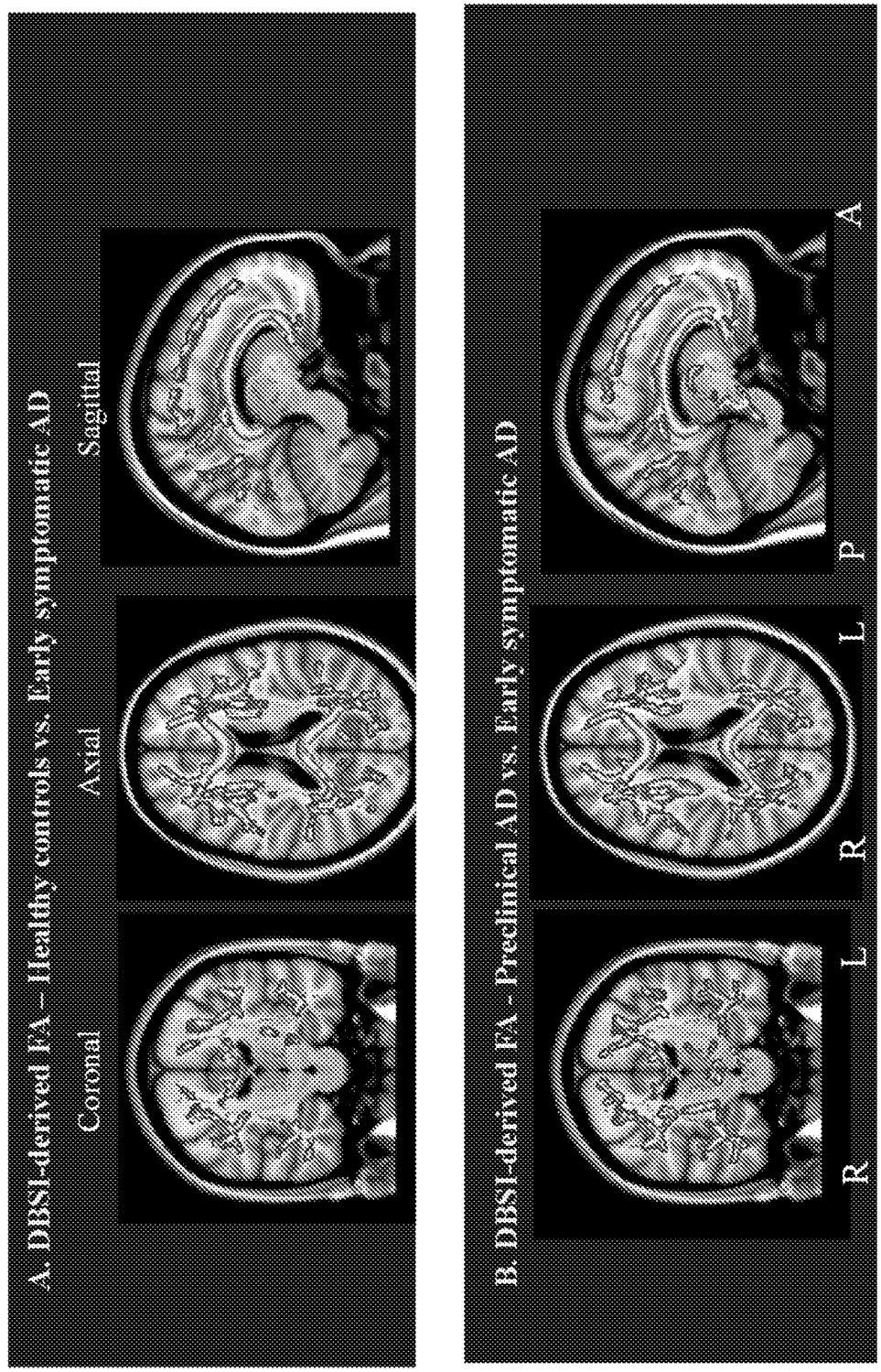
FIG. 76 shows DBSI-detected FA and radial diffusivity in brain images for preclinical AD, early symptomatic AD, and healthy control participants.
Figure 76:
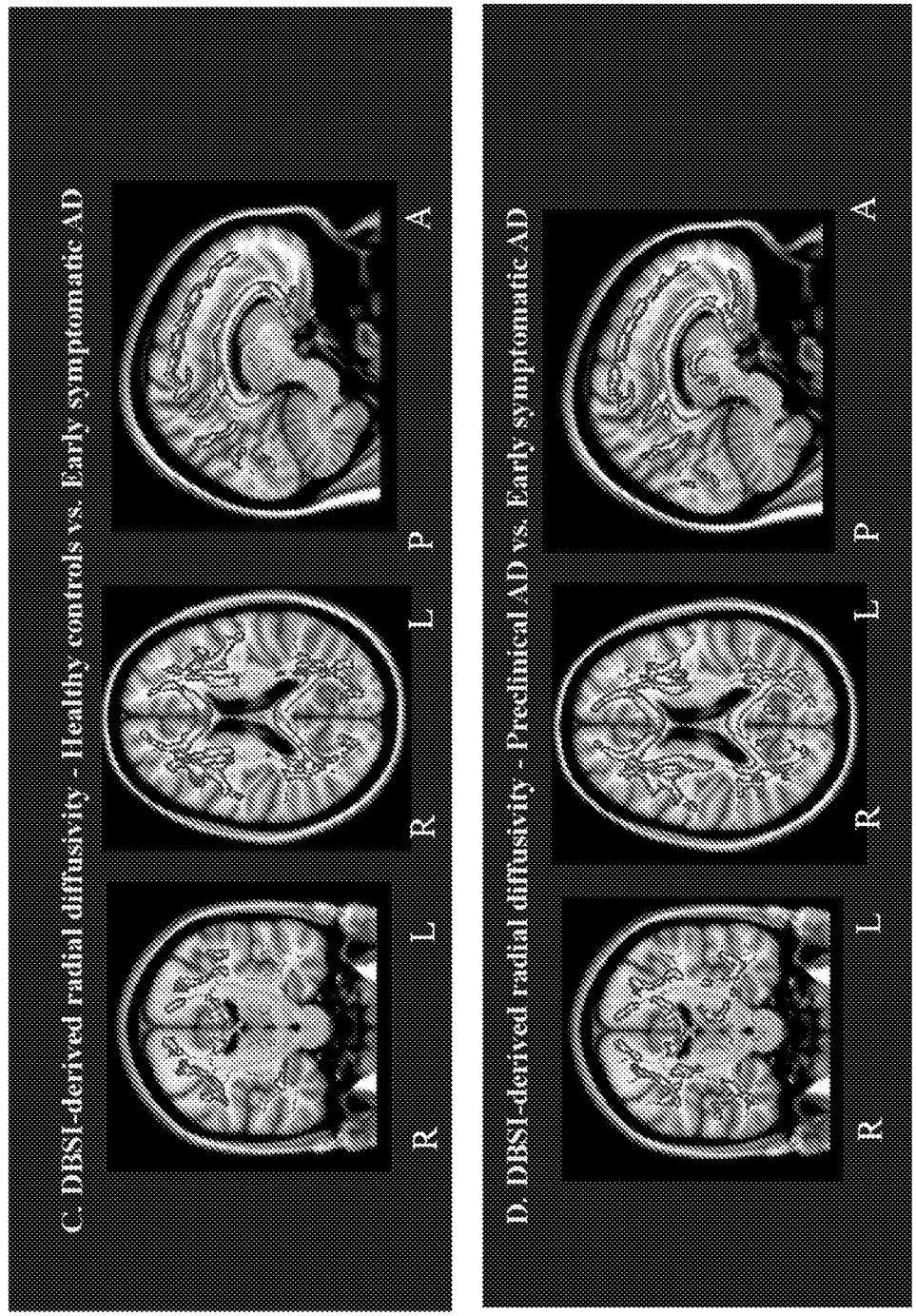
Figure 76:
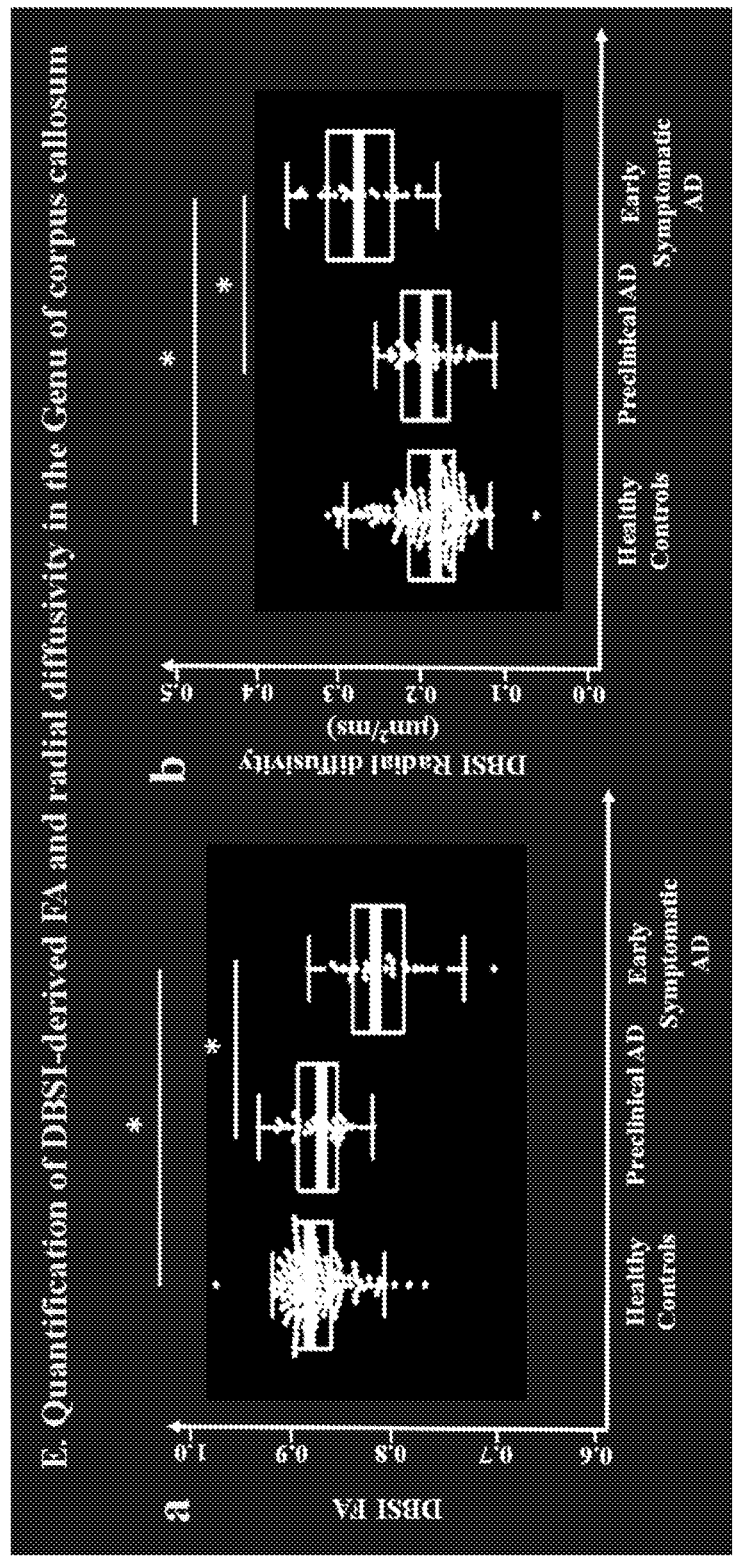

The significantly voxel-wise decrease of DBSI-derived FA was found in the early symptomatic AD cohort when compared to the healthy controls and the preclinical AD cohorts in most of the WM tracts (FIG. 76 and Table 8). FIG. 76 shows diffusion basis spectrum imaging (DBSI) detects decreased FA and increased radial diffusivity in the early symptomatic AD when compared to the preclinical AD and the healthy controls cohorts. Coronal, axial and sagittal views show the voxels (red/yellow clusters, expanded to be visible) in which (1) DBSI-derived FA diffusivity significantly (P<0.05) decreased in the early symptomatic AD after multiple comparison when compared to the healthy controls (A) and the preclinical AD (B) cohorts; (2) DBSI-derived radial diffusivity significantly increased in the early symptomatic AD cohort when compared to the healthy controls (C) and the preclinical AD (D) cohorts. The mean FA skeleton (green) representing the centers of all WM tracts common to participants was overlaid on the Montreal Neurological Institute standard space brain T1-weighted image. (E) Boxplot demonstrates that, in the region of genu of corpus callosum, the DBSI-derived FA (a) is significantly decreased and radial diffusivity (b) is significantly increased in the early symptomatic AD when compared to that in the preclinical AD and the healthy controls cohorts. Thick lines indicate means, boxes indicate $25^{th}$ to $75^{th}$ percentiles, and thin lines indicate $5^{th}$ and $95^{th}$ percentiles. The age, gender, and ApoE ε4 genotype were controlled for in computing the statistical significance of differences. L, left hemisphere; R, right hemisphere; P, posterior; A, anterior; *P<0.05. The significantly voxel-wise increase of DBSI-derived radial diffusivity was also found in the early symptomatic AD cohort when compared to the healthy controls and the preclinical AD cohorts in most of the WM tracts (FIG. 76 and Table 8). There were no differences of DBSI-derived FA and radial diffusivity between the healthy controls and the preclinical AD cohorts. The significant voxels common to all participants in the genu of corpus callosum were extracted to demonstrate there were a significant decrease of DBSI-derived FA (FIG. 76) and a significant increase of DBSI-derived radial diffusivity (FIG. 76) in the early symptomatic AD cohort when compared to the healthy controls and the preclinical AD cohorts (P<0.05). There were no any differences were found among the three cohorts for DBSI-derived axial and mean diffusivities.

Figure 77:
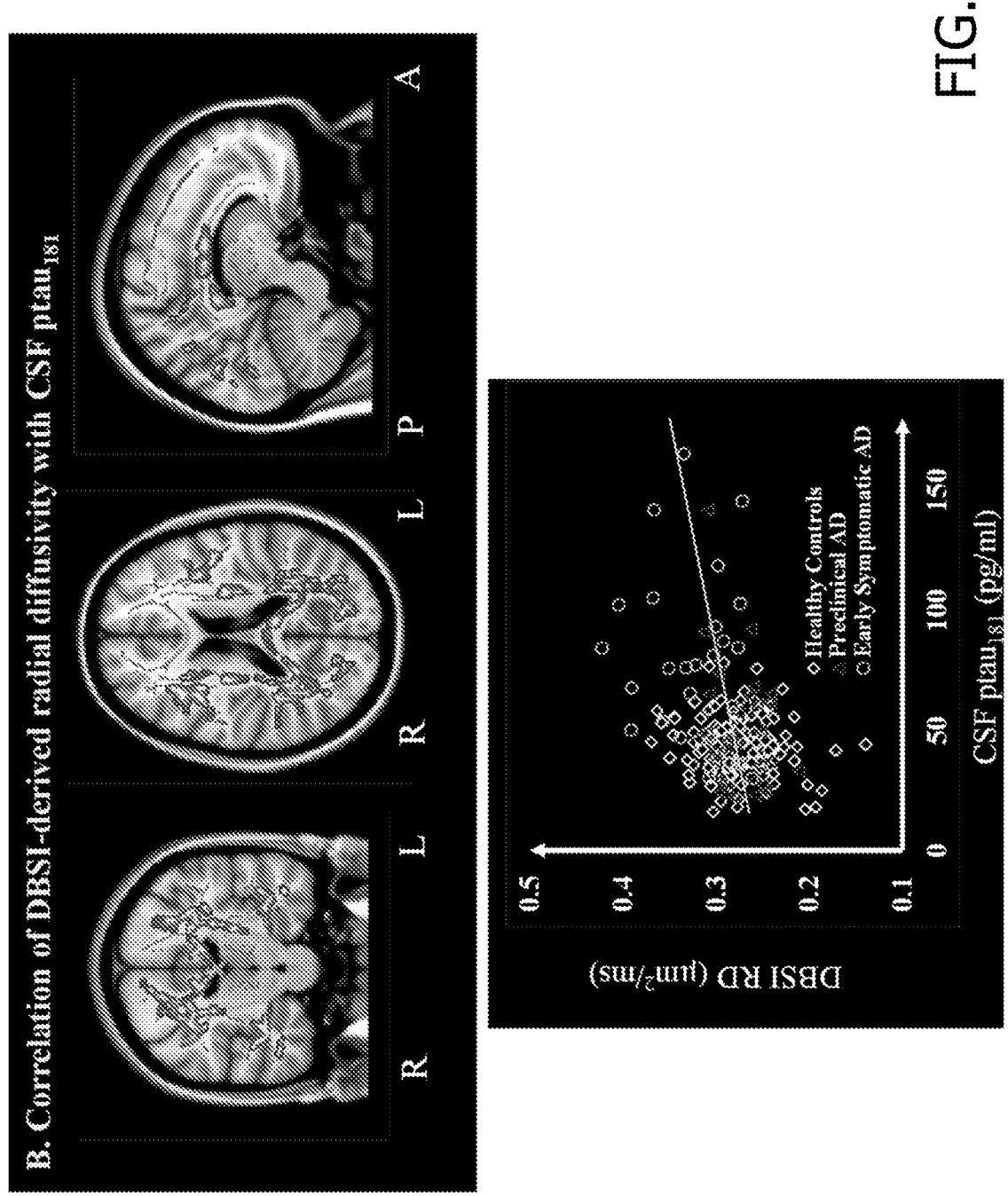
FIG. 77 shows brain image and graphical correlations between DBSI-derived indices and CSF marker of tau pathology.

Significant negative correlation was found between CSF levels of t-tau and DBSI-derived FA in some major WM tracts (FIG. 77 and Table 9). FIG. 77 shows correlations between DBSI-derived indices and CSF marker of tau pathology. Coronal, axial and sagittal views show the voxel-wise significant (P<0.05) (red/yellow clusters, expanded to be visible) correlations between DBSI-derived cellularity diffusivity and CSF t-tau (A), between DBSI-derived radial diffusivity and CSF $ptau_{181}$ (B) and between DBSI-derived mean diffusivity and CSF $ptau_{181}$ (C) The mean FA skeleton (green) representing the centers of all WM tracts common to all participants was overlaid on the Montreal Neurological Institute standard space brain T1-weighted image. Cluster-based thresholding corrected for multiple comparisons. Scatter plots show the correlation between DBSI-derived indices and the CSF marker of tau pathology in the region of splenium of corpus callosum. Diamond marker represents the healthy controls, red triangle represents the preclinical AD and the green circle represents the early symptomatic AD participants. The age, gender and ApoE ε4 genotype were controlled for in computing the statistical significance of differences. L, left hemisphere; R, right hemisphere; P, posterior; A, anterior. No other DBSI-derived indices were associated with CSF levels of t-tau. Significant positive correlations were found between CSF levels of $ptau_{181}$ and DBSI-derived radial and mean diffusivities (FIG. 77 and Table 9). There were no association between CSF levels of $ptau_{181}$ and DBSI-derived cellularity diffusivity, FA and axial diffusivity. The partial correlations were also examined between DBSI imaging markers and CSF biomarkers of tau pathology in those voxels that were significant in the splenium of corpus callosum. When controlling with age, gender and ApoE ε4 genotype, the partial correlation with CSF t-tau was $r_{partial}=-0.33$ (P<0.001) for DBSI-derived FA, and the partial correlation with CSF $ptau_{181}$ was $r_{partial}=0.30$ (P<0.001) for DBSI-derived radial diffusivity and $r_{partial}=0.34$ (P<0.001) for DBSI-derived mean diffusivity.

Innate immune cells, particularly microglia and astrocytes has been reported to mediate inflammatory response in AD and considered as a significant contributor to AD pathogenesis. In AD brain, the highly insoluble amyloid beta peptide deposits and neurofibrillary tangles provide obvious stimuli for neuroinflammation. Amyloid β-induced inflammation has been shown to be mediated via different mechanisms, including inflammasome activation, microglia activation and reactive astrocytes. The persistent immune response stimulated by Amyloid β further promotes pro-inflammatory cytokines to activate more peripheral immune cells and lead to inflammatory cell infiltration, tau hyperphosphorylation and neuronal loss. Detecting and quantifying the early neuroinflammation in AD manifested as immune cell activation and infiltration can enable detection of the mechanism underlying the AD pathogenesis and early disease progression.

To date, three major types of biomarkers of inflammation in AD have been tested, but none have proved ideal. First, PET tracers such as [$^{11}$C]-(R)-PK11195 and [$^{11}$C]-PBR28, targeting the 18 kDa translocator protein, are used for imaging of microglia activation and inflammation in AD animal models and patients. In one prior art study, the activated microglia labelled by the increased [$^{11}$C]-(R)-PK11195 binding was observed in the prodromal amnestic mild cognitive impairment participants with increased Pittsburgh compound B ([$^{11}$C]-PIB) retention for amyloid-β plaque load in brain. In another prior art study, elevated microglial activation was found, as labelled by high [$^{11}$C]-(R)-PK11195 binding within cortical regions, and noted in a group of AD subjects with high [$^{11}$C]-PIB retention. However, the promise of high imaging quality of these PET approaches are limited by issues including genetic polymorphism, lacking of specificity of translocator protein binding for activated microglia and variability of plasma protein binding. Additionally, most of the current translocator protein PET tracers are [$^{11}$C] based and can only be performed at academic centers in proximity to a research cyclotron facility. Second, the elevated levels of CSF YKL40 and other proteins have been reported to be markers of inflammation, and microglial activation suggested by the elevated CSF levels of YKL40 has been observed in preclinical AD and mild cognitive impairment and early AD. CSF level of YKL40 is very promising in discriminating between cognitively normal individuals and patients with mild cognitive impairment and AD, and in predicting disease progression of cognitively normal individuals to mild cognitive impairment. However, CSF analyses have limitations including inter-laboratory variability in measurements of certain markers, the invasiveness of the procedure to obtain CSF for analysis, and the inability to provide information about the anatomic location of pathology using CSF analysis. Third, Gadolinium-based magnetic resonance imaging (MRI) contrast agents in conjunction with T1-Weighted MRI have been proposed to detect inflammation through the detection of blood-brain barrier leakage in multiple sclerosis and AD. However, the long-term safety of gadolinium-based MRI contrast agents remains unknown, and the Food and Drug Administration issued warnings about these agents in 2015. Given these limitations to the currently available biomarkers, a non-invasive, non-radioactive imaging technique capable of quantifying inflammation safely in the general population can significantly advance the understanding of the role of inflammation in pre-symptomatic and early symptomatic AD.

Figure 75:
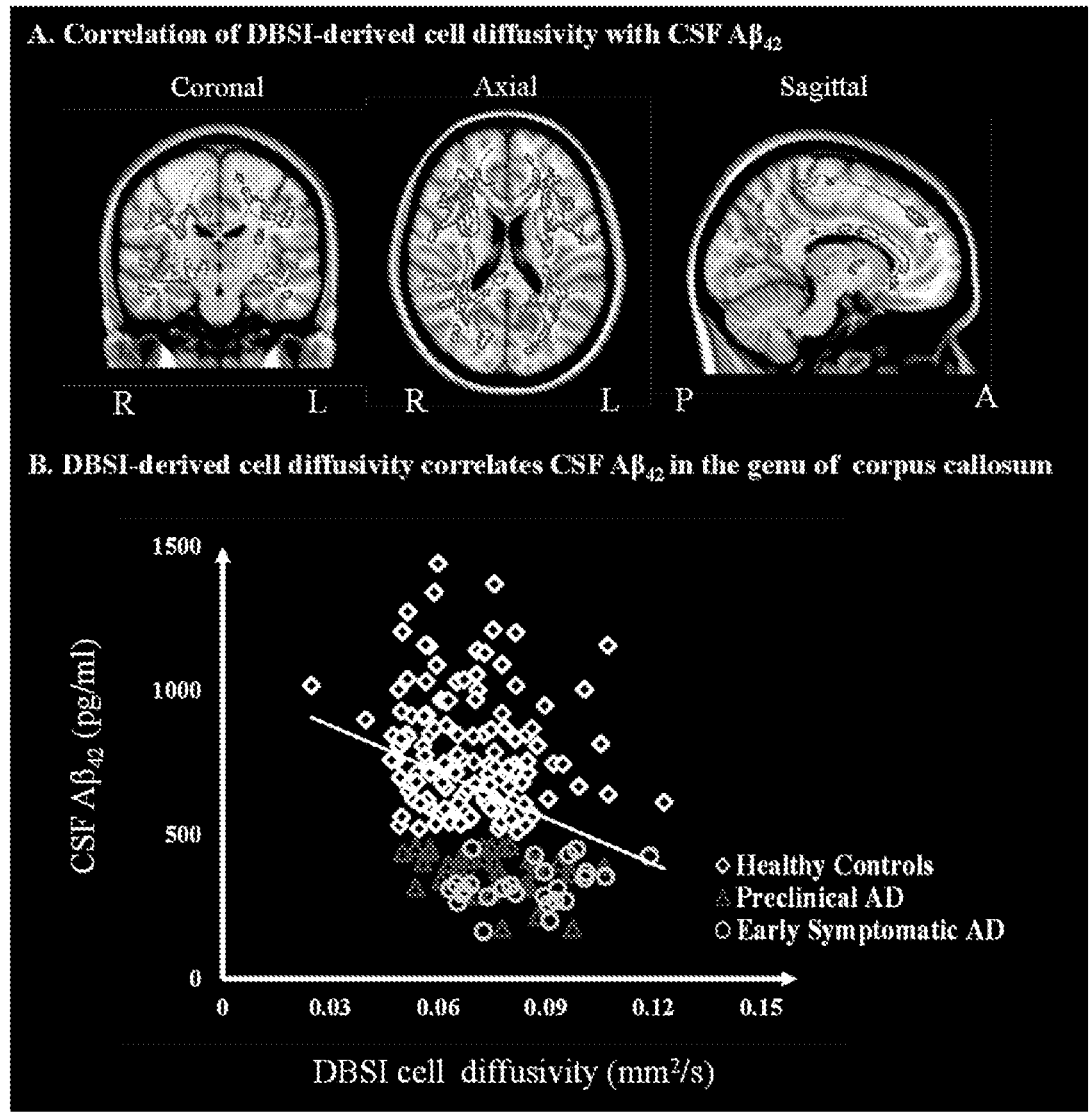
FIG. 75 shows brain image and graphical correlations between DBSI-derived indices and CSF marker of amyloid plaque.

As a novel noninvasive imaging technique, DBSI has demonstrated its capability to image and quantify cellularity infiltration in MS patients and animal models. DBSI-derived cellularity fraction correlated histopathological findings of inflammatory cell infiltration in an in vivo cuprizone treated mouse model. This treatment is well known to result in infiltration of the brain with activated microglia and astrocytes, the same cell types as are involved in neuroinflammation in AD. DBSI-derived cellularity fraction has been considered as a marker for the inflammatory cell infiltration in previous studies. Lack of statistic difference of the DBSI-derived cellularity fraction among the healthy controls, the preclinical and early symptomatic AD suggests that there is no inflammatory cell infiltrated in preclinical and early symptomatic AD. In addition to inflammatory cell infiltration, immune cell activation is another hall mark of inflammation. Microglia/astrocytes activation involves a rapid alteration of cell metabolism and function, which can be accompanied by a graded spectrum of morphological changes that transform highly ramified microglia/astrocytes into amoeboid-phagocytic microglia/astrocytes with the increased cell body size. Histological examination of AD brains as well as cell culture studies have shown that the interaction of microglia with fibrillar amyloid-β leads to their phenotypic activation. A few diffusion MRI techniques have demonstrated their sensitivity to fiber or cell diameters by tracking the changes of water diffusion. The cellularity diffusivity would be increasing with the cell body size increasing. The cellularity diffusivity in each group was quantified to reflect the extent of activated microglia/astrocytes. The observed increase of DBSI-derived cellularity diffusivity in the preclinical and early symptomatic AD suggests the microglial/astrocytes activation may be the early pathological signature in AD, even before WM disruptions (FIG. 74). WM inflammation in AD is mainly manifested as immune cell aviation without significant infiltration, and the significant correlation between DBSI-derived cellularity diffusivity and CSF Aβ$_{42}$ (FIG. 75) suggested the potential causal relationship between the activated microglia/astrocytes and CSF measure of amyloid deposition. FIG. 75 shows correlations between DBSI-derived indices and CSF marker of amyloid plaque. Coronal, axial and sagittal views show the voxel-wise significant (P<0.05) (red/yellow clusters, expanded to be visible) correlations between DBSI-derived cellularity diffusivity and CSF Aβ$_{42}$ (A). The mean FA skeleton (green) representing the centers of all WM tracts common to all participants was overlaid on the Montreal Neurological Institute standard space brain T1-weighted image. Cluster-based thresholding corrected for multiple comparisons. Scatter plots show the correlation between DBSI-derived cellularity diffusivity and the CSF marker of amyloid plaque in the region of genu of corpus callosum. Diamond marker represents the healthy controls, red triangle represents the preclinical AD and the green circle represents the early symptomatic AD participants. The age, gender and ApoE ε4 genotype were controlled for in computing the statistical significance of differences. L, left hemisphere; R, right hemisphere; P, posterior; A, anterior.

Emerging studies have demonstrated that microglial activation can promote Amyloid-β clearance and play important role in neuroprotection in the early stage of AD. However, the chronic inflammation which stimulates the pro-inflammatory cytokines may be a main cause of the neuronal death and pathology damages. The DBSI findings of increased cellularity diffusivity (associated with immune cells activation) with the absence of WM damage in preclinical AD are consistent with the role of neuroprotective role of early inflammation induced by Amyloid-β. And the DBSI findings of further increased cellularity diffusivity accompanied by wide spread WM damage, mainly the myelin damage instead of axonal injury, in the early symptomatic AD are parallel with the detrimental role of chronic inflammation in the later stage of AD. Previous PET studies found the early and protective microglia activation in preclinical AD stage and the two peaks of microglia activation in AD, an early protective peak and a later pro-inflammatory peak. The capability to simultaneously image and detect WM damage while imaging WM inflammation makes DBSI a desired and very unique technique to study the neuroinflammation and neurodegeneration in the pathogenesis and disease progression of AD.

Both cerebral amyloid deposition and persistent activated microglia may induce neuronal damage, resulting in release of aggregated tau protein. CSF levels of t-tau and ptau$_{181}$, which have been considered as the constituent of neurofibrillary tangles, can be used to examine the relationship between AD tau pathology and the WM degeneration detected by DBSI-derived metrics. DBSI-derived FA, radial and mean diffusivities significantly correlated with CSF levels of t-tau and ptau$_{181}$ (FIG. 77), suggesting WM abnormalities is becoming severer with the increasing AD tau pathology. DBSI-derived WM damage indices were found to correlate with the CSF marker of neuronal injury. DBSI-related data disclosed herein is consistent with previous studies demonstrating the widely preserved WM integrity in preclinical phase of AD and white matter degeneration in AD stage.

As discussed herein, DBSI can simultaneously detect and quantify WM cellularity changes and damages in preclinical and early symptomatic AD patients. Moreover, DBSI can be readily and safely translated to clinical trials of patient populations. Consequently, DBSI's application to characterize the role of WM inflammation and damage during AD progression on voxel level is supported herein. Additionally, DBSI's inflammation marker can be validated in both gray matter and white matter regions by using autopsy brains with AD pathologies. Moreover, the rich longitudinal cohort enables validations and establishment of DBSI cell inflammatory marker in AD with other PET markers of inflammation such as DPA-714, PBR28, and PK11195. DBSI application can be expanded to include gray matter in order to extend findings to the whole brain. The PET amyloid and tau imaging for a large amount of participants are available in the cohort for spatial and temporal relationship identification between DBSI-derived indices and PET amyloid and tau imaging.

WM inflammation and damage, simultaneously detectable by DBSI, are the early preclinical features of AD progression. Based on FDA approved standard clinical diffusion MRI sequence with multiple diffusion weightings, DBSI technique is compatible with most clinical MRI scanners. DBSI can noninvasively investigate the role of WM inflammation and damage in AD pathogenesis. Combining DBSI-derived inflammation markers with currently available amyloid-β and tau markers accordingly provides a powerful way to characterize AD pathologies at preclinical and early symptomatic stages.

Figure 79:
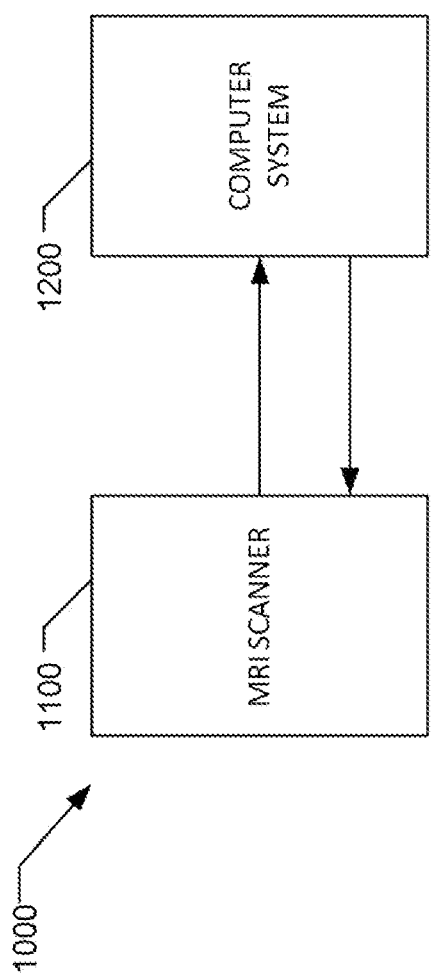
FIG. 79 is a schematic block diagram of an MRI imaging system in one aspect.

In various aspects, the methods described herein may be implemented using an MRI system. FIG. 79 is an illustration of an MRI imaging system 1000 in one aspect. As illustrated in FIG. 79, the MRI system 1000 may include an MRI scanner 1100 operatively coupled and/or in communication with a computer system 1200. In this aspect, the computer system 1200 is configured to receive data including, but not limited to, diffusion data, from the MRI scanner 1100, and is further configured to execute a plurality of stored executable instructions encoding one or more aspects of the MRI method as described herein above. In another aspect, the computer system 1200 may be further configured to operate the MRI scanner 1100 to obtain, for example, diffusion data by executing an additional plurality of stored executable instructions.

Although the present invention is described in connection with an exemplary imaging system environment, embodiments of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well-known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Computer systems, as described herein, refer to any known computing device and computer system. As described herein, all such computer systems include a processor and a memory. However, any processor in a computer system referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

The term processor, as used herein, refers to central processing units, microprocessors, microcontrollers, reduced instruction set circuits (RISC), application specific integrated circuits (ASIC), logic circuits, and any other circuit or processor capable of executing the functions described herein. The above are examples only, and are thus not intended to limit in any way the definition and/or meaning of the term "processor."

As used herein, the term "database" may refer to either a body of data, a relational database management system (RDBMS), or to both. As used herein, a database may include any collection of data including hierarchical databases, relational databases, flat file databases, object-relational databases, object oriented databases, and any other structured collection of records or data that is stored in a computer system. The above examples are example only, and thus are not intended to limit in any way the definition and/or meaning of the term database. Examples of RDBMS's include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one embodiment, a computer program is provided to enable the data processing of the MRI method as described herein above, and this program is embodied on a computer readable medium. In an example embodiment, the computer system is executed on a single computer system, without requiring a connection to a server computer. In a further embodiment, the computer system is run in a Windows® environment (Windows is a registered trademark of Microsoft Corporation, Redmond, Wash.). In yet another embodiment, the computer system is run on a mainframe environment and a UNIX® server environment (UNIX is a registered trademark of X/Open Company Limited located in Reading, Berkshire, United Kingdom). Alternatively, the computer system is run in any suitable operating system environment. The computer program is flexible and designed to run in various different environments without compromising any major functionality. In some embodiments, the computer system includes multiple components distributed among a plurality of computing devices. One or more components may be in the form of computer-executable instructions embodied in a computer-readable medium.

The computer systems and processes are not limited to the specific embodiments described herein. In addition, components of each computer system and each process can be practiced independent and separate from other components and processes described herein. Each component and process also can be used in combination with other assembly packages and processes.

Figure 80:
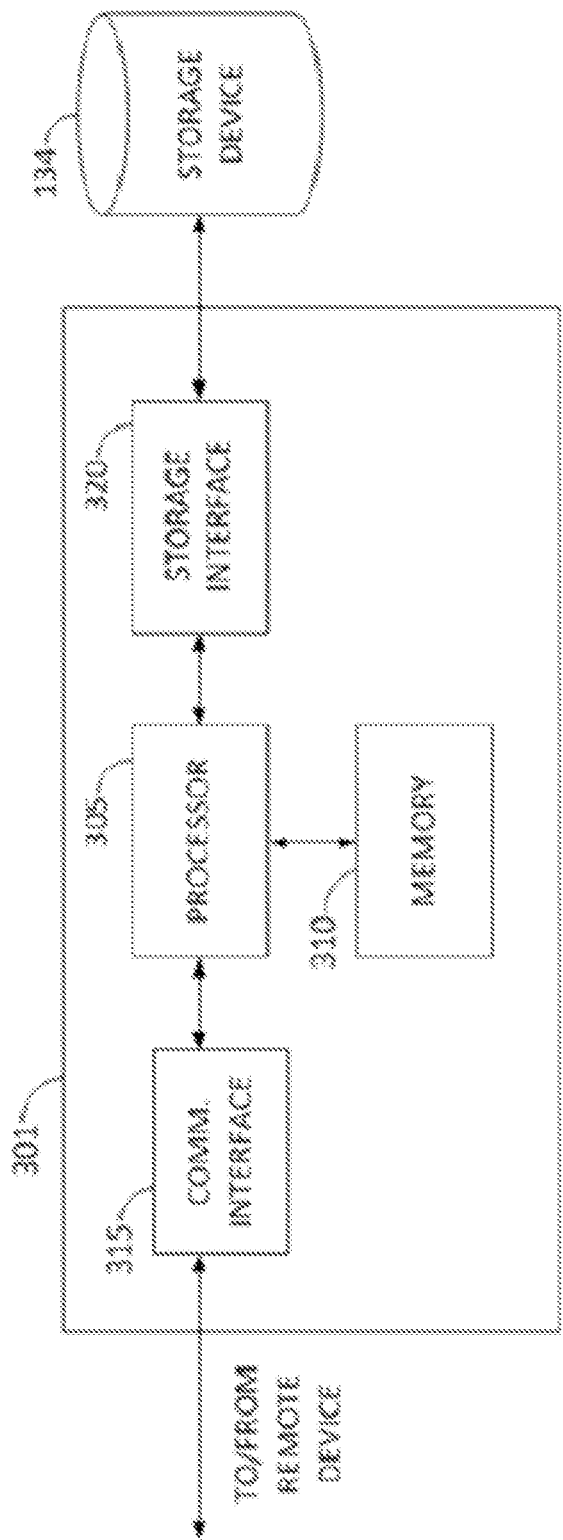
FIG. 80 is a schematic block diagram of an example server system.

In one embodiment, the computer system may be configured as a server system. FIG. 80 illustrates an example configuration of a server system 301 used to receive measurements from the MRI scanner 1100 (not illustrated). Referring again to FIG. 80, server system 301 may also include, but is not limited to, a database server. In this example embodiment, server system 301 performs all of the steps used to implement the MRI imaging method as described herein above.

In this aspect, the server system 301 includes a processor 305 for executing instructions. Instructions may be stored in a memory area 310, for example. The processor 305 may include one or more processing units (e.g., in a multi-core configuration) for executing instructions. The instructions may be executed within a variety of different operating systems on the server system 301, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or any other suitable programming languages).

The processor 305 is operatively coupled to a communication interface 315 such that server system 301 is capable of communicating with a remote device, such as the MRI scanner 1100, a user system, or another server system 301. For example, communication interface 315 may receive requests (e.g., requests to provide an interactive user interface to receive sensor inputs and to control one or more devices of system 1000 from a client system via the Internet.

Processor 305 may also be operatively coupled to a storage device 134. Storage device 134 is any computer-operated hardware suitable for storing and/or retrieving data. In some embodiments, storage device 134 is integrated in server system 301. For example, server system 301 may include one or more hard disk drives as storage device 134. In other embodiments, storage device 134 is external to server system 301 and may be accessed by a plurality of server systems 301. For example, storage device 134 may include multiple storage units such as hard disks or solid state disks in a redundant array of inexpensive disks (RAID) configuration. Storage device 134 may include a storage area network (SAN) and/or a network attached storage (NAS) system.

In some embodiments, processor 305 is operatively coupled to storage device 134 via a storage interface 320. Storage interface 320 is any component capable of providing processor 305 with access to storage device 134. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 134.

Memory area 310 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), registers, hard disk memory, a removable disk, a CD-ROM, or any other form of computer-readable storage medium known in the art. The above memory types are exemplary only, and are thus not limiting as to the types of memory usable for storage of a computer program.

Figure 81:
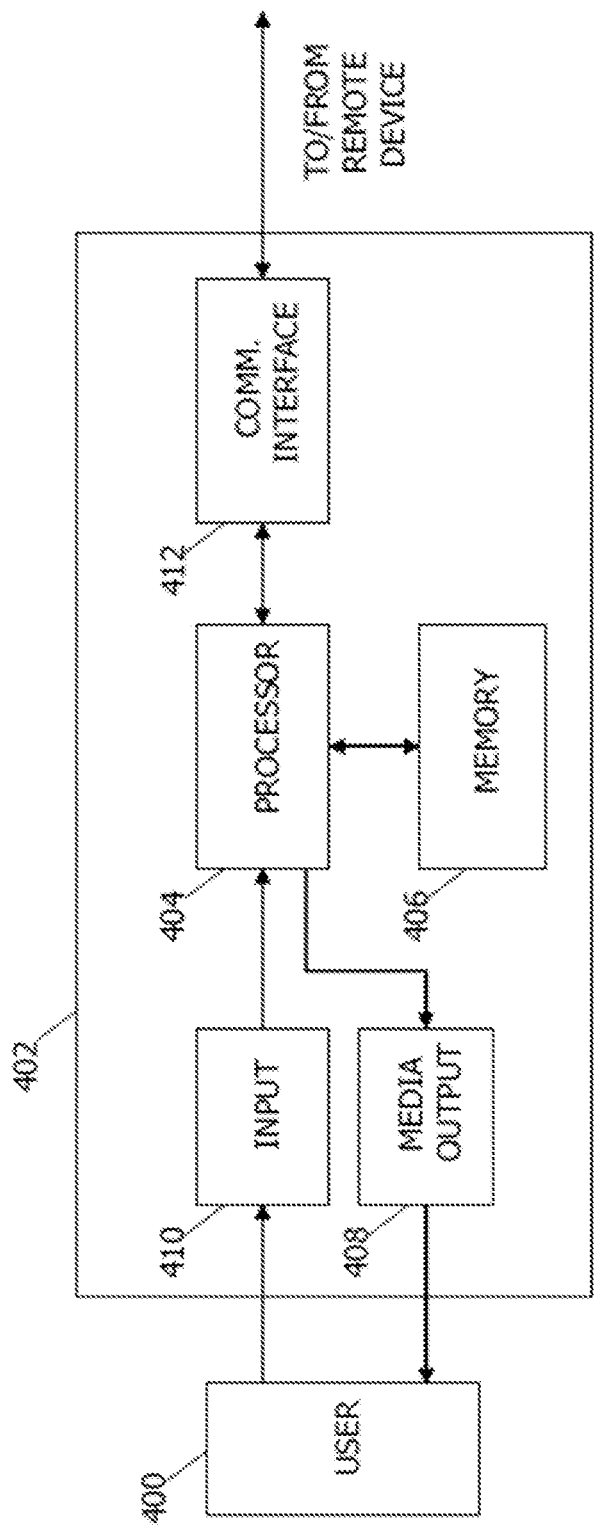
FIG. 81 is a block diagram of an example computing device.

In another embodiment, the computer system may be provided in the form of a computing device, such as a computing device 402 (shown in FIG. 81). Computing device 402 includes a processor 404 for executing instructions. In some embodiments, executable instructions are stored in a memory area 406. Processor 404 may include one or more processing units (e.g., in a multi-core configuration). Memory area 406 is any device allowing information such as executable instructions and/or other data to be stored and retrieved. Memory area 406 may include one or more computer-readable media.

In another embodiment, the memory included in the computing device 402 may include a plurality of modules. Each module may include instructions configured to execute using at least one processor. The instructions contained in the plurality of modules may implement at least part of the method for simultaneously regulating a plurality of process parameters as described herein when executed by the one or more processors of the computing device. Non-limiting examples of modules stored in the memory of the computing device include: a first module to receive measurements from one or more sensors and a second module to control one or more devices of the MRI imaging system 1000.

Computing device 402 also includes one media output component 408 for presenting information to a user 400. Media output component 408 is any component capable of conveying information to user 400. In some embodiments, media output component 408 includes an output adapter such as a video adapter and/or an audio adapter. An output adapter is operatively coupled to processor 404 and is further configured to be operatively coupled to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, client computing device 402 includes an input device 410 for receiving input from user 400. Input device 410 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 408 and input device 410.

Computing device 402 may also include a communication interface 412, which is configured to communicatively couple to a remote device such as server system 302 or a web server. Communication interface 412 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory 406 are, for example, computer-readable instructions for providing a user interface to user 400 via media output component 408 and, optionally, receiving and processing input from input device 410. A user interface may include, among other possibilities, a web browser and an application. Web browsers enable users 400 to display and interact with media and other information typically embedded on a web page or a website from a web server. An application allows users 400 to interact with a server application.

Exemplary methods for diagnosing a condition of a central nervous system in a patient may be performed by the system shown in FIG. 79 and/or the computing devices shown in FIGS. 80 and 81. An exemplary embodiment of a method includes providing a DBSI-MRI data set obtained from the central nervous system of the subject, and transforming the DBSI-MRI data set to obtain at least one DBSI biomarker value. The method also comprises comparing each DBSI biomarker value to at least one corresponding threshold value from a diagnostic database to obtain a relation between each DBSI biomarker value and the at least one corresponding threshold value. The method further comprises diagnosing the condition according to at least one diagnostic rule, wherein each diagnostic rule defines a candidate condition in terms of the relations between the at least one DBSI biomarker value and the at least one corresponding threshold value.

In some embodiments of the exemplary method, the condition is selected from the group consisting of a healthy condition, a preclinical Alzheimer's disease (AD) condition, and an early symptomatic AD condition. In some embodiments, the at least one DBSI biomarker is selected from the group consisting of: a cellularity diffusivity, a fractional anisotropy, and a radial diffusivity. In some embodiments, the diagnostic database comprises a plurality of entries, the plurality of entries comprising a first entry corresponding to the healthy condition, a second entry corresponding to the pre-clinical AD condition, and a third entry corresponding to the early symptomatic AD condition, wherein each entry of the plurality of entries comprises a plurality of threshold values. In some embodiments, the plurality of threshold values for each entry comprise a lower cellularity diffusivity threshold value, an upper cellularity diffusivity threshold value, a lower fractional anisotropy threshold value, an upper fractional anisotropy threshold value, a lower radial diffusivity threshold value, and an upper radial diffusivity threshold value.

In some embodiments of the exemplary method, the at least one diagnostic rule comprises diagnosing the healthy condition if the cellularity diffusivity value is less than the corresponding upper cellularity diffusivity threshold value from the first entry, diagnosing the pre-clinical AD condition if the cellularity diffusivity value is between the corresponding lower cellularity diffusivity threshold value and upper cellularity diffusivity threshold value from the second entry, and diagnosing the early symptomatic AD condition if: the cellularity diffusivity value is between the corresponding lower cellularity diffusivity threshold value and upper cellularity diffusivity threshold value from the third entry of the diagnostic database, the fractional anisotropy value is less than the corresponding upper fractional anisotropy threshold value from the third entry of the diagnostic database, and the radial diffusivity value is greater than the corresponding lower radial diffusivity threshold value from the third entry of the diagnostic database.

In some embodiments of the exemplary method, transforming the DBSI-MRI data set comprises selecting the at least one DBSI biomarker value from a portion of the DBSI-MRI data set corresponding to at least one white matter tract of the subject. In these embodiments, the white matter tract is selected from the group consisting of: corpus callosum, internal capsule, corona radiate, external capsule, cingulate gyrus, hippocampus, superior longitudinal fasciculus, and superior fronto-occipital fasciculus.

Exemplary embodiments of methods, systems, and apparatus for use in diffusion basis spectrum imaging are described above in detail. The methods, systems, and apparatus are not limited to the specific embodiments described herein but, rather, operations of the methods and/or components of the systems and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus described herein.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

It will be understood by those of skill in the art that information and signals may be represented using any of a variety of different technologies and techniques. For example, data, instructions, commands, information, signals, bits, symbols, and/or chips may be represented by voltages, currents, electromagnetic waves, magnetic fields or particles, optical fields or particles, or any combination thereof. Similarly, the various illustrative logical blocks, modules, circuits, and algorithm operations described herein may be implemented as electronic hardware, computer software, or a combination of both, depending on the application and the functionality. Moreover, the various logical blocks, modules, and circuits described herein may be implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general purpose processors include, but are not limited to only including, microprocessors, conventional processors, controllers, microcontrollers, state machines, or a combination of computing devices.

When introducing elements of aspects of the invention or embodiments thereof, the articles "a," "an," "the," and "said" are intended to mean that there are one or more of the elements. The terms "comprising," including," and "having"

are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for diagnosing at least one condition of a central nervous system in a subject, the method comprising:
  receiving, via a computing device including a processor, a diffusion basis spectrum imaging—magnetic resonance imaging (DBSI-MRI) data set obtained from the central nervous system of the subject;
  transforming, via the computing device, the DBSI-MRI data set to obtain at least one DBSI biomarker value including a cellularity diffusivity based on a DBSI signal model;
  generating maps of the at least one DBSI biomarker value derived from the transformation;
  comparing, via the computing device, each of the at least one DBSI biomarker value to at least one corresponding threshold value from a diagnostic database to obtain a relation between each of the at least one DBSI biomarker value and the at least one corresponding threshold value, wherein the at least one corresponding threshold value each is a DBSI biomarker value;
  diagnosing, via the computing device, the at least one condition according to at least one diagnostic rule, wherein each of the at least one diagnostic rule defines a candidate condition of the central nervous system in terms of the relations between the at least one DBSI biomarker value and the at least one corresponding threshold value, and
  verifying the at least one DBSI biomarker by correlating the at least one DBSI biomarker with at least one cerebrospinal fluid (CSF) neural injury marker,
  wherein the at least one condition is selected from the group consisting of a healthy condition, a preclinical Alzheimer's disease (AD) condition, and an early symptomatic AD condition, and the at least one DBSI biomarker is selected from the group consisting of: the cellularity diffusivity, a fractional anisotropy, and a radial diffusivity; and
  wherein the at least one corresponding threshold value includes a plurality of threshold values, and the diagnostic database comprises a plurality of entries, the plurality of entries comprising a first entry corresponding to the healthy condition, a second entry corresponding to the pre-clinical AD condition, and a third entry corresponding to the early symptomatic AD condition, wherein each entry of the plurality of entries comprises the plurality of threshold values, wherein the plurality of threshold values for each entry comprise a lower cellularity diffusivity threshold value, an upper cellularity diffusivity threshold value, a lower fractional anisotropy threshold value, an upper fractional anisotropy threshold value, a lower radial diffusivity threshold value, and an upper radial diffusivity threshold value, wherein the plurality of threshold values are means of relating biomarker values to one condition selected from the group consisting of the healthy condition, the preclinical AD condition, and the early symptomatic AD condition, and
  wherein the at least one diagnostic rule comprises:
    diagnosing the healthy condition if the cellularity diffusivity value is less than the corresponding upper cellularity diffusivity threshold value from the first entry;
    diagnosing the pre-clinical AD condition if the cellularity diffusivity value is between the corresponding lower cellularity diffusivity threshold value and upper cellularity diffusivity threshold value from the second entry; and
    diagnosing the early symptomatic AD condition if:
      the cellularity diffusivity value is between the corresponding lower cellularity diffusivity threshold value and upper cellularity diffusivity threshold value from the third entry;
      the fractional anisotropy value is less than the corresponding upper fractional anisotropy threshold value from the third entry; and
      the radial diffusivity value is greater than the corresponding lower radial diffusivity threshold value from the third entry.

2. The method in accordance with claim 1, wherein transforming the DBSI-MRI data set comprises selecting the at least one DBSI biomarker value from a portion of the DBSI-MRI data set corresponding to at least one white matter tract of the subject, wherein the at least one white matter tract is selected from the group consisting of: corpus callosum, internal capsule, corona radiate, external capsule, cingulate gyrus, hippocampus, superior longitudinal fasciculus, and superior fronto-occipital fasciculus.

3. A central nervous system diagnosis computing device for providing a diagnosis of at least one condition of a central nervous system in a subject, said computing device including a processor in communication with a memory, said processor programmed to:
  retrieve a diffusion basis spectrum imaging—magnetic resonance imaging (DBSI-MRI) data set obtained from the central nervous system of the subject from the memory;
  transform the DBSI-MRI data set to obtain at least one DBSI biomarker value including a cellularity diffusivity based on a DBSI signal model;
  generate maps of the at least one DBSI biomarker value derived from the transformation;
  retrieve a diagnostic database comprising at least one corresponding threshold value from the memory;
  compare each of the at least one DBSI biomarker value to at least one corresponding threshold value from the retrieved diagnostic database to obtain a relation between each of the at least one DBSI biomarker value and the at least one corresponding threshold value, wherein the at least one corresponding threshold value each is a DBSI biomarker value; and
  diagnose the at least one condition according to at least one diagnostic rule, wherein each of the at least one diagnostic rule defines a candidate condition of the central nervous system in terms of the relations between the at least one DBSI biomarker value and the at least one corresponding threshold value,
  wherein the at least one condition is selected from the group consisting of a healthy condition, a preclinical Alzheimer's disease (AD) condition and an early symptomatic AD condition, and the at least one DBSI biomarker is selected from the group consisting of: the cellularity diffusivity, a fractional anisotropy, and a radial diffusivity,
wherein said processor is further programmed to:
verify the at least one DBSI biomarker by correlating the at least one DBSI biomarker with at least one cerebrospinal fluid (CSF) neural injury marker,
wherein the at least one corresponding threshold value includes a plurality of threshold values, and the diagnostic database comprises a plurality of entries, the plurality of entries comprising a first entry corresponding to the healthy condition, a second entry corresponding to the preclinical AD condition, and a third entry corresponding to the early symptomatic AD condition, wherein each entry of the plurality of entries comprises the plurality of threshold values, wherein the plurality of threshold values are means of relating biomarker values to one condition selected from the group consisting of the healthy condition, the preclinical AD condition, and the early symptomatic AD condition,
wherein the plurality of threshold values for each entry comprise a lower cellularity diffusivity threshold value, an upper cellularity diffusivity threshold value, a lower fractional anisotropy threshold value, an upper fractional anisotropy threshold value, a lower radial diffusivity threshold value, and an upper radial diffusivity threshold value, and
wherein the at least one diagnostic rule comprises:
diagnosing the healthy condition if the cellularity diffusivity value is less than the corresponding upper cellularity diffusivity threshold value from the first entry;
diagnosing the pre-clinical AD condition if the cellularity diffusivity value is between the corresponding lower cellularity diffusivity threshold value and upper cellularity diffusivity threshold value from the second entry; and
diagnosing the early symptomatic AD condition if:
the cellularity diffusivity value is between the corresponding lower cellularity diffusivity threshold value and upper cellularity diffusivity threshold value from the third entry;
the fractional anisotropy value is less than the corresponding upper fractional anisotropy threshold value from the third entry; and
the radial diffusivity value is greater than the corresponding lower radial diffusivity threshold value from the third entry.

4. The computing device in accordance with claim 3, wherein said processor is further configured to select the at least one DBSI biomarker value from a portion of the DBSI-MRI data set corresponding to at least one white matter tract of the subject, wherein the at least one white matter tract is selected from the group consisting of: corpus callosum, internal capsule, corona radiate, external capsule, cingulate gyrus, hippocampus, superior longitudinal fasciculus, and superior fronto-occipital fasciculus.

5. At least one non-transitory computer-readable storage media for providing a diagnosis of at least one condition of a central nervous system in a subject, the at least one non-transitory computer-readable storage media having computer-executable instructions embodied thereon, wherein, when executed by at least one processor, the computer-executable instructions cause the at least one processor to:
transform a diffusion basis spectrum imaging—magnetic resonance imaging (DBSI-MRI) data set to obtain at least one DBSI biomarker value, wherein the DBSI-MRI data set is obtained from the central nervous system of the subject including a cellularity diffusivity based on a DBSI signal model;
generate maps of the at least one DBSI biomarker value derived from the transformation;
compare each of the at least one DBSI biomarker value to at least one corresponding threshold value from a stored diagnostic database to obtain a relation between each of the at least one DBSI biomarker value and the at least one corresponding threshold value, wherein the at least one corresponding threshold value each is a DBSI biomarker value; and
diagnose the at least one condition according to at least one diagnostic rule, wherein each of the at least one diagnostic rule defines a candidate condition of the central nervous system in terms of the relations between the at least one DBSI biomarker value and the at least one corresponding threshold value,
wherein the at least one condition is selected from the group consisting of a healthy condition, a preclinical Alzheimer's disease (AD) condition and an early symptomatic AD condition, and the at least one DBSI biomarker is selected from the group consisting of: the cellularity diffusivity, a fractional anisotropy, and a radial diffusivity,
wherein the computer-executable instructions further cause the at least one processor to:
verify the at least one DBSI biomarker by correlating the at least one DBSI biomarker with at least one cerebrospinal fluid (CSF) neural injury marker,
wherein the at least one corresponding threshold value includes a plurality of threshold values, and the diagnostic database comprises a plurality of entries, the plurality of entries comprising a first entry corresponding to the healthy condition, a second entry corresponding to the pre-clinical AD condition, and a third entry corresponding to the early symptomatic AD condition, wherein each entry of the plurality of entries comprises the plurality of threshold values, wherein the plurality of threshold values are means of relating biomarker values to one condition selected from the group consisting of the healthy condition, the preclinical AD condition, and the early symptomatic AD condition,
wherein the plurality of threshold values for each entry comprise a lower cellularity diffusivity threshold value, an upper cellularity diffusivity threshold value, a lower fractional anisotropy threshold value, an upper fractional anisotropy threshold value, a lower radial diffusivity threshold value, and an upper radial diffusivity threshold value, and
wherein the at least one diagnostic rule comprises:
diagnosing the healthy condition if the cellularity diffusivity value is less than the corresponding upper cellularity diffusivity threshold value from the first entry;
diagnosing the pre-clinical AD condition if the cellularity diffusivity value is between the corresponding lower cellularity diffusivity threshold value and upper cellularity diffusivity threshold value from the second entry; and
diagnosing the early symptomatic AD condition if:
the cellularity diffusivity value is between the corresponding lower cellularity diffusivity threshold value and upper cellularity diffusivity threshold value from the third entry;

the fractional anisotropy value is less than the corresponding upper fractional anisotropy threshold value from the third entry; and the radial diffusivity value is greater than the corresponding lower radial diffusivity threshold value from the third entry.

6. The at least one non-transitory computer-readable storage media in accordance with claim 5, wherein the computer-executable instructions cause the at least one processor to transform the DBSI-MRI data set by selecting the at least one DBSI biomarker value from a portion of the DBSI-MRI data set corresponding to at least one white matter tract of the subject, wherein the at least one white matter tract is selected from the group consisting of: corpus callosum, internal capsule, corona radiate, external capsule, cingulate gyrus, hippocampus, superior longitudinal fasciculus, and superior fronto-occipital fasciculus.

* * * * *

UNITED STATES PATENT AND TRADEMARK OFFICE
CERTIFICATE OF CORRECTION

PATENT NO. : 11,672,468 B2
APPLICATION NO. : 16/097457
DATED : June 13, 2023
INVENTOR(S) : Yong Wang et al.

It is certified that error appears in the above-identified patent and that said Letters Patent is hereby corrected as shown below:

In the Specification

In Column 1, Lines 23-26 should read:
-- This invention was made with government support under AG026276, AG003991 and AG054567 awarded by the National Institutes of Health. The government has certain rights in the invention. --.

Signed and Sealed this
Twenty-sixth Day of November, 2024

Katherine Kelly Vidal
*Director of the United States Patent and Trademark Office*